United States Patent
Narine et al.

(10) Patent No.: US 7,538,236 B2
(45) Date of Patent: May 26, 2009

(54) BIOPLASTICS, MONOMERS THEREOF, AND PROCESSES FOR THE PREPARATION THEREOF FROM AGRICULTURAL FEEDSTOCKS

(76) Inventors: Suresh Narine, 6307 132nd Street, Edmonton, Alberta (CA) T6H 3Y8; Peter Sporns, 5315 35th Avenue, Edmonton, Alberta (CA) T6L 1C5; Jin Yue, 2151, Michner Park, Edmonton, Alberta (CA) T6H 4N1

( * ) Notice: Subject to any disclaimer, the term of this patent is extended or adjusted under 35 U.S.C. 154(b) by 0 days.

(21) Appl. No.: 11/649,620

(22) Filed: Jan. 4, 2007

(65) Prior Publication Data

US 2007/0175793 A1    Aug. 2, 2007

Related U.S. Application Data

(60) Provisional application No. 60/755,770, filed on Jan. 4, 2006.

(51) Int. Cl.
C07C 51/34   (2006.01)
C07C 45/40   (2006.01)
C07C 59/147  (2006.01)

(52) U.S. Cl. ............... 554/133; 568/469.9; 554/120

(58) Field of Classification Search .......... 554/120, 554/124, 133; 568/469.9
See application file for complete search history.

(56) References Cited

U.S. PATENT DOCUMENTS

| | | | |
|---|---|---|---|
| 2,450,858 A | 10/1948 | Fitzpatrick et al. | |
| 2,813,113 A | 11/1957 | Goebel et al. | |
| 3,112,329 A | 11/1963 | Pryde | |
| 4,591,602 A | 5/1986 | DeVillez | |
| 4,978,465 A | 12/1990 | Sturwold | |
| 5,278,327 A | 1/1994 | Eierdanz et al. | |
| 5,302,670 A | 4/1994 | Frische et al. | |
| 5,401,493 A | 3/1995 | Lohrmann et al. | |
| 5,427,790 A | 6/1995 | Frische et al. | |
| 5,514,368 A | 5/1996 | Wangemann et al. | |

(Continued)

FOREIGN PATENT DOCUMENTS

CA     2039755     10/1991

(Continued)

OTHER PUBLICATIONS

Pryde, E.H. et al., Ozonization of Soybean Oil. The preparation and some properties of aldehyde oils, 1961, The Journal of the American Oil Chemist Society, vol. 38, pp. 375-379.*

(Continued)

*Primary Examiner*—Daniel M Sullivan
*Assistant Examiner*—Yate' K Cutliff
(74) *Attorney, Agent, or Firm*—Patrick J. Hagan; Dann, Dorfman, Herrell and Skillman, P.C.

(57) ABSTRACT

The present invention relates generally to polymers and monomers derived from agricultural feedstocks, and more particularly to methods for the production of monomers from renewable agricultural resources such as feedstocks, for example canola, flax and tallow, and polymers, in particular polyurethanes produced from monomers derived from such feedstocks. The present invention also relates to novel processes for the production of short-chain alcohols, as well as hydroxyl wax esters, from renewable feedstocks. An improved apparatus for carrying out ozonolysis reactions is also disclosed.

17 Claims, 87 Drawing Sheets

A schematic representation of the production of GIII-Polyol as described in Example 7

U.S. PATENT DOCUMENTS

| | | | |
|---|---|---|---|
| 5,595,965 | A | 1/1997 | Wiggins |
| 5,777,201 | A | 7/1998 | Poutre et al. |
| 5,885,948 | A | 3/1999 | Glenn, Jr. et al. |
| 5,919,741 | A | 7/1999 | Jaynes et al. |
| 5,973,173 | A | 10/1999 | Josten et al. |
| 6,025,417 | A | 2/2000 | Willett et al. |
| 6,080,707 | A | 6/2000 | Glenn, Jr. et al. |
| 6,080,708 | A | 6/2000 | Glenn, Jr. et al. |
| 6,316,649 | B1 | 11/2001 | Cermak et al. |
| 6,420,493 | B1 | 7/2002 | Ryckis-Kite et al. |
| 6,428,767 | B1 | 8/2002 | Burch |
| 6,433,121 | B1 | 8/2002 | Petrovic et al. |
| 6,444,713 | B1 | 9/2002 | Pach et al. |
| 6,465,401 | B1 | 10/2002 | Kodali et al. |
| 6,465,569 | B1 | 10/2002 | Kurth |
| 6,548,580 | B1 | 4/2003 | Rhode et al. |
| 6,559,213 | B2 | 5/2003 | Wesch |
| 6,768,029 | B1 * | 7/2004 | Khan et al. .......... 568/469 |
| 2002/0001661 | A1 | 1/2002 | Gopal |
| 2002/0013396 | A1 | 1/2002 | Benecke et al. |
| 2002/0155080 | A1 | 10/2002 | Glenn, Jr. et al. |
| 2003/0088054 | A1 | 5/2003 | Chasar et al. |
| 2003/0090016 | A1 | 5/2003 | Petrovic |

FOREIGN PATENT DOCUMENTS

| | | |
|---|---|---|
| CA | 2156155 | 8/1994 |
| CA | 2147089 | 10/1995 |
| CA | 2314943 | 2/2001 |
| DE | 72783 | 11/1969 |
| EP | 0476553 | 3/1992 |
| EP | 0170201 | 9/1992 |
| EP | 0767199 | 4/1997 |
| EP | 0656019 | 1/1998 |
| EP | 0712834 | 7/1999 |
| EP | 0904445 | 2/2002 |
| EP | 1264850 | 12/2002 |
| EP | 1173524 | 3/2003 |
| JP | 05201835 | 8/1993 |
| JP | 05202222 | 8/1993 |
| JP | 08183823 | 7/1996 |
| WO | 8603502 | 6/1986 |
| WO | 8605502 | 9/1986 |
| WO | 8805446 | 7/1988 |
| WO | 9218591 | 10/1992 |
| WO | 9303004 | 2/1993 |
| WO | 9522576 | 8/1995 |
| WO | 9607632 | 3/1996 |
| WO | 9607751 | 3/1996 |
| WO | 9811871 | 3/1998 |
| WO | 9811872 | 3/1998 |
| WO | 9811873 | 3/1998 |
| WO | 9926618 | 6/1999 |
| WO | 9926619 | 6/1999 |
| WO | 9938489 | 8/1999 |
| WO | 9938491 | 8/1999 |
| WO | 0001658 | 1/2000 |
| WO | 0015684 | 3/2000 |
| WO | 0031015 | 6/2000 |
| WO | 0041515 | 7/2000 |
| WO | 0078699 | 12/2000 |
| WO | 0104225 | 1/2001 |
| WO | 0156756 | 8/2001 |
| WO | 0170842 | 9/2001 |
| WO | 0198404 | 12/2001 |
| WO | 0240627 | 5/2002 |
| WO | 02060839 | 8/2002 |
| WO | 03008476 | 1/2003 |
| WO | 03014271 | 2/2003 |
| WO | 03020782 | 3/2003 |
| WO | 03031424 | 4/2003 |

OTHER PUBLICATIONS

Pryde, E.H. et al., Alcohols from ozonolysis products of unsaturated fatty esters, 1976, Journal of the American Oil Chemist Society, vol. 53, pp. 90, 93.*

Byrdwell, W.C. et al, Wlectrospray ionization Ms of high M.S. TAG oligomers, 2004, Journal of American Oil Chemist Society, vol. 81, No. 1, pp. 13.*

Guo, A. et al., Polyols and polyurethanes from hydroformylation of soybean oil, 2002, Journal of Polymers and the Environment, vol. 10, No. 1/2, pp. 49.*

Petrovic, Z. et al., Structure and properties of Polyurethanes prepared from triglyceride polyols oby ozonolysis, Jan. 8, 2005, Biomacromolecules, vol. 6 (2), pp. 713, 715.*

Elfman-Borjesson, I. et al., "Analysis of Non-Polar Lipids by HPLC no a Diol Column", J. High Resol. Chromatogr., 20:516-518 (1997).

Ferry, J.D., "Viscoelastic Properties of Polymers", John Wiley & Sons, Inc. (Ed.), New York, Chapter 11pp. 270-271 (1980).

Flory, P.J., Principles of Polymer Chemistry, Cornell University Press, Ithaca, NY, pp. 458-464 (1953).

Gibson, L.J. et al., Cellular solids: structure & properties, Oxford, New York, Pergamon Press, pp. 120-122 (1988).

Guo, A. et al., "Polyols and polyurethanes from hydroformylation of soybean oil", J. Polym. & Environ., 10: 49-52 (2002).

Guo, A. et al., "Rigid polyurethane foams based on soybean oil", Journal of Applied Polymer Science, 77: 467-473 (2000).

Guo, A. et al., "Structure and properties of halogenated and nonhalogenated soy-based polyols", J. Polym. Sci: Part A: Polym. Chem., 38: 3900-3910 (2000).

Hu, Y. et al., "Rigid polyurethane foam prepared from a rape seed oil based polyol", J. Appl. Polym. Sci., 84: 591-597 (2002).

Hutchinson, J.M., "Characterising the glass transition and relaxation kinetics by conventional and temperature-modulated differential scanning calorimetry", Thermochimica Acta, 324: 165-174 (1998).

Hutchinson, J.M., "Studying the glass transition by DSC and TMDSC, Journal of Thermal Analysis and Calorimetry", 72: 619-629 (2003).

Lin, S.H., "Industrial wastewater treatment IN a new gas-induced ozone reactor", Journal of Hazardous Materials, B98, 295-309 (2003).

Ishida, H. et al., "Mechanical characterization of copolymers based on benzoxazine and epoxy", Polymer, 37: 4487-4495 (1996).

James, H.M. et al., "Theory of the Increase in Rigidity of Rubber During Cure", J. Chem. Phys., 15: 669-683 (1947).

Javni, I. et al., "Soybean oil based polyisocyanurate cast resins", Journal of Applied Polymer Science, 90: 3333-3337 (2003).

Javni, I. et al., "Thermal stability of polyurethanes based on vegetable oils", J. Appl. Polym. Sci., 77: 1723-1734 (2000).

John, J. et al., "Characterization of polyurethane foams from soybean oils", J. Appl. Polym. Sci., 86: 3097-3107 (2002).

Pegoraro, M., "Gas Transport Properties of Siloxane Polyurethanes", Journal of Applied Polymer Science, 57(4): 421-430 (1995).

Khandare, P.M. et al., "The measurement of the glass transition temperature of mesophase pitches using a thermomechanical device", Carbon, 34: 663-669 (1996).

Khot, S.N. et al., "Development and application of triglyceride-based polymers and composites", J. Appl. Polym. Sci., 82: 703-723 (2001).

Kissinger, H.E., "Reaction Kinetics in Differential Thermal Analysis", Anal. Chem., 29: 1702-1706 (1957).

Szycher, M., Isocyanate Chemistry, in Sycher's Handbook of Polyurethanes, CRC Press, New York, pp. 4-1 to 4-40 (1999).

McKenna, G.S. In Comprehensive Polymer Science: vol. 2, Polymer Properties, Booth C., Price, C., Eds.; Pergamon: Oxford, pp. 311-362 (1989).

Neff, W.E. et al., "Oxidative Stability of Purified Canola Oil Triacylglycerols with Altered Fatty-Acid Compositions as Affected by Triacylglycerol Composition and Structure", J. Am. Oil Chem. Soc., 71: 1101-1109 (1994).

Nielson, L.E. et al., "Mechanical Properties of Polymers and Composites", 2nd ed., Marcel Dekker, NY pp. 139-255 (1994).

O'Brien, R.D., Fats and Oils: Formulating and Processing for Applications, CRC Press, Boca Raton, FL, pp. 16-17 (2004).

Painter, P.C. et al., "A Simple Model for the Swelling of Polymer Networks", J. Chem. Phys., 99: 1409-1418 (1993).

Petrovic, Z.S. et al., "Thermal-Degradation of Segmented Polyurethanes", J. Appl. Poly. Sci., 51(6): 1087-1095 (1994).

Petrovic, Z.S. et al., "Soy-oil-based segmented polyurethanes", Journal of Polymer Science Part B—Polymer Physics, 43: 3178-3190 (2005).

Petrovic, Z.S. et al., "Structure and properties of polyurethanes prepared from triacylglycerol polyols by ozonolysis", Biomacromolecules, 6: 713-719 (2005).

Petrovic, Z.R. et al., "Structure and Properties of Polyurethanes Based on Halogenated and Nonhalogenated Soy-Polyols", J. Polymer Sci Part A: Polym. Chem. 38: 4062-4069 (2000).

Petrovic, Z.S. et al., "Effect of OH/NCO molar ratio on properties of soy-based polyurethane networks", J. Polym. & Environ., 10: 5-12 (2002).

Carlson, K.D., "Vemonia galamensis Seed Oil: A New Source for Epoxy Coatings", Pryde, E.H. et al. (Eds.), New Sources of Fats and Oils, American Oil Chemists Society, Champaign, IL, pp. 297-318 (1981).

Salunkhe, D.K. et al. in World Oilseeds: Chemistry, Technology and Utilization; Van Nostrand Reinhold, New York, pp.87-89 (1992).

Saxena, P.K. et al., "The Effect of Castor Oil on the Structure and Properties of Polyurethane Elastomers", J. Appl. Polym. Sci., 44: 1343-1347 (1992).

Son, T. W. et al., "Thermal and phase behavior of polyurethane based on chain extender, 2,2-bis-[4-(2-hydroxyethoxy)phenyl]propane", Polym. J., 31: 563-568 (1999).

Thomas, T.J. et al., "Thermogravimetric and Mass-Spectrometric Study of the Thermal-Decomposition of Pbct Resins", J. Appl. Polym. Sci., 24: 1797-1808 (1979).

Williams, R.J., "Methods for Determination of Glass Transitions in Seeds", Annals of Botany, 74: 525-530 (1994).

Wunderlich, B., "The tribulations and successes on the road from DSC to TMDSC in the 20th century the prospects for the 21st century", Journal of Thermal Analysis and Calorimetry, 78: 7-31 (2004).

Yu, T.L. et al., "Morphology of polyurethanes with triol monomer crosslinked on hard segments", J. Polym. Sci. Part B: Polym. Phys., 37: 2673-2681 (1999).

Zlatanic, A. et al., "Structure and Properties of Triolein-Based Polyurethane Networks", Biomacromolecules, 3: 1048-1056 (2002).

Barrett, L.W. et al., "Naturally functionalised triglyceride oils in interpenetrating polymer networks", J. Am. Oil Chem. Soc., 70: 523-534 (1993).

Carlson, K.D. et al., "Chemical epoxidation of a natural unsaturated epoxy seed oil from Vernonia galamensis and a look at epoxy oil markets", J. Am . Oil Chem. Soc., 62: 934-939 (1985).

Coats, A.W. et al., "Kinetic parameters from Thermogravimetric Data", Nature, 201: 68 (1964).

Coleman, M.M. et al., "Hydrogen-bonding in polymers. 4. infrared temperature studies of a simple polyurethane", Macromolecules, 19: 2149-2157 (1986).

Cooney, J.D. et al., "Thermal Degradation of Poly(Ethylene-Terephthalate) - a Kinetic Analysis of Thermogravimetric Data", J. Appl. Polym. Sci., 28:2887-2902 (1983).

Czech, P. et al., "Polyurethane networks based on hyperbranched polyesters: Synthesis and molecular relaxations", J. Non-Cryst. Solis, 351: 2735-2741 (2005).

Firestone, D., Physical and Chemical Characteristics of Oils, Fats and Waxes, AOCS Press, pp. 56 and 85 (1999).

Darwant, B., "Bond dissociation energies in simple molecules", [Washington] U.S. National Bureau of Standards, pp. 18-19 (1970).

Dwan'Isa, J.-P. et al., "Novel Biobased Polyurethanes Synthesized from Soybean Phosphate Ester Polyols: Thermomechanical Properties Evaluations" , J. Polym & Environ., 11: 161-168 (2003).

Eisenberg, A., Physical Properties of Polymers, American Chemical Society: Washington, DC, pp. 61-95 (1993).

Khoe, S.N. eta l., "Rigid urethane foams frmo hydroxymethylated linseed oil and polyol esters", J. Am. Oil Chem. Soc., 49: 615-618 (1972).

Lyon, C.D. eta l., "Rigid Urethance Foams from Hydroxymethylated Castor-oil, Safflower Oil, Oleic Safflower Oil and Polyol Esters of Castor Oils", J. Am. Oil Chem. Soc., 51(8): 331-334 (1974).

* cited by examiner

Figure 1: Production of Polyol and Subsequent Interesterification

Figure 2: Synthesis reaction of Polyols from Canola Oil

Figure 3: HPLC of Reaction Mixture (upper trace) and Fraction 76 (lower trace) After Hydrogenation a) Tristearin
b) Frac 76

Figure 5: Electrospray Ionization Mass Spectrometry of Fraction 76
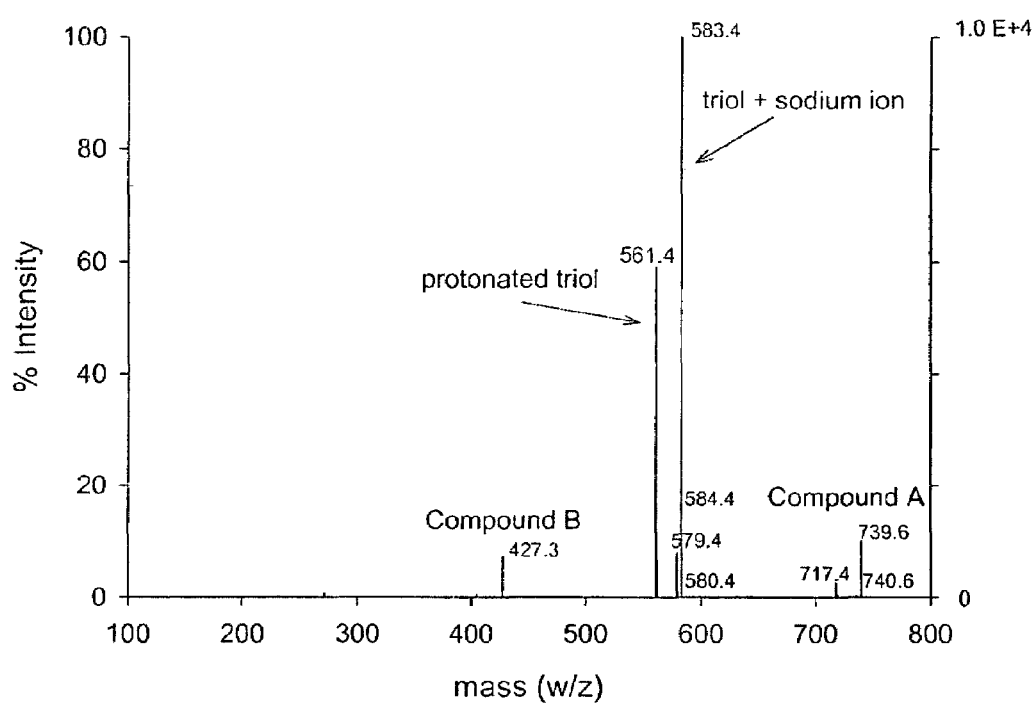

Figure 6: TLC Plate of Product after Ozonolysis
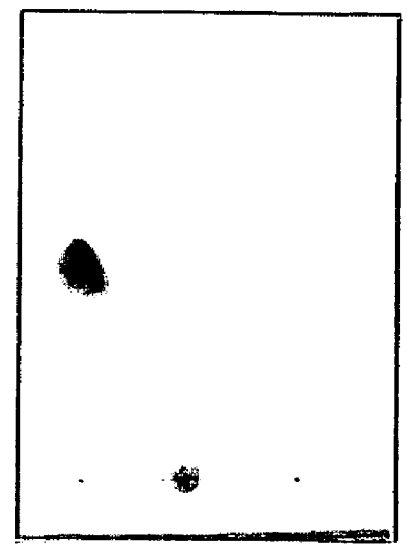

Figure 7: GC of Products of First and Second Hydrogenation
(A) Product after First Hydrogenation
(B) Product after Second Hydrogenation
1= Nonanal, retention time= 5.7min
2= Nonanol, retention time= 8.4 min
3= Nonanoic acid, retention time= 13.7min
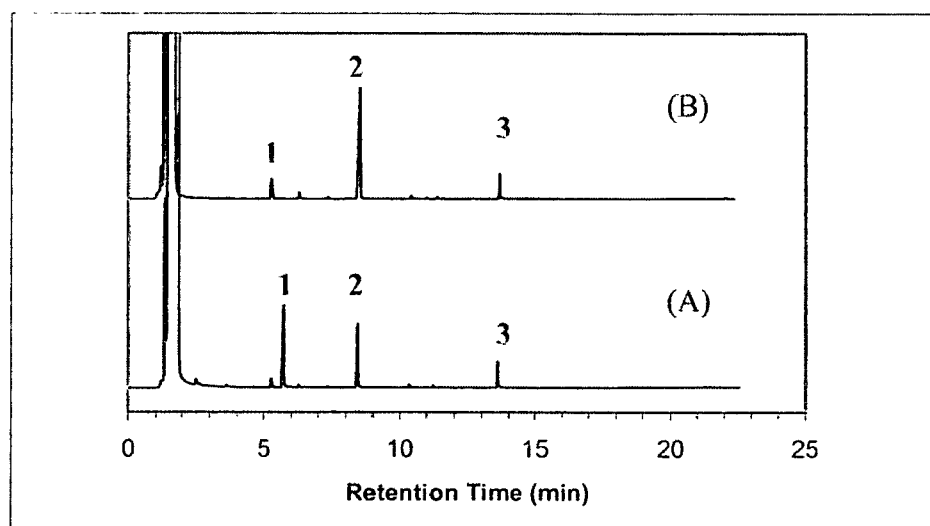

Figure 8: Side Products from Canola Oil
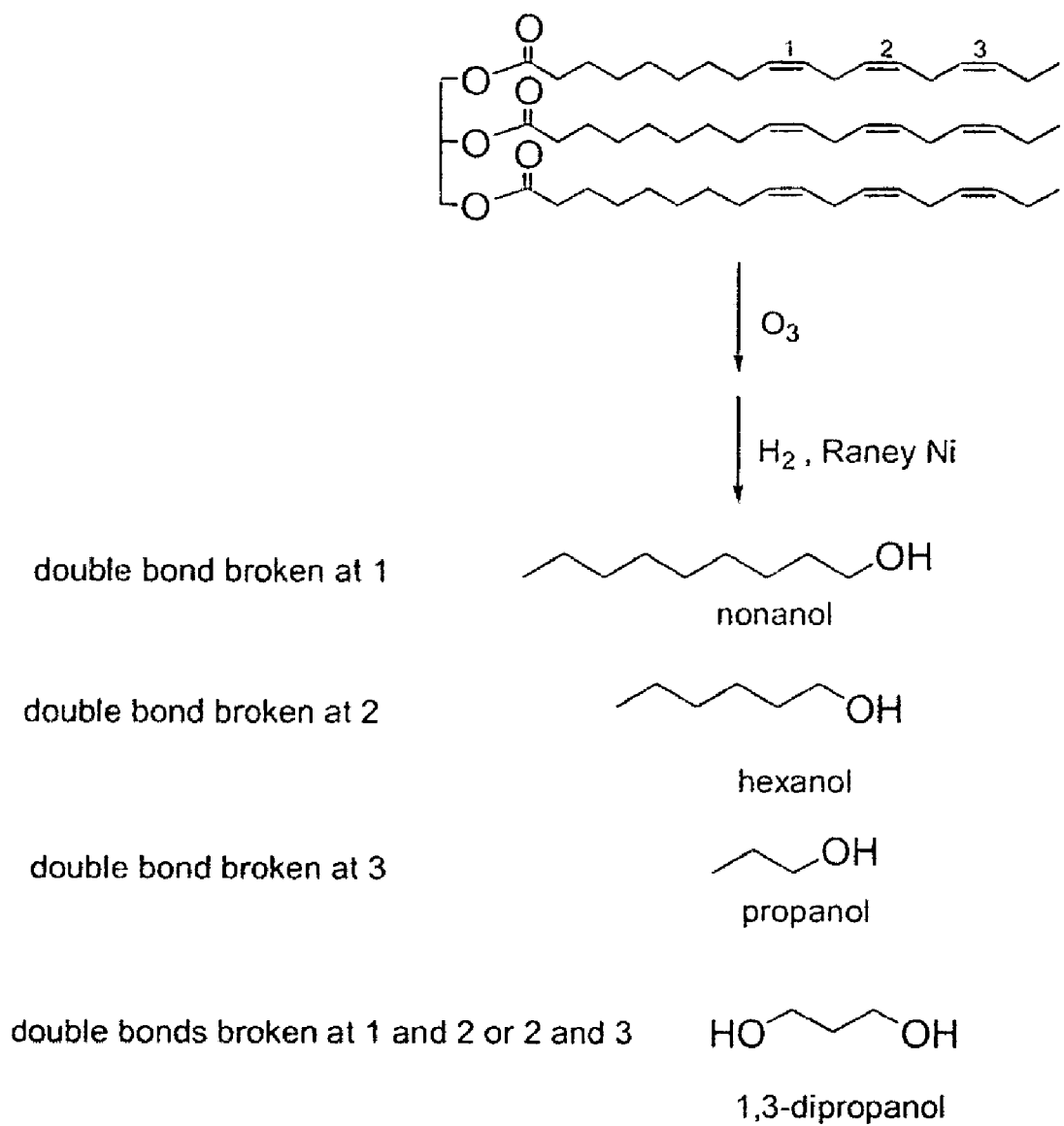

Figure 9: GC of Products before and after Distillation
(a) before Distillation
(b) after Distillation
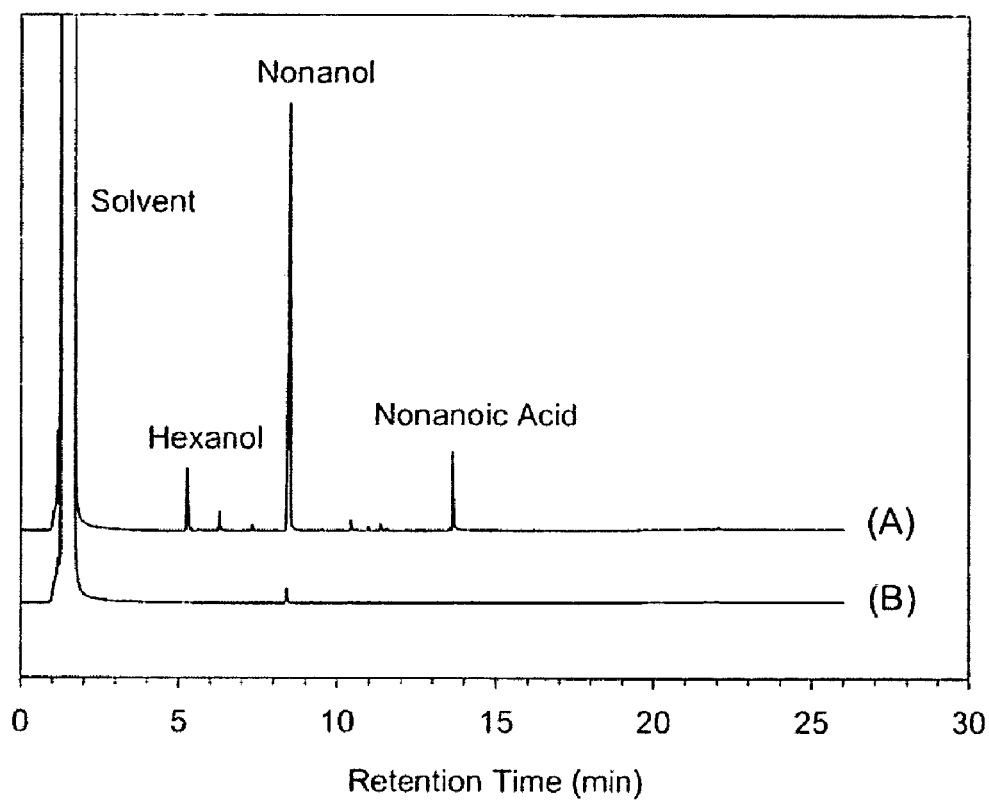

Figure 10: HPLC of Polyol Product
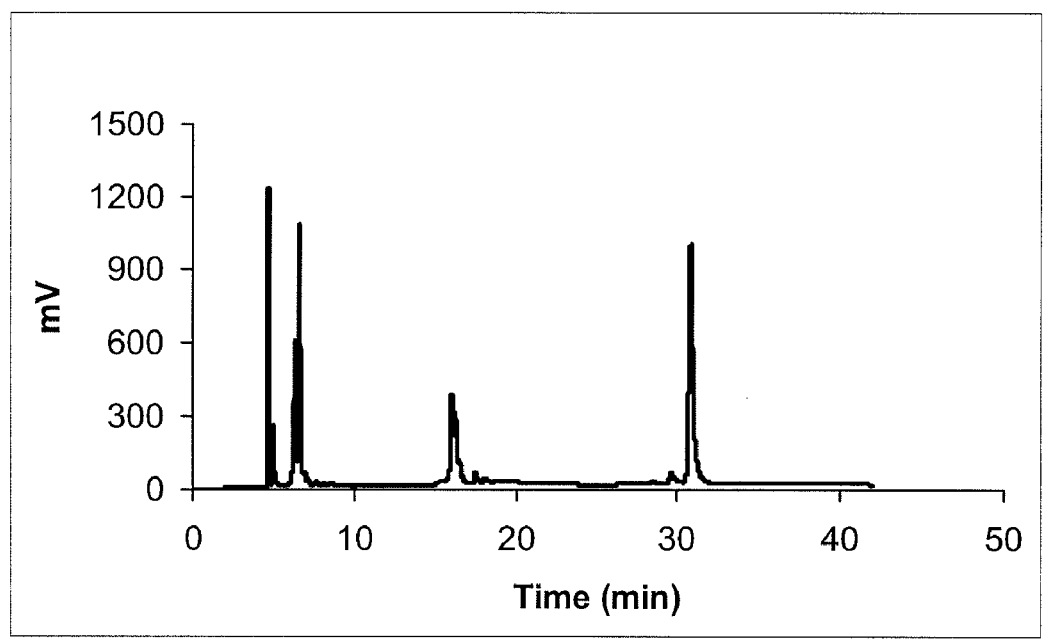

Figure 11: HPLC of Triacylglycerol, Mono-ol, Diol and Triol
Sample A: Triacylglycerol; Sample B: Mono-ol
Sample C: Diol; Sample D: Triol
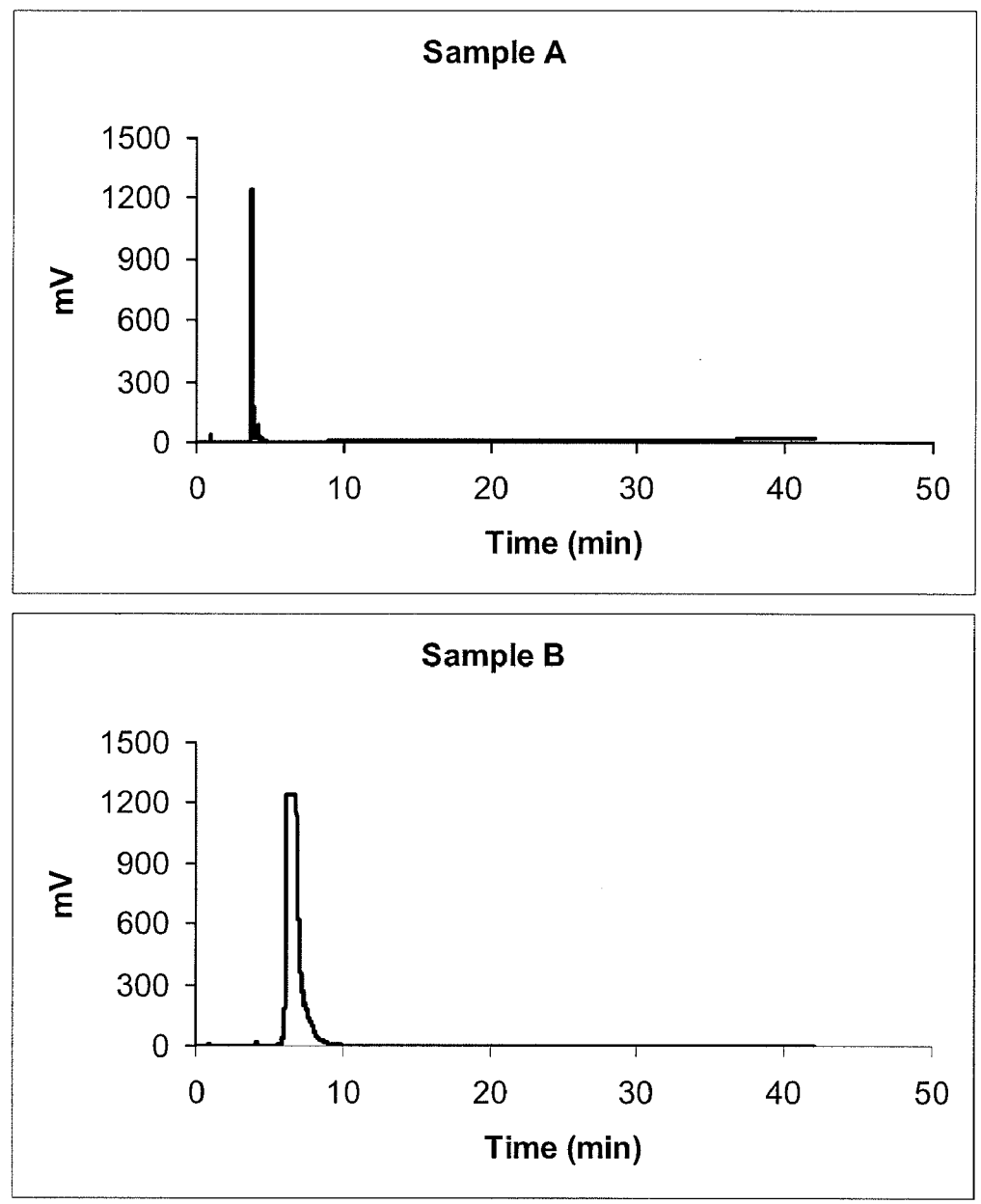

Figure 12: FTIR spectra of Triacylglycerol, Mono-ol, Diol and Triol
   A: Triglycerol
   B: Mono-ol
   C: Diol
   D: Triol
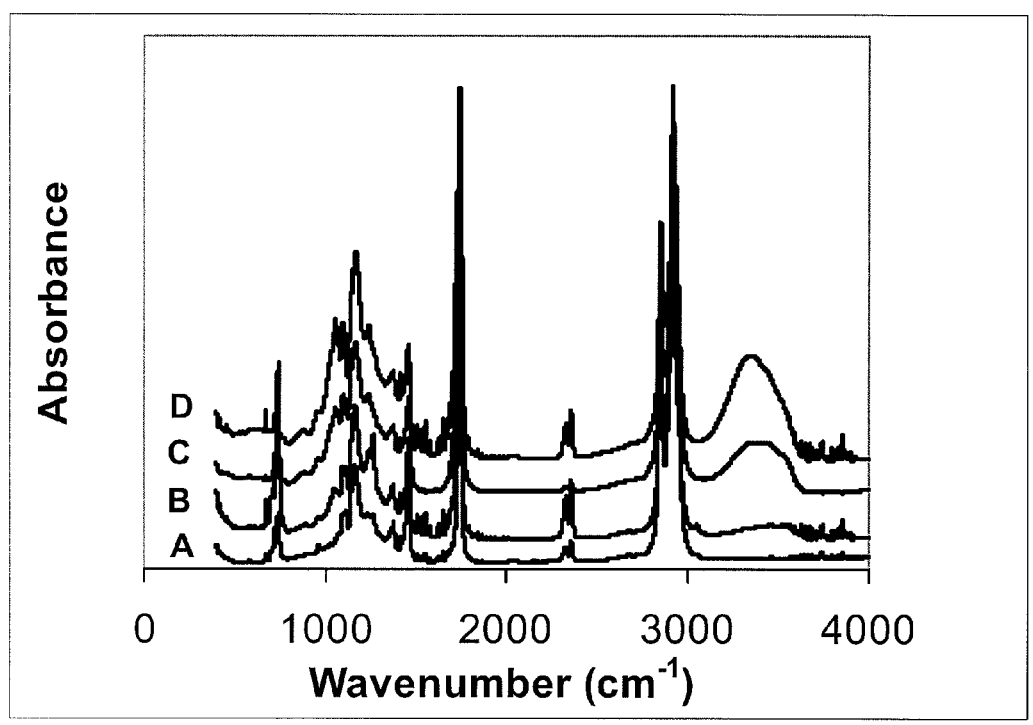

Figure 13: $^1$H-NMR of Triacylglycerol, Mono-ol, Diol and Triol
  A: Triglycerol
  B: Mono-ol
  C: Diol
  D: Triol
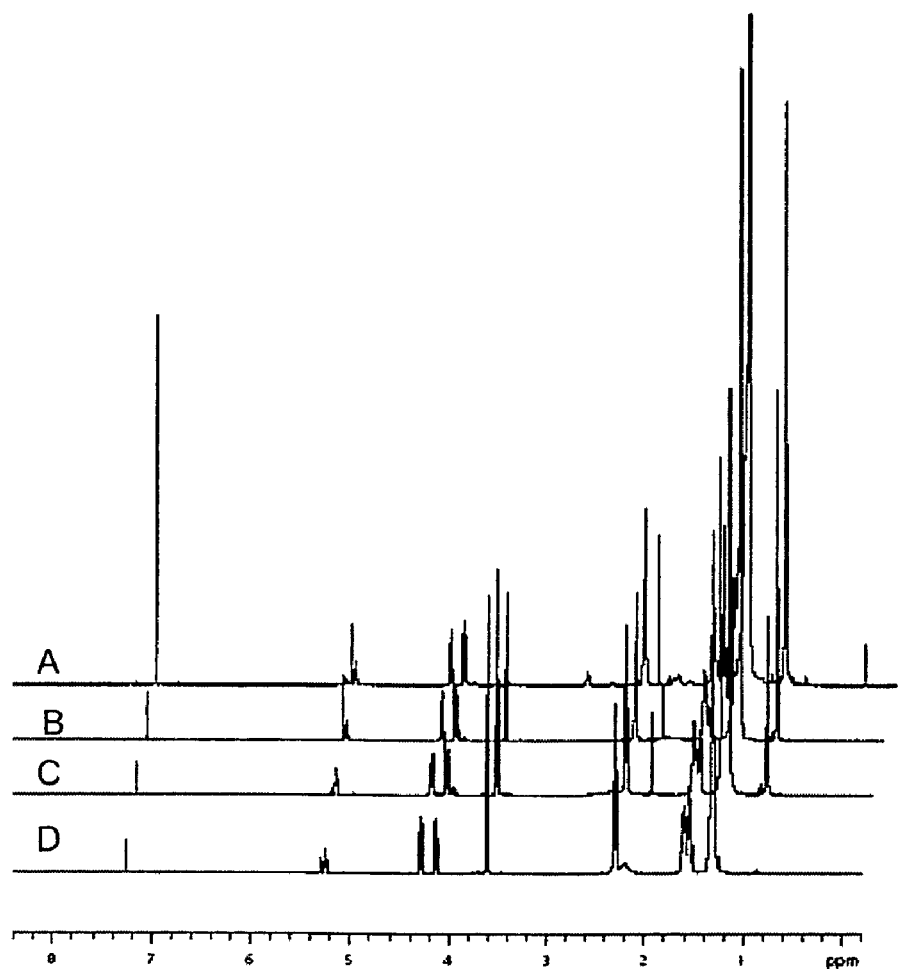

Figure 14: Mass Spectrometry of Mono-ol, Diol and Triol
Sample B: Mono-ol
Sample C: Diol
Sample D: Triol
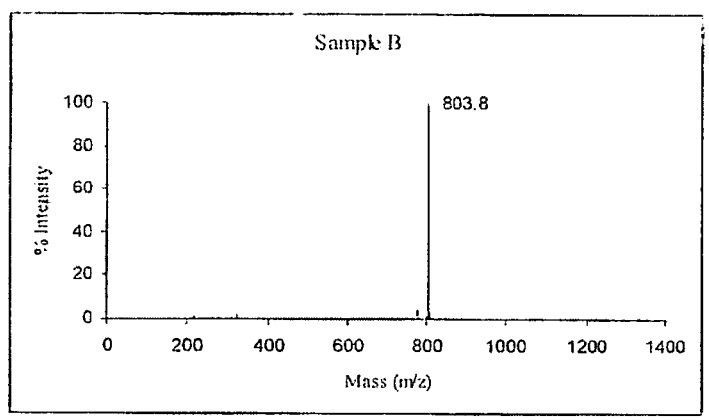
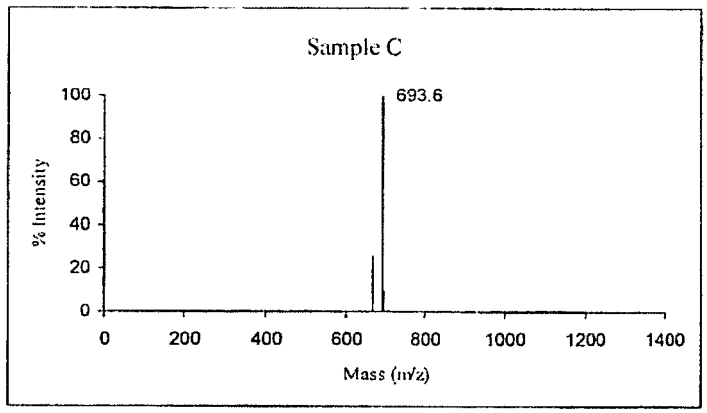
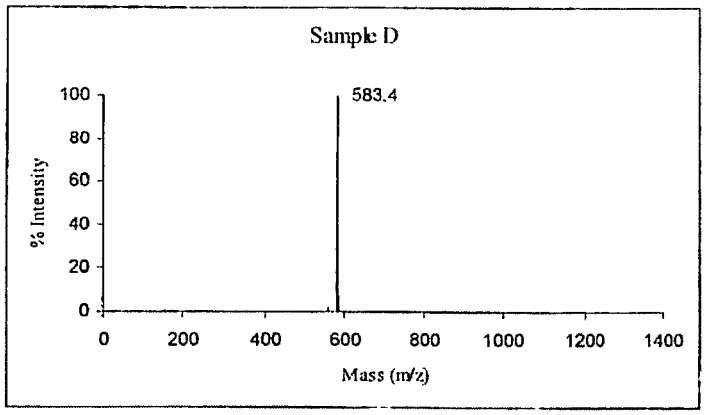

Figure 15: Transesterification Reaction of Triol
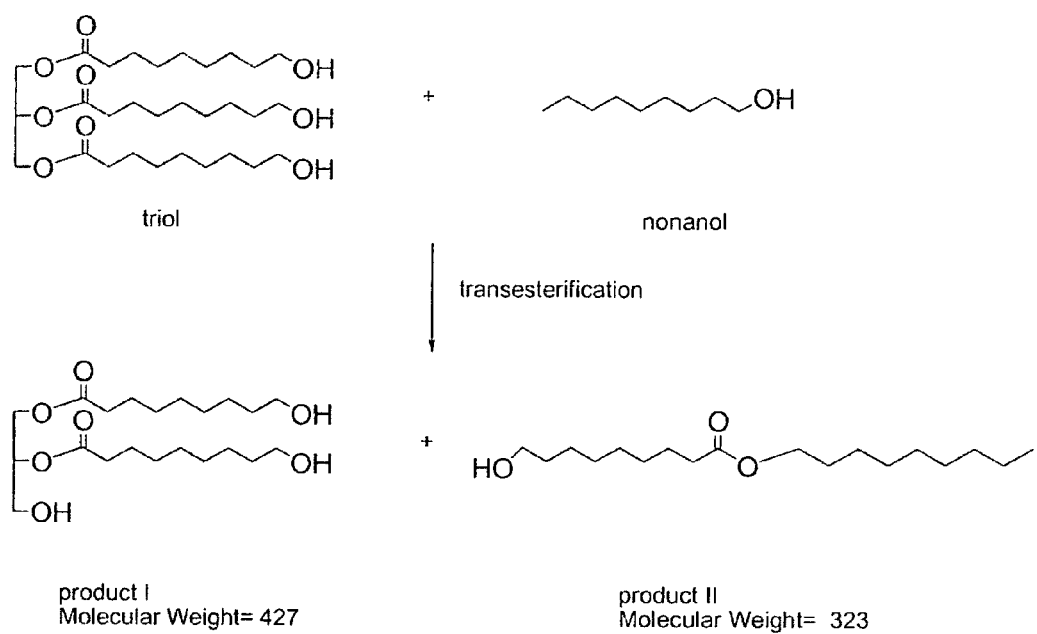

Figure 16: MS of Transesterified Product
　　　　Product I: Transesterified Product with Molecular Weight 427.2
　　　　Product II: Transesterified Product with Molecular Weight 323.3
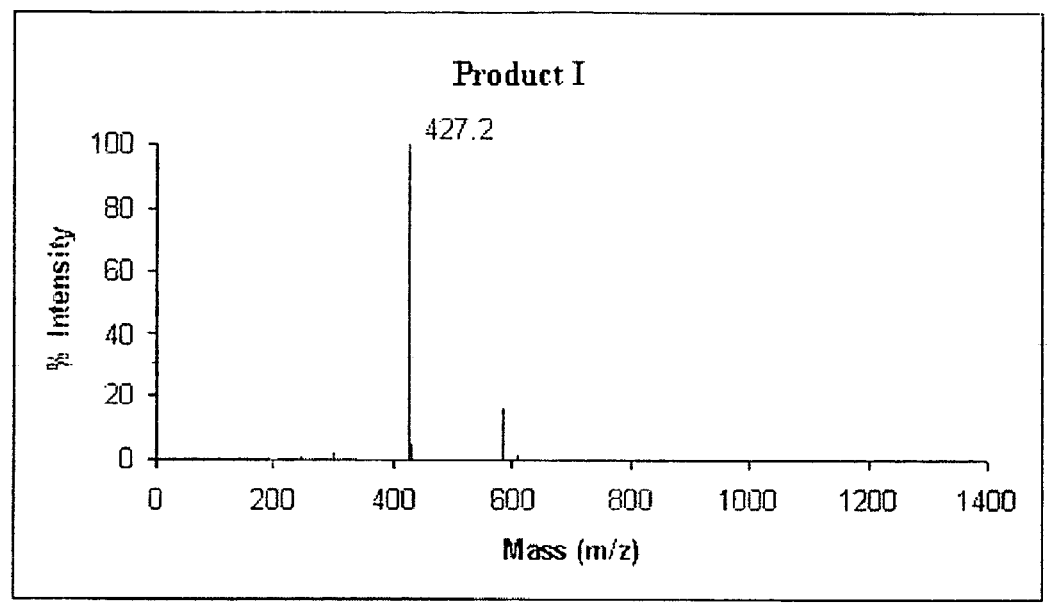
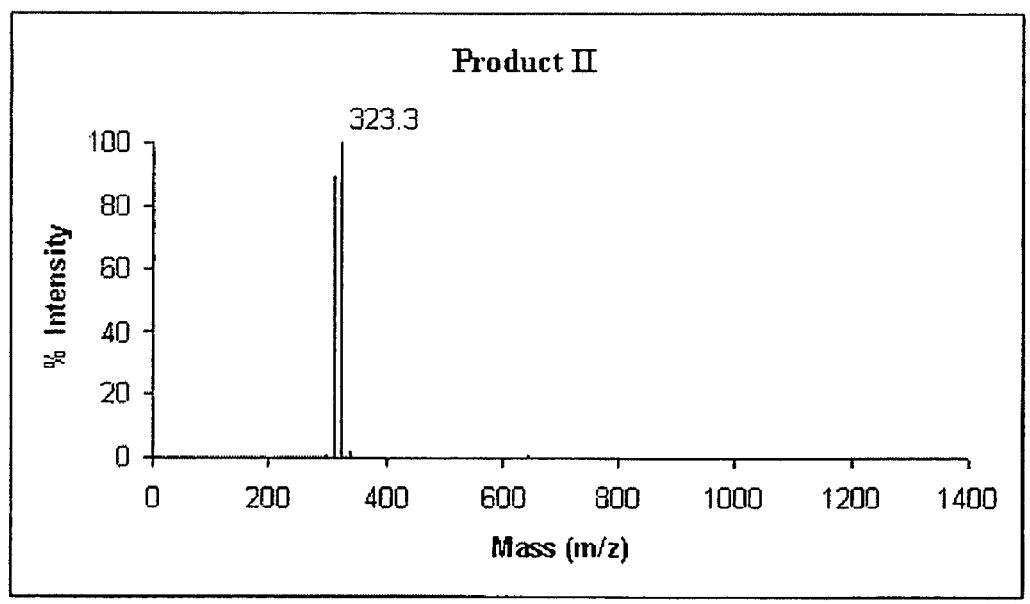

GC graph of Canola based reaction products, which was ozonized at 0°C with air as a supply gas for 8h. (a) before distillation. (b) after distillation.

Figure 18: FTIR spectra of: (a) Canola oil (b) Flax oil (c) Canola-air polyol (d) Flax-air polyol (e) Canola-oxygen polyol.
Figure 18(a): FTIR spectra in the range 400-4000 cm$^{-1}$.
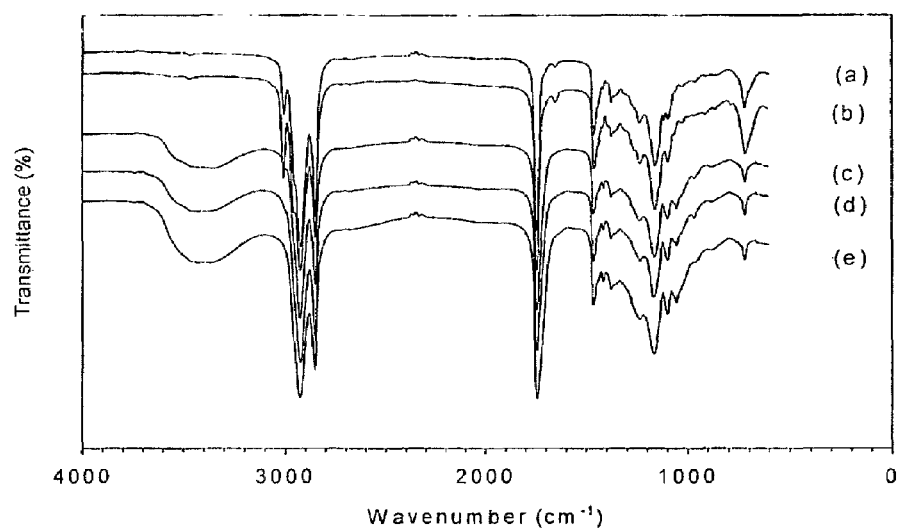
Figure 18(b): Enlargement of the FTIR band at 1650cm$^{-1}$ characteristic of C=C double bond.
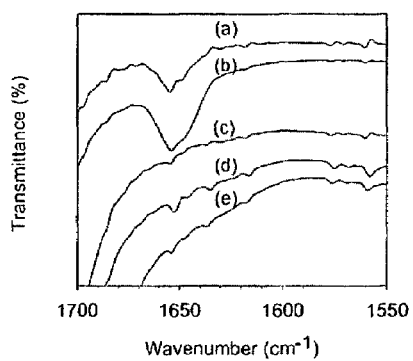
Figure 18(c): Enlargement of the FTIR band at 3006 cm$^{-1}$ characteristic of unsaturated C-H stretches.
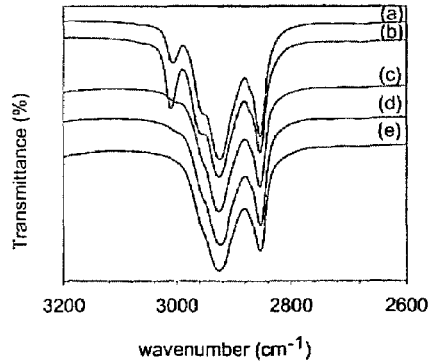

Figure 19: HPLC chromatograghy of Canola-air polyol, ozonized for 8h at 0°C.
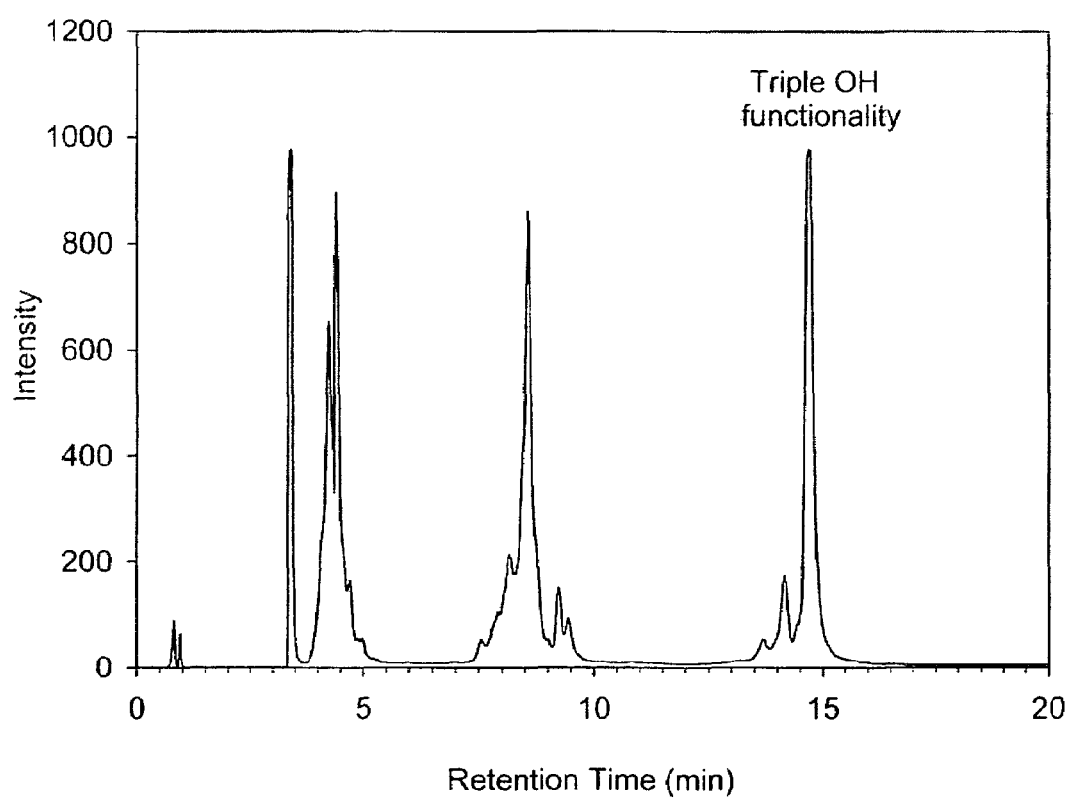

Figure 20a: DSC crystallization curves of:
(a) Canola oil
(b) Flax oil
(c) Canola-air polyol (d) Flax-air polyol
(e) Canola-oxygen polyol and
(f) Hydrogenated Canola oil
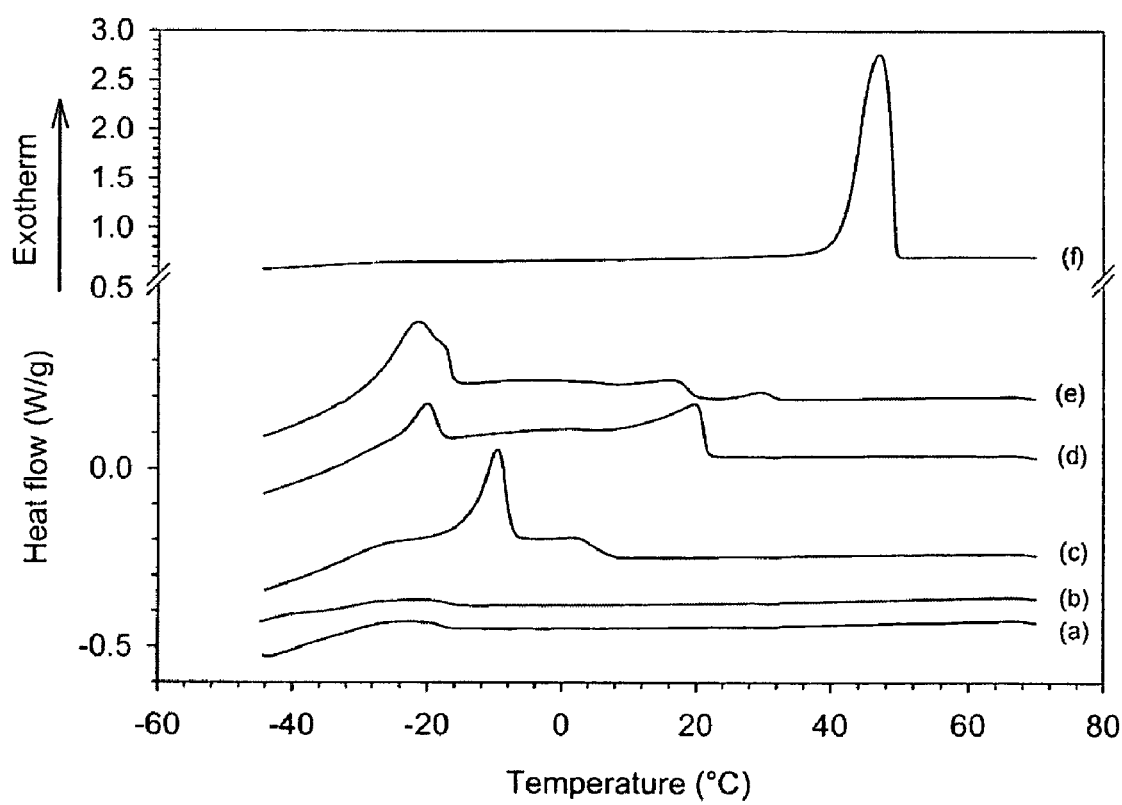

Figure 20b: DSC melting curves of:
(a) Canola oil
(b) Flax oil
(c) Canola-air polyol
(d) Flax-air polyol
(e) Canola-oxygen polyol and
(f) Hydrogenated Canola oil.
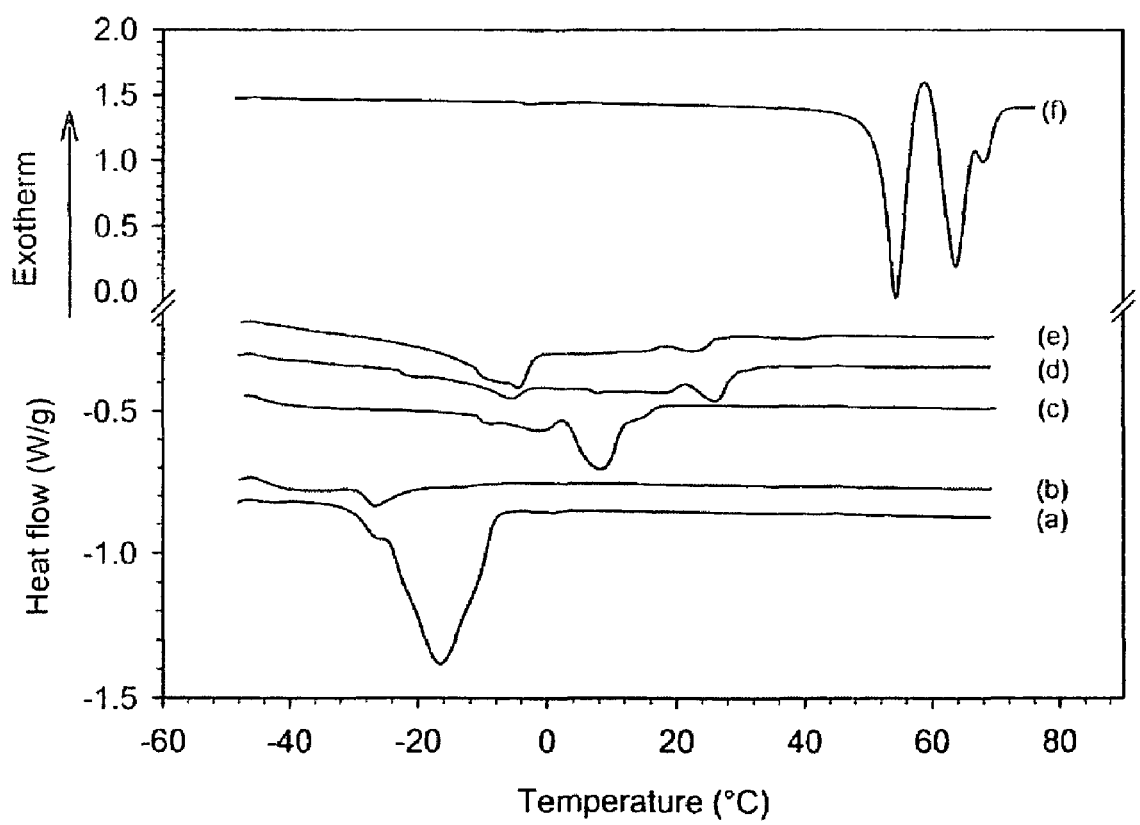

Figure 21: Viscosity of: (a) Flax oil (b) Canola oil, (c) Canola-air polyol, (d) Flax-air polyol, (e) Canola-oxygen polyol.
Figure 21(a): Viscosity as a function of time.
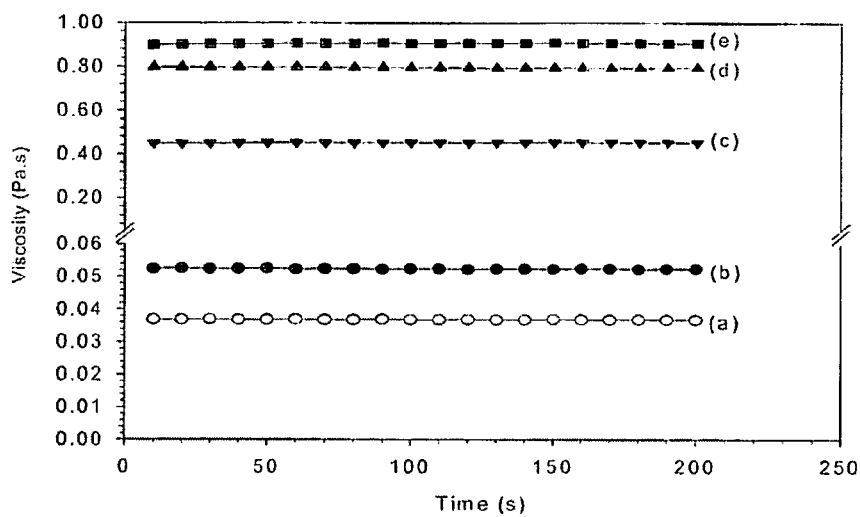
Figure 21(b): Viscosity as a function of temperature.
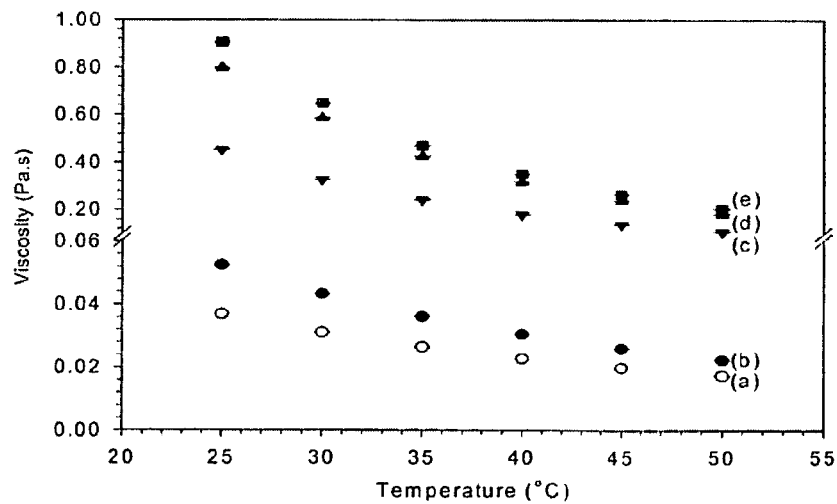

Figure 22: FTIR spectra of elastomers with OH/NCO molar ratio 1.0
(a) canola oil based polyurethane (COBPU); (b) flax oil based polyurethane (FOBPU); and (c) soybean oil based polyurethane (SOBPU).
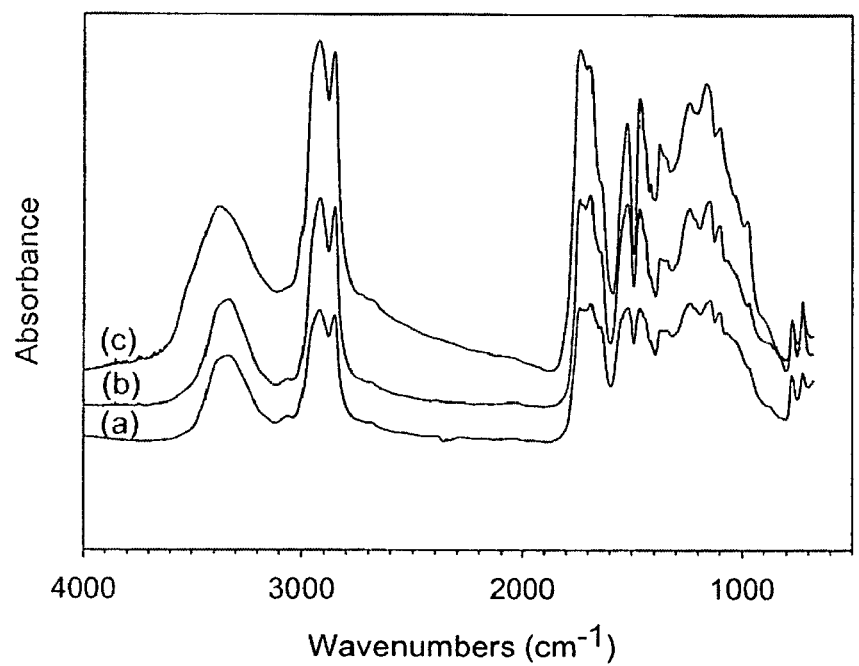

Figure 23: Reversing heat flow vs. temperature of elastomers with OH/NCO molar ratio 1.0. (a) canola oil based polyurethane (COBPU) (b) flax oil based polyurethane (FOBPU).
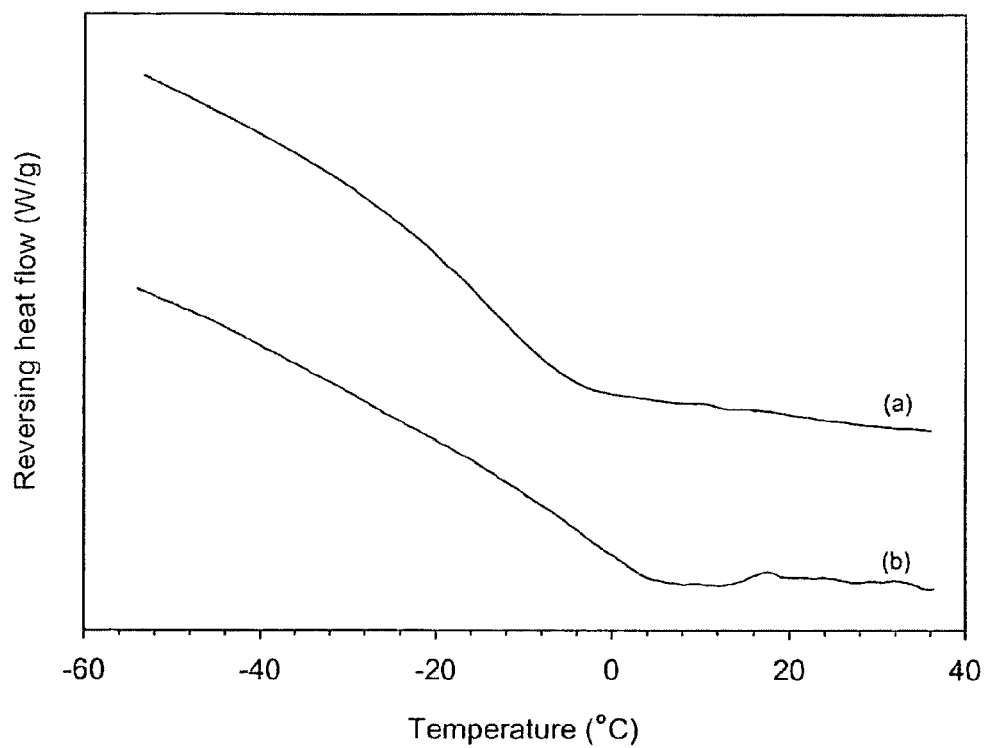

Figure 24: Thermomechanical analysis curves of elastomers with OH/NCO molar ratio 1.0 (a) canola oil based polyurethane (COBPU) (b) flax oil based polyurethane (FOBPU).
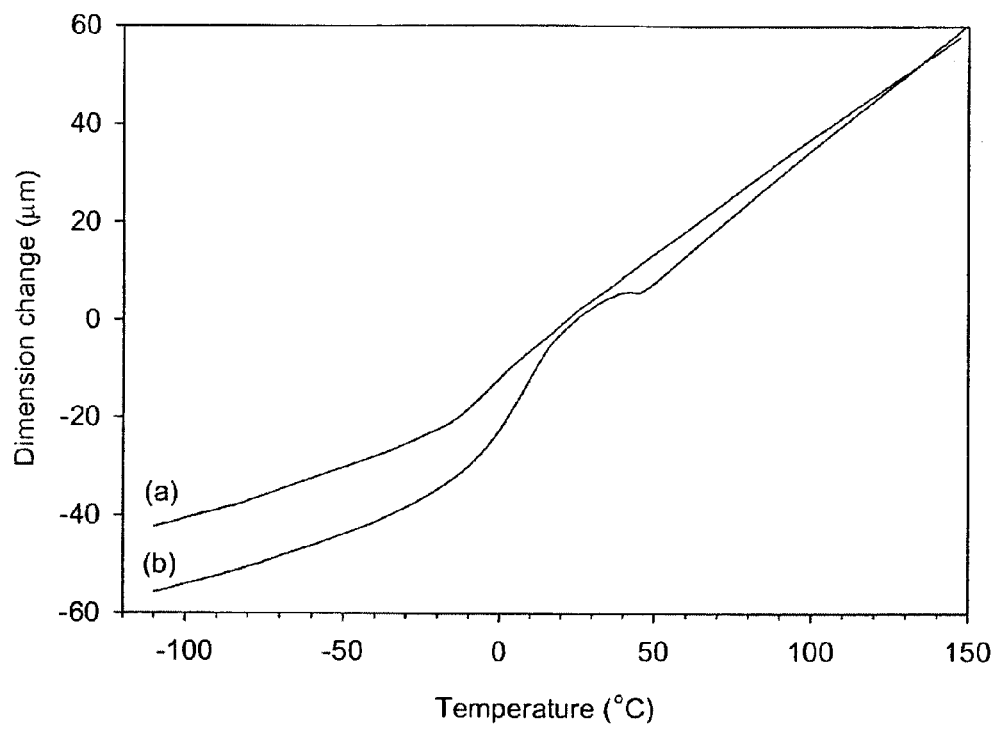

Figure 25: Storage moduli elastomers with OH/NCO molar ratio 1.0 (a) canola oil based polyurethane (COBPU) (b) flax oil based polyurethane (FOBPU) and (c) soybean oil based polyurethane (SOBPU).
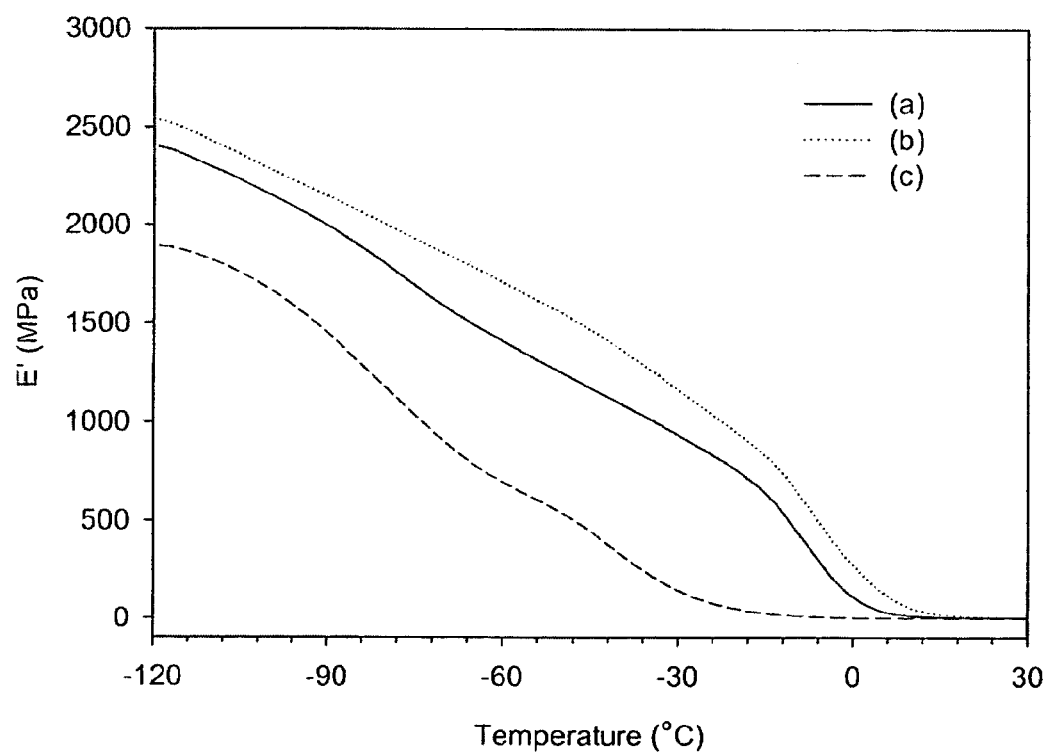

Figure 26(a): TGA of elastomers with OH/NCO molar ratio 1.0 (a) canola oil based polyurethane (COBPU) (b) flax oil based polyurethane (FOBPU) and (c) soybean oil based polyurethane (SOBPU).
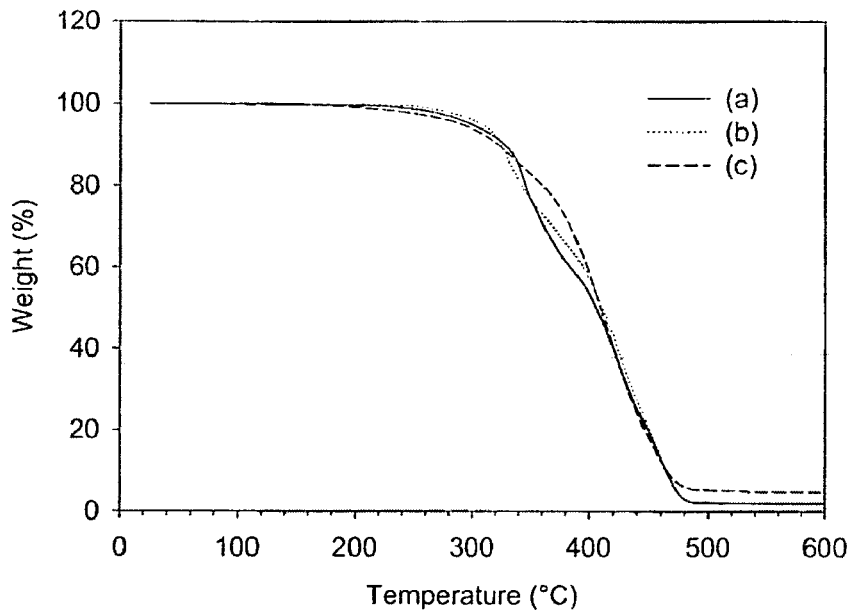
Figure 26(b): Derivative TGA curves elastomers with OH/NCO molar ratio 1.0 (a) canola oil based polyurethane (COBPU) (b) flax oil based polyurethane (FOBPU) and (c) soybean oil based polyurethane (SOBPU).
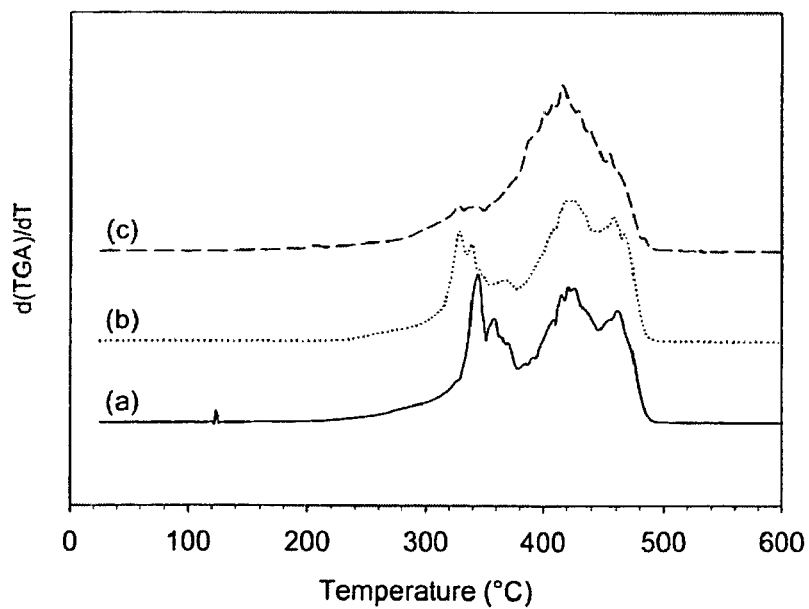

Figure 27: Nominal stress-strain of elastomers with OH/NCO molar ratio 1.0 (a) canola oil based polyurethane (COBPU), (b) flax oil based polyurethane (FOBPU) and (c) soybean oil based polyurethane (SOBPU).
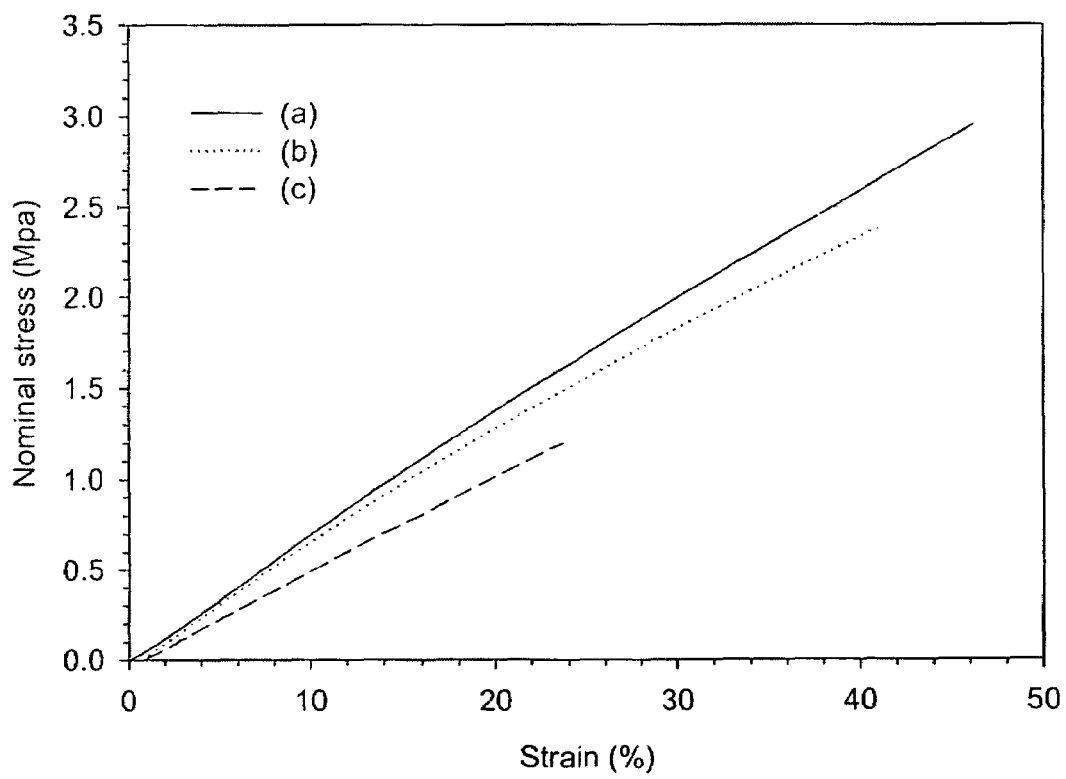

Figure 28: FTIR spectra of polyurethane foams. ( —— ) Canola oil based polyurethane (Canola-PU), ( ······ ) Soybean oil based polyurethane (Soybean-PU), and ( - - ) Castor oil based polyurethane (Castor-PU).
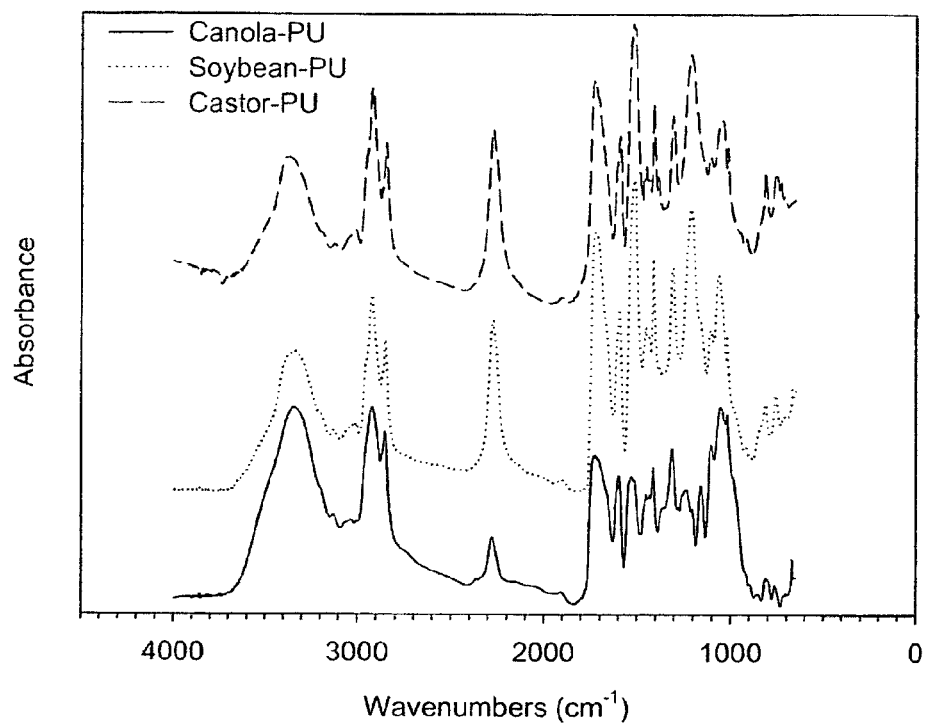

Figure 29(a): Storage moduli of polyurethane foams. Insert: first derivatives relative to temperature of storage moduli. (— —) Canola oil based polyurethane (Canola-PU), (·····) Soybean oil based polyurethane (Soybean-PU), and (     ) Castor oil based polyurethane (Castor-PU).
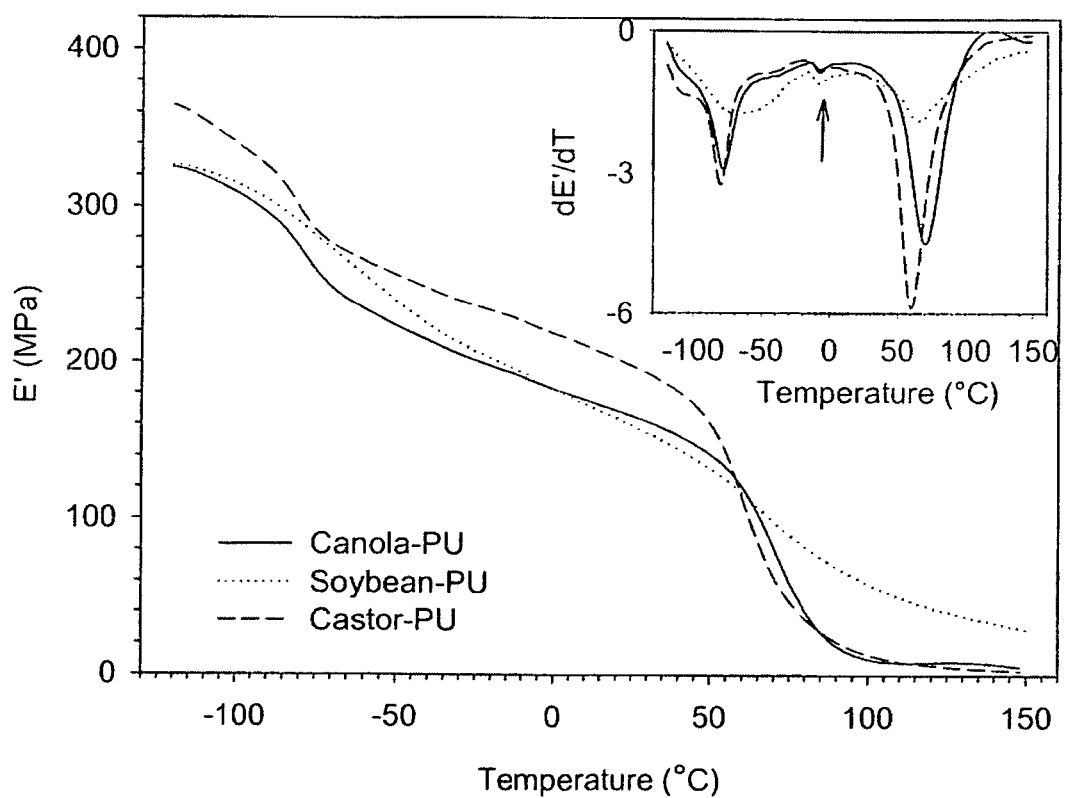

Figure 29(b): Loss moduli. (— —) Canola oil based polyurethane (Canola-PU), (·····) Soybean oil based polyurethane (Soybean-PU), and (— — —) Castor oil based polyurethane (Castor-PU).
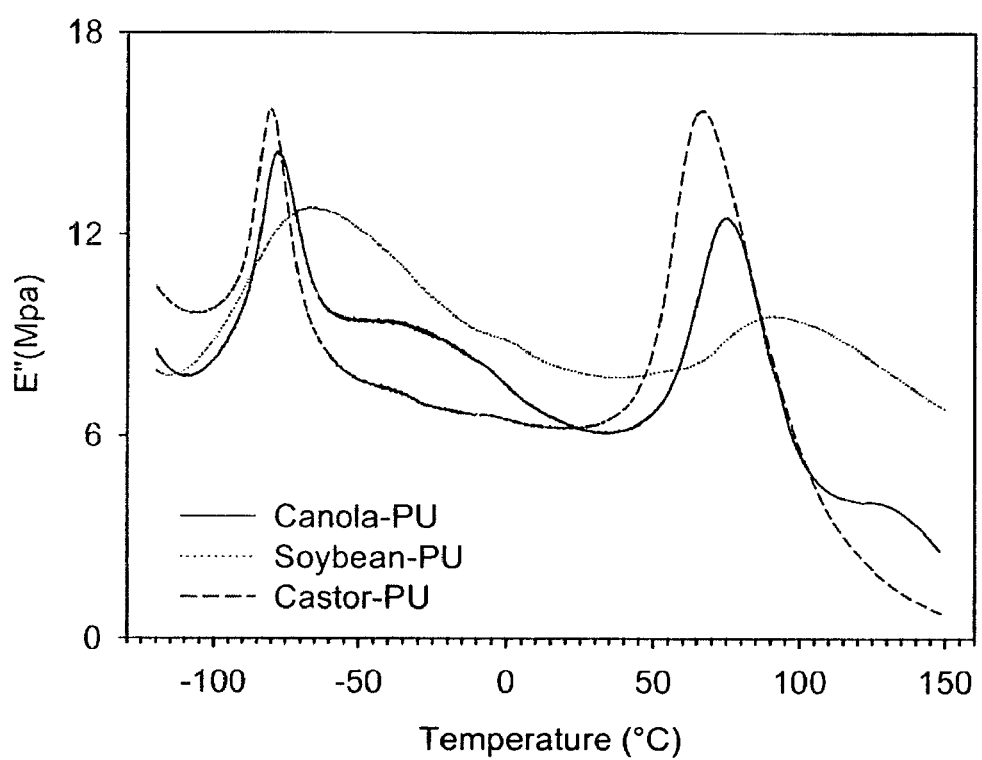

Figure 29(c): Tan δ of polyurethane foams. ( ⎯⎯ ) Canola oil based polyurethane (Canola-PU). ( ····· ) Soybean oil based polyurethane (Soybean-PU), and ( ‑ ‑ ) Castor oil based polyurethane (Castor-PU).
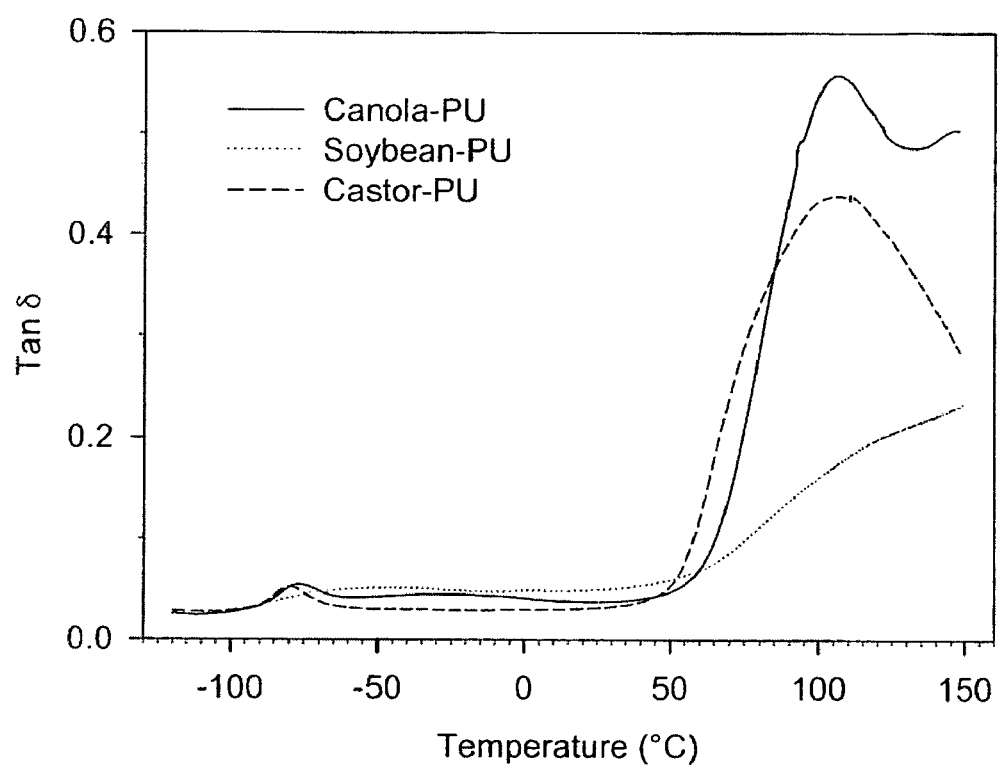

Figure 30(a): TGA curves of polyurethane foams in nitrogen. (———) Canola oil based polyurethane (Canola-PU), (······) Soybean oil based polyurethane (Soybean-PU), and (— — —) Castor oil based polyurethane (Castor-PU).
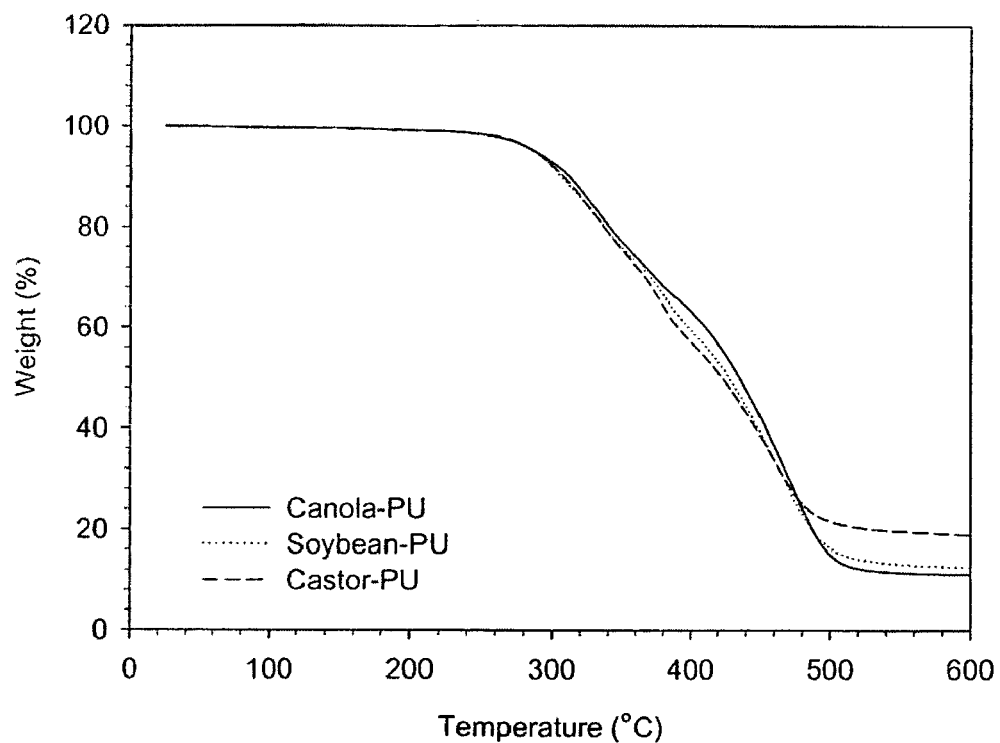

Figure 30(b): Derivative TGA curves polyurethane foams. ( —— ) Canola oil based polyurethane (Canola-PU), (······) Soybean oil based polyurethane (Soybean-PU), and ( – – ) Castor oil based polyurethane (Castor-PU).
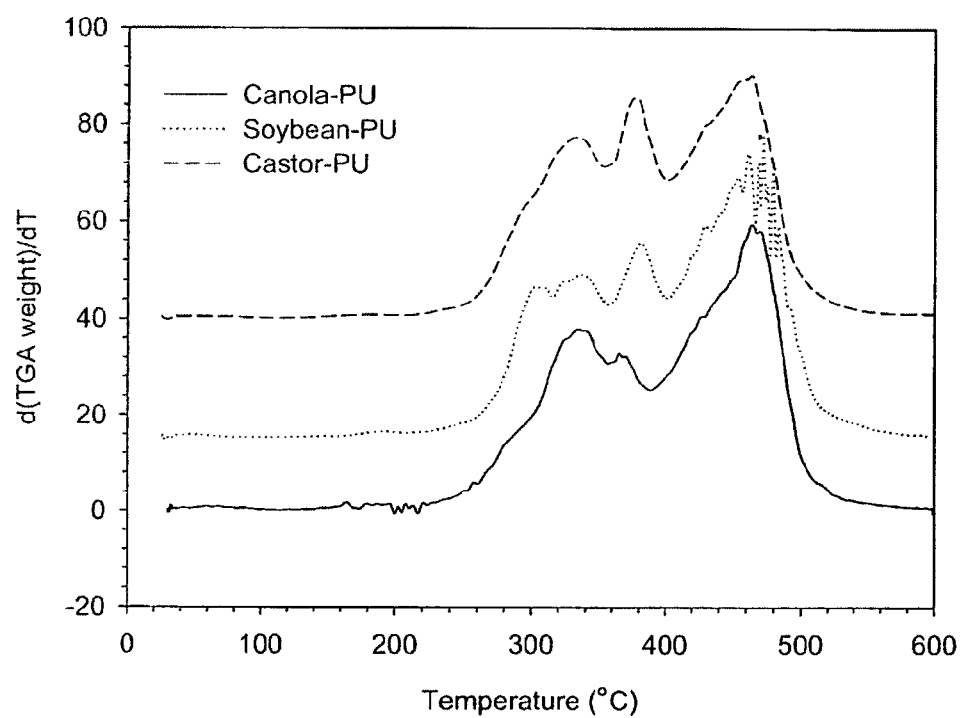

Figure 31: Compressive strength vs. strain of polyurethane foams. (———) Canola oil based polyurethane (Canola-PU), (·····) Soybean oil based polyurethane (Soybean-PU), and (— — —) Castor oil based polyurethane (Castor-PU).
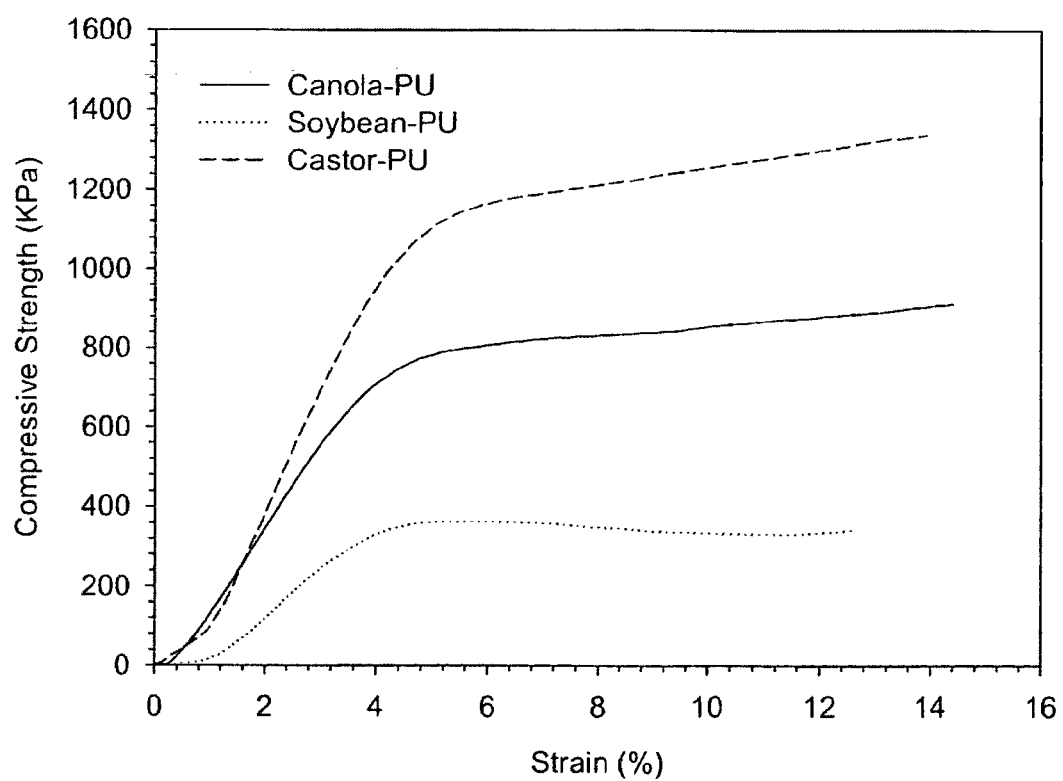

Figure 32(a): Scanning electron micrograph of the Canola oil based polyurethane (Canola-PU).
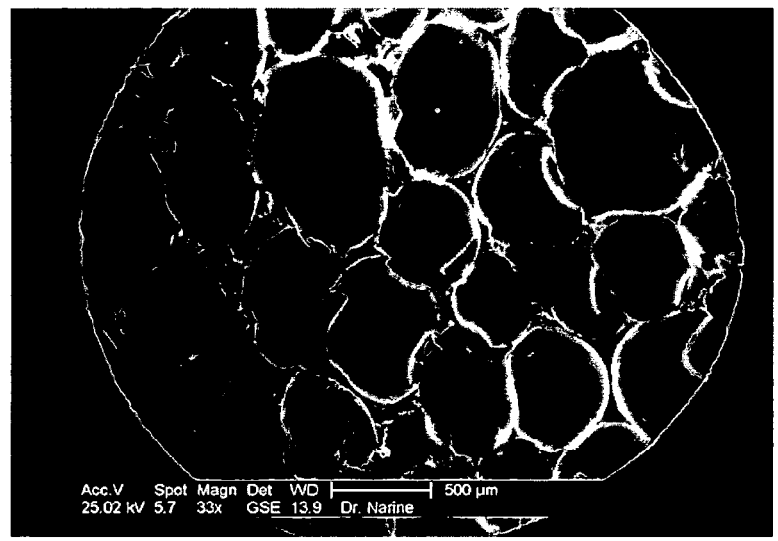

Figure 32(b): Scanning electron micrograph of the Soybean oil based polyurethane (Soybean-PU).
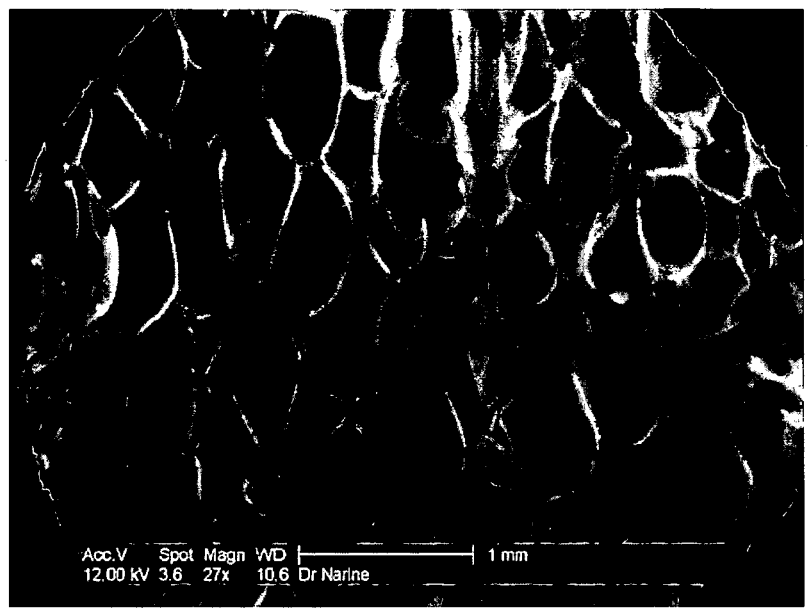

Figure 32(c): Scanning electron micrograph of the Castor oil based polyurethane (Castor-PU).
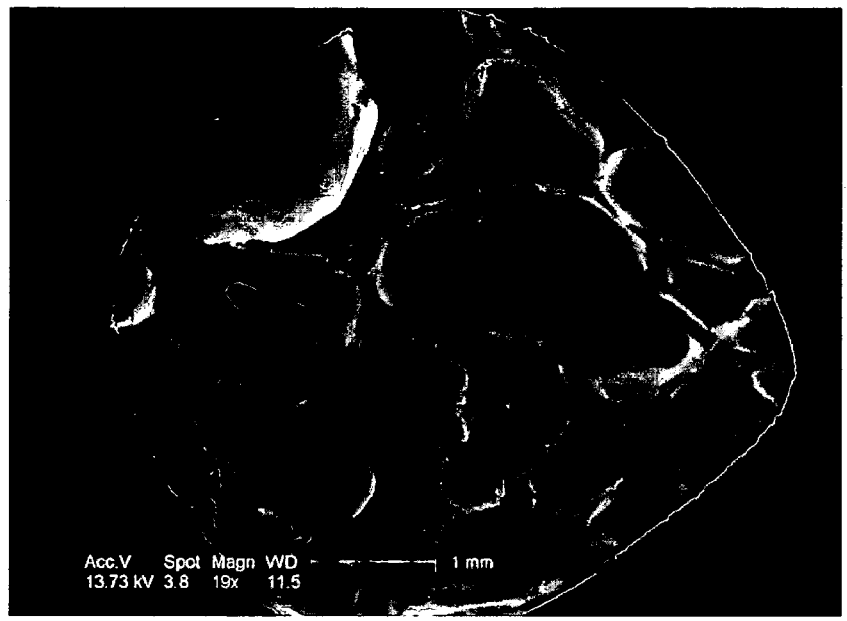

Figure 33: HPLC of Polyols Produced with Pd-C, Raney Ni System
1: Diol. Retention time: 15.03mins
2: Triol. Retention time: 25.48mins
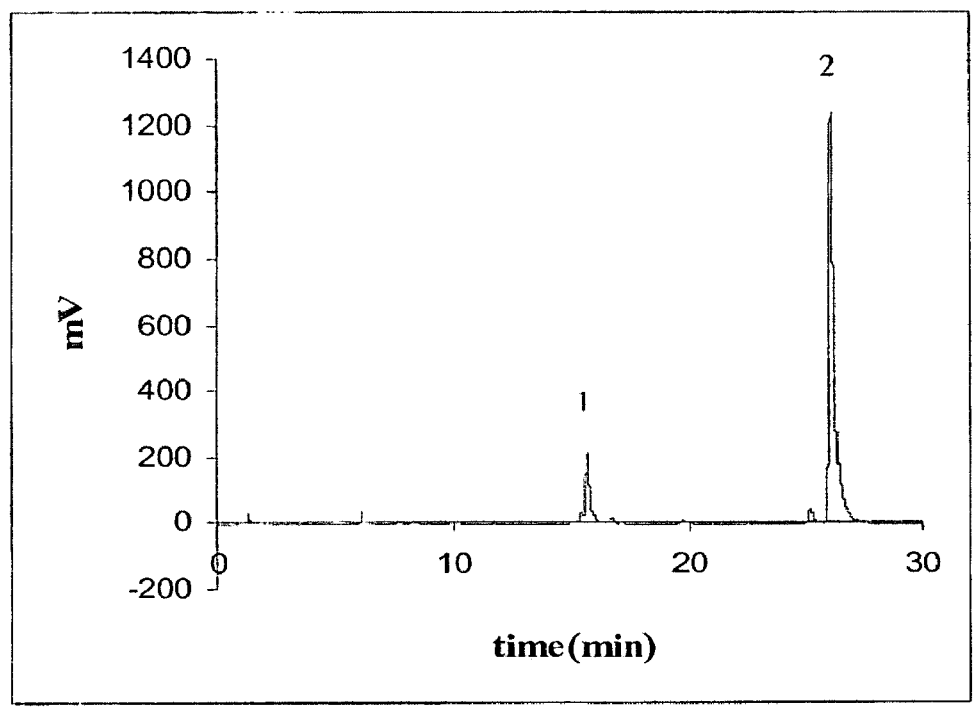

Figure 34: HPLC of Polyols Produced with Zinc, Raney Nickel System
1: Unreacted TAGs. Retention time: 5.53mins
2: Diol. Retention time: 15.03mins
3: Triol. Retention time: 25.48mins
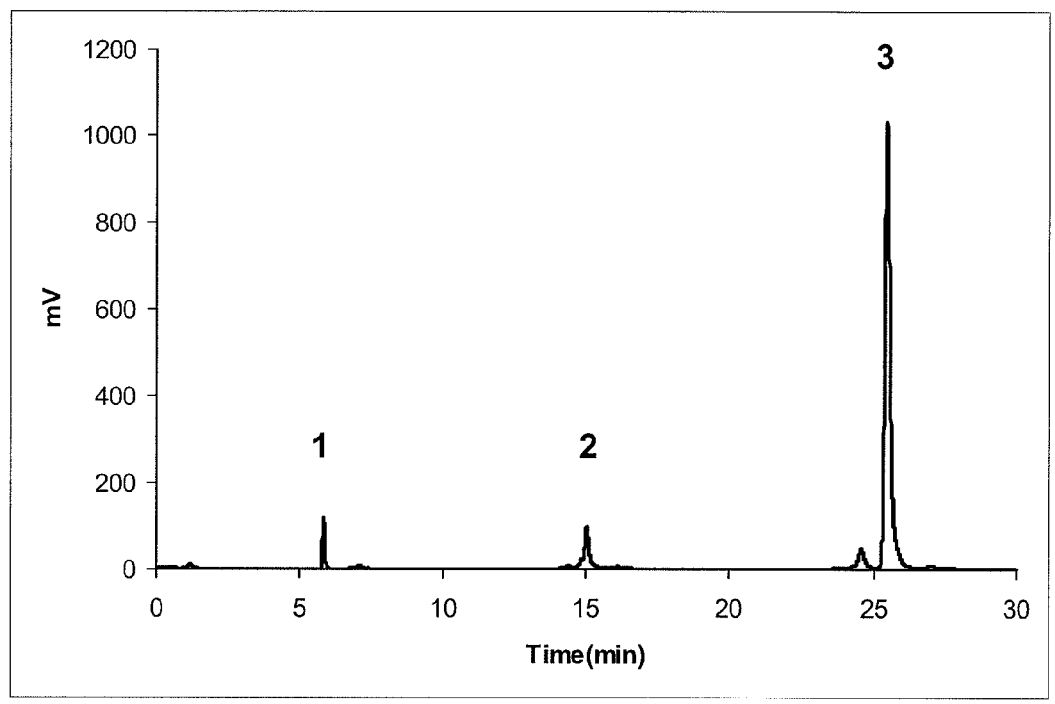

Figure 35: HPLC of Polyols Produced with Recycled Ethyl Acetate
1: Diol. Retention time: 15.03mins
2: Triol. Retention time: 25.48mins
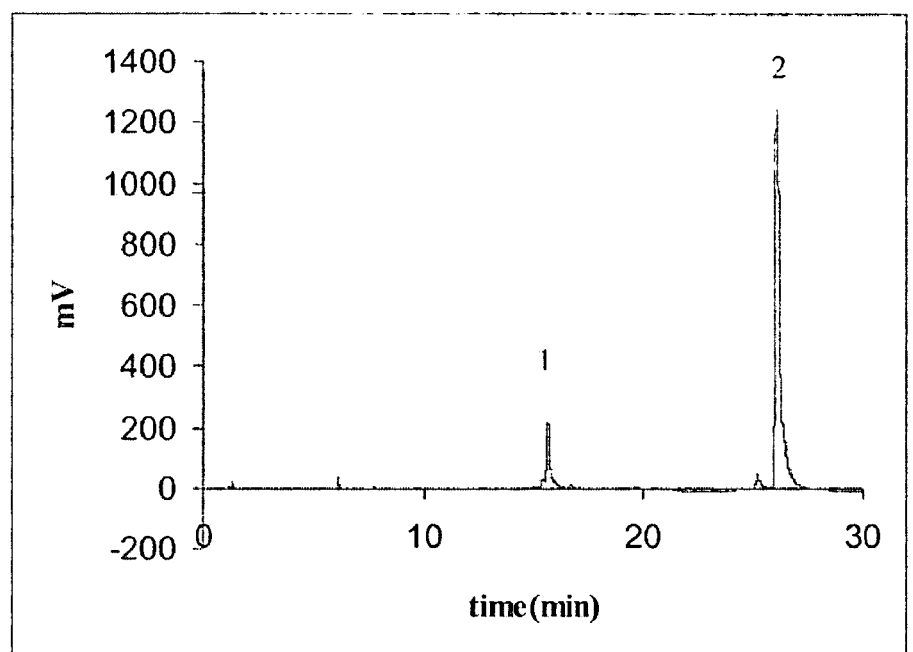

Figure 36(a): Viscosity as a function of time, of: (a) Ethyl Acetate Canola Oil Based Polyols, (b) Recycled Ethyl Acetate Canola Oil Based Polyols.
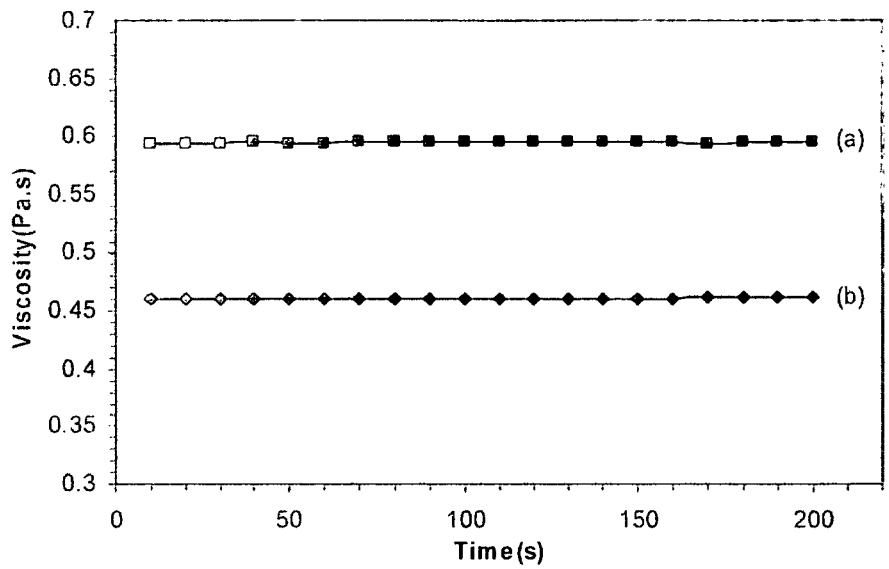
igure 36(b): Viscosity as a function of temperature of: (a) Ethyl Acetate Canola Oil Based Polyols, (b) Recycled Ethyl Acetate Canola Oil Based Polyols..
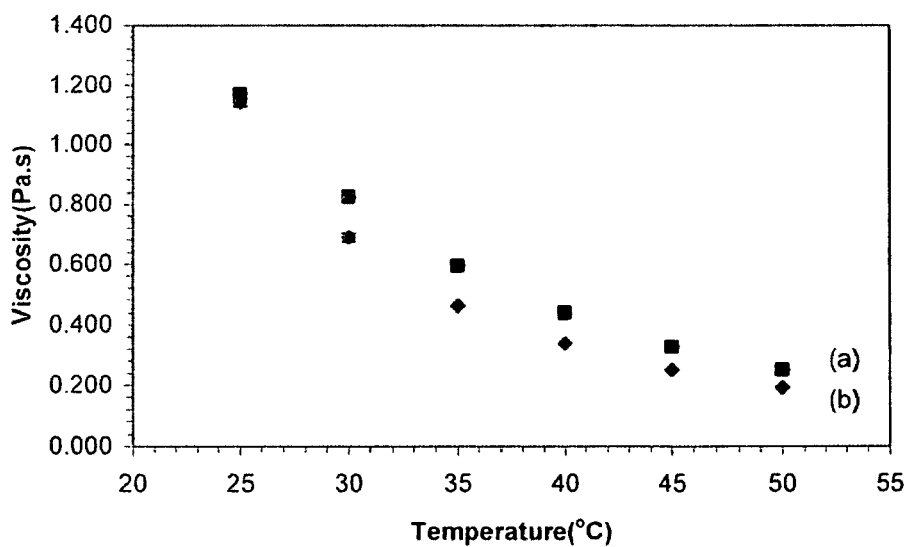

Figure 37(a): Storage moduli of polyurethane foams. (a) Ethyl Acetate Canola Oil Based PU (EACOBPU) and (b) Recycled Ethyl Acetate Canola Oil Based PU (REACOBPU)
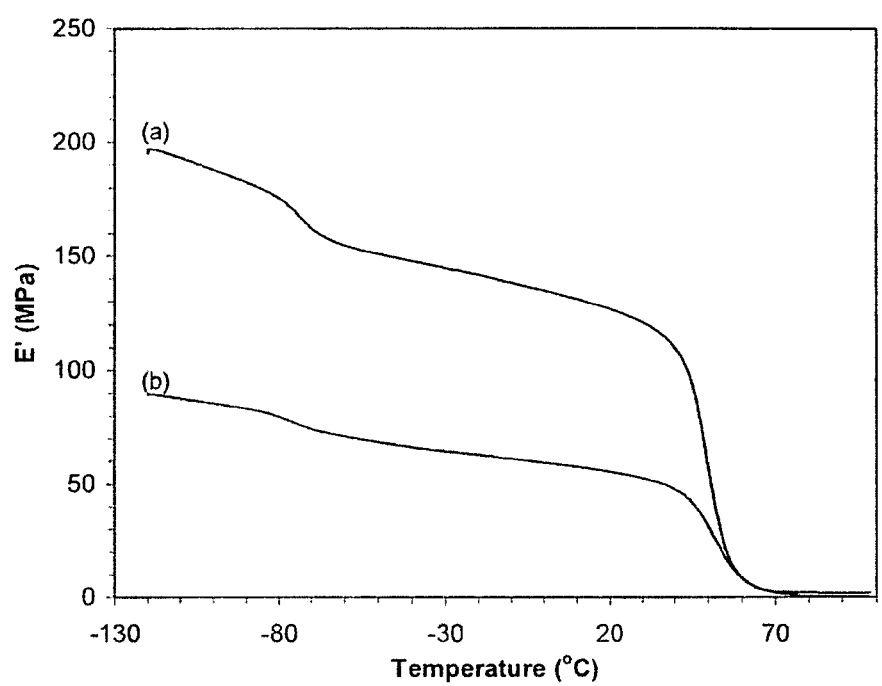

Figure 37(b): Loss moduli. (a) Ethyl Acetate Canola Oil Based PU (EACOBPU) and (b) Recycled Ethyl Acetate Canola Oil Based PU (REACOBPU)
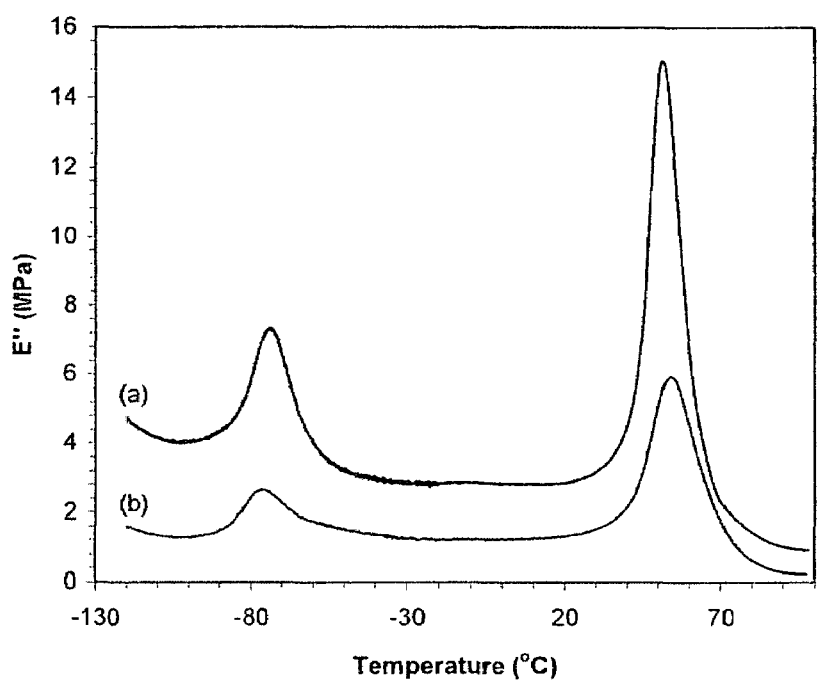

Figure 37(c): Tan δ of polyurethane foams. (a) Ethyl Acetate Canola Oil Based PU (EACOBPU) and (b) Recycled Ethyl Acetate Canola Oil Based PU (REACOBPU)
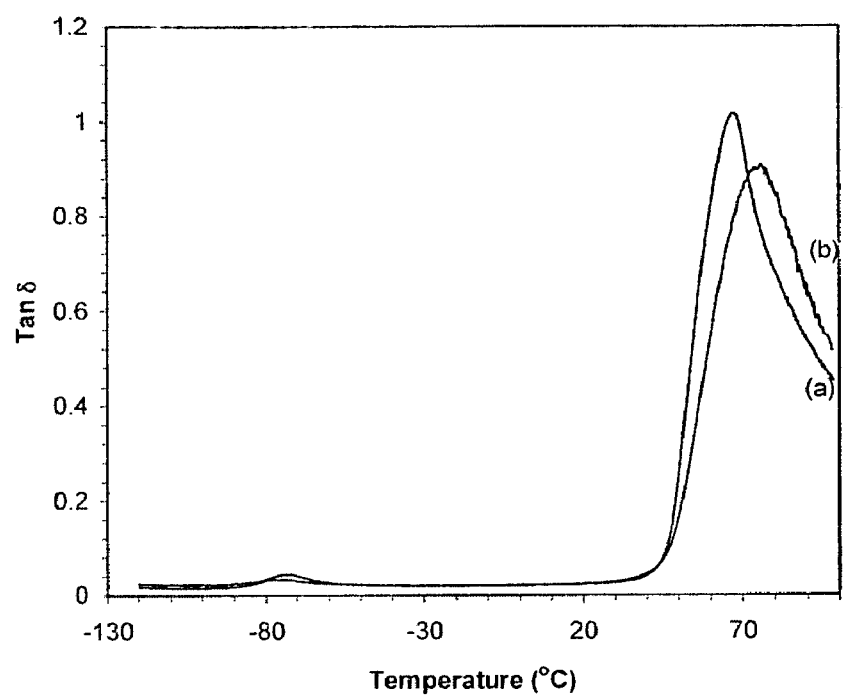

Figure 38: Compressive strength vs. strain of polyurethane foams. (a) Ethyl Acetate Canola Oil Based PU (EACOBPU) and (b) Recycled Ethyl Acetate Canola Oil Based PU (REACOBPU)
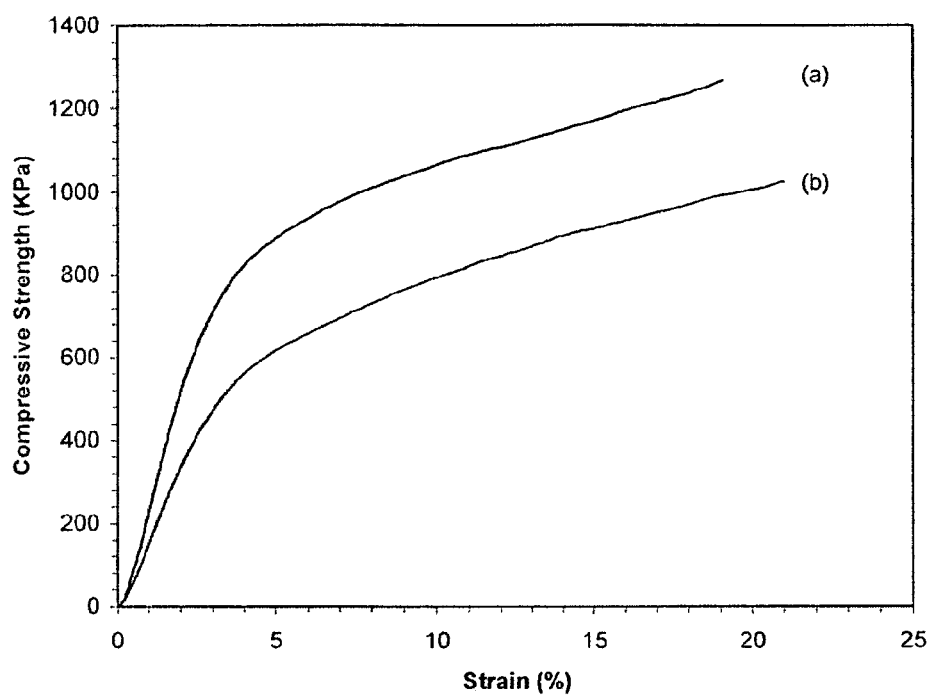

Figure 42 A schematic representation of the production of GIII−Polyol as described in Example 7
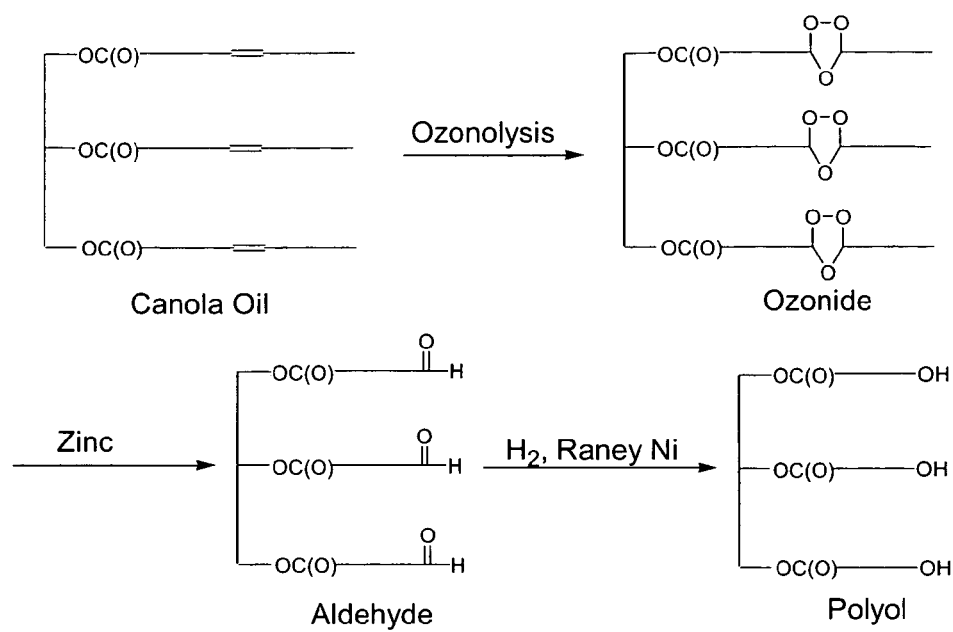

Figure 43 HPLC graphs of GII-Polyol and GIII-Polyol product synthesized from canola oil Figure 44 HPLC standard curves of (a) triol, (b) diol and (c) mono-ol Figure 45 FTIR spectra of GIII-PU plastic sheets with (a) OH/NCO molar ratio 1.0/1.0, (b) OH/NCO molar ratio 1.0/1.1 and (c) OH/NCO molar ratio 1.0/1.2
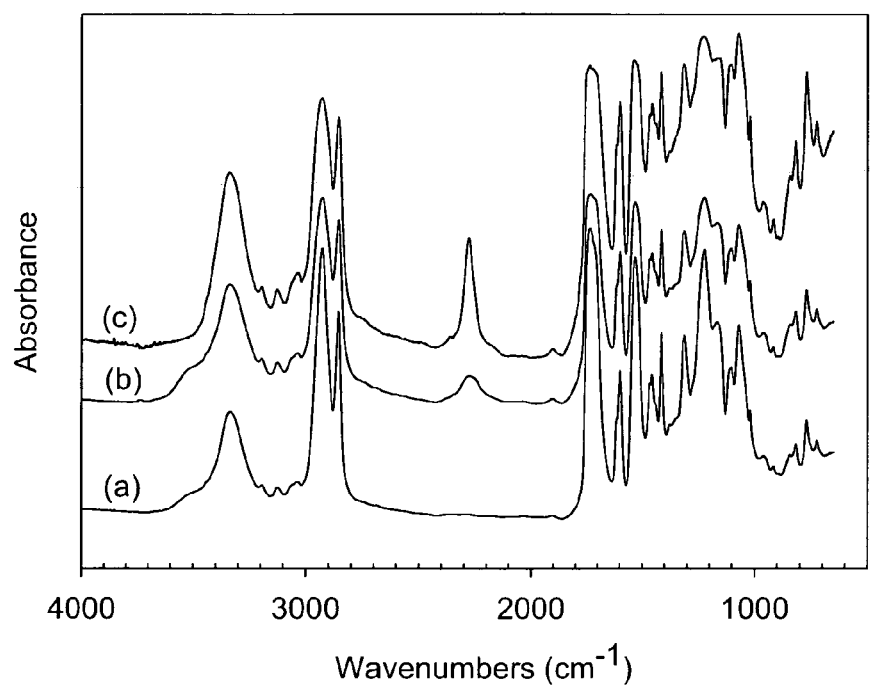

Figure 46 Master curve of E' at a reference temperature of $T_g$ + 5°C for GIII–PU plastic sheet with OH/NCO molar ratio 1.0/1.2
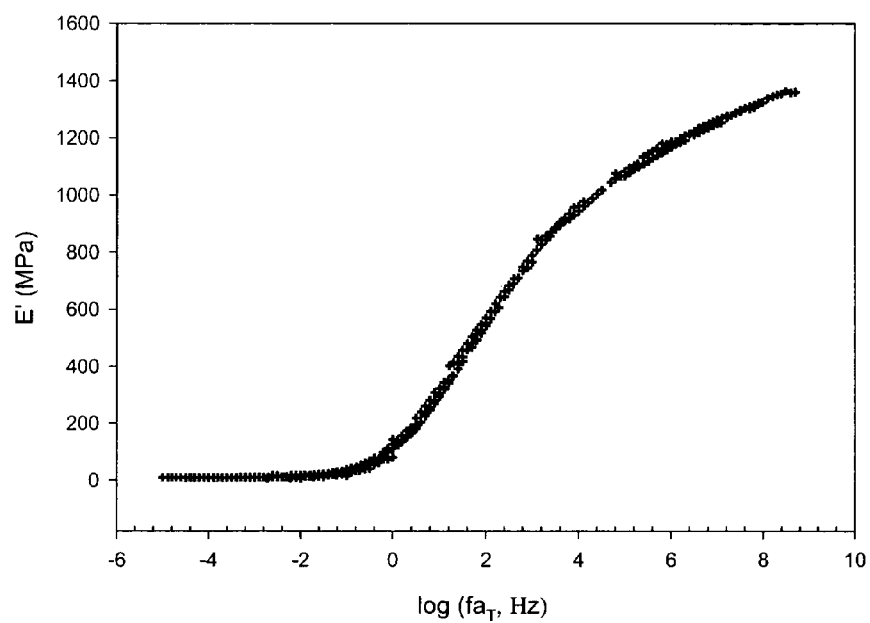

Figure 47 DSC curves of the GIII-PU plastic sheets with (a) OH/NCO molar ratio 1.0/1.0, (b) OH/NCO molar ratio 1.0/1.1 and (c) OH/NCO molar ratio 1.0/1.2
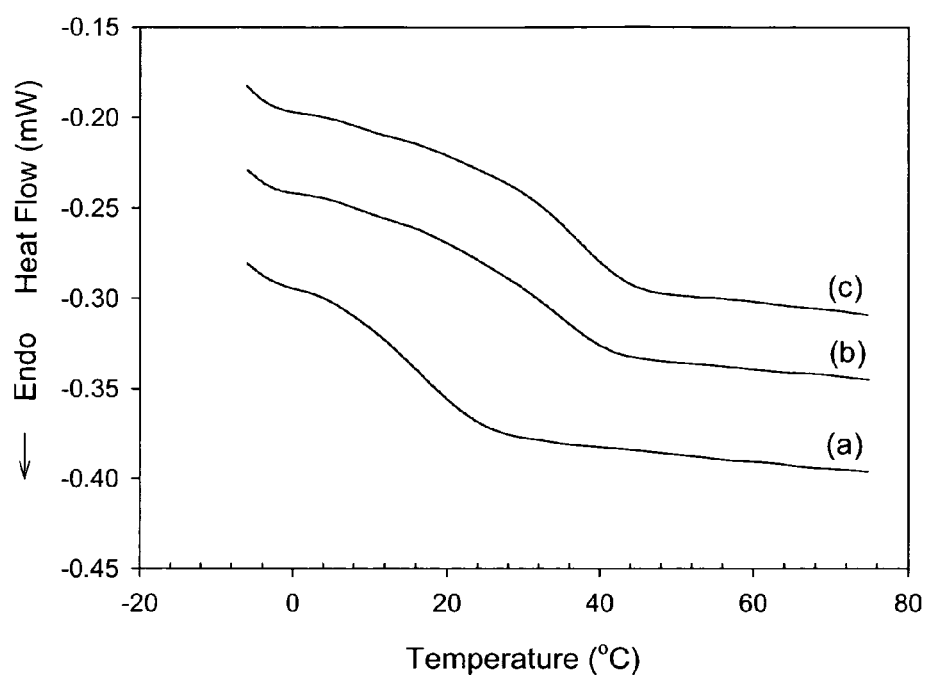

Figure 48 Storage moduli vs. temperature of the GIII-PU plastic sheets, obtained from DMA carried out at a frequency of 1Hz with (a) OH/NCO molar ratio 1.0/1.0, (b) OH/NCO molar ratio 1.0/1.1 and (c) OH/NCO molar ratio 1.0/1.2
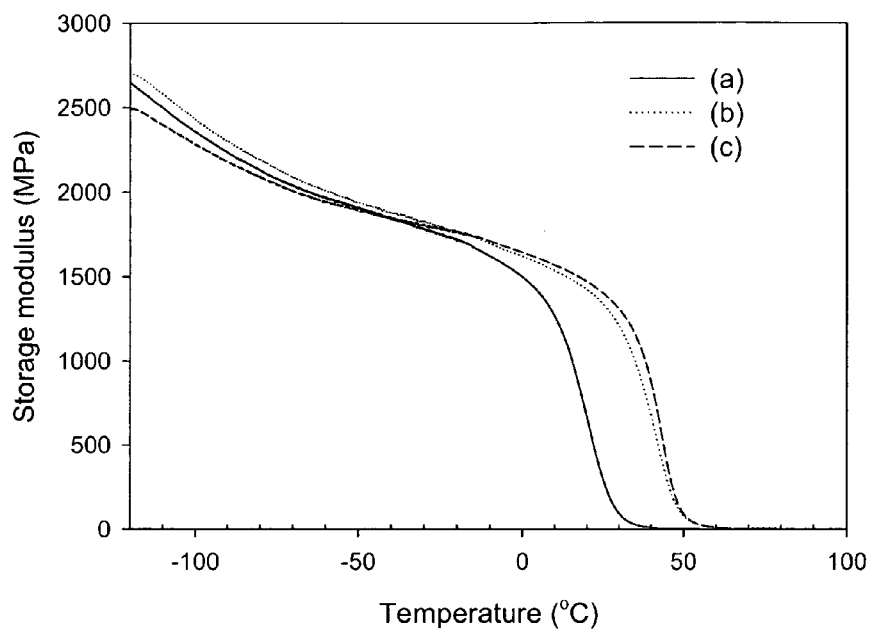

Figure 49 Changes in the loss (E″) moduli with temperature of the GIII−PU plastic sheets, obtained from DMA carried out at frequency of 1Hz with (a) OH/NCO molar ratio 1.0/1.0, (b) OH/NCO molar ratio 1.0/1.1 and (c) OH/NCO molar ratio 1.0/1.2
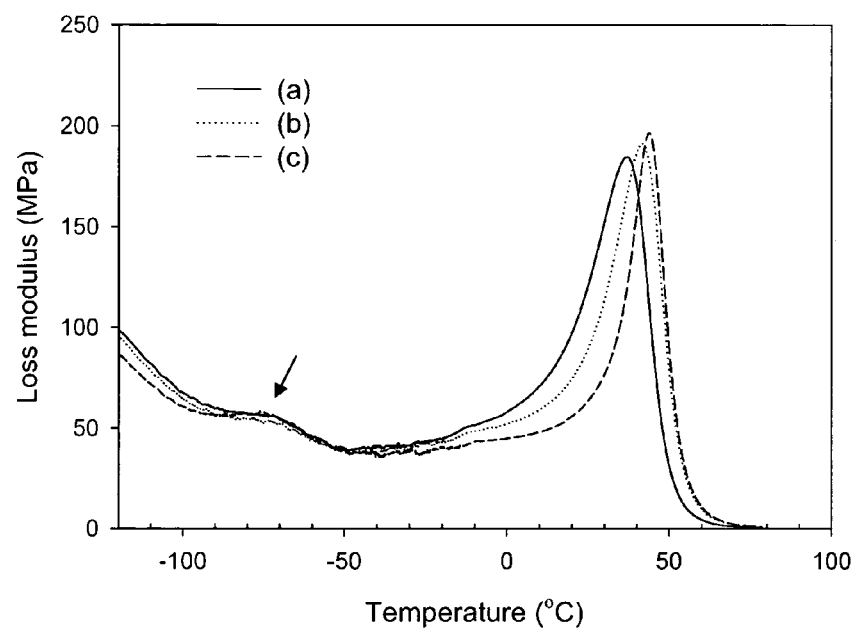

Figure 50 Temperature dependence of tangent δ (tan δ) of the GIII-PU plastic sheets measured by DMA with (a) OH/NCO molar ratio 1.0/1.0, (b) OH/NCO molar ratio 1.0/1.1 and (c) OH/NCO molar ratio 1.0/1.2
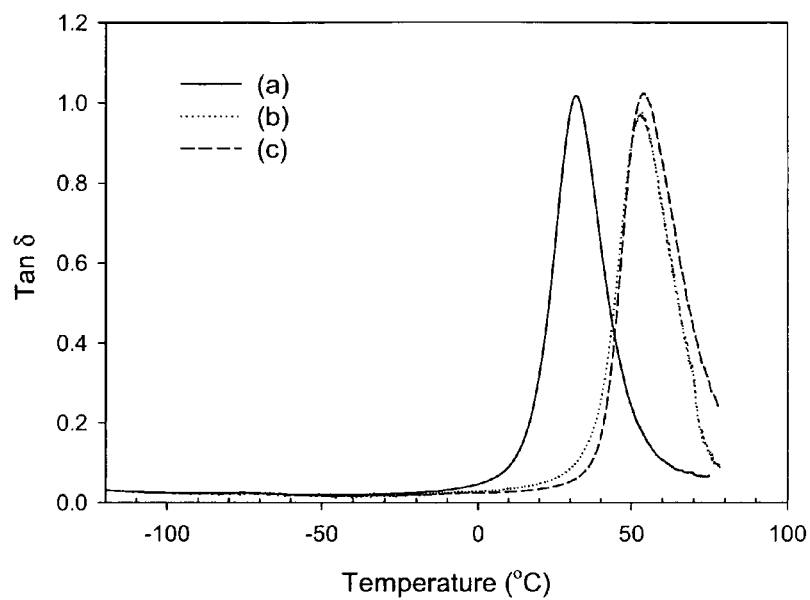

Figure 51(a) TGA curves of the GIII-PU plastic sheets with (a) OH/NCO molar ratio 1.0/1.0, (b) OH/NCO molar ratio 1.0/1.1 and (c) OH/NCO molar ratio 1.0/1.2
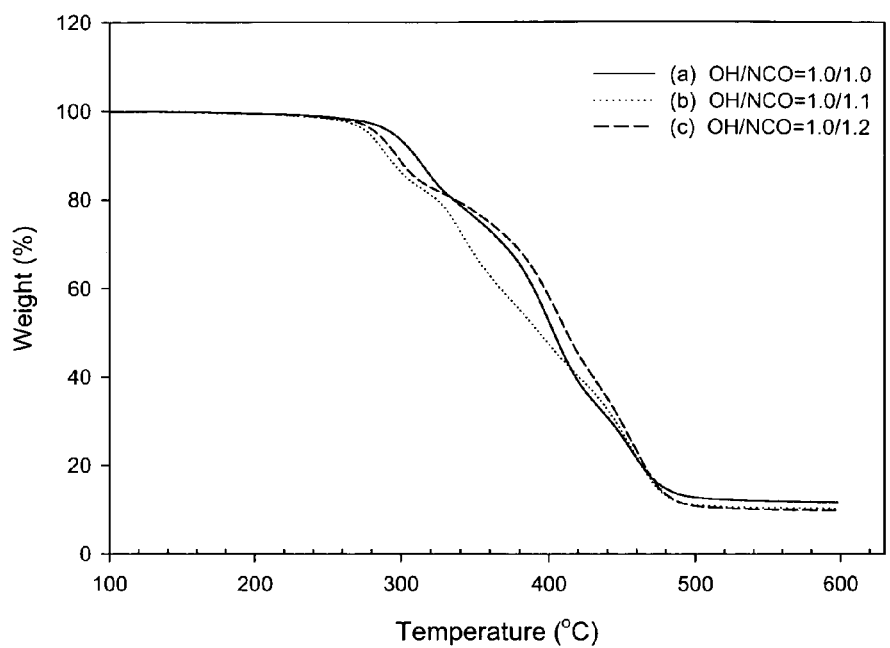

Figure 51(b) Derivative of TGA (DTGA) curves of the GIII-PU plastic sheets with (a) OH/NCO molar ratio 1.0/1.0, (b) OH/NCO molar ratio 1.0/1.1 and (c) OH/NCO molar ratio 1.0/1.2
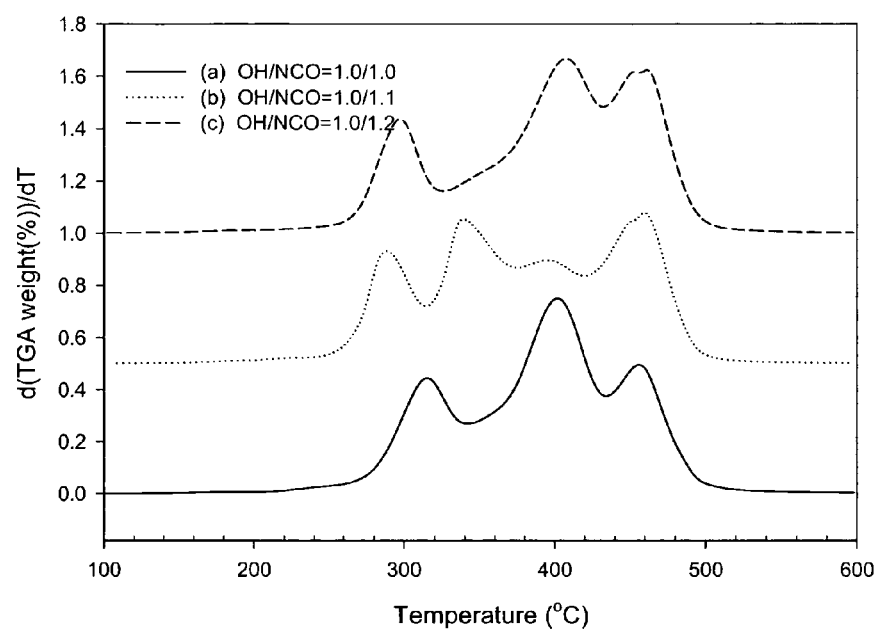

Figure 52 Stress vs. strain curves for the GIII-PU plastic sheets with (a) OH/NCO molar ratio 1.0/1.0, (b) OH/NCO molar ratio 1.0/1.1 and (c) OH/NCO molar ratio 1.0/1.2
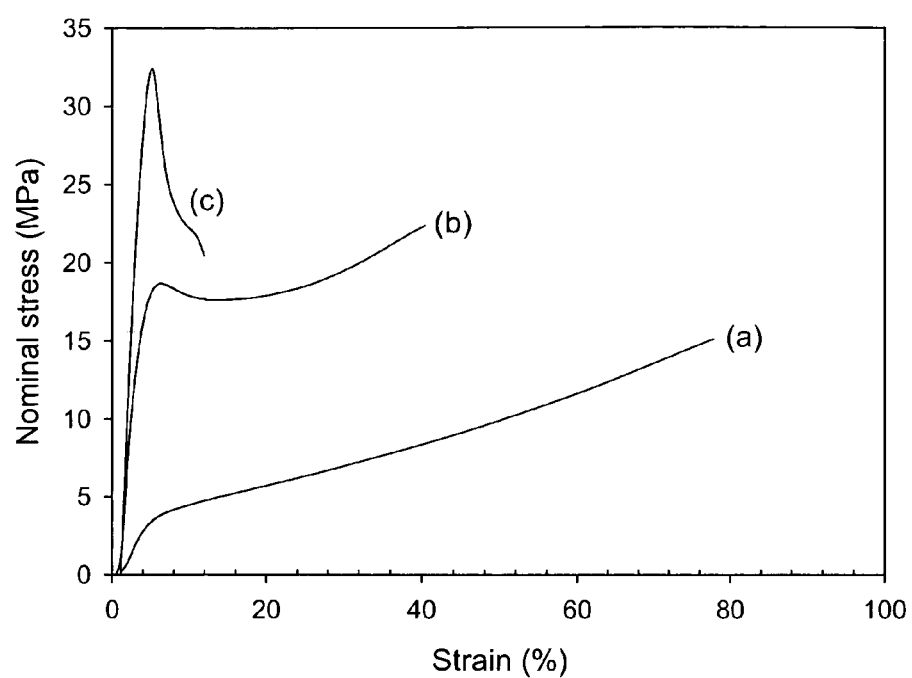

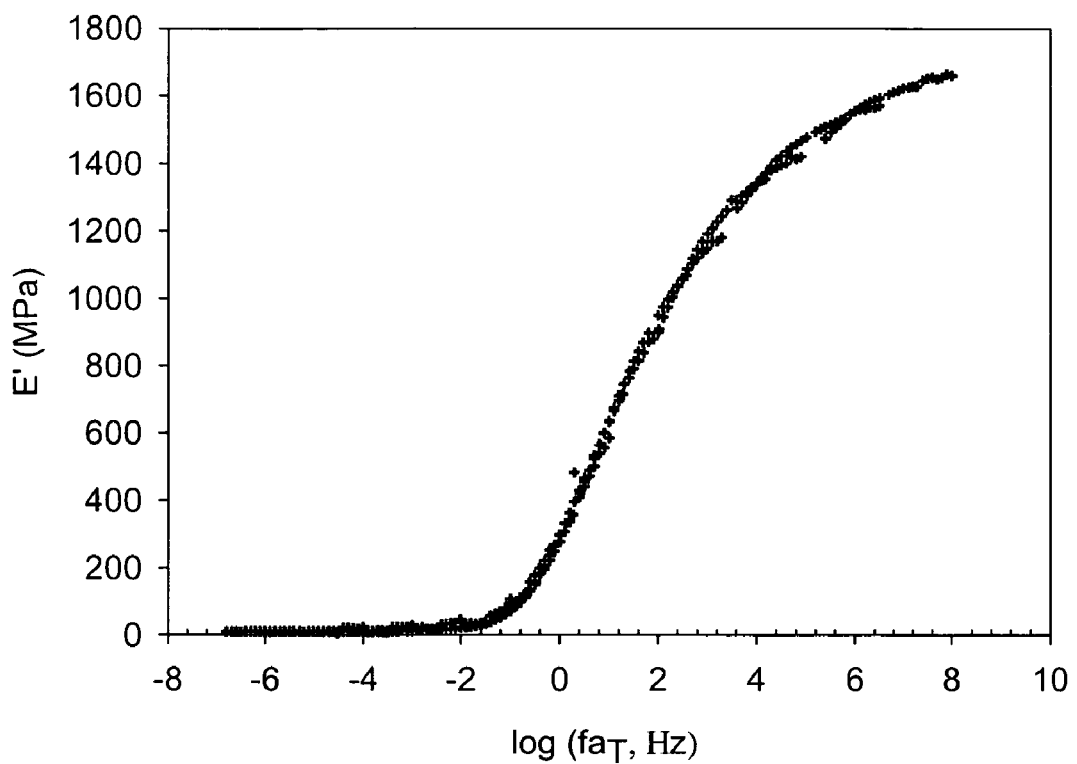
Figure 53 Master curve of E' at a reference temperature of $T_g$ + 5°C for GIII–PU elastomers

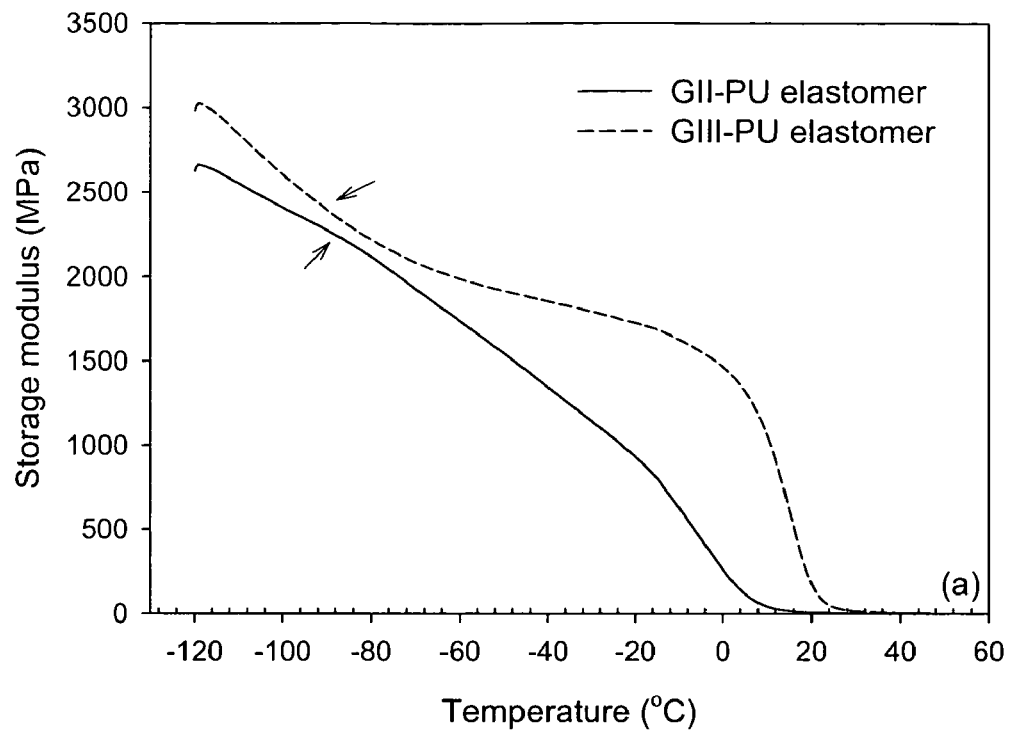
Figure 54(a) Storage moduli vs. temperature, obtained from DMA carried out at a frequency of 1Hz for PU elastomers

Figure 54(b) Storage moduli vs. temperature, obtained from DMA carried out at a frequency of 1Hz for PU foams
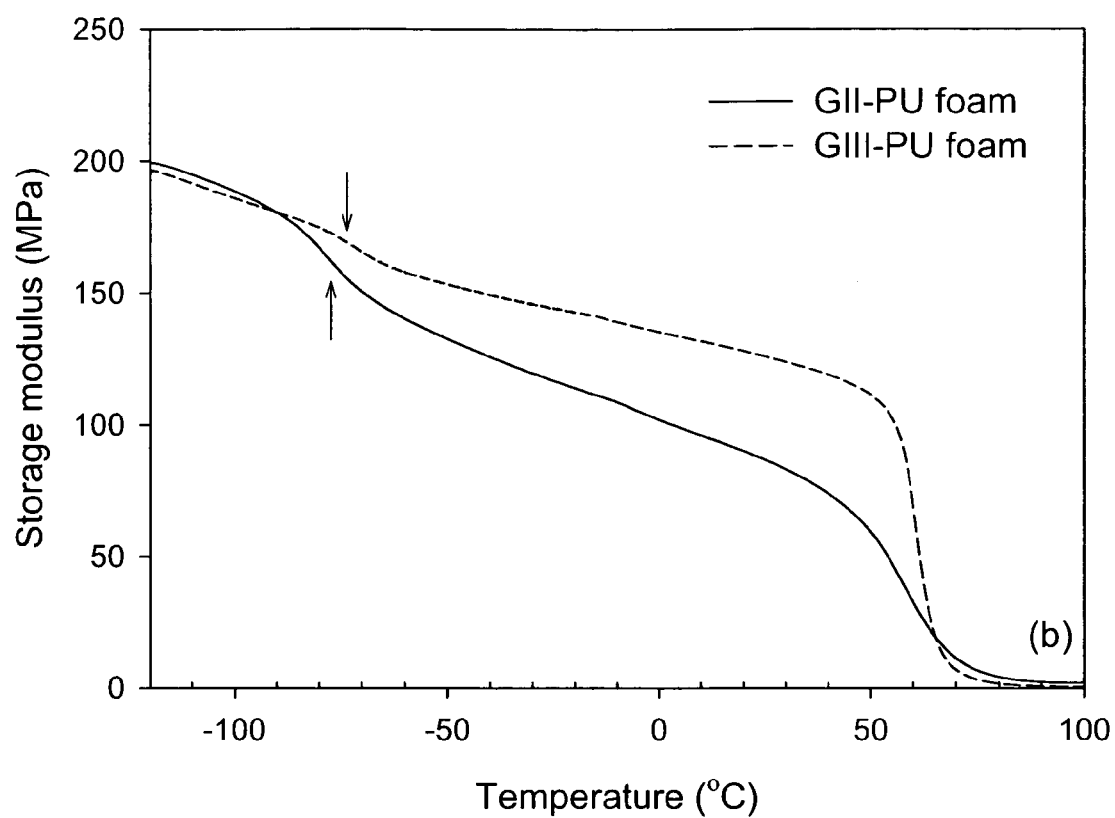

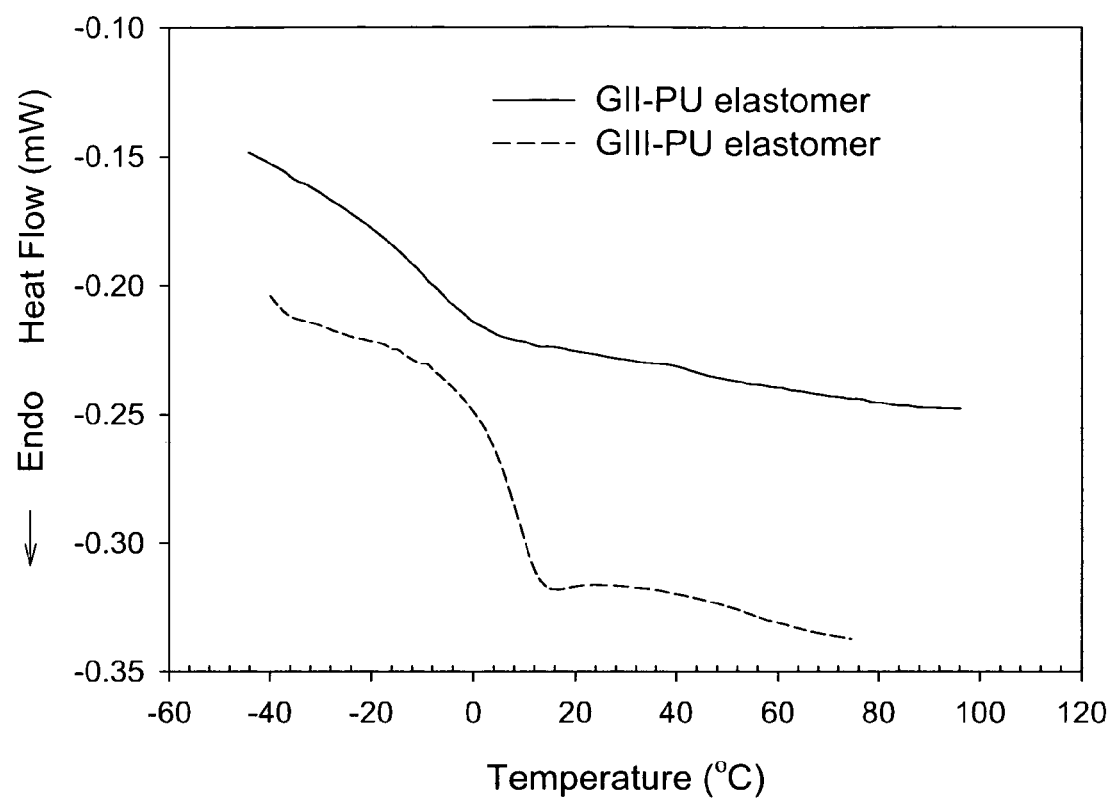
Figure 55 DSC curves of the PU elastomers

Figure 56(a) Changes in the loss (E″) moduli with temperature, obtained from DMA carried out at frequency of 1Hz for PU elastomers
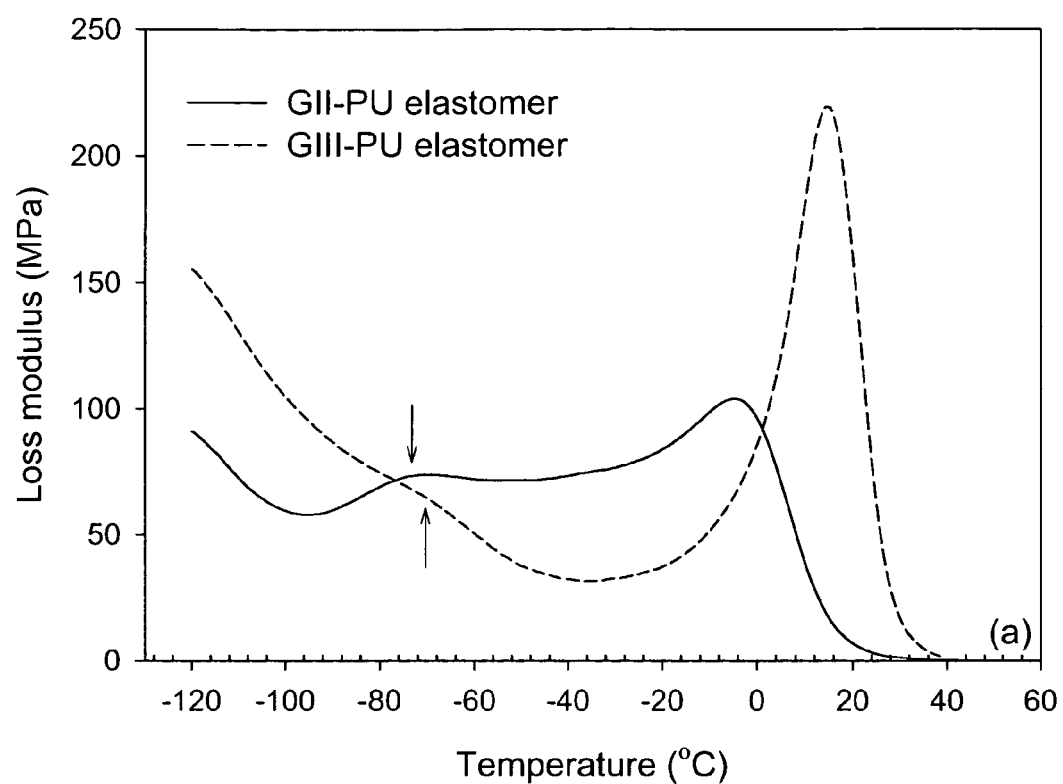

Figure 56(b) Changes in the loss (E″) moduli with temperature, obtained from DMA carried out at frequency of 1Hz for PU foams
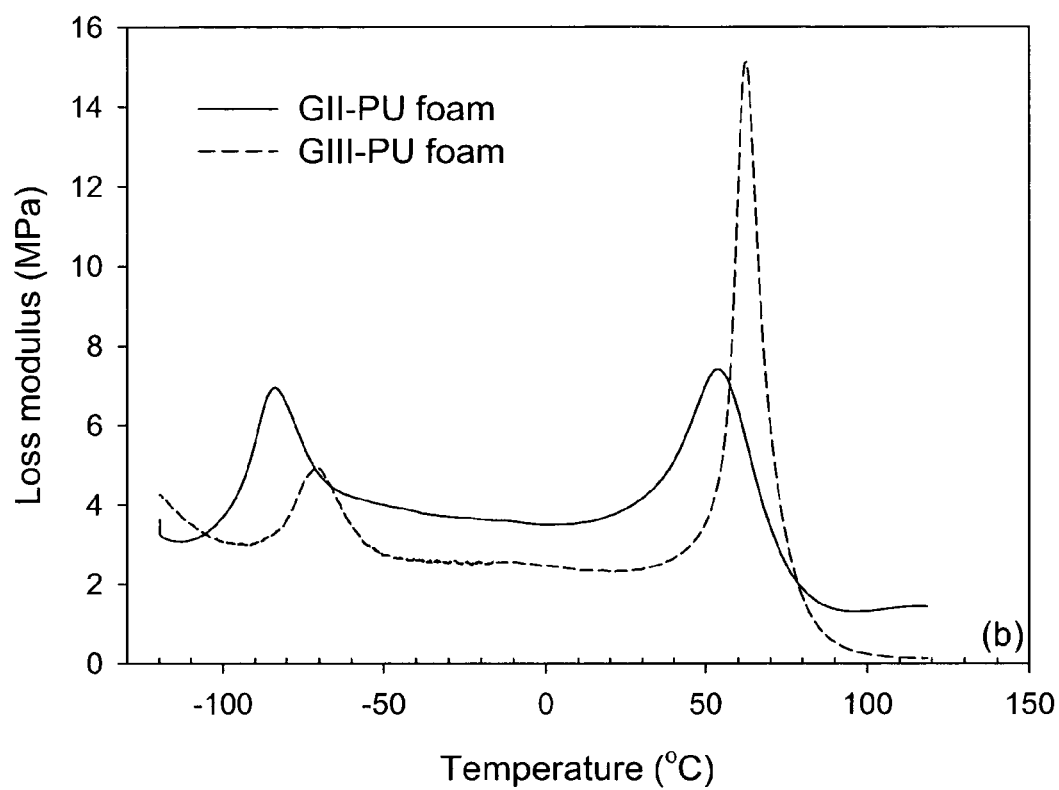

Figure 57 Temperature dependence of tangent δ (tan δ) of PU elastomers measured by DMA
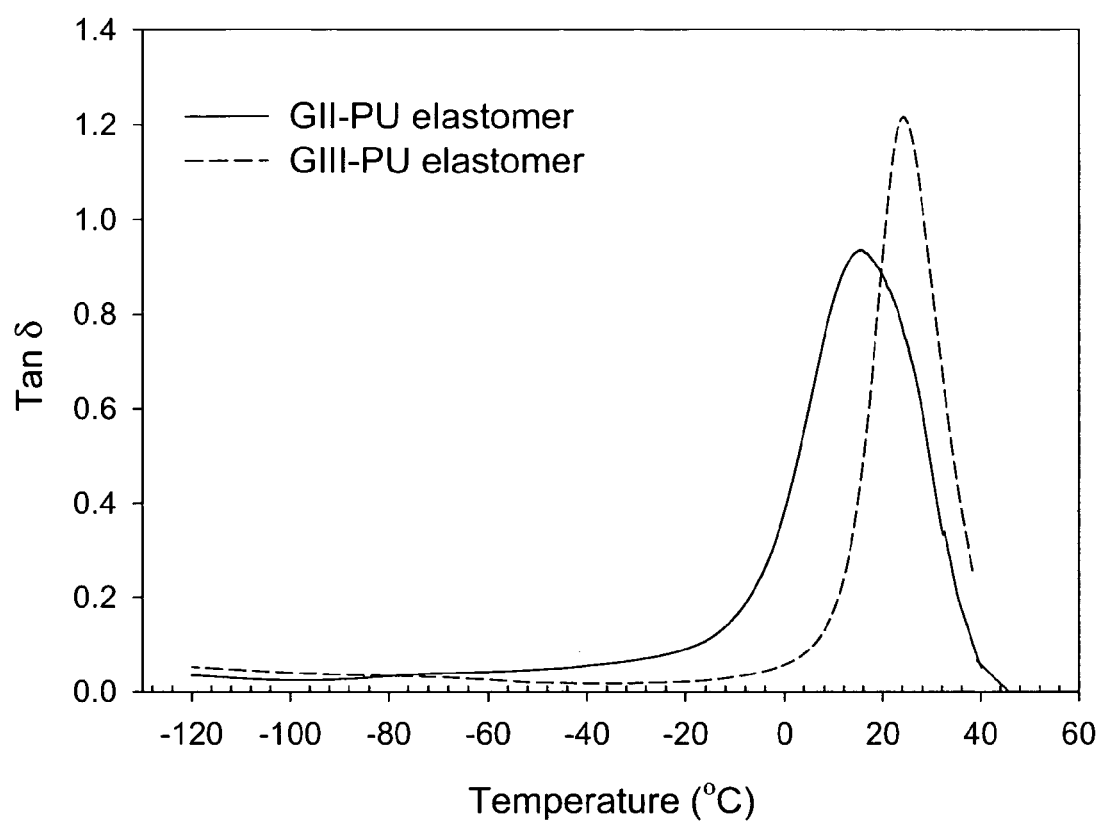

Figure 58 Stress vs. strain curves for the PU elastomers
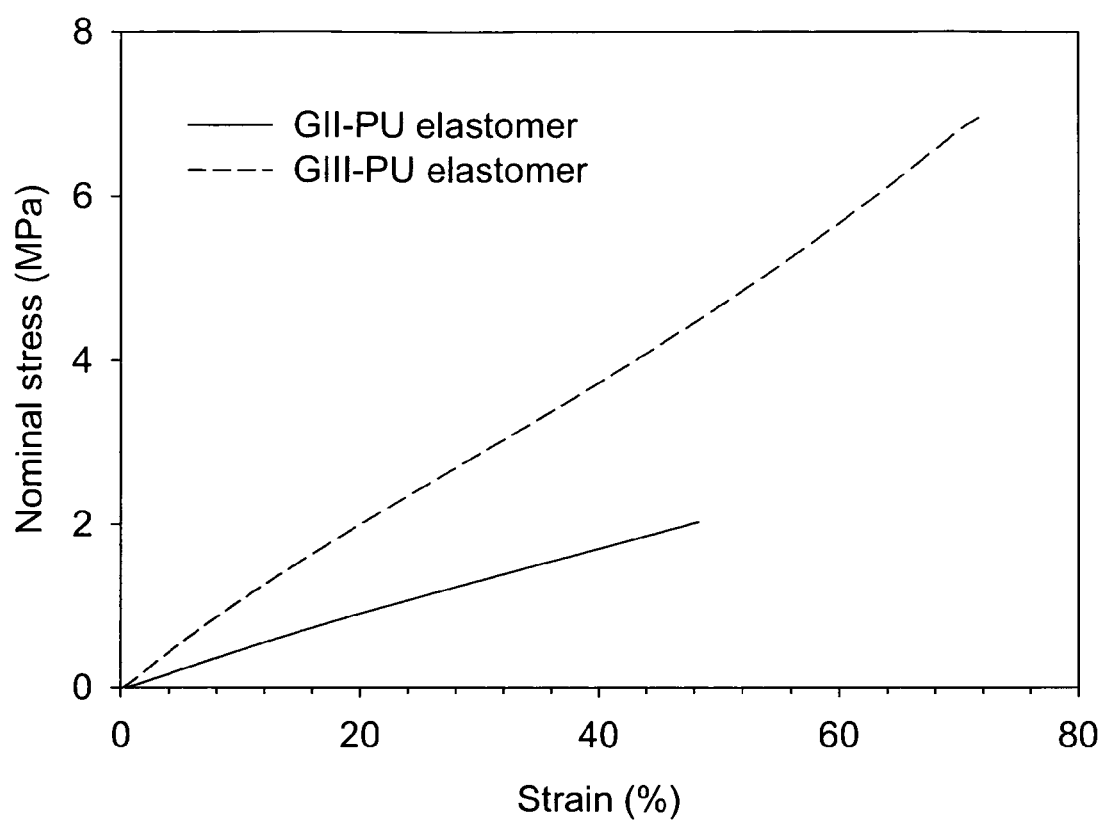

Figure 59 Compressive strength vs. strain of PU foams
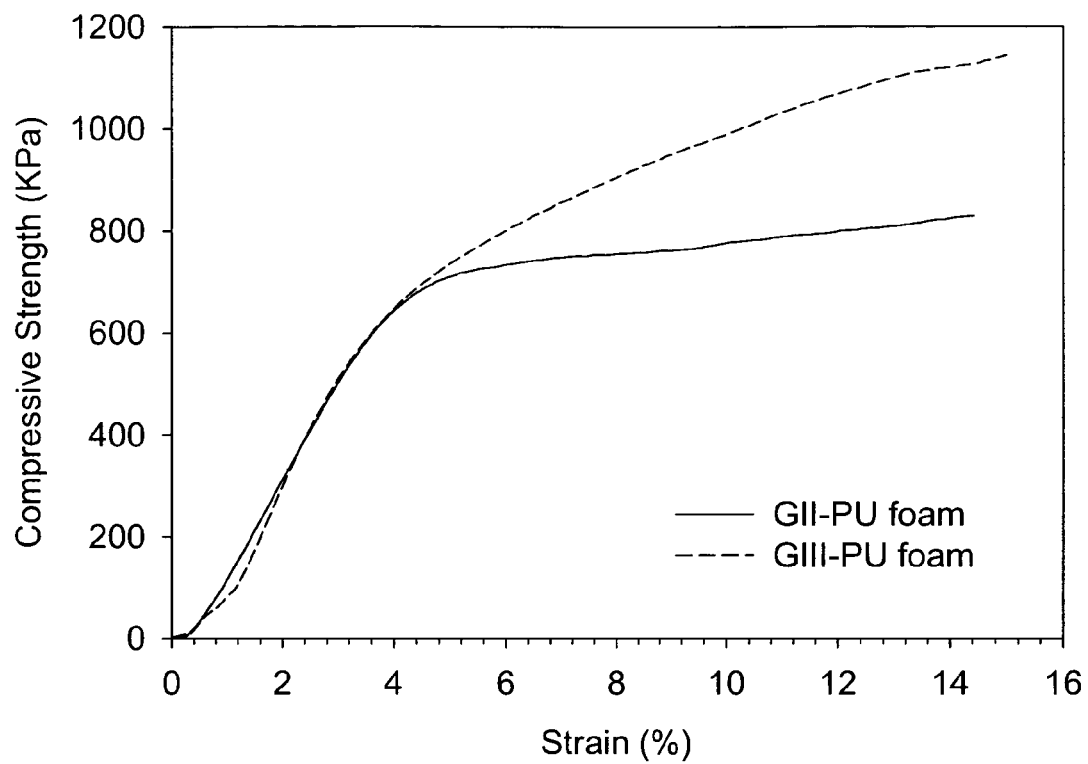

Figure 60 Scanning electron micrograph of the PU. (a) GII-PU foams and (b) GIII-PU foams
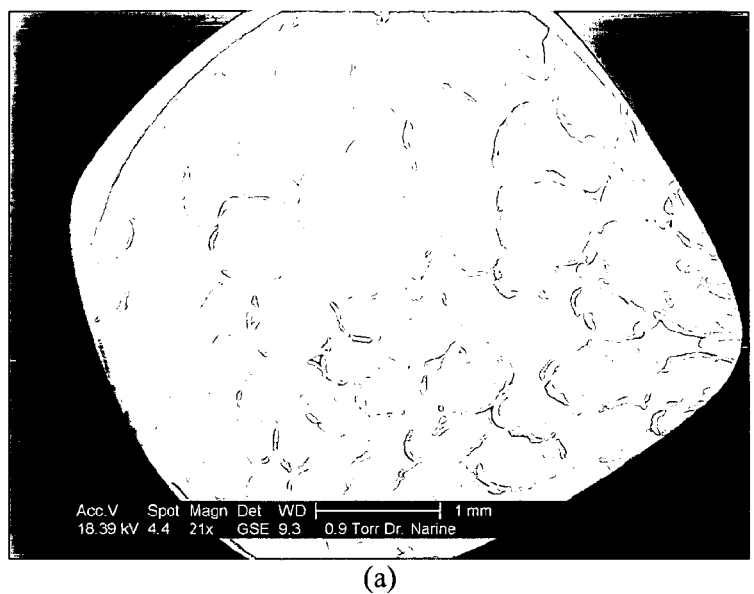
(a)
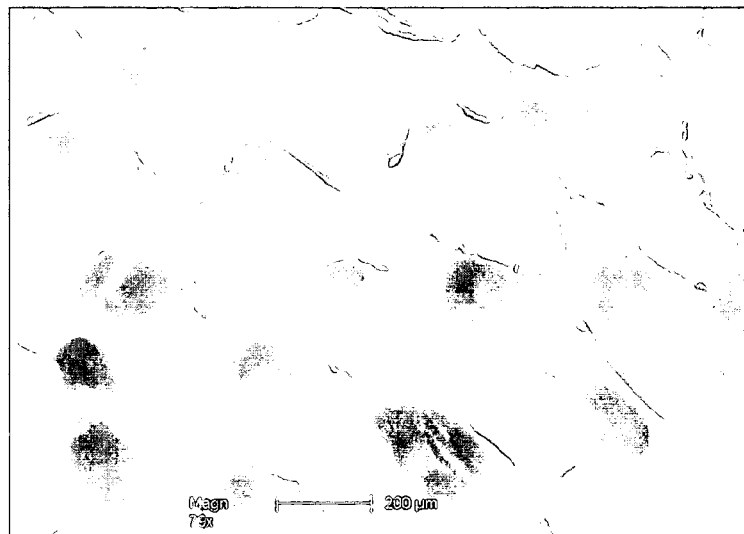
(b)

Figure 61 : Synthesis of nonyl-9-hydroxynanoate from canola oil
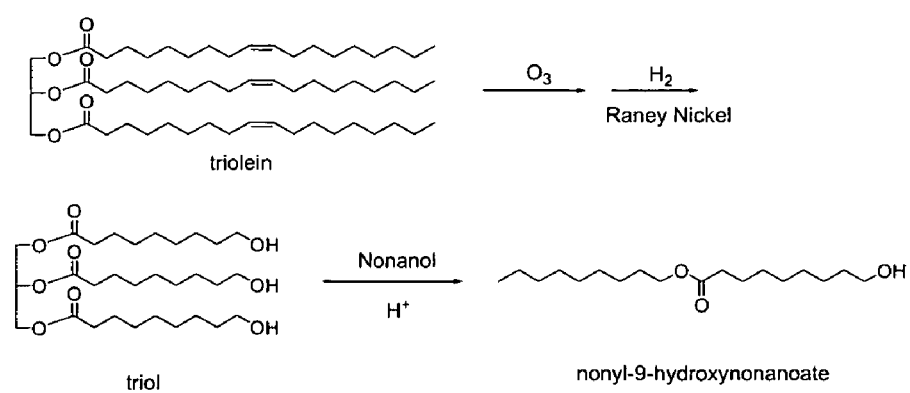

Figure 62: IR of nonyl-9-hydroxynonanoate
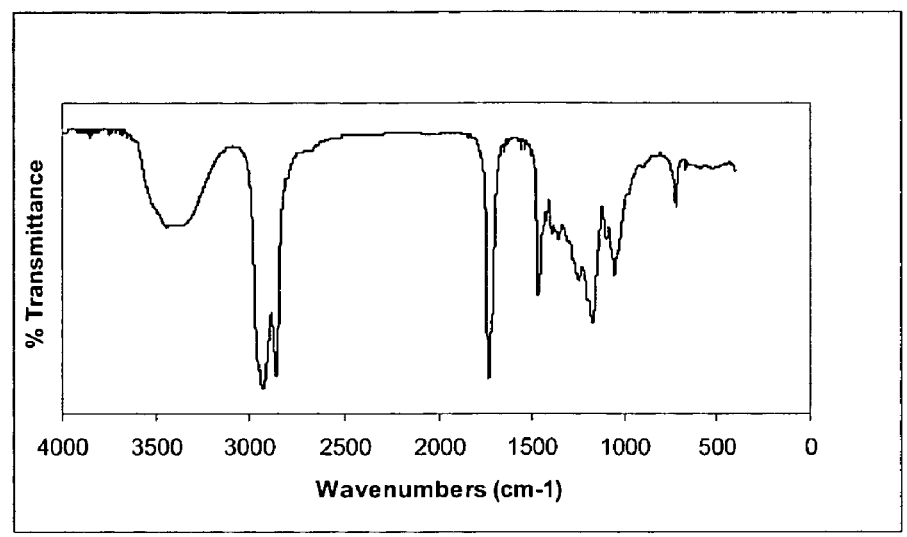

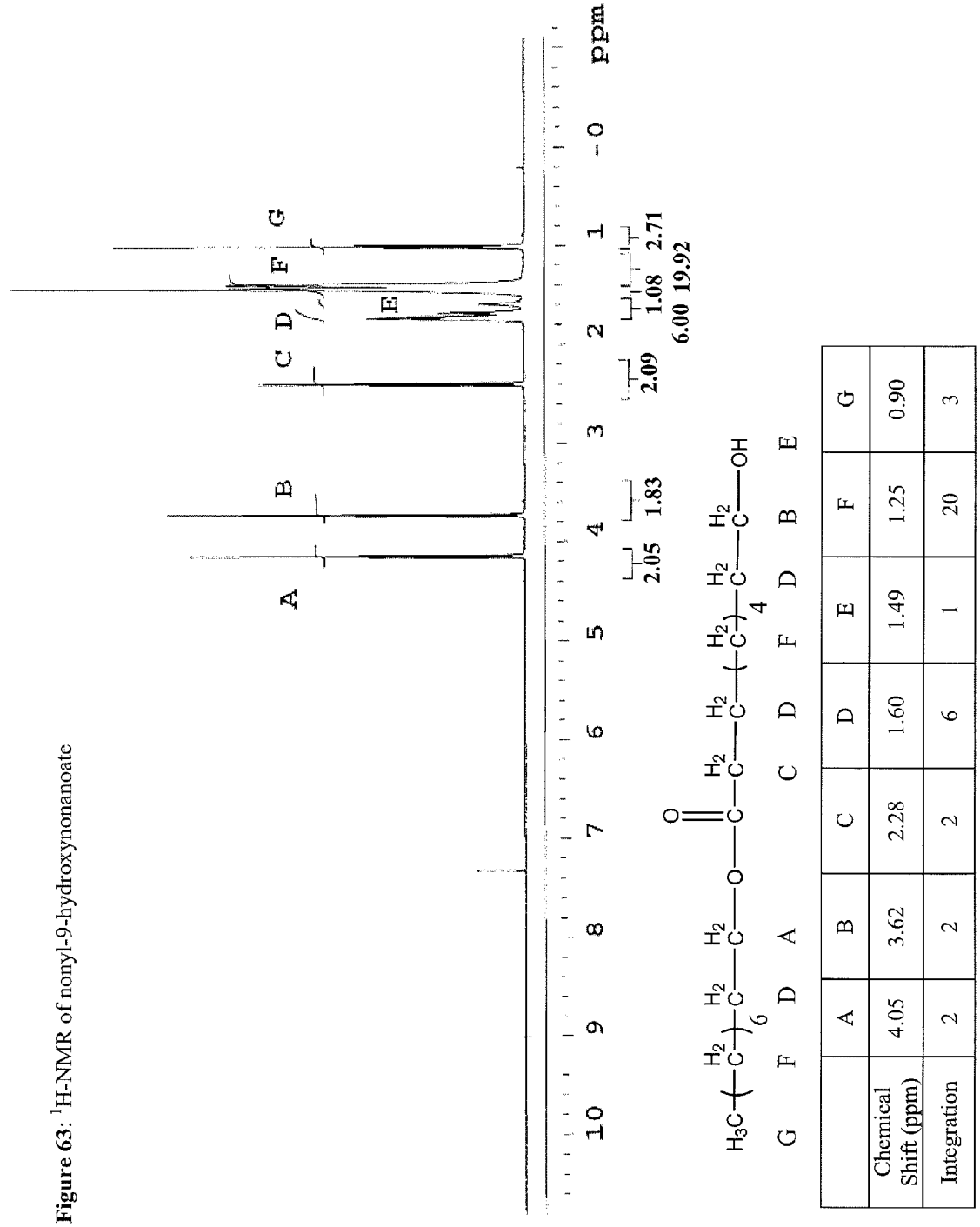
Figure 63: $^1$H-NMR of nonyl-9-hydroxynonanoate

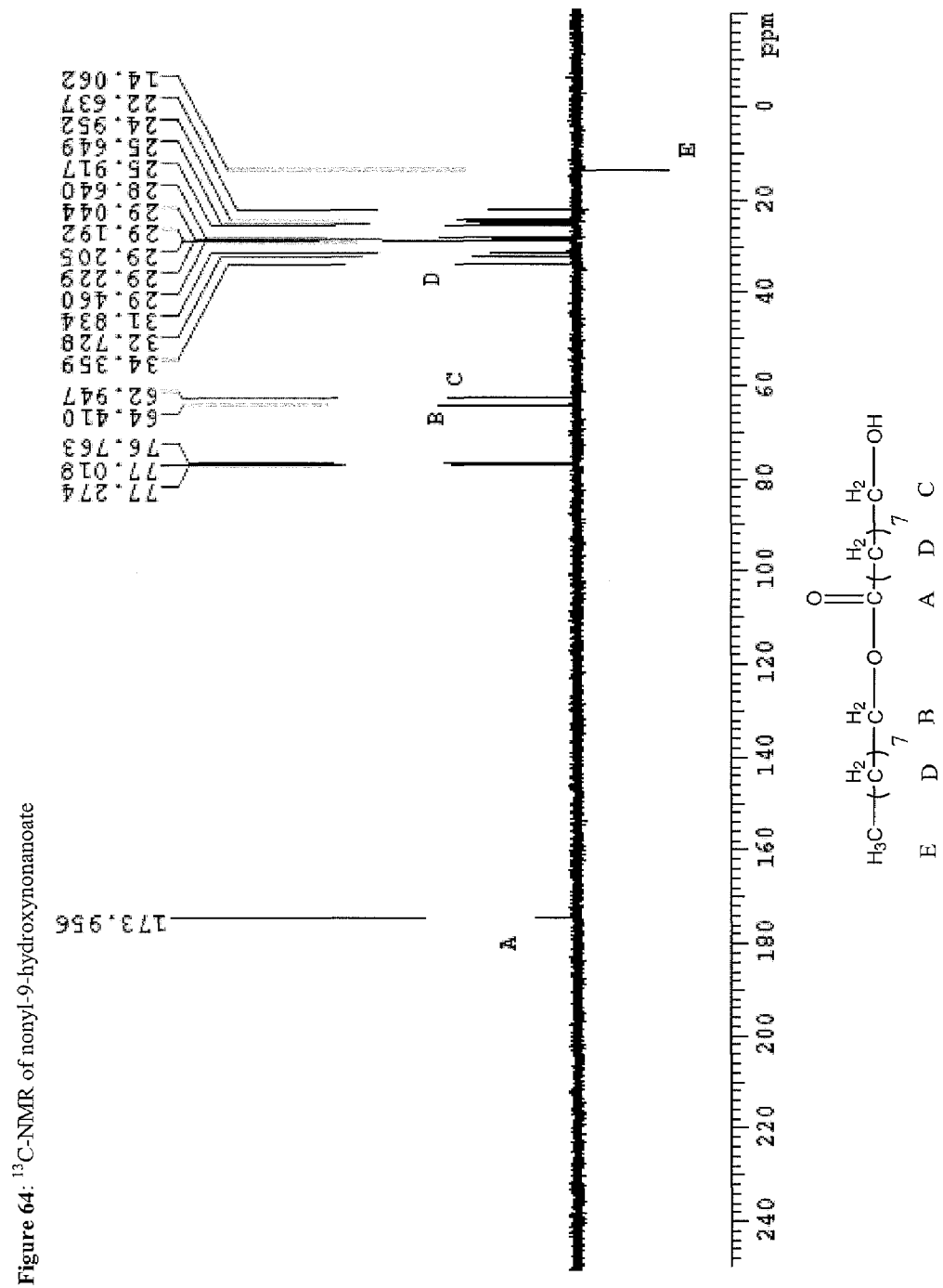
Figure 64: $^{13}$C-NMR of nonyl-9-hydroxynonanoate

Figure 65: Mass Spectrometry of nonyl-9-hydroxynonanoate
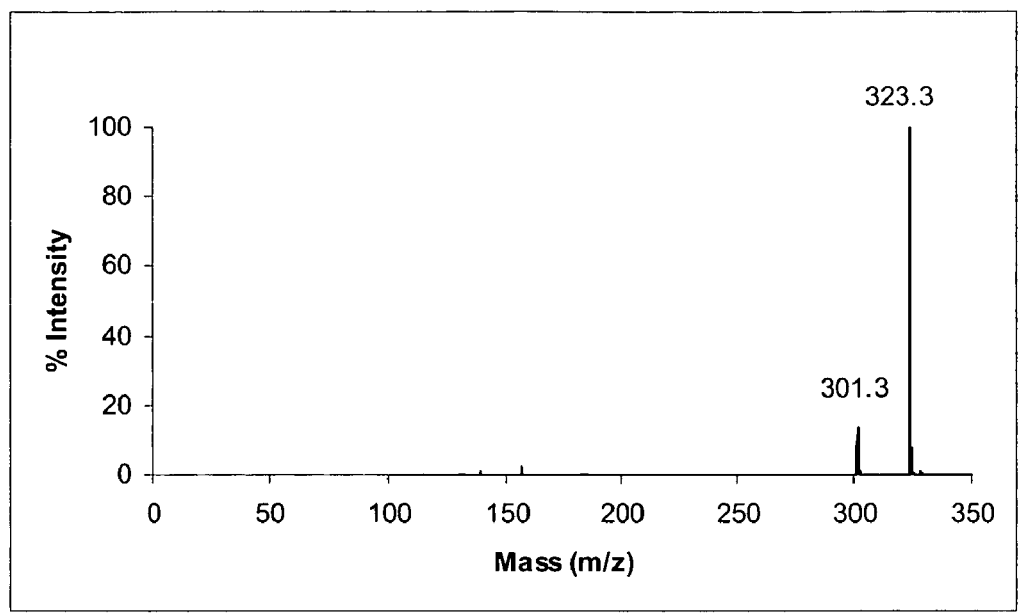

Figure 66 Viscosity of designer polyols synthesized with different ozonolysis time as a function of temperature.
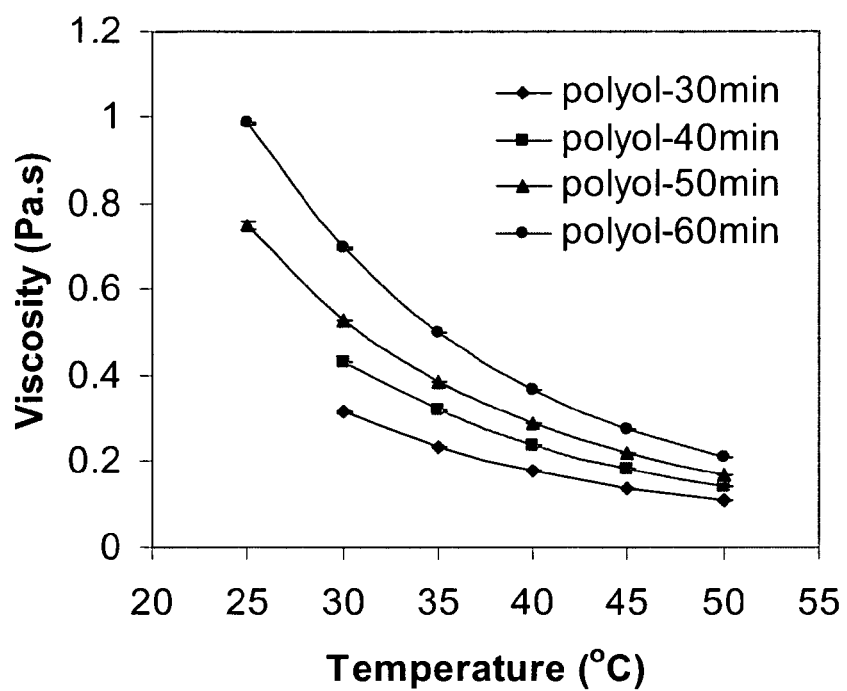

Figure 67 DSC curves of the PU elastomers prepared from polyols with different ozonolysis time.
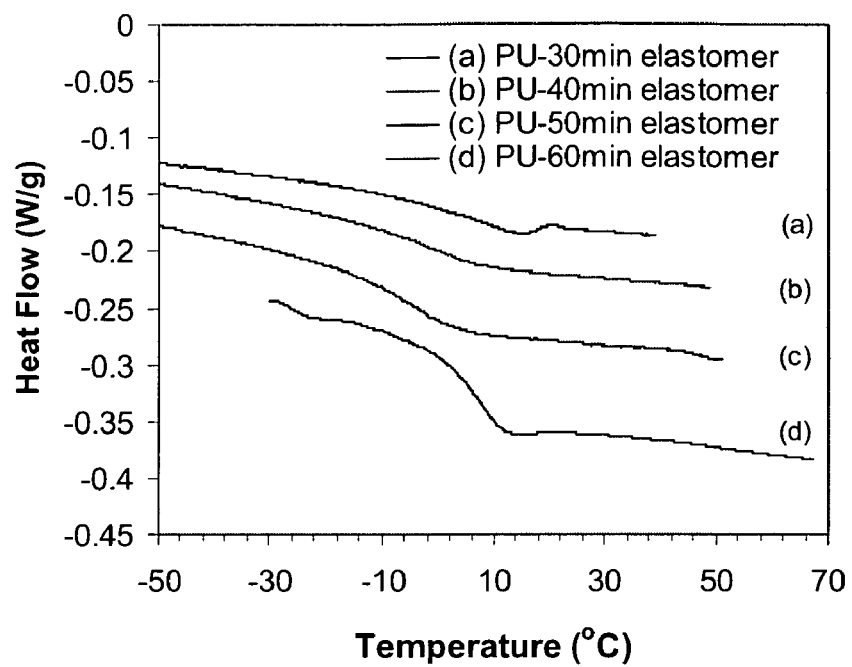

Figure 68 Storage moduli vs. temperature of the PU elastomers prepared from polyols with different ozonolysis time.
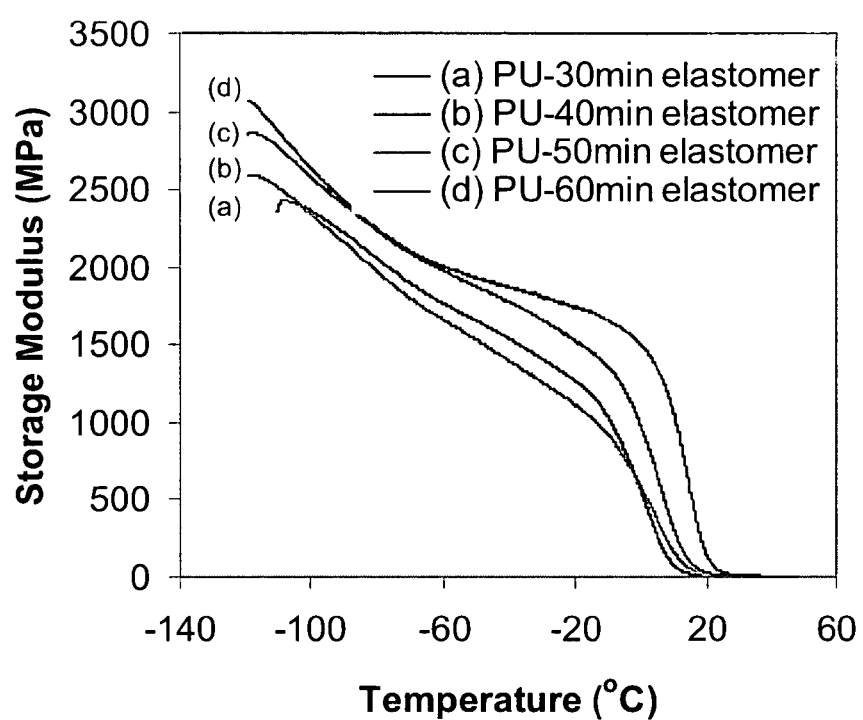

Figure 69 Loss (E″) moduli with temperature of the PU elastomers prepared from polyols with different ozonolysis time.
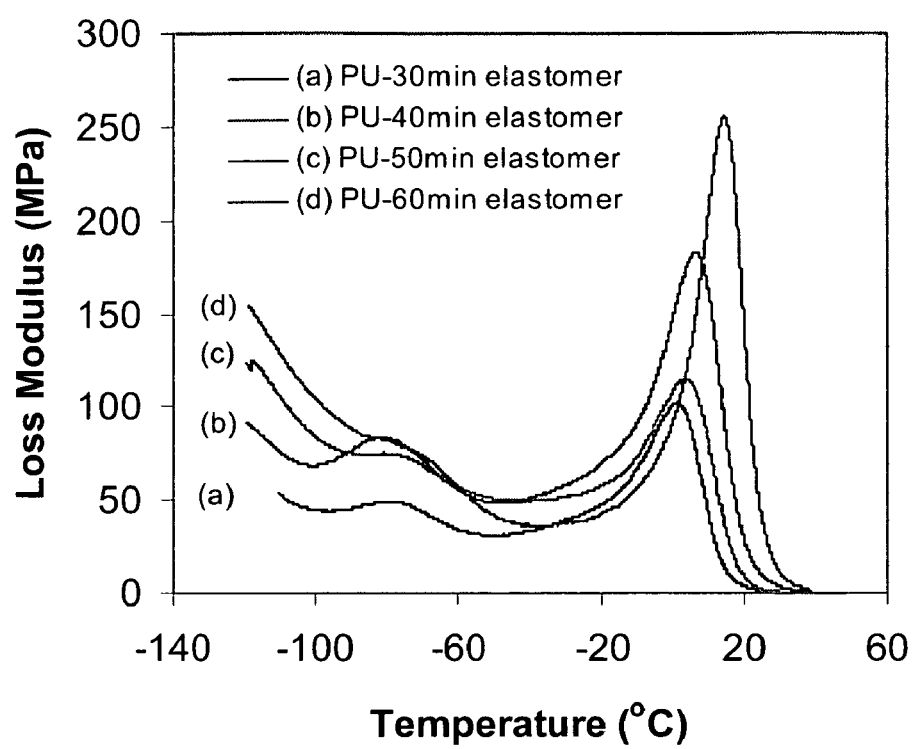

Figure 70 Stress vs. strain curves for the PU elastomers prepared from polyols with different ozonolysis time.
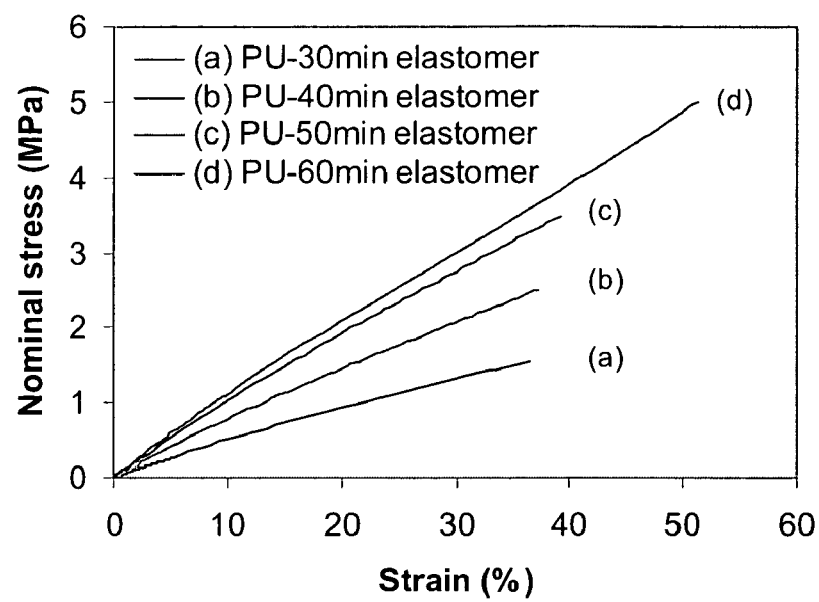

Figure 71 DSC curves of the PU prepared from polyols with different ozonolysis time.
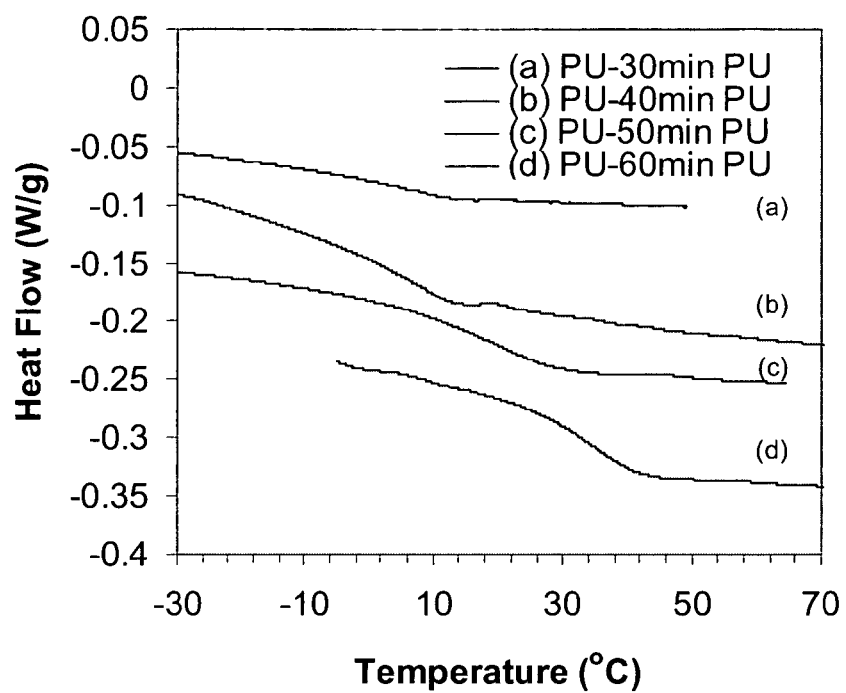

Figure 72 Storage moduli vs. temperature of the PU prepared from polyols with different ozonolysis time.
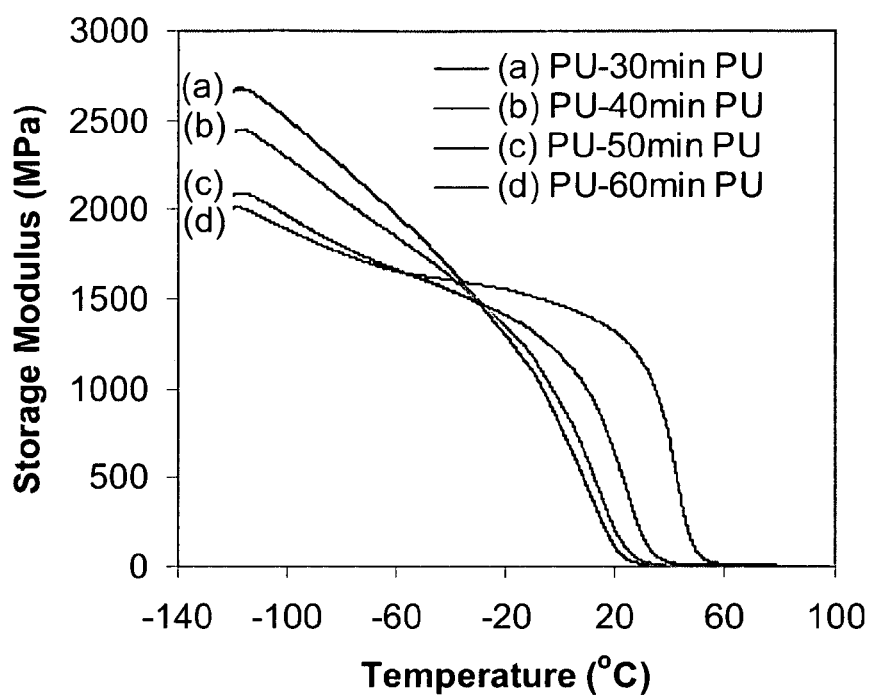

Figure 73 Stress vs. strain curves for the PU prepared from polyols with different ozonolysis time.
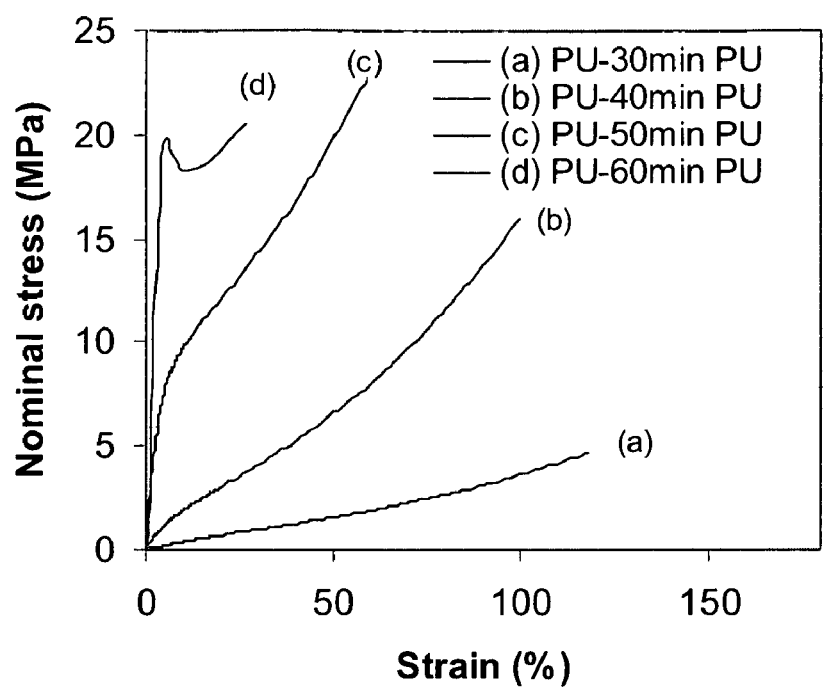

BIOPLASTICS, MONOMERS THEREOF, AND PROCESSES FOR THE PREPARATION THEREOF FROM AGRICULTURAL FEEDSTOCKS

CROSS-REFERENCE TO RELATED APPLICATION

The present invention claims priority to U.S. Provisional Application No. 60/755,770, filed Jan. 4, 2006, the contents of which are incorporated herein by reference in their entirety.

BACKGROUND OF THE INVENTION

1. Field of the Invention

The present invention relates generally to monomers and polymers derived from agricultural feedstocks, and more particularly to methods for the production of monomers from renewable agricultural resources such as feedstocks, for example canola, flax and tallow, and polymers, in particular polyurethanes, produced from such monomers.

2. Brief Description of the Related Art

With the realization that oil resources are becoming increasingly hard to find and expensive to produce, many industries that use oil as their source of raw material are looking to other sources, preferably renewable sources. At present, the production of plastics is still mainly based on the use of oil resources and a very large subgroup (about 10%) of the plastics industry includes the production of various polyurethanes (American Plastics Council (http://www.americanplasticscouncil.org). Accessed Apr. 10, 2005).

The preparation of polymers from renewable sources is of significant economic and scientific importance. As an inexpensive, readily available renewable resource, attention has been paid to renewable resources such as vegetable oils which are abundant and varied as a source for polymeric materials. Since they are composed of triacylglycerols containing predominantly unsaturated fatty acids, native North American vegetable oils are chemically relatively unreactive. But other functional groups such as hydroxyl, epoxy, or carboxyl groups can be introduced at the positions of double bonds (Petrovic, Z. R., Guo, A.; Zhang, W., *J Polymer Sci A Polym. Chem* 38: 4602 (2000) to produce reactive raw materials, which have been utilized in producing valuable polymeric materials. Present methods of using vegetable oils in polyurethane production require alcohol functionality to form what are widely referred to as polyols.

Vegetable oils are predominantly made up of triacylglycerol molecules and have complex structures (O'Brien, R. D., *Fats and Oils: Formulating and Processing for Applications*, CRC press, Boca Raton, Fla., pp 16-17, 2004). Triacylglycerol molecules are constituted by three fatty acids (varying from 14 to 22 carbons each in length for North American seed oils) and connected to a glycerol backbone through ester linkages. The fatty acids constituting most common North American seed oils have 0 to 3 double bonds which provide the sites of reactivity to convert the triacylglycerol structure of the vegetable oil into a triacylglycerol polyol, the raw material suitable for polymer production. Some triacylglycerol oils such as castor and vernonia oils develop specialized functional hydroxyl or epoxy groups and the others (such as canola, flax or linseed oils) have a double-bond functionality which provides reaction sites which enables them to be processed into high-value biochemicals for various industries (Pryde, E. H., L. H. Privcen, and K. D. Mukherjee (Eds.), *New Sources of Fats and Oils*, American Oil Chemists Society, Champaign, Ill., 1981).

In polymer applications, certain grades of vegetable oils and their derivatives, such as polyol products, have been industrially explored as an alternative feedstock to produce additives or components for composites or polymers with definite advantages when compared with fossil and mineral raw materials (Pryde, E. H., L. H. Privcen, and K. D. Mukherjee (Eds.), *New Sources of Fats and Oils*, American Oil Chemists Society, Champaign, Ill., 1981).

In the polymer field (which includes materials such as poly vinyl chloride (PVC) and polyurethane, and the like), plant oils based materials with varying physical, mechanical and thermal properties have been produced (Salunkhe, D. K., J. K. Chavan, R. N. Adsule, S. S. Kadam, in *World Oilseeds: Chemistry, Technology, and Utilization*; Van Nostrand Reinhold, New York, pp 87-89, 1992; John, J., M. Bhattacharya and R. B. Turner, Characterization of polyurethane foams from soybean oil, *J. Appl. Polym. Sci.* 86, 3097-3107 (2002); Khot, S. N., J. J. Lascala, E. Can, S. S. Morye, G. I. Williams, G. R. Palmese, S. H. kusefoglu and R. P. Wool, Development and application of triglyceride-based polymers and composites, ibid. 82: 703-723 (2001)), but much more needs to be done to widen the pool of biochemical feedstock, enhance the yields, optimize the processes, and broaden the products.

Polyurethanes which have a wide range of applications (elastomers, rigid set resins, flexible slab, and foams) are traditionally industrially produced by reacting petroleum based polyols with isocyanates (Szycher, M., *Szycher's Handbook of polyurethanes*, CRC Press, Boca Raton, Fla., 1999). In recent years, naturally functionalized triacylglycerol oils (Barrett, L. W., L. H. Sperling, C. J. Murphy, Naturally functionalised triglyceride oils in interpenetrating polymer networks. *J. Am. Oil Chem. Soc.* 70: 523-534 (1993); Carlson K. D. and S. P. Chang, Chemical epoxidation of a natural unsaturated epoxy seed oil from Vernonia galamensis and a look at epoxy oil markets., ibid. 62: 934-939. (1985)) as well as vegetable oil polyols have attracted attention for making a multitude of plastic products including various polyurethanes (PUs) (Khoe, T. H., F. H. Otey, and E. N. Frankel, Rigid urethane foams from hydroxymethylated linseed oil and polyol esters, ibid. 49: 615-618 (1972); Lyon, C. K., V. H. Garret and E. N. Frankel, Rigid urethane foams from hydroxymethylated castor oil, safflower oil, oleic safflower oil, and polyol esters of castor acids., ibid. 51: 331-334 (1974); Guo, A., Y. Cho and Z. S. Petrovic, Structure and properties of halogenated and nonhalogenated soy-based polyols., *J. Polym. Sci: Part A: Polym. Chem.* 38: 3900-3910 (2000); Guo, A., D. Demydov, W. Zhang and Z.S. Petrovic, Polyols and polyurethanes from hydroformylation of soybean oil., *J. Polym. & Environ.* 10: 49-52 (2002); Hu, Y. H., Y. Gao, D. N. Wang, C. P. Hu, S. Zu. L. Vanoverloop and D. Randall, Rigid polyurethane foam prepared from a rape seed oil based polyol., *J. Appl. Poly. Sci.,* 84: 591-597 (2002); Dwan'Isa, J.-P. Latere, A. K. Mohanty, M. Misra, L. T. Drzal and M. Kazemizadeh, Novel Biobased Polyurethanes Synthesized from Soybean Phosphate Ester Polyols: Thermomechanical Properties Evaluations., *J. Polym. & Environ.* 11: 161-168 (2003)).

The alcohol functionality also can already be found in some natural oils such as castor oil (Saxena, P. K., S. R. Srinivasan, J. Hrouz, and M. Ilavsky, The Effect of Castor Oil on the Structure and Properties of Polyurethane Elastomers, *J. Appl. Polym. Sci.* 44: 1343-1347 (1992)).

Alternately research groups have sought to introduce alcohol functionality utilizing the reactivity of double bonds to hydroformylate (Lyon, C. K., V. H. Garret, and E. N. Fankel, Rigid Urethane Foams from Hydroxymethylated Castor-oil, Safflower Oil, Oleic Safflower Oil and Polyol Esters of Castor Acids, *J. Am. Oil Chem. Soc.* 51(8): 331-334 (1974)) or introduce epoxides that can later be opened in various ways (Hu, Y. H., Y. Gao, D. N. Wang, C. P. Hu, S. Zu, L. Vanoverloop, and D. Randall, Rigid Polyurethane Foam Prepared from a Rape Seed Oil Based Polyol, *J. Appl. Polm. Sci.* 84: 591-597 (2002)).

For example, Frankel and group (Khoe, T. H., F. H. Otey, and E. N. Frankel, Rigid urethane foams from hydroxymethylated linseed oil and polyol esters, *J. Am. Oil. Chem. Soc.* 49: 615-618 (1972); Lyon, C. K., V. H. Garret and E. N. Frankel, Rigid urethane foams from hydroxymethylated castor oil, safflower oil, oleic safflower oil and polyol esters of castor acids, Ibid. 51: 331-334 (1974)) have produced derivatives of castor, safflower, and flax oils with enhanced hydroxyl groups, and Petrovic and group (Guo, A., D. Demydov, W. Zhang, and Z. S. Petrovic, Polyols and polyurethanes from hydroformylation of soybean oil, *J. Polym. & Environ.* 10-49-52 (2002)) have produced soybean oil based polyols.

The second method involves epoxidation of unsaturated fatty acids followed by alcoholysis reactions to introduce hydroxyl functionality. Petrovic and his group have successfully used it to produce polyols from soybean oil (Guo, A., Y. Cho, and Z. S. Petrovic, Structure and properties of halogenated and nonhalogenated soy-based polyols, *J. Polym. Sci. Part A: Polym. Chem.* 38: 3900-3910 (2000)). Hu and coworkers (Hu, Y. H., Y. Gao, D. N. Wang, C. P. Hu, S. Zu, L. Vanoverloop and D. Randall, Rigid polyurethane foam prepared from a rape seed oil based polyol, *J. Appl. Polym. Sci.* 84: 591-597 (2002)) have used this reaction to produce polyols from canola oil. The above technologies yielded heterogeneous triacylglycerol polyols with hydroxyl functionality situated in the middle of the fatty acid chains, causing significant steric hindrance during crosslinking reactions in the production of polymers.

However, the polyols produced so far by the reported technologies have their hydroxyl groups located in the middle of the triacylglycerol fatty acid chains leaving pendant chains of the triacylglycerol (also known as dangling chains) unsupported, which significantly limits the rigidity of the resulting polyurethanes. Significant steric hindrance to crosslinking (especially by bulky aromatic diisocyanates) are introduced by the —OH groups being located in the middle of the fatty-acid moieties, leading to less than optimized cross-linking density. Moreover, these dangling chains which are imperfections in the final polymer network, do not support stress if the network is under load and act as plasticizers which reduce the polymer rigidity and increase its flexibility.

Ozonolysis was used to obtain polyols with aerminal primary hydroxyl groups and different functionalities from trilinolein, low-saturation canola oil, and soybean oil (Petrovic, Z. S., W. Zhang, and I. Javni, Structure and properties of polyurethanes prepared from triacylglycerol polyols by ozonolysis, *Biomacromolecules*, 6: 713-719 (2005). In this study, ozonation of the oils was carried out in methylene chloride/methanol at −30 to −40° C., and sodium borohydride was used as the reducing agent.

It has been shown that polyurethanes produced using vegetable oils present some excellent properties such as enhanced hydrolytic and thermal stability, as shown with soybean oil based PUs (Zlatanic, A., A. S. Petrovic and K. Dusek, Structure and Properties of Triolein-Based Polyurethane Networks., *Biomacromolecules*, 3: 1048-1056 (2002)).

In terms of other useful materials derived from feedstocks, wax esters consist of a fatty acid esterified to a fatty alcohol. A number of waxes are produced commercially in large amounts for use in cosmetics, lubricants, polishes, surface coatings, inks and many other applications.

In view of the above, there remains a need for novel methods for the production of monomers and polymers having terminal hydroxyl functional groups from renewable resources, such as feedstocks. In particular, the use of renewable feedstocks, such as vegetable oils including canola and flax, to produce monomers capable of producing high-quality polymers, such as polyurethane foams and elastomers, utilizing reactions which are easily and inexpensively performed at an industrial scale would be highly desirable. The development of novel methods of producing wax esters is also highly desirable.

SUMMARY OF THE INVENTION

Included in the scope of the invention is a method of introducing terminal hydroxyl functionality by way of ozonolysis of double bonds found in renewable feedstocks, followed by reduction to afford hydroxyl containing monomers, useful in the production of polymers, in particular, polyurethanes, and the like.

In one aspect, the present invention provides a method for producing a polyol from a renewable feedstock comprising one or more unsaturated fatty acid triacylglycerols, wherein the method comprises the steps of:
 (a) ozonolysis of two or more double bonds in the unsaturated fatty acids of the one or more triacylglycerols of the feedstock under conditions effective to afford two or more corresponding ozonide functionalities;
 (b) subjecting the products of step (a) to reductive hydrogenation under conditions effective to produce one or more corresponding polyols,
 wherein the one or more polyols comprise at least one triacylglycerol containing at least two primary hydroxyl groups.

In another aspect of the invention, step (a) further comprises reducing the ozonolysis products to produce two or more corresponding aldehyde functionalities.

In yet another aspect of the present invention, the invention provides a method for producing a polyol from a renewable feedstock as noted above, wherein ozone used in the ozonolysis step (a) is substantially uniformly distributed throughout the reaction mixture.

In another aspect of the invention, the ozonolysis conditions of step (a) are selected to optimize the primary hydroxyl functionality of the one or more polyols. The ozonolysis conditions may include ozonolysis time, ozone flow rate, and concentration of the renewable feed stock.

In another aspect of the invention, the ozonolysis reaction is performed at or above 0° C. In another aspect, the ozonolysis reaction is performed at room temperature.

In yet another aspect of the present invention the method for the production of a polyol from a renewable feedstock further comprises the step of separating the one or more polyols from the reaction mixture of step (b) under conditions suitable to separate the polyols.

In yet another aspect of the present invention there is provided a method for producing a polyurethane polymer which comprises reacting a polyol prepared by the methods of the present invention with a suitable isocyanate to afford the polyurethane polymer.

In yet another aspect of the present invention is a polyurethane polymer prepared from a polyol prepared by the process of the present invention and an isocyanate.

In yet another aspect of the present invention is provided a method for the production of nonanol, hexanol, propanol, and/or 1,3-propanediol from a renewable feedstock comprising a fatty acid triacylglycerol having at least one unsaturated fatty acid chain, the method comprising the steps of:

(a) ozonolysis of the double bonds in the fatty acid chain of the triacylglycerol of the feedstock;

(b) subjecting the products of step (a) to reductive hydrogenation to produce nonanol, hexanol, propanol, and/or 1,3-propanediol.

In yet another aspect of the present invention is provided a method for the production of hydroxyl wax ester from a renewable feedstock comprising one or more unsaturated fatty acid triacylglycerols, wherein the method comprises the steps of:

(a) ozonolysis of the double bonds in the unsaturated fatty acids of the one or more triacylglycerols of the feedstock;

(b) subjecting the products of step (a) to reductive hydrogenation to produce at least one of a corresponding mono-ol, at least one of a corresponding polyol, or a mixture thereof, in the presence of a short chain alcohol;

wherein the at least one mono-ol, the at least one polyol, or the mixture thereof, comprises a triacylglycerol containing at least one terminal hydroxyl group, and wherein the reaction conditions are sufficient to afford transesterification between the triacylglycerol containing at least one terminal hydroxyl group and the short chain alcohol, thereby affording said hydroxyl wax ester.

In yet another aspect of the present invention there is provided an improved apparatus for carrying out ozonolysis reactions, the improvement comprising:

a longitudinally disposed agitator operatively connected to a motor, the longitudinally disposed agitator comprising a plurality of pitched blades, wherein the longitudinally disposed agitator extends downwardly into a reaction vessel having an upper and a lower end, the reaction vessel comprising an ozone inlet channel disposed at the lower end and extending across the diameter of the reaction vessel, the ozone inlet channel having two apertures for ozone input at opposing ends thereof and a plurality of pores for release of ozone into the reaction vessel.

In another aspect, the present invention provides a method for the production of a hydroxyl wax ester from a renewable feedstock comprising one or more unsaturated fatty acid triacylglycerols, wherein the method comprises the steps of:

a. ozonolysis of the double bonds in the unsaturated fatty acids of the one or more triacylglycerols of the feedstock;

b. subjecting the products of step (a) to reductive hydrogenation to produce at least one corresponding mono-ol, at least one corresponding polyol, or a mixture thereof, wherein the at least one mono-ol, the at least one polyol, or the mixture thereof comprises a triacylglycerol containing at least one terminal hydroxyl group; and c. subjecting the products of step (b) to transesterification with a short chain alcohol to produce said hydroxyl wax ester.

In one aspect, the renewable feedstock is canola oil. In another aspect, the short chain alcohol is nonanol and the hydroxyl wax ester is nonyl-9-hydroxynonanoate.

In yet another aspect, the invention provides a compound having the formula:

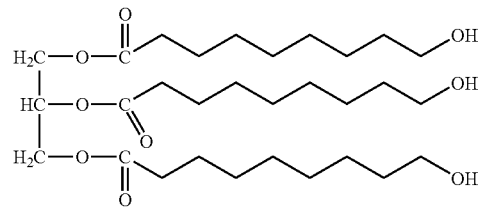

wherein said compound is isolated in substantially pure form.

In still another aspect of the present invention, the method for the production of a polyol from a renewable feedstock further comprises the selection of ozonolysis conditions in order to produce polyols for forming polyurethane products having harder or softer properties. In another aspect of the present invention, the ozonolysis conditions comprise at least one of ozonolysis time, ozone flow rate, and concentration of the renewable feedstock.

Numerous advantages are afforded by this route of modifying renewable feedstocks such as vegetable oils via ozonolysis of double bonds found in renewable feedstocks, followed by reduction to produce polyols. Methods of the present invention based on ozonolysis and hydrogenation for the production of polyols from unsaturated triacylglycerols afford polyol products and can introduce terminal multiple alcohol functional groups into the triacylglycerol that can then be used as a starting material for the production of polyurethane products. The polyols so produced locates the hydroxyl functionality at the terminal end of the fatty acid chain, greatly enhancing reactivity and reducing steric hindrances to crosslinking molecules.

These and other aspects will become apparent upon reading the following detailed description of the invention and by reference to the following figures.

BRIEF DESCRIPTION OF THE DRAWINGS

FIG. 5 shows the electrospray Ionization Mass Spectrometry of Fraction 76;

FIG. 6 shows a Thin Layer Chromatography plate of products after ozonolysis as described in Example 2;

FIG. 7 is a gas chromatogram of first and second hydrogenation products of Example 2; (A) is a chromatogram of the product after the first hydrogenation step; (B) is a chromatogram of the product after the second hydrogenation step;

FIG. 8 illustrates various side products obtained in the reaction described in Example 2;

FIG. 9 shows GC chromatographs recorded before and after distillation step of Example 2;

FIG. 10 shows an HPLC chromatogram of the polyol product of Example 2;

FIG. 12 shows FTIR spectra of samples of product of Example 2;

FIG. 13 shows the NMR spectra of samples of product of Example 2;

FIG. 14 shows mass spectra of samples of product of Example 2;

FIG. 15 shows possible products of transesterification reactions including the production of hydroxyl wax ester of Example 6;

FIG. 16 shows the mass spectra of products of the transesterification reactions of FIG. 15;

FIG. 18 is an FTIR spectra of: (a) Canola oil (b) Flax oil (c) Canola-air polyol (d) Flax-air polyol (e) Canola-oxygen polyol;

FIG. 18a is an FTIR spectra in the range 400-4000 cm$^{-1}$;

FIG. 18b is an enlargement of the FTIR band at 1650 cm$^{-1}$ characteristic of C=C double bond;

FIG. 18c is an enlargement of the FTIR band at 3006 cm$^{-1}$ characteristic of unsaturated C—H stretches;

FIG. 19 is an HPLC chromatography of Canola-air polyol, ozonized for 8h at 0° C.;

FIG. 20 represents DSC curves of: (a) Canola oil (b) Flax oil (c) Canola-air polyol (d) Flax-air polyol (e) Canola-oxygen polyol and (f) Hydrogenated Canola oil;

FIG. 20a shows crystallization curves;

FIG. 20b shows melting curves;

FIG. 21 illustrates the viscosity of: (a) Flax oil (b) Canola oil, (c) Canola-air polyol, (d) Flax-air polyol, (e) Canola-oxygen polyol;

FIG. 21a) illustrates viscosity as a function of time;

FIG. 21b) illustrates viscosity as a function of temperature;

FIG. 22 is an FTIR spectra of an elastomer with OH/NCO molar ratio 1.0 (a) canola oil based polyurethane (COBPU) (b) flax oil based polyurethane (FOBPU) and (c) soybean oil based polyurethane (SOBPU);

FIG. 23 shows reversing heat flow vs. temperature of elastomers with OH/NCO molar ratio 1.0(a) canola oil based polyurethane (COBPU) (b) flax oil based polyurethane (FOBPU);

FIG. 24 illustrates thermomechanical analysis curves of an elastomer with OH/NCO molar ratio 1.0 (a) canola oil based polyurethane (COBPU) (b) flax oil based polyurethane (FOBPU);

FIG. 25 illustrates the Storage moduli of elastomers with OH/NCO molar ratio 1.0 (a) canola oil based polyurethane (COBPU) (b) flax oil based polyurethane (FOBPU) and (c) soybean oil based polyurethane (SOBPU);

FIG. 26a shows the TGA of an elastomer with OH/NCO molar ratio 1.0 (a) canola oil based polyurethane (COBPU) (b) flax oil based polyurethane (FOBPU) and (c) soybean oil based polyurethane (SOBPU);

FIG. 26b shows Derivative TGA curves of an elastomer with OH/NCO molar ratio 1.0 (a) canola oil based polyurethane (COBPU) (b) flax oil based polyurethane (FOBPU) and (c) soybean oil based polyurethane (SOBPU);

FIG. 27 graphically illustrates the nominal stress-strain of elastomers with OH/NCO molar ratio 1.0 (a) canola oil based polyurethane (COBPU), (b) flax oil based polyurethane (FOBPU) and (c) soybean oil based polyurethane (SOBPU)

FIG. 28 is an FTIR spectra of polyurethane foams (———) Canola oil based polyurethane (Canola-PU), (· · · ·) Soybean oil based polyurethane (Soybean-PU), and (– – –) Castor oil based polyurethane (Castor-PU);

FIG. 29a illustrates the Storage moduli of polyurethane foams. Insert: first derivatives relative to temperature of storage moduli;

FIG. 29b illustrates the Loss moduli;

FIG. 29c illustrates the Tan δ; of (———) Canola oil based polyurethane (Canola-PU), (· · · ·) Soybean oil based polyurethane (Soybean-PU), and (– – –) Castor oil based polyurethane (Castor-PU);

FIG. 30a is TGA curves of polyurethane foams in nitrogen;

FIG. 30b represents derivative TGA curves of canola and soybean oil based polyurethane foams; (———) Canola oil based polyurethane (Canola-PU), (· · · ·) Soybean oil based polyurethane (Soybean-PU), and (– – –) Castor oil based polyurethane (Castor-PU);

FIG. 31 shows the compressive strength vs. strain of polyurethane foams (———) Canola oil based polyurethane (Canola-PU), (· · · ·) Soybean oil based polyurethane (Soybean-PU), and (– – –) Castor oil based polyurethane (Castor-PU);

FIG. 32a is a scanning electron micrograph of the Canola oil based polyurethane (Canola-PU);

FIG. 32b is a scanning electron micrograph of the Soybean oil based polyurethane (Soybean-PU);

FIG. 32c is a scanning electron micrograph of the Castor oil based polyurethane (Castor-PU);

FIG. 33 is a HPLC of polyols produced with Pd-C, Raney Ni System;

FIG. 34 is a HPLC of polyols produced with Zinc, Raney Nickel System;

FIG. 35 is a HPLC of polyols produced with Recycled Ethyl Acetate

FIG. 36(a) represents the Viscosity as a function of time of: (a) Ethyl Acetate Canola Oil Based Polyols, (b) Recycled Ethyl Acetate Canola Oil Based Polyols.

FIG. 36(b) represent the Viscosity as a function of temperature of: (a) Ethyl Acetate Canola Oil Based Polyols, (b) Recycled Ethyl Acetate Canola Oil Based Polyols;

FIG. 37(a) represents the Storage moduli of polyurethane foams.

FIG. 37(b) represents the Loss moduli. FIG.

37(c) represents the Tan δ of polyurethane foams. (a) Ethyl Acetate Canola Oil Based PU (EACOBPU) and (b) Recycled Ethyl Acetate Canola Oil Based PU (REACOBPU);

FIG. 38 represent the Compressive strength vs. strain of polyurethane foams. (a) Ethyl Acetate Canola Oil Based PU (EACOBPU) and (b) Recycled Ethyl Acetate Canola Oil Based PU (REACOBPU)

Figure 39:
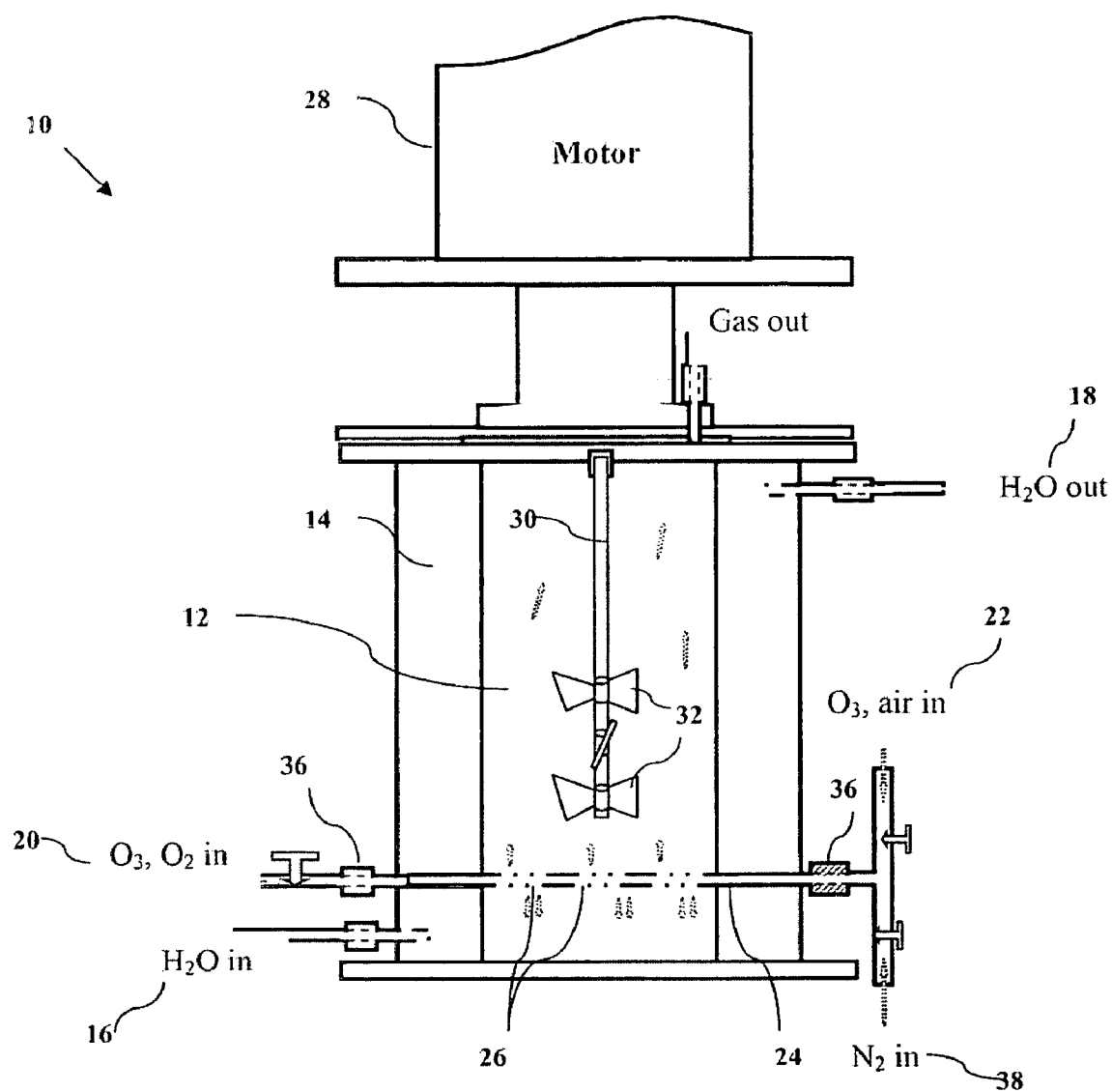

FIG. 39 shows a schematic of one embodiment of a reactor for use with the ozonolysis processes of the present invention.

Figure 40A:
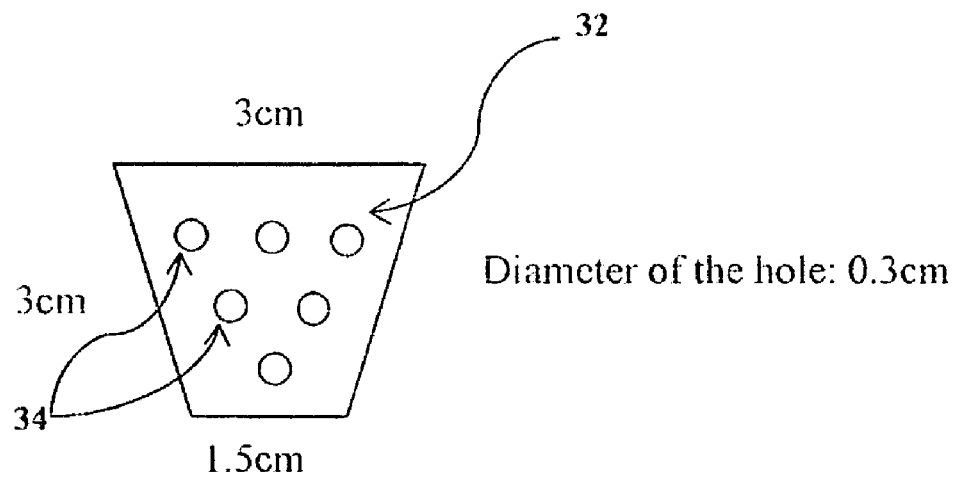
Figure 40B:
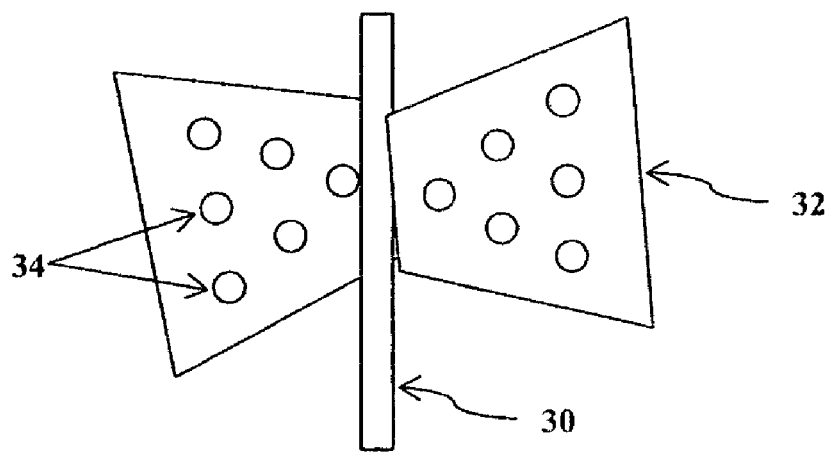

FIGS. 40(a) and 40(b) illustrate the agitator blades of the ozonolysis reactor and their angle of attachment to the agitator rod in accordance with one embodiment of the present invention.

Figure 41:
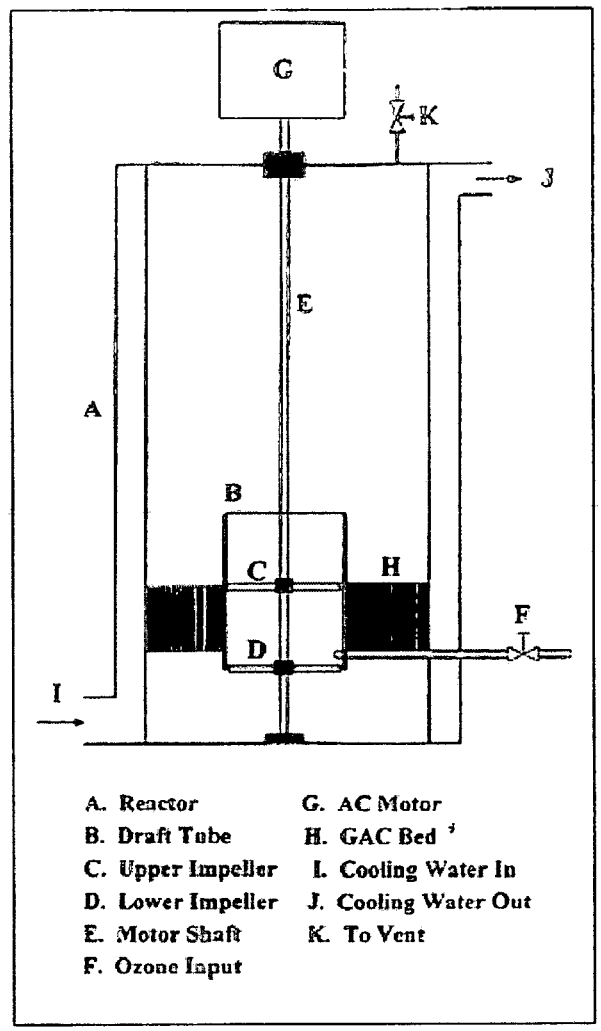

FIG. 41 illustrates a prior art ozonolysis reactor.

Figure 43A:
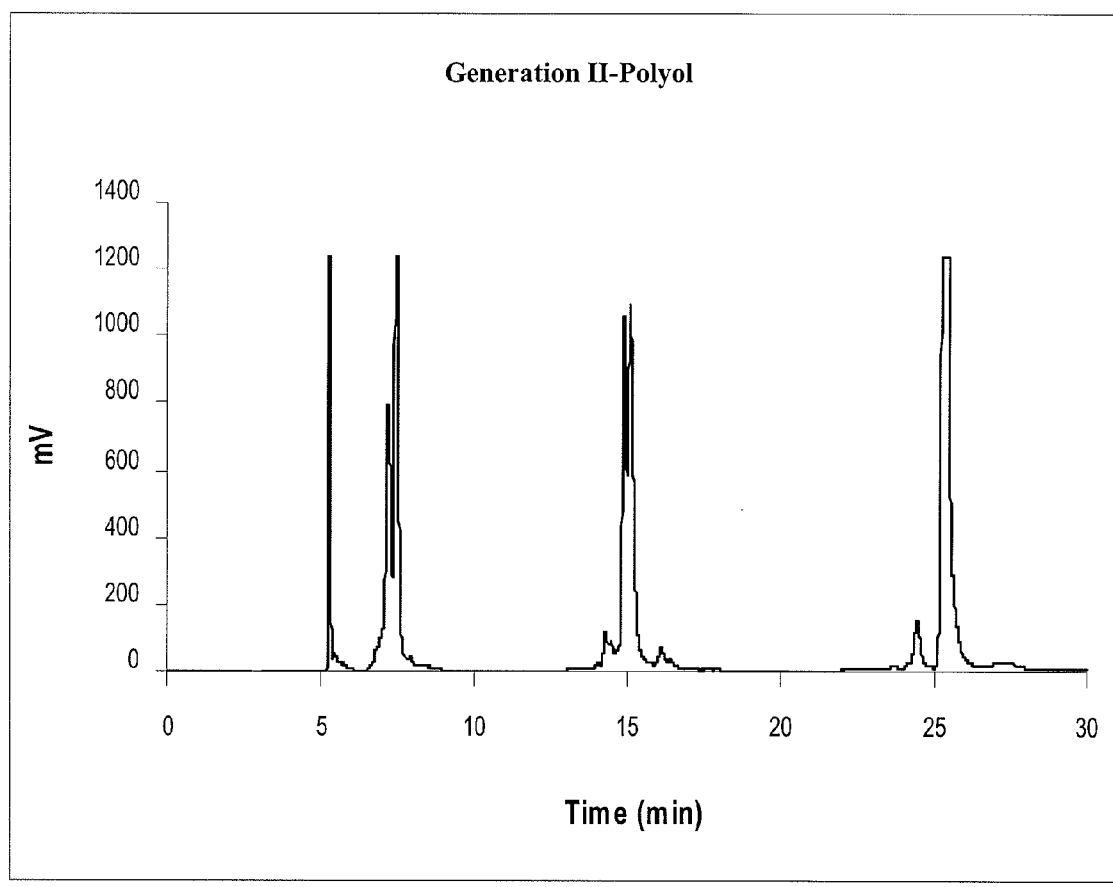
Figure 43B:
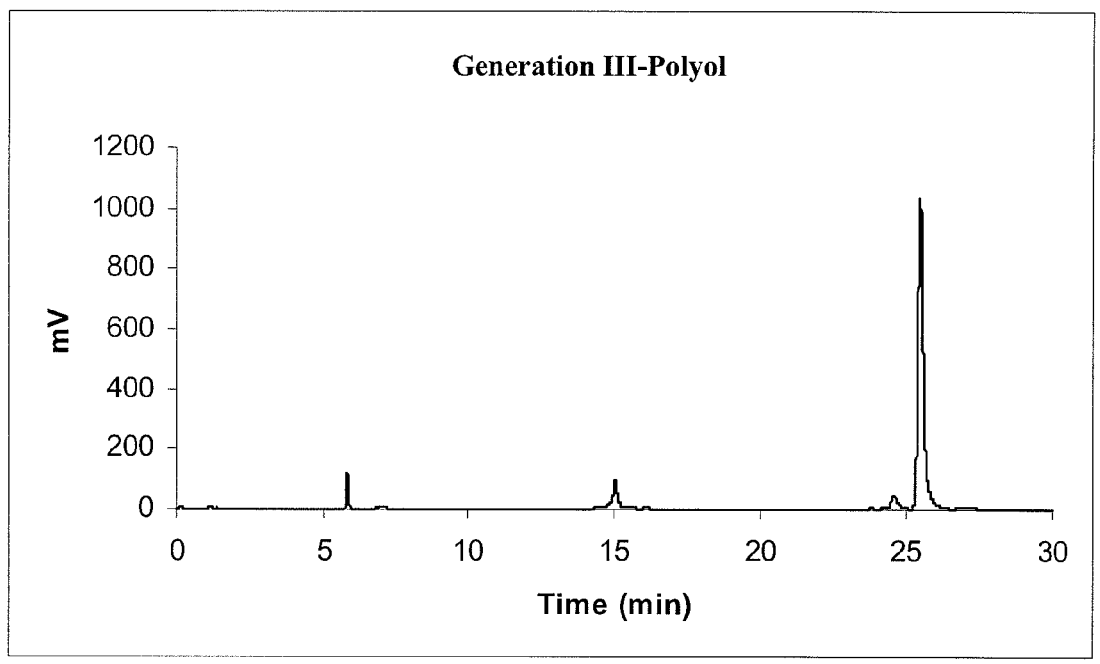
Figure 44A:
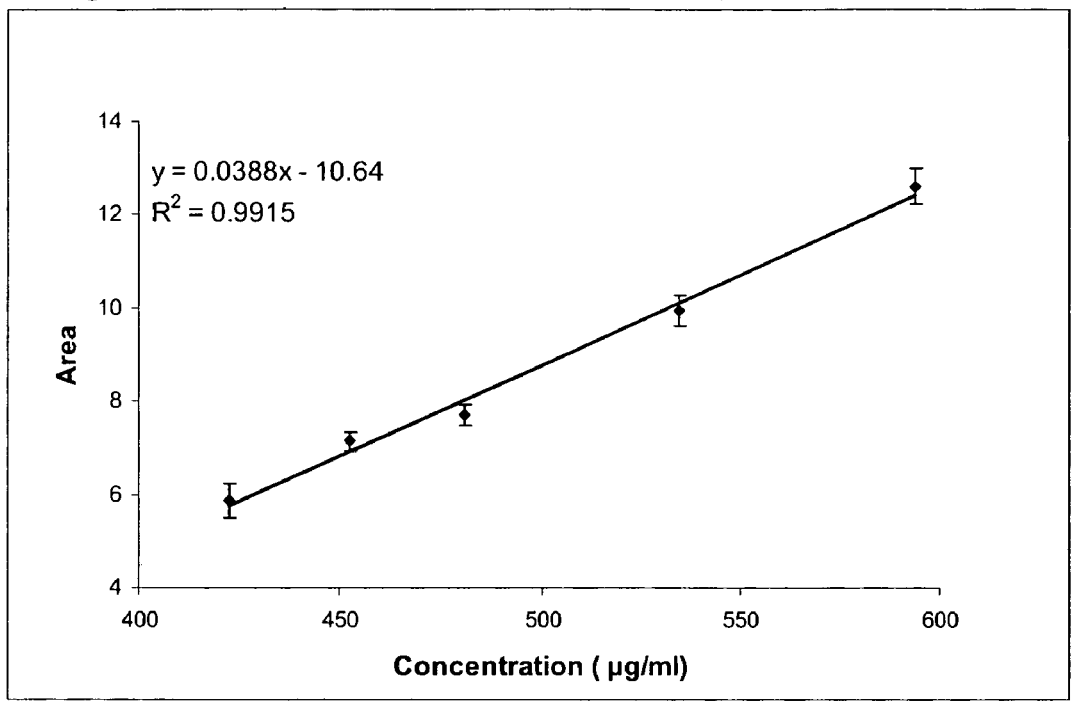
Figure 44B:
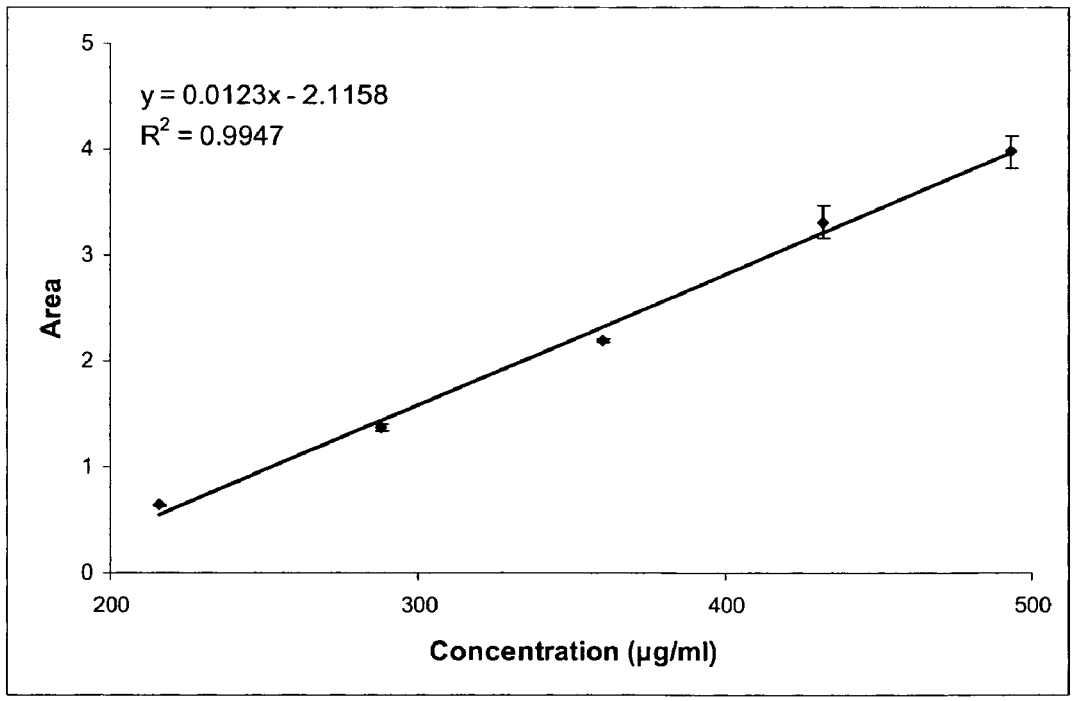
Figure 44C:
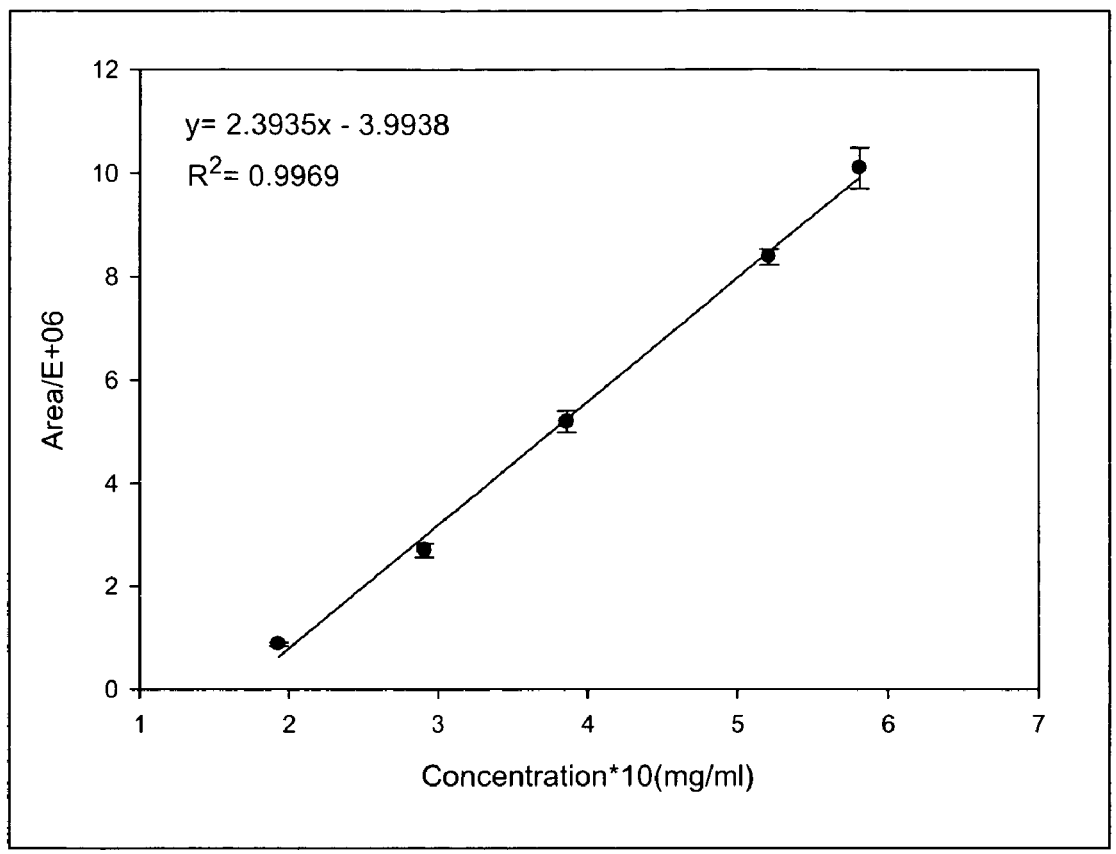

FIG. 42 is a schematic representation of the production of GIII-Polyol as described in Example 7;

FIG. 43 shows HPLC graphs of GII-Polyol and GIII-Polyol product synthesized from canola oil;

FIG. 44 shows HPLC standard curves of (a) triol, (b) diol and (c) mono-ol;

FIG. 45 represents FTIR spectra of GIII-PU plastic sheets with (a) OH/NCO molar ratio 1.0/1.0, (b) OH/NCO molar ratio 1.0/1.1 and (c) OH/NCO molar ratio 1.0/1.2;

FIG. 46 represents the Master curve of E' at a reference temperature of $T_g+5°$ C. for GIII-PU plastic sheet with OH/NCO molar ratio 1.0/1.2;

FIG. 47 represents DSC curves of the GIII-PU plastic sheets with (a) OH/NCO molar ratio 1.0/1.0, (b) OH/NCO molar ratio 1.0/1.1 and (c) OH/NCO molar ratio 1.0/1.2;

FIG. 48 represents storage moduli vs. temperature of the GIII-PU plastic sheets, obtained from DMA carried out at a frequency of 1 Hz with (a) OH/NCO molar ratio 1.0/1.0, (b) OH/NCO molar ratio 1.0/1.1 and (c) OH/NCO molar ratio 1.0/1.2;

FIG. 49 represents changes in the loss (E") moduli with temperature of the GIII-PU plastic sheets, obtained from DMA carried out at frequency of 1 Hz with (a) OH/NCO molar ratio 1.0/1.0, (b) OH/NCO molar ratio 1.0/1.1 and (c) OH/NCO molar ratio 1.0/1.2;

FIG. 50 represents the temperature dependence of tangent δ (tan δ) of the GIII-PU plastic sheets measured by DMA with (a) OH/NCO molar ratio 1.0/1.0, (b) OH/NCO molar ratio 1.0/1.1 and (c) OH/NCO molar ratio 1.0/1.2;

FIG. 51(*a*) represents TGA curves of the GIII-PU plastic sheets with (a) OH/NCO molar ratio 1.0/1.0, (b) OH/NCO molar ratio 1.0/1.1 and (c) OH/NCO molar ratio 1.0/1.2;

FIG. 51(*b*) represents the derivative of TGA (DTGA) curves of the GIII-PU plastic sheets with (a) OH/NCO molar ratio 1.0/1.0, (b) OH/NCO molar ratio 1.0/1.1 and (c) OH/NCO molar ratio 1.0/1.2;

FIG. 52 shows stress vs. strain curves for the GIII-PU plastic sheets with (a) OH/NCO molar ratio 1.0/1.0, (b) OH/NCO molar ratio 1.0/1.1 and (c) OH/NCO molar ratio 1.0/1.2;

FIG. 53 shows master curve of E' at a reference temperature of $T_g+5°$ C. for GIII-PU elastomers;

FIG. 54 represents storage moduli vs. temperature, obtained from DMA carried out at a frequency of 1 Hz for (a) PU elastomers (b) PU foams;

FIG. 55 represents DSC curves of the PU elastomers;

FIG. 56 represent changes in the loss (E") moduli with temperature, obtained from DMA carried out at frequency of 1 Hz for (a) PU elastomers (b) PU foams;

FIG. 57 represents temperature dependence of tangent δ (tan δ) of PU elastomers measured by DMA;

FIG. 58 represents stress vs. strain curves for the PU elastomers;

FIG. 59 represents compressive strength vs. strain PU foams;

FIG. 60 represents scanning electron micrograph of the PU. (a) GII-PU foams and (b) GIII-PU foams;

FIG. 61 is a transesterification reaction to make nonyl-9-hydroxynonanoate.

FIG. 62 is a FTIR spectrum of nonyl-9-hydroxynonanoate.

FIG. 63 is a $^1$H-NMR spectrum of nonyl-9-hydroxynonanoate.

FIG. 64 is a $^{13}$C-NMR spectrum of nonyl-9-hydroxynonanoate.

FIG. 65 shows the electron spray mass spectrometry of nonyl-9-hydroxynonanoate.

FIG. 66 represents the viscosity of designer polyols synthesized with different ozonolysis time as a function of temperature.

FIG. 67 represents DSC curves of the PU elastomers prepared from polyols with different ozonolysis time;

FIG. 68 represents storage moduli vs. temperature of the PU elastomers prepared from polyols with different ozonolysis time;

FIG. 69 represents changes in the loss (E") moduli with temperature of the PU elastomers prepared from polyols with different ozonolysis time;

FIG. 70 shows stress vs. strain curves for the PU elastomers prepared from polyols with different ozonolysis time;

FIG. 71 represents DSC curves of the PU prepared from polyols with different ozonolysis time;

FIG. 72 represents storage moduli vs. temperature of the PU prepared from polyols with different ozonolysis time; and FIG. 73 shows stress vs. strain curves for the PU prepared from polyols with different ozonolysis time.

DETAILED DESCRIPTION OF EMBODIMENTS

The present invention provides novel, versatile and efficient processes and conditions for the preparation of monomers and polymers useful in the preparation of plastics and the like.

The present invention also provides a method of introducing hydroxyl functionality by way of ozonolysis of double bonds found in renewable feedstocks, followed by reduction to afford hydroxyl containing monomers, useful in the production of polymers, in particular, polyurethanes.

In one embodiment, the present invention provides a method for producing a polyol from a renewable feedstock comprising one or more unsaturated fatty acid triacylglycerols, wherein the method comprises the steps of:
  (a) ozonolysis of two or more double bonds in the unsaturated fatty acids of the one or more triacylglycerols of the feedstock under conditions effective to afford two or more corresponding ozonide functionalities;
  (b) subjecting the products of step (a) to reductive hydrogenation under conditions effective to produce one or more corresponding polyols,
wherein the one or more polyols comprise at least one triacylglycerol containing at least two primary hydroxyl groups.

In another embodiment of the invention, step (a) further comprises subjecting the ozonolysis products to zinc reduction to produce two or more corresponding aldehyde functionalities.

In yet another embodiment, the invention provides a method for producing a polyol from a renewable feedstock as noted above, wherein ozone used in the ozonolysis step (a) is substantially uniformly distributed throughout the reaction mixture. One example of how this substantially uniform distribution of ozone may be accomplished is provided with reference to a novel ozonolysis vessel as described and claimed herein. The person skilled in the art would readily choose other forms of apparatus to achieve the ozone distribution desired based on the information provided herein.

In another embodiment of the invention, the ozonolysis conditions of step (a) are selected to optimize the primary hydroxyl functionality of the one or more polyols. The ozonolysis conditions may include ozonolysis time, ozone flow rate, and concentration of the renewable feed stock.

In another embodiment of the invention, the ozonolysis reaction is performed at or above 0° C. In another embodiment, the ozonolysis reaction is performed at room temperature.

In another embodiment, the invention provides a method for the production of a polyol from a renewable feedstock further comprising the step of separating the one or more polyols from the reaction mixture of step (b) under conditions suitable to separate the polyols.

In another embodiment, the one or more polyols produced are isolated in greater than 90% purity relative to non-polyol components contained in or produced during the production of the one or more polyols. In another embodiment, the one or more polyols produced are isolated in greater than 95% purity relative to non-polyol components contained in or produced during the production of the one or more polyols.

In yet another embodiment, the present invention also provides a method for producing a polyurethane polymer which comprises reacting a polyol prepared by the methods of the present invention with a suitable isocyanate to afford the polyurethane polymer.

In another embodiment, the present invention provides a method for the production of nonanol, hexanol, propanol, and/or 1,3-propanediol from a renewable feedstock comprising a fatty acid triacylglycerol having at least one unsaturated fatty acid chain, the method comprising the steps of:
  (a) ozonolysis of the double bonds in the fatty acid chain of the triacylglycerol of the feedstock;
  (b) subjecting the products of step (a) to reductive hydrogenation to produce nonanol, hexanol, propanol, and/or 1,3-propanediol; and
  (c) separating nonanol, hexanol, propanol, and/or 1,3-propanediol from the products of step (b) by wiped-blade molecular distillation.

In another embodiment, the present invention provides a method for the production of a hydroxyl wax ester from a renewable feedstock comprising one or more unsaturated fatty acid triacylglycerols, wherein the method comprises the steps of:
  (a) ozonolysis of the double bonds in the unsaturated fatty acids of the one or more triacylglycerols of the feedstock;
  (b) subjecting the products of step (a) to reductive hydrogenation to produce at least one of a corresponding mono-ol, at least one of a corresponding polyol, or a mixture thereof, in the presence of a short chain alcohol;
wherein the at least one mono-ol, the at least one polyol, or the mixture thereof, comprises a triacylglycerol containing at least one terminal hydroxyl group, and wherein the reaction conditions are sufficient to afford transesterification between the triacylglycerol containing at least one terminal hydroxyl group and the short chain alcohol, thereby affording said hydroxyl wax ester.

In yet another embodiment, the present invention also provides novel polyurethane polymers prepared from a polyol prepared by the process of the present invention and an isocyanate.

In another embodiment, the present invention provides an improved apparatus for carrying out ozonolysis reactions, the improvement comprising:
  a longitudinally disposed agitator operatively connected to a motor, the longitudinally disposed agitator comprising a plurality of pitched blades,
  wherein the longitudinally disposed agitator extends downwardly into a reaction vessel having an upper and a lower end,
  the reaction vessel comprising an ozone inlet channel disposed at the lower end and extending across the diameter of the reaction vessel,
  the ozone inlet channel having two apertures for ozone input at opposing ends thereof and a plurality of pores for release of ozone into the reaction vessel.

In another embodiment, the present invention provides a method for the production of a hydroxyl wax ester from a renewable feedstock comprising one or more unsaturated fatty acid triacylglycerols, wherein the method comprises the steps of:

a. ozonolysis of the double bonds in the unsaturated fatty acids of the one or more triacylglycerols of the feedstock;
  b. subjecting the products of step (a) to reductive hydrogenation to produce at least one corresponding mono-ol, at least one corresponding polyol, or a mixture thereof, wherein the at least one mono-ol, the at least one polyol, or the mixture thereof comprises a triacylglycerol containing at least one terminal hydroxyl group; and
  c. subjecting the products of step (b) to transesterification with a short chain alcohol to produce said hydroxyl wax ester.

In one embodiment, the renewable feedstock is canola oil. In another embodiment, the short chain alcohol is nonanol and the hydroxyl wax ester is nonyl-9-hydroxynonanoate.

In yet another embodiment, the invention provides a compound having the formula:

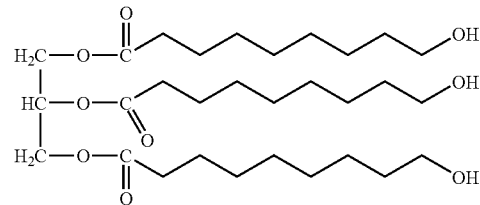

wherein said compound is isolated in substantially pure form.

In one embodiment, the method for the production of a polyol from a renewable feedstock further comprises the selection of ozonolysis conditions in order to produce polyols for forming polyurethane products having harder or softer properties. In another embodiment, the ozonolysis conditions comprise at least one of ozonolysis time, ozone flow rate, and concentration of the renewable feedstock.

Figure 1:
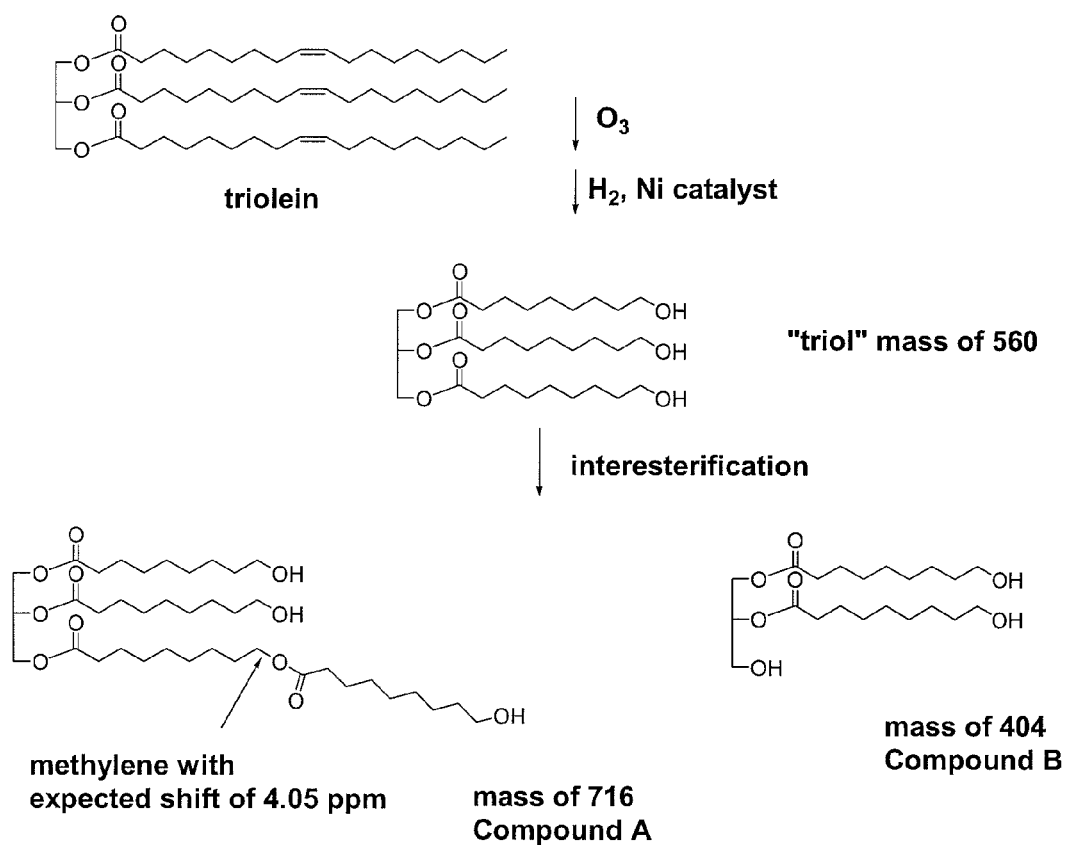
FIG. 1 is a schematic representation of the production of polyols and subsequent interesterification reactions as described in Example 1.

Therefore, in one embodiment of the present invention is provided a method for the production of polyols from unsaturated fatty acid triacylglycerols (TAGs) such as those depicted in FIG. 1. Such polyols can then be used as a starting material for the production of polyurethane products with appropriate isocyanate crosslinkers (M. Szycher, Isocyanate Chemistry, in *Sycher's Handbook of Polyurethanes*, CRC Press, New York, pp. 4-1 to 4-40, 1999).

In one embodiment, the method to produce the polyols includes ozonolysis of the double bonds in unsaturated fatty acids found in the triacylglycerols, followed by a reductive hydrogenation to produce the corresponding polyol. This sequence of reactions can afford several advantages over other approaches to produce alcohol functional groups in triacylglycerols. While highly unsaturated vegetable oils such as canola or flaxseed contains many different unsaturated fatty acids, the first double bond for all of these fatty acids is always found at carbon nine. In addition these vegetable oils contain a very small percentage of saturated fatty acids (D. Firestone, Physical and Chemical Characteristics of Oils, Fats, and Waxes. AOCS Press, 1999). Thus, the alcohol formed, be it a monohydroxyl functionalized triacylglycerol (also referred to as a mono-ol), dihydroxyl functionalized triacylglycerol (also referred to as a diol), or trihydroxyl functionalised triacylglycerol (also referred to as a triol), from such highly unsaturated vegetable oils is more homogeneous than the starting triacylglycerols in the case where the triacylglycerol comprises different unsaturated fatty acids all resulting in the same primary alcohol upon ozonolysis and subsequent reductive hydrogenation. In addition the primary alcohols formed at the C9 group of the fatty acid triacylglycerol chains are reactive primary alcohols, with the chance of forming a single alcohol group on a triacylglycerol (chain terminators) very low.

As used in the context of the present invention, the various chemical terms are to be given their ordinary meaning as would be understood by persons skilled in the art, unless provided otherwise.

The term "polyol" as used in the context of the present invention is meant to include triglycerides having a hydroxyl functionality in at least two of the three chains within the triacylglycerol. Accordingly, "diol", and "triol" as used herein are meant to refer to those triacylglycerols having two and three hydroxyl functionalities present in the triacylglycerol, respectively, and are meant to be included in the term "polyol".

To demonstrate this method, ozonolysis and hydrogenation of triolein was undertaken to produce a triol product with primary alcohol functional groups at position nine of each fatty acid ester in the original triacylglycerol. Further details regarding methods for carrying out the procedure are set out in Example 1 below and as described below. The polyols produced by the procedure of Example 1 are also referred to herein as "Generation I-Polyol" or "GI-Polyol".

To prevent any potential complications, reaction conditions are chosen to avoid increasing the molecular complexity of the products formed. For example, in one embodiment the ozonolysis is alternated with nitrogen flushing so that the production of acid groups is minimized. Acid groups are detrimental to the polyurethane forming process (M. Szycher, Isocyanate Chemistry, in *Sycher's Handbook of Polyurethanes*, CRC Press, New York, pp. 4-1 to 4-40, 1999). Also as described in Example 1 below, in one embodiment the hydrogenation step is carried out twice to insure that no unreacted double bonds would remain in the final product.

Figure 2:
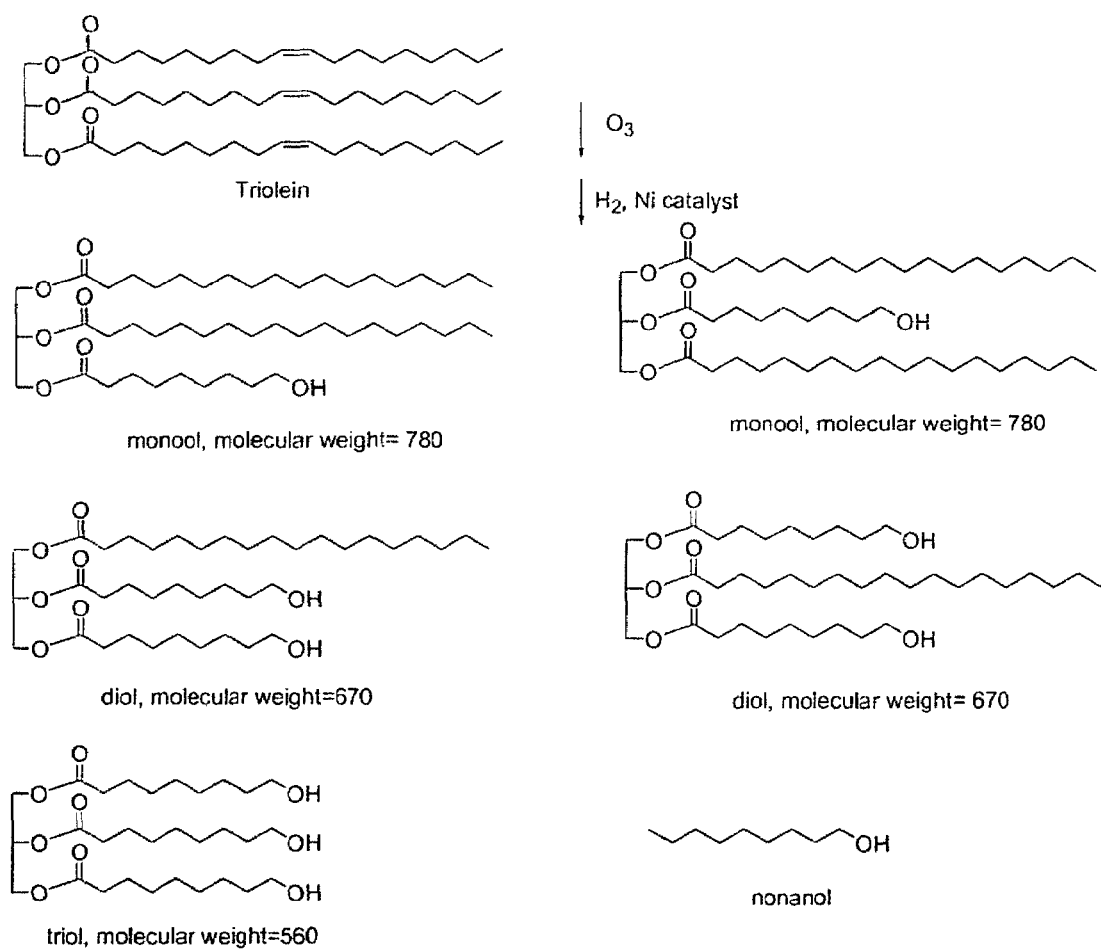
FIG. 2 depicts the processes of the present invention with triolein found in Canola oil as a starting material to illustrate the production of polyols.

Additional products are afforded by the present methods for the preparation of polyols. For example, FIG. 2 further illustrates various potential products that may be formed when triolein is used as a starting material for methods of the present invention.

Thus, the present invention further includes methods for the preparation of polyols that include the separation of the polyol products formed after these reactions. The methods for separation which can be used can be any method which allows for the separation of the polyol products. In one embodiment, methods to separate the polyol products on the basis of the number of alcohol functional groups may be used such as with the use of diol derivatized silica gel. Other separation methods known to those skilled in the art, such as flash chromatography or gel permeation chromatography, for example, may also be used.

Figure 3:
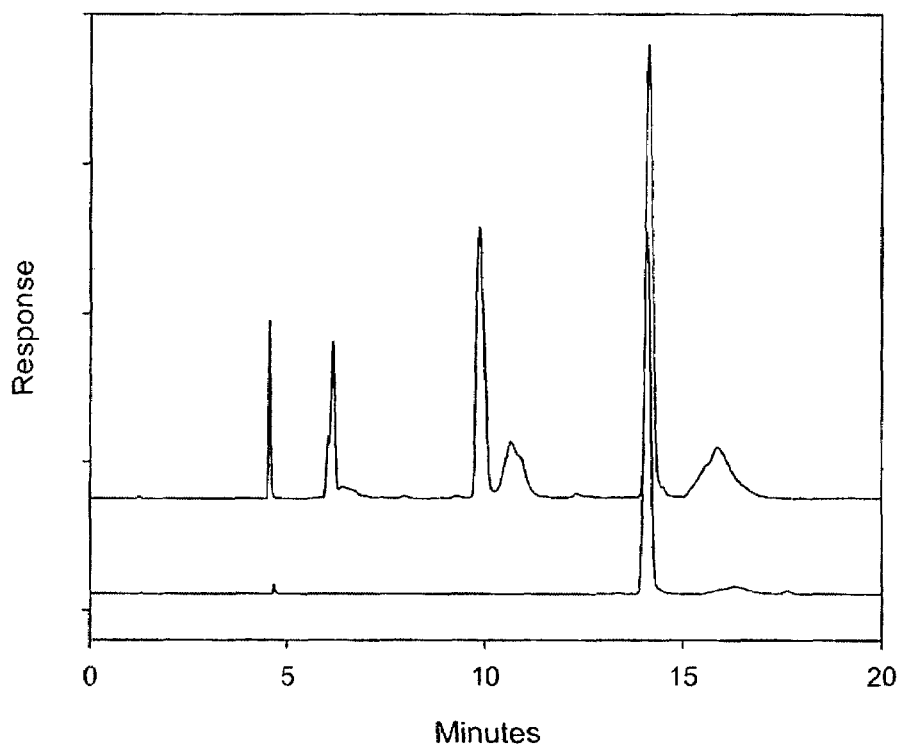
FIG. 3 is an HPLC of Reaction Mixture (upper trace) and Fraction 76 (lower trace) after Hydrogenation.

In one embodiment, the method of Elfman-Borjesson and Harrod (Elfman-Borjesson, I. and M. Harrod, Analysis of Non-Polar Lipids by HPLC on a Diol Column. *J. High Resol. Chromatogr.* 20: 516-518 (1997)) is modified to give the required chromatography. The use of the diol column [Betasil Diol-100 (5 μm particle size) 250×4 mm] provides that lipid materials are separated on the basis of the number of alcohol functional groups present in the triacylglycerol. Using the diol column, unreacted triacylglycerol was observed to have the shortest retention time; followed by triacylglycerols with a single alcohol group; then two alcohol groups and finally the longest retained material on the column was that that contained three alcohol groups. As can be seen in FIG. 3, the major product of the reactions (peak at 14.2 minute retention time) appeared in the region (longest retention time) where a triacylglycerol containing three alcohol groups would appear. When the peaks were integrated, the peak at 14.2 retention time made up about one third (33.9%) of the total material.

Figure 4:
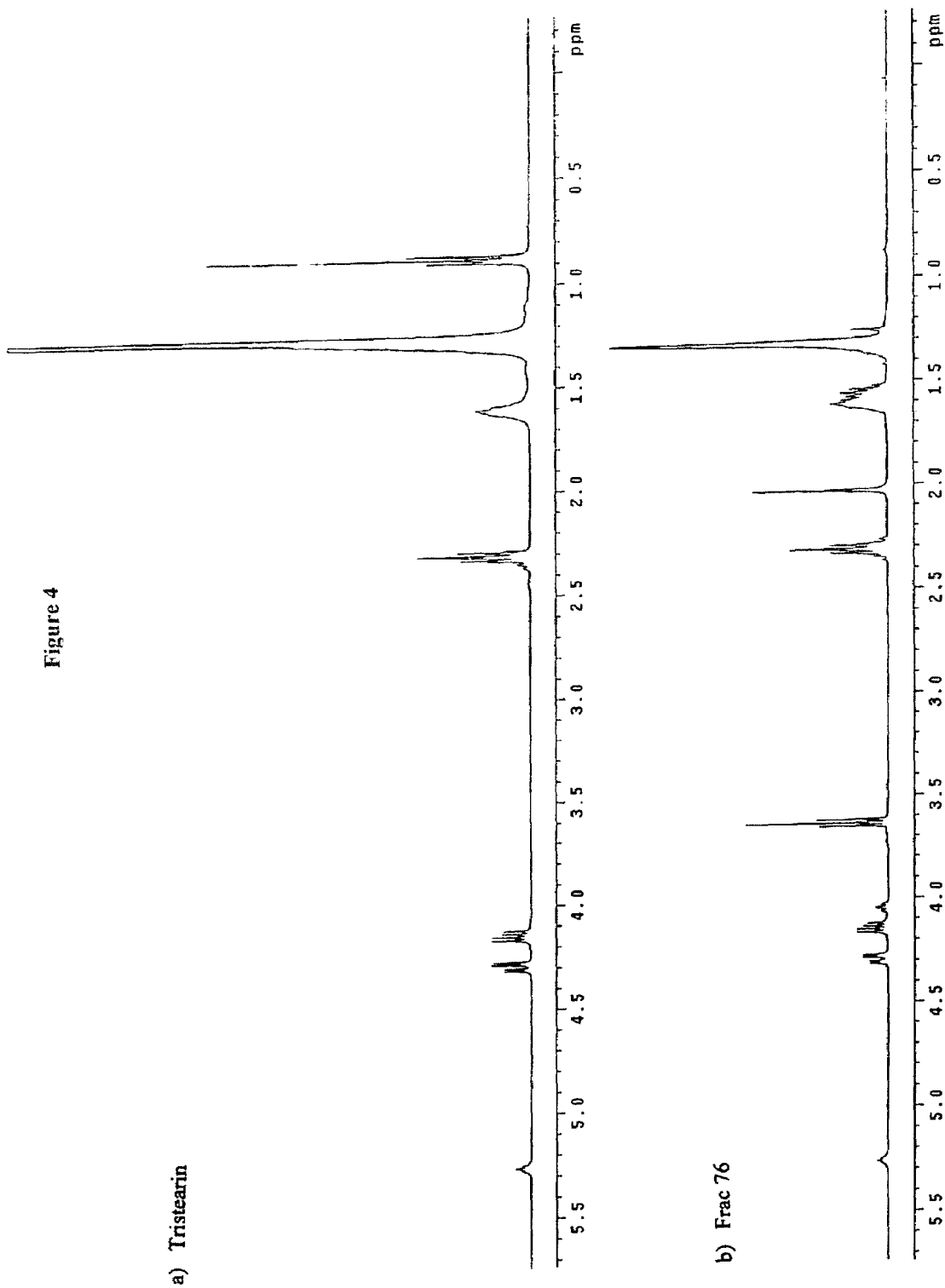
FIG. 4 is an NMR Comparison of Fraction 76 and Tristearin.

To further confirm the reaction products, a larger amount of product material for spectral analysis was isolated using silica gel derivatized with diol groups. Column chromatography using a larger mesh material was carried out. The fractions isolated were analyzed using thin layer chromatography and those containing larger amounts of material were subjected to our HPLC analysis. One of the purer fractions (fraction 76, see FIG. 3) was evaporated and analyzed extensively using NMR (FIG. 4) and mass spectrometry (FIG. 5). This purified material corresponded to the major product that was noted in the final reaction mixture.

The proton NMR of this purified fraction (FIG. 4) was observed to be very close to the anticipated "triol" compound of FIG. 1. but there seemed to be an excess of protons for the fatty alcohol ester groups and there was an NMR unexplained triplet at 4.05 ppm. However on the positive side a comparison with the proton NMR of tristearin indicated many of the expected proton shifts. The methyl protons of tristearin (0.95 ppm) were not present in the fraction 76 NMR. Moreover there was a new triplet at 3.65 ppm that was in the region expected for protons on methylene alcohol groups. Also the pattern of the glycerol proton peaks at 5.27, 4.30 and 4.16 ppm were virtually identical to the coupling pattern seen in tristearin. The presence of the triol in the purified fraction 76 was confirmed by accurate mass spectroscopy.

While not wishing to be bound by any particular theory, experimenting with structural variations using estimates found in ChemDraw (ChemDraw Ultra, Version 8, CambridgeSoft Corporation, MA., USA) gave a likely explanation for the impurity observed in both the NMR and seen in the HPLC. The unexplained triplet at 4.05 ppm could be explained by compound A (FIG. 1) produced as a result of interestification. This would also explain the excess fatty alcohol ester protons. The conditions for interesterification in the reaction conditions of Example 1 were ideal with some acid formed as a result of the ozonolysis and the final reaction products containing numerous reactive primary alcohols. Moreover, it is preferable that alcohols such as methanol and ethanol are to be avoided as solvents of the reactions of the present invention as significant transesterification to the methyl and ethyl esters could be effected. To further confirm the interesterification reaction, electrospray mass spectroscopy (FIG. 5) indicated the expected mass peaks for the triol (protonated form at 561.4, sodium form at 583.4), but also higher mass peaks at 717.6 and 739.6 which corresponded to the protonated and sodium form of compound A of FIG. 1. In addition there was also a small peak at 427.3 that was likely indicative of the sodium form of compound B (FIG. 1). It could also not be ruled out that the interesterification reaction occurred to some extent during sample preparation for spectral analysis.

As such, another important aspect of the present invention is that even when interesterification is observed under certain reaction conditions, one of the products of interesterification also contains hydroxyl terminal functionalities that are available for crosslinking with isocyanate groups. The introduction of multiple alcohol functional groups into the triacylglycerol is important so that chain-terminating triacylglycerols with only a single alcohol are not present to a significant extent.

In the present invention, the renewable feedstock that may be used for the production of polyols is any which contains unsaturated fatty acid triacylglycerols which allow for the formation of the polyol products using the methods of the present invention. In one embodiment, polyols may be prepared from feedstocks such as unsaturated seed oils, for example canola, which in turn may be used, inter alia, in the production of polyurethane products. Canola vegetable oil contains more than 90% of unsaturated fatty acids, including oleic acid, linoleic acid and linolenic acid (D. Firestone, Physical and Chemical Characteristics of Oils, Fats, and Waxes. AOCS Press, 1999), which all have a double bond at carbon nine. Other feedstocks which contain some degree of unsaturated fatty acids and therefore may be used for the production of polyols include linseed, sunflower, tung, lesqueralla, flaxseed, Jatupha, camelina sativa, hump, peanut, palm, soy, cottonseed, corn, cashew nuts, calendula, mustard, sesame, safflower, sunflower, rapeseed, olive, castor, jojoba, brazil nuts, avocado, and kenaf oils.

Methods of the present invention also afford a variety of products besides the polyols of the present invention. Such additional products depend in part upon the starting renewable feedstock. In particular, depending on the feedstock, a number of short straight chain alcohols may also be produced by the methods of the present invention. Short chain alcohols are potential chain-terminators in reactions using isocyanates to crosslink the polyol compounds, and may serve to promote interesterification of the polyols, which can result in increasing heterogeneity of the polyol feedstock, or in the formation of chain-terminating compounds.

Accordingly, in one embodiment, such short chain alcohols are removed from the polyols. In one embodiment, the short chain alcohols are removed using wiped-blade molecular distillation.

GC may be used to identify and quantify the short-chain alcohols. Column chromatography may be used to separate pure mono-ol, diol and triol, and then $^1$H and $^{13}$C NMR as well as mass spectrometry may be used to uniquely identify these products once the short chain alcohols are removed from the reaction mixtures. Such an identification procedure facilitates the use of a simple HPLC method to determine the composition of mixtures of polyol product, for use as a quality-control mechanism in designing novel polyol feedstock.

Solvents for use in the present ozonolysis and hydrogenation reactions are those that afford production of the polyol products. In one embodiment, the solvents for hydrogenation comprise ethyl acetate. Ethyl acetate is a comparatively benign solvent for use in an industrial setting.

To further illustrate the flexibility of the present methods with different renewable feedstocks as starting materials, details surrounding a preferred embodiment for this process using canola oil as a starting material follow, additional details of which are set out in Example 2 below. Polyols produced by the process described in Example 2 are also referred to herein as "Generation II-Polyol" or "GII-Polyol".

Different analysis methods may be used to determine the products formed after each step of the reactions. In one embodiment, after ozonolysis was complete, TLC plates were run on the organic layer, the aqueous layer, as well as the starting material, with the developing solvent being 10% of ethyl acetate in hexane (FIG. 6). As can be seen from FIG. 6, for the same retention factor ($R_f$) value of 0.6, the spot for the organic fraction became much smaller than that of the glycerides in the canola oil and another spot showed up on the base line. It demonstrated that most of the triacylglycerols in the canola oil reacted with ozone to produce ozonide, which was much more polar than the TAGs.

In the present embodiment using canola oil as the starting material, nonanol was produced as a side product only when the double bonds between carbon 9 and carbon 10 were broken and the ozonide of the short nine carbon chain cleaved from the TAG was completely reduced by hydrogen. Otherwise, some nonanal would still remain in the hydrogenation product.

Based on this, the presence of nonanal, easily tested by GC, may be used as an indicator of the completion of hydrogenation. The second hydrogenation step was performed because a significant amount of nonanal was detected after the first hydrogenation (FIG. 7, curve A). This ensured that the ozonide and the double bonds were almost completely reduced as evidenced by the nonanal peak which almost disappeared after the second hydrogenation as shown in FIG. 7, curve B. Therefore, the reaction conditions for the hydrogenation reaction of the present invention can be any operable conditions which yield the desired polyol product and, if desired, the maximum quantity of nonanol bi-product. A preferred temperature range for the hydrogenation processes is from about 120° C. to about 140° C., although this temperature can be higher or lower depending upon the reagents, reaction conditions and the solvent used. Typical reaction times for the ozonolysis and hydrogenation reactions are between 2 and 3 hours, although longer or shorter times may be used if necessary.

In addition to nonanol, other short chain side products were produced and purified by the methods of the present invention, such as the small chain mono alcohols, propanol and hexanol, as illustrated in FIG. 8. Such separation procedure is desired because, on one hand, all these small side products are potential chain terminators to the cross-linking reactions in the production of polyurethanes and on the other hand, they are very valuable materials in the chemical industry. As such, another aspect of the present invention is a method for the production and purification of by-products from the present processes. In one embodiment, wiped blade molecular distillation may be utilized to separate the short chain molecules from the triacylglycerol polyols as described herein. Further separation of the short chain by-products by conventional techniques such as distillation and crystallization may be carried out. GC chromatographs recorded before and after distillation demonstrated that the end-product polyols were substantially free of short-chain by products except of a small amount of nonanol, i.e. <1% as shown in FIG. 9.

After the short chain by-products were removed from the polyols by wiped blade molecular distillation, in one embodiment, an HPLC analysis method modified from Elfman-Borjesson and Harrod (Elfman-Borjesson, I. and M. Harrod, Analysis of Non-Polar Lipids by HPLC on a Diol Column. *J. High Resol. Chromatogr.* 20: 516-518 (1997)) was developed to separately identify the different polyols. A special diol column [Betasil Diol-100 (5 μm particle size) 250×4 mm] was used to separate the polyols on the basis of the number of hydroxide groups present on the end of triacylglycerol chains, FIG. 10. As four main peaks were separated, it was logical to assign them according to their position. Starting from the first with the shortest retention time, the peaks were assigned to the unreacted TAGs, followed by TAGs with a single alcohol group (mono-ol); then TAGs with two alcohol groups (diol) and finally TAGs with three alcohol groups (triol) the most retained material, respectively. To further confirm the expected reaction products, flash chromatography was performed to separate the different polyols and TLC run on each fraction. Finally, fractions 28-50, 131-143, 264-289, 366-378 were respectively combined and named as samples A, B, C and D, and analyzed by HPLC, NMR, IR and Mass spectrometry.

Figure 11:
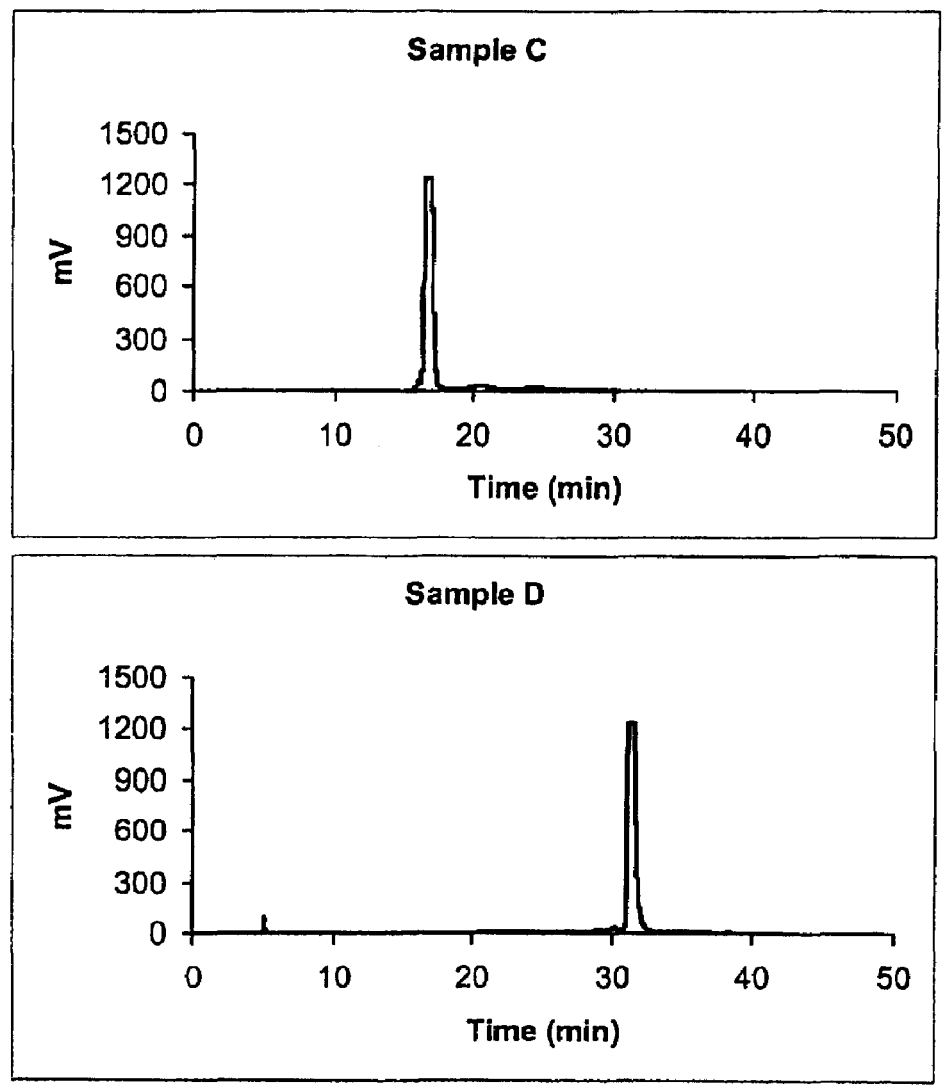
FIG. 11 shows HPLC chromatograms of samples of product of Example 2.

As can be seen in FIG. 11, each sample HPLC demonstrated a single peak with a retention time matching that of one of the four peaks shown in FIG. 10., i.e. 4.04, 5.86, 15.94, and 30.92 min for samples A, B, C and D respectively.

The FTIR spectra of the four samples are shown in FIG. 12. The 1650 cm$^{-1}$ characteristic C=C double bond stretch was reduced to very small bumps in all the spectra, confirming that almost all the double bonds in the canola oil have been reduced. The absorption band centered at 3300 cm$^{-1}$ characteristic of hydroxyl group, was missing in the sample A, but appears in the samples B, C and D with a tendency to grow bigger and broader from B to D. This pattern qualitatively corroborate the peak assignments of FIG. 10 to the four main fractions i.e. TAG, mono-ol diol, and triol.

The FTIR indications were quantitatively verified by $^1$H-NMR. Two peaks in the $^1$H-NMR of the samples (FIG. 13), the triplet at 0.88 ppm representing the terminal methyl groups of the fatty acids, and the triplet at 3.60 ppm representing the methylene protons adjacent to hydroxyl group are very important and warrant careful attention. From sample A to D, there was a tendency for the methyl peaks to decrease and the methylene peaks to increase. For sample D, the peak representing the methyl protons had completely disappeared, and in Sample A, no peaks representing the methylene protons were present. This proves that sample A was the unreacted TAG with terminal methyl groups on the end of all three fatty acid chains. Similarly, D was proven to be the triol product with three hydroxyl groups present on the end of the chains (instead of the methyl groups) and according to the integrations of the methyl and methylene groups, sample B and C were mono-ol and diol products. The purity of the triol product obtained is estimated at 95% from the $^1$H-NMR. It is expected that the flash chromatography technique described in Example 2 may be used to purify triol obtained from other feedstocks using the methods of the invention.

Mass spectroscopy provided additional strong evidence to further confirm the identity of the products. FIG. 14 shows that samples B, C and D had mass peaks at 803.7, 693.6, 583.4 respectively, which corresponded to the protonated and sodium adducts of saturated mono-ol, diol and triol.

The short chain alcohols which were produced and separated in one embodiment as side products may be used as a solvent for hydrogenation, as set out in Example 6 below. The resulting products were separated by wiped blade molecular distillation and flash chromatography then identified by MS and NMR. It was found that the polyol products were transesterified in the presence of nonanol and other short chain alcohols. The transesterification reaction involved here is shown in FIG. 15. FIG. 16(a) shows a mass peak at 427.3 corresponding to the protonated and sodium adduct of transesterified product I. FIG. 16(b) shows a mass peak at 323.3 corresponding to the protonated and sodium adducts of the transesterified product II.

Importantly, the formed transesterification product II of FIG. 15 was a wax ester, a member of a very important class of compounds used in cosmetics, lubricants, polishes, surface coatings, inks and many other applications. In its own right, the production of wax ester such as those produced here, are of notable commercial importance, and it is of great significance to realize the potential of this reaction process to be tailored for the production of wax ester. A generalized procedure for preparing the hydroxyl wax ester is set out in Example 6 below.

For the purpose of polyurethane formation, however, it is of paramount importance to remove the short chain alcohol products, because not only they act as chain terminators, but also cause deterioration of the polyol product by transesterification. Clearly, the use of the recycled short chain alcohols as solvents is to be avoided in the production of polyols, as the transesterification degrades and makes more complex the glyceride polyol fraction after distillation As such, an important aspect of the present invention is a method for the production of hydroxyl wax esters. In another aspect of the present invention, the process may be tailored to produce an excess of hydroxyl wax esters.

Another aspect of the present invention is the ability to readily optimize the processing conditions of the present invention to maximize triglyeride mono, diol and triol products by way of using different conditions. Furthermore, using novel processes of the present invention it is also possible to produce different "grades" of polyol products suitable for elastomers, rigid foams or flexible foams and the like with specific molecular profiles as indicated by the unique mixture of triacylglycerol, mono-ol, diol and triol products by controlling the conditions of the claimed processes.

Therefore, in another embodiment of the present invention, there is provided a method for the preparation of various grades of polyols from renewable resources, such as renewable feedstocks comprising oils such as canola and flax oils and the like, based on the ozonolysis and hydrogenation reactions of the present invention. Details of one embodiment of the present invention are further provided in Example 3 below, and as follows. In particular, the dramatic effect of crystallization on polyol viscosities is evidenced by analyzing DSC measurements. This effect as expected diminished when the temperature increased. HPLC and GC measurements can be used to establish basic correlations between molecular diversity of the three types of polyols produced, and their physicochemical properties, such as hydroxyl number, acidity number, and viscosity.

In Example 3 below, three grades of polyols were synthesized: (i) polyols from canola oil using oxygen gas supply to generate the ozone, and referred to as canola-oxygen; (ii) polyols from canola oil using air supply to generate the ozone, and referred to as canola-air; and (iii) polyols from flax oil using air supply to generate the ozone, and referred to as flax-air.

Figure 17:
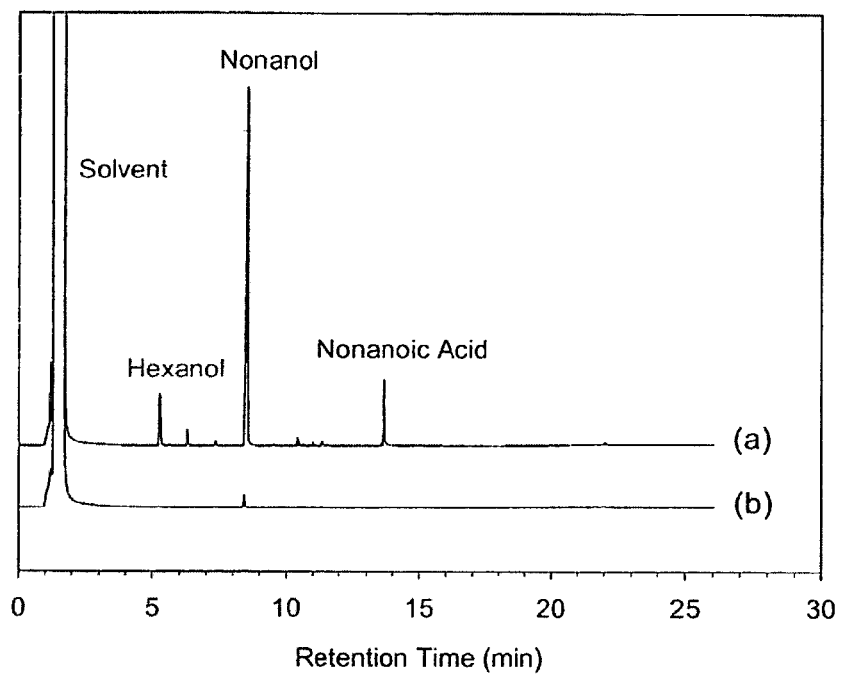
FIG. 17 is a GC graph of Canola based reaction products, ozonized at 0° C. with air as a supply gas for 8h. (a) before distillation. (b) after distillation.

GC chromatographs recorded before and after distillation demonstrated that the end-product polyols were practically free of short-chain by-products apart from a small amount of nonanol (<1%) as illustrated in FIG. 17, for a canola-air polyol sample. The GC chromatographs obtained for the other two grades of polyols also confirmed that the potential chain terminators of the cross-linking reactions which jeopardize the production of polyurethanes were removed effectively. High-value alcohols and acids such as nonanol and nonanoic acid were recovered with a relatively high yield in addition to hexanol and propanol. Table 1 gives calculated and GC-determined experimental amounts of the 3-carbon derivatives (propanol and propionic acid), the 6-carbon derivatives (hexanol and hexanoic acid), and the 9-carbon derivatives (nonanol and nonanoic acid) of short chain by-product, in grams produced before distillation from 100 g canola and flax oil. The calculations were based on the amount of TAGs (in 100 g) compiled by Firestone (Firestone, D., Editor, In *Physical and Chemical Characteristics of Oils, Fats, and Waxes*, AOCS press, Washington, D.C., 1999) for flax oil and by Neff et al. (Neff, W. E., T. L. Mounts, W. M. Rinsch, H. Konishi and M. A. El-Agaimi, Oxidative stability of purified canola oil triacylglycerols with altered fatty acid compositions as affected by triaglycerol composition and structure, *J. Am. Oil Chem. Soc.* 71: 1101-1109 (1994)) for canola oil. The amount of the 9-carbon derivatives by-products was much higher than the others, implying that mostly it is the double bond functionality at carbon number nine which is cleaved.

TABLE 1

Calculated and experimental amounts in grams of short chain by-product from 100 g canola and flax oil. (Errors are standard deviations, n = 3).

| | Propanol equivalent | Hexanol equivalent | Nonanol equivalent | 1,3 propanediol |
|---|---|---|---|---|
| Canola (theoretical) | 1.70 | 7.46 | 28.60 | 10.00 |
| Canola-air | 0.44 ± 0.19 | 2.59 ± 0.29 | 11.85 ± 1.09 | 0.72 ± 0.21 |
| Canola-oxygen | 0.28 ± 0.06 | 4.09 ± 0.18 | 23.53 ± 0.32 | 0.59 ± 0.04 |
| Flax (theoretical) | 11.44 | 5.50 | 9.85 | 33.07 |
| Flax-air polyol | 0.49 ± 0.19 | 1.61 ± 0.54 | 5.92 ± 0.68 | 0 |

Propanol equivalent includes the 3-carbon derivatives (propanol and propionic acid); hexanol equivalent includes the 6-carbon derivatives (hexanol and hexanoic acid), and nonanol equivalent includes the 9-carbon derivatives (nonanol and nonanoic acid).

The production of separate primary alcohols demonstrates that the ozonolysis and hydrogenation reactions effectively cleave the double bonds and add hydroxyl functionality to both of the severed ends. Furthermore, depending on the processing conditions, more or less of the double bonds can be cleaved. This places significant power in the hands of the process engineer, as one can therefore tailor the process to prepare "designer" polyols which impart specific and desirable physical properties.

It is possible to produce different "grades" of polyol products suitable for plastic sheets, rigid foams, flexible foams or expanded "soft" foams by adjusting the ozonolysis and hydrogenation reaction times, ozone flow rate and concentration of the starting vegetable oil. By selecting appropriate ozonolysis conditions, the primary hydroxyl functionality of the polyols can be optimized for the production of various polyurethane products. Polyol mixtures with higher proportions of primary hydroxyl groups can be used to prepare polyurethane polymers in the form of rigid foams and plastic sheets. In these instances, higher cross-linking densities result due to the higher proportions of primary hydroxyl groups in the polyols. Polyol mixtures with lower proportions of primary hydroxyl groups can be used to prepare polyurethane polymers in the form of elastomers and compressible foams, as lower proportions of primary hydroxyl groups results in lower cross-linking densities. The person skilled in the art will readily select appropriate conditions based on the desired polyurethanes.

For instance, the polyol product produced in Example 5 below is suitable for making hard, brittle plastic sheets and rigid foams.

To obtain softer grades of polymer one can
a) Reduce ozonolysis time or/and
b) Reduce ozone flow rate or/and
c) Increase the concentration of the starting vegetable oil in the starting solution.

With the current HPLC analysis method and high purity HPLC standards of mono-ol, diol and triol, it is possible to know quantitatively the ratios of each triol, diol and mono-ol fractions. Furthermore the ability to produce different grades of polyol mixtures has been demonstrated in the present application.

The FTIR spectra of the starting oils and the different polyols are shown in FIG. 18a. The spectra are dominated by absorptions arising from triacylglycerols, which form the major component of vegetable oils (See, for example, the SDBS-Web library at http://www.aist.go.jp/RIODB/SDBS. Accessed Apr. 2, 2005). The absorption bands common to all the samples and present in all spectra are those between 2800 and 3000 $cm^{-1}$ characteristic of saturated C—H stretching modes, the carbonyl absorption band present at 1730 $cm^{-1}$ characteristic of the ester and the absorption triplet (1238, 1166 and 1100 $cm^{-1}$) characteristic of the triacylglycerol ester. In the small wavenumbers range, the intensity of the sharp 722 $cm^{-1}$ absorption peak representative of the amount of saturated carbon chains (>4C) was reduced by approximately half, clearly revealing a reduction of carbon chains as expected for this procedure. Even in the presence of these strong absorptions, it was possible to see spectral contributions arising from particular functional groups. An absorption band at 3300 $cm^{-1}$, characteristic of the hydroxyl group, was missing in the spectra of the original canola and flax starting oils, but appeared in the spectra of the polyols. The band at 1650 $cm^{-1}$ characteristic of C=C double bond absorption disappeared after completion of the overall reaction indicating a significant loss of double bonds (FIG. 18b). Other evidence of double bond saturation was the reduction of the small absorption line at 3006 $cm^{-1}$, indicative of unsaturated C—H stretches, to a very small shoulder of the strong 2925 $cm^{-1}$ absorption peak in the case of air-fed reactions, and complete disappearance for the oxygen-fed reactions (FIG. 18c). Based on the above, it was confirmed that polyols were produced from vegetable oils by ozonolysis and hydrogenation reactions.

The hydroxyl and acidity numbers and the refractive indices of the polyols derived from canola and flax oils are shown in Table 2. The acidity numbers were similar for canola-air and flax-air polyols whereas the hydroxyl number of canola-based polyols was observed to be higher than that of flax-based polyols. As expected, since more oxygen was readily available to cleave double bonds during the ozonolysis reaction, the polyols obtained with oxygen as a supply gas were observed to have higher hydroxyl and acidity numbers than the polyols obtained with air. The method can produce polyols with relatively lower hydroxyl values than other technologies, because it produces only primary alcohol groups (preferred due to the superior strength they introduce in the polyurethanes) rather than secondary alcohol groups which have the possibility of more than one available position on each carbon chain. Theoretically there is a maximum hydroxyl value of 294 mg KOH/g that can be obtained when producing polyols with 3 primary alcohols from canola and flax oils. The hydroxyl value for the polyol was lower than the theoretical maximum hydroxyl value due to incomplete ozonolysis reactions as well as chemical properties of the starting material. Triacylglycerol oils contain a mixture of saturated and unsaturated fatty acids, which means that single and double hydroxyl groups will be produced since the starting triacylglycerol does not always contain three unsaturated fatty acids. Single and double hydroxyl groups can also be produced if the ozonolysis reaction does not cleave all the double bonds on all the fatty acids. As such, hydroxyl numbers do not provide a good measure of the poly-hydroxyl nature of the polyol across various different compounds. However, within a class of compounds (such as within the primary polyols produced by the methods described herein) it can serve as a good comparison measure.

Nonetheless, the functionality of polyols produced by the methods described herein produce superior polyurethanes, regardless of the lowered hydroxyl numbers.

TABLE 2

Calculated and experimental amounts in grams of short chain by-product from 100 g canola and flax oil. (Errors are standard deviations, n = 3).

|  | Hydroxyl number (mg KOH/g) | Acidity number (mg KOH/g) | Viscosity at 25° C. (Pa · s) ± 5 × 10$^{-4}$ | $n_D^{35}$ ± 5 × 10$^{-4}$ |
|---|---|---|---|---|
| Canola oil | 3.51 ± 0.18 | 0 | 0.0524 | 1.4670 |
| Canola-air | 152.4 ± 0.3 | 22.9 ± 0.3 | 0.4527 | 1.4663 |
| Canola-oxygen | 176.4 ± 0.5 | 51.7 ± 0.1 | 0.9067 | 1.4658 |
| Flax oil | 5.97 ± 0.41 | 0.16 ± 0.0 | 0.0369 | 1.4760 |
| Flax-air | 128.7 ± 2.4 | 23.1 ± 0.2 | 0.7970 | 1.4675 |

Evidence that a triply-hydroxylated polyol was produced in the present embodiment is shown in the HPLC chromatograph of the canola-air polyol (FIG. 19). The appearance of the sharp peak at a retention time around 15 minutes indicated a polyol that contained three carbon chains with primary hydroxyl groups. The first group of peaks centered at the retention time around 4.5 minutes and the second group of peaks centered around 8.5 minutes correlate to the single and double-hydroxyl groups produced during the reaction respectively. Similar phenomena were also observed in the other two polyols produced.

The DSC melting profiles shown in FIG. 20b further evidence the suitability of the polyols to processing within standard polyurethane-forming capital equipment present in plants currently. The thermograms of hydrogenated oils which contain the maximum stearic acid amount are also displayed for comparison. The polyols thermograms show some similarities and their crystallization and melting peaks were stronger and more clearly defined than those of the vegetable oils. Clearly, depending on the polyol, various levels of crystallinity were present in the sample at higher temperatures. From the DSC crystallization profiles (FIG. 20a), the first crystallization peak of the flax-air polyol was shown to be higher than that of the canola-air polyol (19.9° C. for Flax air against 2.3° C. for canola air). Table 3 summarizes the crystallization temperatures and melting temperatures (temperatures determined with ±0.5° C. uncertainty). Compared to standard values for commercially available polyols, the polyols synthesized were well within acceptable tolerances for standard capital equipment. Presence of crystals can be a barrier to mass transfer of crosslinkers, which can be either a problem or a benefit, depending on what type of polyurethane is being processed. Furthermore, the presence of crystals clearly affects the viscosity of the sample, which results in different requirements on the shear and pumping systems of the plant, etc. However these variances in crystallinity and viscosity can be manipulated well within the plant environment to create polyurethanes with desirable properties.

TABLE 3

Crystallization and melting temperatures obtained from DSC

|  | Crystallization | | | Melting | | |
|---|---|---|---|---|---|---|
|  | $T_{1C}$ (° C.) | $T_{2C}$ (° C.) | $T_{3C}$ (° C.) | $T_{1M}$ (° C.) | $T_{2M}$ (° C.) | $T_{3M}$ (° C.) |
| Canola oil | -25.4 | | | -16.6 | | |
| Canola-air | -9.6 | 2.3 | | -8.7 | -0.7 | 8.21 |
| Canola-oxygen | -25.4 | 16.8 | 29.6 | -4.5 | 23.2 | 39.7 |
| Flax oil | -22.5 | | | -26.6 | | |
| Flax-air | -20.1 | 19.9 | | -20.4 | -5.7 | 26.3 |

Due to hydrogen bonding induced by hydroxyl groups of the polyols, the measured viscosities of the polyols were significantly higher than those of the starting oils, and those with higher hydroxyl numbers demonstrate the highest viscosities. FIG. 21a shows the viscosity of the samples measured at 25° C. as a function of time indicating Newtonian behavior. The viscosity of the starting oils and the sample polyols decreased with increasing temperature (FIG. 21b) as expected for such materials. The viscosities of the flax-based polyol were higher than those of canola-air polyols, despite the fact that the hydroxyl number of the former was relatively lower. This was due to the effect of crystallization on viscosity. Because the first crystallization peak of the flax-air polyol was higher than that of the canola-air polyol, when measurements of viscosity were taken at 25° C., crystalline structure had already begun to form within the flax-air polyol, attributing to a much greater viscosity. Canola-oxygen polyol displayed an even greater viscosity at the same temperature due to its higher hydroxyl value as well as a crystallization peak at 29.6° C. As expected, this effect dramatically diminished when the temperature increased, and the gap between the polyols viscosities narrowed substantially as seen in FIG. 21b.

In yet another embodiment of the present invention, polyols synthesized from agricultural feedstock, such as canola and flax oils, and soybean oil-derived polyols and crude castor oil obtained commercially, and as described herein were reacted with aliphatic diisocyanates and aromatic diisocyanates to produce polyurethane (PU) polymers, further details of which are set out in Example 4 below.

The reaction of aliphatic 1,6-hexamethylene diisocyanate (HDI) with polyols synthesized from canola, flax and soybean oils was observed to yield PU elastomers. The reaction of aromatic diphenylmethane diisocyanate (MDI) with polyols synthesized from canola and soybean oils was observed to yield rigid PU foams.

Such PUs were characterized for their thermal and mechanical properties with dynamic mechanical analysis (DMA), thennomechanical analysis (TMA), differential scanning calorimetry (DSC), and thennogravimetric analysis (TGA) as well as tensile and compressive properties measurements. The glass transition temperatures ($T_g$) of the PU elastomers were found to be lower $T_g$s (<0° C.) than those of the PU rigid foams (>56° C.).

In the case of the elastomers, the formation of hydrogen bonds was evidenced by FTIR measurements. The TGA thermographs showed clearly two well-defined steps of degradation for all the elastomers. In the first step, up to 30% weight loss, the fastest rate of loss was found at 345° C. for canola-based PU, and at 330° C. for flax-based PU while soy-based PU lost most of the weight in the second step. With the same OH/NCO molar ratio, the elastomers made from canola-based polyol showed slightly higher Young's modulus and tensile strength than those made from flax-based polyol and soy-based polyols.

The PU foams produced from canola-based polyols performed better with higher compressive strength and modulus and more uniform cellular structure. The flax-based polyols were not suitable to produce PU foams.

The FTIR spectra for the three elastomers (designates as COBPU, FOBPU and SOBPU, see Example 4 below) with OH/NCO molar ratio of 1.0 are shown in FIG. 22. The —NCO group absorption band centered at 2270 cm$^{-1}$ was clearly missing, and a strong 3340 cm$^{-1}$ absorbance band characteristic of the N—H group and an absorbance band characteristic of the C═O group centered around 1700 cm$^{-1}$ were present in all the FTIR spectra. FTIR measurements confirmed that almost all of the diisocyanate groups reacted during polymerization and formed urethane linkages, urea and amide groups.

The existence of hydrogen bonds, a very important feature of polyurethanes which has a significant effect on material properties, was directly observed in the FTIR spectra as seen in FIG. 22. The band centered around 1700 cm$^{-1}$ split into two resolved branched peaks indicating the presence of hydrogen bonded urethane carbonyl (C═O) groups (Yu, T. L., T. L. Lin, Y. M. Tsai and W. J. Liu, Morphology of polyurethanes with triol monomer crosslinked on hard segments., *J. Polym. Sci.: Polym. Phys.*, 37: 2673-2681 (1999)). Based on the fact that the wave number of the hydrogen bonded urethane C═O group is usually lower than that of non-hydrogen bonded C═O groups (Coleman, M. M., K. H. Lee, D. J. Skrovanek and D. C. Painter, Hydrogen-bonding in polymers. 4. Infrared temperature studies of a simple polyurethane., *Macromolecules*, 19: 2149-2157 (1986)), the position of hydrogen bonded C═O groups was assigned to the 1690 cm$^{-1}$ wavelength, and that of non hydrogen bonded C═O groups to the 1740 cm$^{-1}$ wavelength. The N—H group is another strong proton donor which can forms hydrogen bond as well, but it was not resolved from the FTIR spectra due to its vibration region overlap with the O—H vibration region (around 3300 cm$^{-1}$).

For COBPU and FOBPU elastomers, the intensity ratio of hydrogen bonded to non hydrogen bonded peaks was observed to be higher than that of the SOBPU sheet, indicating that more hydrogen bonds were formed for the former two PUs than the latter. Since the presence of hydrogen bonds would enable the material to dissipate energy without breaking covalent bonds, they are a dominating factor in the resulting mechanical properties which are discussed later.

The glass transition temperature ($T_g$) of crosslinked PUs are affected by several factors including the relative amounts of the soft (polyols) and hard (diisocyanate) segments, the cross linking density, and the amount of hydrogen bonding. As expected, $T_g$s increased with decreasing OH/NCO molar ratio. At Low OH/NCO molar ratio, the PUs exhibit a higher $T_g$ because the excess NCO groups continue to react with the existing urethane groups and form more crosslinked structures. On the other hand, when OH/NCO>1, the excess OH groups may act as plasticizers and as a result, decrease $T_g$. This trend is consistent with what has been reported by Petrovic et al (Petrovic, Z. S., W. Zhang, A. Zlatanic, C. C. Lava and M. Ilavsky, Effect of OH/NCO molar ratio on properties of soy-based polyurethane networks., *J. Polym. & Environ.*, 10: 5-12 (2002)).

FIG. 23 shows an example of the reversing heat flow vs. temperature curves obtained for COBPU and FOBPU with the OH/NCO molar ratio of 1.0. The $T_g$s were determined from the shift of heat capacity with temperature and the results for the different OH/NCO molar ratios are listed in Table 4. It is obvious that $T_g$s increased with the decreasing OH/NCO molar ratio for both COBPU and FOBPU elastomers.

Typical TMA curves of COBPU and FOBPU elastomers are shown in FIG. 24. TMA analysis evidenced the strong dependence of the PUs thermal behavior on the type of polyol used in their formulation. The $T_g$s were determined from the intersect of two tangents, one to the low-temperature thermal expansion curve and the other to the thermal-expansion curve beyond the transition following the ASTM E 1545 standard. The deflection observed in the TMA graphs of the FOBPU samples extending from around 0 to 45° C. fell in their melting temperature range accounting for the imprecision in the determination of $T_g$ by TMA. The $T_g$s determined from TMA were lower compared to DMA and MDSC, but the trend was the same: the lowest $T_g$ was recorded for COBPU and the highest was observed for FOBPU. The glass transition determination is not unique because it is both thermodynamic and kinetic in nature (McKenna, G. S. In *Comprehensive Polymer Science: Vol. 2, Polymer Properties*; Booth C., Price, C., Eds.; Pergamon: Oxford, pp 311-362, 1989) (Table 4)

FIG. 25 shows the evolution with temperature of the storage moduli (E') of the COBPU, FOBPU, and SOBPU elastomers with OH/NCO molar ratio of 1.0 and illustrates typical dynamic mechanical behavior of our samples. At the same temperature, E' of SOBPU was much lower than those of the other two PUs. A β-transition at approximately −70° C. was observed for both COBPU and SOBPU samples, which was not found for FOBPU samples. The $T_g$ of the SOBPU (−43° C.) was also lower than that of COBPU and FOBPU samples. This is probably due to a smaller amount of hydrogen bonding in SOBPU compared to COBPU and FOBPU and the presence in SOBPU networks of dangling chains created because of hydroxyl groups located in the middle of the chains. The dangling chains cause significant steric hindrance to further cross-linking, and result in lower cross-linking densities

TABLE 4

Tg (° C.) of the polyurethane elastomers.

| molar ratio | Canola oil based PU elastomers | | | Flax oil based PU elastomers | | |
|---|---|---|---|---|---|---|
| (OH/NCO) | DMA | TMA | MDSC | DMA | TMA | MDSC |
| 1.0:0.8 | −11 | −26 | −20 | −8 | −12 | −8 |
| 1.0:1.0 | −8 | −17 | −15 | −6 | −16 | −4 |
| 1.0:1.2 | −5 | −14 | −9 | −5 | −10 | −3 |

Based on the theory of rubber elasticity (22), the cross-linking density ($v_e$) was determined as:

$$E' = 3v_e RT \qquad (2)$$

where E' is the storage modulus in the rubbery plateau above $T_g$ (ca. T=$T_g$+40° C.), R is the gas constant.

The values of $v_e$ obtained for COBPU were 2.3×10$^2$, 3.3×10$^2$ and 4.8×10$^2$ M/m$^3$, for OH/NCO molar ratios of 1.0:0.8, 1.0:1.0 and 1.0:1.2 respectively, and in the case of FOBPU they were 3.5×10$^2$, 5.3×10$^2$ and 8.3×10$^2$ M/m3. This indicates that the flexibility of the polymer chains was reduced in the higher cross-linked networks increasing the $T_g$ and thus shifting the rubbery state to higher temperatures.

The measured glass transition temperature is dependent upon the physical property measured, the type of measuring apparatus and the experimental parameters used. Changes in heat capacity, viscosity, dielectric relaxation, or thermal expansion coefficients used to probe the shift from glassy to rubbery state, could yield very different $T_g$ values (Eisenberg, A. In *Physical Properties of Polymers*; American Chemical Society: Washington, D.C., pp 61-96 (1993)). DSC is very sensitive to any additional phenomenon which occurs near the $T_g$ process and its evaluation is affected (Hutchinson, J. M., Characterising the glass transition and relaxation kinetics by conventional and temperature-modulated differential scanning calorimetry., *Thermochimica Acta* 324: 165-174 (1998)). The temperature variation rate has also a direct influence on the heat capacity, especially at $T_g$, with heat transfer effects complicating the process (Hutchinson, J. M., Studying the glass transition by DSC and TMDSC., *Journal of Thermal Analysis and Calorimetry*, 72: 619-629 (2003)). Standard DSC does often provide only a weak indication of $T_g$ and sometimes does not reveal its existence at all, as our measurements have shown. MDSC, however, minimizes this problem by providing not only the total heat flow signal but also the heat capacity and its kinetic components. The total heat flow is divided into Reversing Heat Flow and Nonreversing Heat Flow. Reversing Heat Flow is the heat capacity component of the total heat flow and is calculated by converting the measured heat capacity into a heat flow signal using the classical heat flow equation as a theoretical basis. As a result, $T_g$ can be determined from the Reversing Heat Flow signal (Wunderlich, B., The tribulations and successes on the road from DSC to TMDSC in the $20^{th}$ century the prospects for the $21^{st}$ century., *Journal of Thermal Analysis and Calorimetry*, 78: 7-31 (2004)). If TMA does not always show a clear glass transition (as shown with the mentioned imprecision in our TMA determination of $T_g$), it however yields repeatable measurements associated with $T_g$s (Khandare, P. M.; J. W., Zondlo and A. S., Pavlovic, The measurement of the glass transition temperature of mesophase pitches using a thermomechanical device., *Carbon*, 34: 663-669 (1996)). The DMA provides the most credible information on changes that occur during glass transition and therefore is well-suited to measuring $T_g$. DMA is very sensitive to the glass transition because the mechanical properties such as modulus and damping, measured by DMA depend strongly on the material's relaxation time which undergoes large changes during the glass transition (Williams, R. J., Methods for Determination of Glass Transitions in Seeds, *Annals of Botany* 74: 525-530, (1994)). The DMA traces are frequency dependent but yield unambiguous peaks for the $T_g$.

TGA curves of the PU elastomers with OH/NCO molar ratio of 1.0 and their derivatives (DTGA) are shown in FIGS. 26a and 26b respectively. Decompositions started at approximately 160° C., losing weight very slightly until 300° C., where a rapid drop followed and ended at approximately 490° C. The initial rate loss (for weight loss <10%) was slightly lower for FOBPU than for COBPU and SOBPU. In the temperature range of 160-300° C., the shapes of the weight loss curves of all the PUs were similar and in the temperature range of 300-400° C., totally different. DTGA data (FIG. 26b) reveal two main degradation processes, one correlated with the first 25-30% of the weight loss, and the second with the remaining weight loss. The shapes of the DTGA curves were practically the same. COBPU had its fastest rate of loss at 345° C., and FOBPU and SOBPU both had their fastest rate of loss at 330° C. SOBPU lost most of the weight in the second step, while COBPU and FOBPU both lost around 25% of the weight in the first step.

The degrading process is complex but it is known that the first stage of degradation is dominated by urethane bond decomposition and that the amount of residue is correlated with the amount of unreacted isocyanate in polymers (Petrovic Z. S., Z. Zavargo, J. H. Flynn, and W. J. Macknight, Thermal-Degradation of Segmented Polyurethanes, *J. Appl. Poly. Sci.*, 51 (6): 1087-1095 (1994)). Javni et al. (Javni, I., Z. S. Petrovic, A. Guo and R. Fuller, Thermal stability of polyurethanes based on vegetable oils., ibid. 77: 1723-1734 (2000)) previously reported that although the early stage of degradation is dominated by urethane bonds decomposition, the polyol component may contribute to the weight loss at higher conversions, causing an increase of activation energy. This suggests that the first step of the COBPU and FOBPU losses is likely due to a higher conversion of —NCO groups to urethane bonds compared to that in SOBPU samples and that the difference in the fastest weight loss (330° C. vs. 340° C.) could be linked to differences in the activation energies introduced by the different polyol types.

Tensile properties were characterized for the PU elastomers. The stress vs. strain curves for the PU sheets with OH/NCO molar ratio 1:1 are shown in FIG. 27. Similar results were obtained for the other two sets of specimen with different molar ratio and summarized in Table 5. Young's modulus and tensile strength at break increased with increasing diisocyanate content, which are well known features in urethanes. With the same OH/NCO molar ratio, COBPU had the highest Young's modulus, tensile strength at break and largest elongation, while SOBPU had the lowest. The higher strength and modulus of COBPU was due to its high hydrogen bonds content and the excessive density of crosslinks which hindered molecular motion.

TABLE 5

Mechanical properties of polyurethane elastomers at various OH/NCO molar ratios. Errors are standard deviations, n = 5.

|  | Molar ratio (OH/NCO) | Young's Modulus (MPa) | Strength at break (MPa) | Strain at break (%) |
|---|---|---|---|---|
| Canola based polyol/HDI | 1:0.8 | 3.08 ± 0.07 | 1.00 ± 0.05 | 41.59 ± 3.86 |
|  | 1:1 | 4.82 ± 0.15 | 1.58 ± 0.13 | 43.05 ± 3.19 |
|  | 1:1.2 | 5.71 ± 0.18 | 2.09 ± 0.17 | 44.29 ± 3.32 |
| Flax based polyol/HDI | 1:0.8 | 2.76 ± 0.13 | 0.99 ± 0.08 | 46.90 ± 3.49 |
|  | 1:1 | 4.58 ± 0.17 | 1.39 ± 0.09 | 40.54 ± 3.54 |
|  | 1:1.2 | 5.83 ± 0.26 | 1.79 ± 0.10 | 41.72 ± 1.74 |
| Soybean based polyol/HDI | 1:0.8 | 1.51 ± 0.04 | 0.29 ± 0.06 | 26.35 ± 0.79 |
|  | 1:1 | 2.80 ± 0.23 | 0.55 ± 0.04 | 22.93 ± 2.27 |
|  | 1:1.2 | 3.32 ± 0.26 | 0.63 ± 0.04 | 22.44 ± 0.59 |

The FTIR spectra of Canola-PU, Soybean-PU and Castor-PU foams are shown in FIG. 28. A broad absorption band at 3340 cm$^{-1}$ characteristic of the hydrogen bonded N—H group and an absorbance band centered around 1720 cm$^{-1}$ characteristic of the C═O group were present in all the FTIR spectra (Szycher, M., *Szycher's Handbook of polyurethanes*, CRC Press, Boca Raton, Fla., 1999). However, both bands were not symmetrical. The asymmetrical shape of the band around 1720 cm$^{-1}$ showed that the hydrogen bonded C═O group vibration region was overlapping with the free C═O group vibration region. In the case of N—H wavelength region, a shoulder was observed around 3400-3500 cm$^{-1}$ which is usually assigned to free N—H group, indicating that only part of the N—H group were hydrogen bonded. The decrease of the degree of hydrogen bond formation was due to the steric hindrance effect of the isocyanate aromatic rings and the restriction of hard segment mobility of the chemical crosslinking. In addition, the band centered at 2270 cm$^{-1}$ characteristic of the —NCO group observed in all spectra indicated that the isocyanate had not completely reacted with the polyols. For the same OH/NCO molar ratio, its relative intensity in Soybean-PU and Castor-PU was higher than that in Canola-PU foams. Furthermore, Canola-PU foams had a relatively higher N—H peak than the other two foams. These clear differences, even if precise quantitative analyses of the FTIR results are lacking, showed that the —NCO amount left after the reaction was lower and the urethane linkages amount was higher in the case of Canola-PU foams. This was therefore attributed to the difference in polyol structure, particularly the dangling chains content and their location. Canola based polyol was constituted of 30% (on a molar basis) pendant chains, whereas in the soybean polyol and in the castor oil, every molecule with hydroxyl functionality provided a portion of the fatty acid chain as a dangling chain. Furthermore, Canola based polyol contained only primary terminal hydroxyl groups located at carbon 9 whereas soybean polyol and castor oil contained secondary functional hydroxyl groups all located in the middle of the fatty acid chains which resulted in significantly higher steric hindrance to further crosslinking.

Dynamic mechanical behavior of Canola-PU, Soybean-PU and Castor-PU foams with plots of the storage modulus (E'), loss modulus (E") and tangent δ (tan δ) as a function of temperature are shown in FIG. 29a, FIG. 29b and FIG. 29c, respectively. The storage modulus, E', as highlighted by its first derivative (insert in FIG. 29a) dropped first gradually then exhibited a relatively rapid drop around −90° C. and another large drop around 50° C. during the transition from glassy to rubbery states. The first rapid drop was attributed to the β-transition and the second to the glass transition. The β-transition may be related to the rotation (Petrovic, Z. S., W. Zhang, and I. Javni, Structure and properties of polyurethane prepared from triacylglycerol polyols by ozonolysis, *Biomacromolecules*, 6: 713-719 (2005)) or backbone chain motion of the short groups (Nielsen, L. E. and R. F. Landel, *Mechanical Properties of Polymers and Composites*, 2$^{nd}$ ed. Marcel Dekker, NY, 1994) in the fatty acid chains. Below $T_g$, the E' of Castor-PU foams was the highest. Once $T_g$ is reached, the E' begins to decrease rapidly. The E' for Soybean-PU foams decreased at a slower rate and plateaued at a higher level than Canola-PU and Castor-PU foams. In the case of soybean polyol based PU foams, the dangling chains acted as a plasticizer which broadened its transition range and reduced its storage modulus. Generally, with the increase of crosslinking density, the transition region broadens, and the modulus drops at a lower rate and plateaus at a higher level. At least part of the broadening of the transition region was due to the heterogeneities in the molecular weight between crosslinks.

The $T_g$s listed in Table 6 were determined with a very good accuracy from FIG. 29a following ASTM E1640-99 standard.

TABLE 6

Glass Transition Temperatures and Compressive Properties of PU Foams

|  | Canola PU | Soybean PU | Castor PU |
| --- | --- | --- | --- |
| $T_g$ | 58 | 67 | 56 |
| Compressive strength (KPa) | 770 ± 145 | 410 ± 50 | 1170 ± 140 |
| Modulus (MPa) | 22.2 ± 7.5 | 14.4 ± 1.4 | 30.1 ± 3.4 |

Soybean-PU had a higher $T_g$ because it had a higher OH number and hence a higher crosslinking density. Crosslinks hinder the polymer segmental motion by introducing restrictions on the molecule motion of a chain therefore increasing $T_g$.

A weak transition at about 0° C. was observed for all the PU foams as clearly revealed by the first derivative of E' (arrow in the insert of FIG. 29a). This weak transition was also observed in the loss modulus curves shown in FIG. 29b. In the case of Canola-PU, it appeared as a broad shoulder between −50° C. to 10° C. Petrovic et al. (Petrovic, Z. S., W. Zhang, and I. Javni, Structure and properties of polyurethane prepared from triacylglycerol polyols by ozonolysis, *Biomacromolecules*, 6: 713-719 (2005)) reported the same phenomena for similar PU systems. In addition, it was found that the two main loss modulus peaks of Soybean-PU foams were much broader than for the other two foams, indicating a broader distribution in crosslinking density. Similar behavior was observed for the tan δ curves shown in FIG. 29c TGA curves and their calculated derivatives (DTGA), shown in FIGS. 30a and 30b respectively, illustrate the degradation behavior of the PU foams. The decompositions of the PU foams started at higher temperature than in the PU elastomers (approximately 200° C. against 160° C.). (S. S. Narine, X. Kong, L. Bouzidi and P. Sporns, (In Press, January 2007), *Physical Properties of Polyurethanes Produced from Polyols from Seed Oils: I Elastomers*, J. Am. Oil Chem. Soc.). The DTGA curves show two separate main features which are associated with two distinct degradation stages. The first feature which ends at around 400° C. had well-resolved peaks specific to each structure (3 peaks for Soybean-PU and Castor-PU, and 2 peaks for Canola-PU). The second feature was a relatively broad signal which ended abruptly and was practically the same for all specimens. In the first stage, the fastest rate of loss was at 335° C. for Canola-PU, and at 380° C. for Soybean-PU and Castor-PU. The second stage involved an estimated weight loss of 70% with the fastest rate of loss situated at 470° C. for all samples.

The degrading process is complex and depends on several factors such as urethane bonds, polyol type, dangling chains and unreacted isocyanate. The degradation started at a higher temperature than that of the elastomers mainly because the MDI aromatic rings used to prepare the foams affect the activation energy of the formed urethane groups, and delay their dissociation. In the first stage, the similarity of all the samples degradation processes could be explained by similar conversion of —NCO groups to urethane bonds and the differences in the fine structure and shifts of maximum loss rate peaks could be explained by the differences in the activation energies introduced by the dangling chains present in the soybean polyol and castor oil. The second stage where most of the weight loss occurred could be correlated to a similar decomposition process of the polyols backbone.

The mechanical properties of the foams were characterized by compressive stress-strain measurements and the results are shown in FIG. 31. After an initial near-linearity of stress to strain up to about 3%, the specimens exhibited relatively abrupt yielding, followed by a sustained plateau region over which there was a little increase in stress with increasing strain. The initial linear region determines the modulus of the foam. The broad plateau region resulted from a plastic collapse or cell wall buckling of the foams, which was referred to as the collapse stress.

Young's modulus was calculated according to the ASTM D1621-00 standard. With a density of 160 kg/m$^3$, the Canola-PU foam had a compressive strength of 770±145 KPa and a modulus of 22.2±7.5 MPa. The Castor-PU foam yielded the highest compressive strength (1170±140 KPa) and modulus (30.1±3.4 MPa). With the same density, the modulus and compressive strength of the Soybean-PU foam was substantially lower (14.4±1.4 MPa and 415±50 KPa respectively).

The compressive strength and modulus depend primarily on the cellular structure of the foam, i.e. the material of the cell walls and the size and shape of the cells. The lowest compressive strength of soybean-PU samples was the result of the plasticizing effect of the dangling chains combined with a smaller amount of hard segments. The plasticizer weakens the network under load and lowers the compressive strength and Young's modulus. The hard segments confer to the PU foams high modulus, especially when they are of non-uniform size and therefore more difficult to disrupt. The high compressive strength and modulus of castor-PU foams was mainly due to the size and shape of the cells and the thickness of the cell walls and will be discussed later.

The cross-sectional surfaces of the foams observed with SEM are shown in FIG. 32. Canola-PU foams had small pores of approximately 0.25-mm diameter, uniformly distributed with relatively thin walls (FIG. 32a). Soybean-PU foams had a less uniform structure composed of larger elongated strips-like pores interconnected by smaller pores of different sizes (FIG. 32b). In the case of Castor-PU foams, the cells were very coarse even observed by naked eye and had the largest wall width (FIG. 32c) which resulted in the highest compressive strength and modulus. The relatively poor quality of the Castor-PU foam microstructure might be attributed to its inadequate optimization of the surfactant used in its formulation. It is known (Szycher, M., Szycher's Handbook of polyurethanes, CRC Press, Boca Raton, Fla., 1999) that the role of the surfactant is to stabilize the cell walls by lowering the surface tension between the cells and prevent their coalescence, resulting in smaller cells uniformly distributed over the network. Meanwhile, catalysts are added to accelerate reactions according to the requirement. The final cellular structure is a balance between the network formation and the blowing reaction. In the case of Castor-PU foams, when the amounts of catalysts were reduced to 0.5 parts, finer cells with narrow distribution were obtained.

In yet another embodiment of the present invention, polyols synthesized via modified ozonolysis and hydrogenation methods from agricultural feedstock (which are set out in Example 5 below), such as canola oil-derived polyols, and as described herein were reacted with aromatic diisocyanates to produce polyurethane (PU) polymers, such as rigid foams.

The HPLC was performed on the products from the modified ozonolysis and hydrogenation method. HPLC of polyols produced with Pd-C, Raney Ni System and HPLC of polyols produced with Zinc, Raney Nickel System are shown in FIG. 33 and FIG. 34 respectively. It can be seen that with the new method in both procedures, the peak of mono-ol which is a chain terminator in the cross linking has disappeared, the saturated fat peak was very small and that the peak of triol was much bigger compared to diol peak.

Using the recycled ethyl acetate as the solvent for the new ozonolysis method with Pd-C, Raney Ni System as the catalyst for hydrogenation, polyols with a large amount of triol and almost free of mono-ol were also produced. FIG. 35 shows the HPLC performed on these polyols to qualitatively verify their quality.

FIG. 36a shows the viscosity of the polyols measured at 35° C. as a function of time indicating Newtonian behavior. The viscosity of the starting oils and the sample polyols decreased with increasing temperature (FIG. 36b) as expected for such materials. The viscosities of the canola oil based polyol synthesized using ethyl acetate were higher than those of canola oil based polyol synthesized using recycled ethyl acetate.

Such PUs were characterized for their thermal and mechanical properties with dynamic mechanical analysis (DMA), as well as compressive property measurements.

Dynamic mechanical behavior of Ethyl Acetate Canola Oil Based PU (EACOBPU) and Recycled Ethyl Acetate Canola Oil Based PU (REACOBPU) foams, with plots of the storage modulus (E'), loss modulus (E") and tangent δ (tan δ) as a function of temperature are shown in FIG. 37a, FIG. 37b and FIG. 37c, respectively. The $T_g$ of the Ethyl Acetate Canola Oil Based PU (EACOBPU) and Recycled Ethyl Acetate Canola Oil Based PU (REACOBPU) foams were 50 and 51° C., respectively.

The mechanical properties of the foams were characterized by compressive stress-strain measurements and the results are shown in FIG. 38. Young's modulus was calculated according to the ASTM D1621-00 standard. With a density of 160 kg/m$^3$, the EACOBPU foam had a compressive strength of 1028±126 KPa and a modulus of 23.3±6.6 MPa. The REACOBPU foam yielded the highest compressive strength (812±110 KPa) and modulus (15.5±3.1 MPa).

It was decided to carry out further experiments, as it was felt that the foregoing methods produced a material that contained mono-ol and saturated TAGs in amounts which resulted in the production of polyurethanes with cross-linking densities that could be further optimized. Mono-ol acts as a chain terminator when polyols are crosslinked with diisocyanate to produce polyurethane and the saturated TAGs which are not involved in the reaction act as plasticizers. It was also believed that the hydroxyl number of GII-Polyol (produced by the process described in Example 2) could be further optimized.

In view of the above, further methods were developed for the production of monomers having terminal hydroxyl functional groups with optimal hydroxyl number and the possibility for controlling triol, diol, mono-ol and TAGs contents to afford the production of polymers having a large spectrum of physical properties.

Methods of the present invention have been developed which utilize ozonolysis followed by either: (a) zinc reduction, followed by hydrogenation; or, (b) hydrogenation without zinc reduction. These methods result in further optimized production of polyols from unsaturated triacylglycerols and introduce terminal multiple alcohol functional groups into the triacylglycerol that can then be used as a starting material for the production of polyurethane products. In accordance with the present invention, the polyols so produced locate the hydroxyl functionality at the terminal end of the fatty acid chain, in order to optimize reactivity and reduce steric hindrances to crosslinking molecules to the lowest level possible.

The production of separate primary alcohols demonstrates that the ozonolysis, followed by either zinc reduction and hydrogenation reactions, or hydrogenation reaction without zinc reduction reaction, effectively cleaves the double bonds and adds hydroxyl functionality to both of the severed ends. Furthermore, depending on the processing conditions, more or less of the double bonds can be cleaved. This places significant power in the hands of the process engineer, as one can therefore tailor the process to prepare "designer" polyols which impart specific and desirable physical properties.

Example 7 describes an alternate procedure for the production of polyols. Polyols produced by the process of Example 7 will be referred to herein as "Generation III-Polyol" or "GIII-Polyol". In the production of GIII-Polyol, ethyl acetate (EA) was used in both ozonolysis and hydrogenation steps. EA efficiently dissolves the starting material, the intermediate product and the final product, and therefore increases the reaction rate and conversion. EA is mild and cheap, which makes it a satisfactory solvent for industrial use.

EA is an ideal replacement for the caustic and carcinogenic Methylene chloride which is typically used as an unparticipating solvent for ozonolysis. Unlike methylene chloride which when subjected to the action of ozone, could produce phosgene, a highly toxic and severely poisonous chemical, EA is a food grade solvent which doesn't react with ozone.

GIII-Polyol produced by ozonolysis of Canola oil, then zinc reduction of the ozonide to aldehyde at room temperature and atmospheric pressure, followed by hydrogenation of the aldehyde were found to have a hydroxyl number as close to the maximum value possible as determined assuming that all the double bonds have been cleaved.

GIII-Polyol produced by ozonolysis of Canola oil followed by hydrogenation of the ozonolysis reaction product were found to have a hydroxyl number as close to the maximum value possible as determined assuming that all the double bonds have been cleaved.

FIG. 42 is a schematic representation of the production of polyols as described in Example 7. As illustrated in FIG. 42, ozonolysis of two or more double bonds in the unsaturated fatty acids of the triacylglycerols of the canola oil (in this case, three double bonds are shown to be participating in this reaction) affords corresponding ozonide functionalities. Subjecting the products of the ozonolysis reaction to zinc reduction yields corresponding aldehyde functionalities (in the case of the embodiment shown in FIG. 42, three aldehyde functionalities are shown within the triacylglycerol molecule). Subsequent reductive hydrogenation yields a corresponding polyol, which in the embodiment shown in FIG. 42 is a polyol containing three primary hydroxyl groups.

Along with triol, the production of mono-ol and diol is unavoidable since there are a certain amount of triacylglycerols (TAG) containing saturated fatty acids, which in the case of canola oil are mainly stearic and palmitic acids. Furthermore, the incomplete conversion of the double bonds to hydroxyl groups contributes to the production of mono-ol and diol.

HPLC has now become a major analytical technique for the analysis of a wide range of compounds too involatile or too labile to be analyzed by gas chromatography. It is widely used in the fields of biochemistry, pharmacy and food chemistry. However, in the area of making polyols from renewable sources, there have been no reports to date on using HPLC methods for qualitative and quantitative analysis of such polyols.

A practical HPLC method was applied for qualitative and quantitative analysis of polyols. The gradient described in Example 8 gives a good and fast separation between the different components. A diol column (ElfmanBorjesson, I. Harrod, M., Analysis of non-polar lipids by HPLC on a diol column, *Hrc—Journal of High Resolution Chromatography*, 20 (9), 516-518, (1997)) was used to separate the components of the polyol on the basis of the number of hydroxyl groups present at the end of TAG chains.

The HPLC peaks were logically assigned according to the succession of their retention times. Starting from the shortest retention time, the peaks were consecutively assigned to the saturated TAGs, followed by TAGs with a single alcohol group (mono-ol); then TAGs with two alcohol groups (diol) and finally TAGs with three alcohol groups (triol), the most retained material.

The peak with retention time of 5.8 min was assigned to saturated TAGs, the peak with a retention time of 7.6 min was assigned to mono-ol, the peak with a retention time of 15.0 min was assigned to diol, and the peak with a retention time of 25.5 min was assigned to triol.

HPLC graphs of GIII-Polyol were compared with GII-Polyol and are shown in FIG. 43. As aforementioned, GII-Polyol refers to polyols produced by the process described in Example 2. GII-Polyol had a relatively large amount of mono-ol and saturated TAGs, compared to GIII-Polyol which was mainly constituted of triol, a small amount of saturated TAGs and is almost free of mono-ol.

In order to identify the contents of each component in the products, the HPLC standard curves of the components of the reaction product used for the production of PU i.e. diol, triol and mono-ol and saturated TAG were prepared. Standard samples which are not commercially available were obtained from the reaction product by flash chromatography separation as described in Example 8. FIG. 44(*a*), FIG. 44(*b*) and FIG. 44(*c*) show the standard curves for triol, diol, mono-ol and saturated TAG respectively. All curves show linearity with correlation coefficients above 0.99.

The content (in percentage mass) of triol and diol of GII-Polyol and GIII-Polyol are listed in Table 7 along with the maximum theoretical values possible. Theoretical values were calculated using published data of TAG composition and structure of canola oil (Neff, W. E., Mounts, T. L., Rinsch, W. M., Konishi, H., Elagaimy, M. A., Oxidative Stability of Purified Canola Oil Triacylglycerols with Altered Fatty-Acid Compositions as Affected by Triacylglycerol Composition and Structure, *Journal of the American Oil Chemists Society*, 71(10) 1101-1109 (1994)) assuming that all the double bonds of TAGs were broken and replaced by hydroxyl groups.

TABLE 7

Composition and Conversion of Polyol

| | Mass Percentage (%) | | |
|---|---|---|---|
| | GII-Polyol | GIII-Polyol | Theoretical Value |
| Triol | 22 | 60.2 ± 1.2 | 75 |
| Diol | 38 | 26.0 ± 0.5 | 22 |
| Conversion (%) | 60 | 86.2 ± 1.7 | — |

Conversion was calculated as the ratio of the mass of diol and triol in the polyol product to the maximum possible mass of triol and diol theoretically obtained assuming that all the double bonds in the starting vegetable oil were cleaved.

The viscosity of GIII-Polyol at room temperature (0.9860 Pa·s) was almost double of that of GII-Polyol (0.4527 Pa·s). The higher viscosity in the former was due to the higher hydroxyl content which introduced additional hydrogen bonds in these polyols.

GIII-Polyol synthesized via modified ozonolysis and hydrogenation methods from agricultural feedstock, such as canola oil-derived polyols, and as described herein (Example 7) were reacted with aromatic diisocyanates to produce polyurethane (PU) plastics in the form of plastic sheets. The production of PU plastic sheets from GIII-Polyol from canola oil is described in Example 10.

The FTIR spectra are shown in FIG. 45 for the three GIII-PU plastics with different OH/NCO molar ratios. A strong 3340 cm$^{-1}$ absorbance band characteristic of the N—H group and an absorbance band characteristic of the C=O group centered around 1700 cm$^{-1}$ were present in all the FTIR spectra demonstrating the formation of urethane linkages in all the samples. As shown in FIG. 45, the intensities of the N—H group absorption band increased with decreasing OH/NCO molar ratio. This evidenced that the concentration of the urethane linkages in the GIII-PU plastics with OH/NCO molar ratio 1.0/1.2 is much higher than those of the other two formulations. Furthermore, the —NCO group absorption band centered at 2270 cm$^{-1}$ was clearly missing in the case of OH/NCO molar ratio 1.0/1.0, while it increased significantly with decreasing OH/NCO molar ratio, indicating that GIII-PU plastics with OH/NCO molar ratio 1.0/1.2 contained more unreacted —NCO groups than the other two.

FTIR spectroscopy gives useful qualitative information about the molecular structure of the PU, but in order to obtain quantitative information, other methods, such as DMA (which is used to determine the cross-linking density) should be used.

plastic sheet with OH/NCO molar ratio 1.0/1.2. The extended frequency range obtained by the superposition is $10^{-5}$ to $10^9$ Hz. The pseudo-equilibrium modulus of the cross-linking network, G' (G'=E'/3), is related to $v_e$ through Eq. (1). $\rho$ was determined according to ASTM D 792-00 standard and assumed to be a constant when the $M_c$ was calculated at temperature of $T_g+5°$ C. The results are listed in Table 8.

TABLE 8

$T_g$ (° C.) obtained by DSC and DMA, density and parameters of cross-linking networks of the polyurethane plastic sheets.

| molar ratio (OH/NCO) | $T_g$ from DSC (° C.) | $T_g$ from DMA (° C.) | E' (MPa)* | $\rho$ at 23° C. (g/cm$^3$) | $v_e$ (mol/cm$^3$) | $M_c$ (g/mol) |
|---|---|---|---|---|---|---|
| 1.0/1.0 | 15.3 ± 0.6 | 22.7 ± 0.6 | 5.1 | 1.133 | 6.8 × 10$^{-4}$ | 1662 |
| 1.0/1.1 | 34.3 ± 0.6 | 41.3 ± 0.6 | 8.3 | 1.145 | 1.0 × 10$^{-3}$ | 1217 |
| 1.0/1.2 | 36.7 ± 0.6 | 43.0 ± 1.0 | 6.1 | 1.156 | 7.6 × 10$^{-4}$ | 1682 |

*E' at rubbery plateau from master curve

The elastic behavior of polymer networks can be described by either the affine or the phantom network models.

In the affine network model (Flory, P. J., *Principles of Polymer Chemistry*, Ithaca (N.Y.), Cornell University Press, (1953)), the storage modulus G' is given by:

$$G' = \frac{E'}{3} = v_e RT = \frac{\rho RT}{M_c} \quad (1)$$

where R is the gas constant, $v_e$ the cross-linking density, T the absolute temperature, $M_c$, the number-average molecular weight between crosslinks, and $\rho$ the density of the GIII-PU plastic sheets.

The phantom network model (James, H. M., and E. Guth, Theory of the Increase in Rigidity of Rubber During Cure, *J. Chem. Phys.*, 15: 669-683 (1947)) which usually describes the elasticity of perfect networks, considers the effect of elastically active junctions. However, most of the networks have less than perfect elasticity in real networks. For example, non-idealities such as dangling chains will decrease the cross-linking density $v_e$ and entrapped entanglements will increase it. The molecular chains will also interact with each other and reduce the junction fluctuations.

In the case of strong interactions, the junctions do not fluctuate at all and are displaced affinely with macroscopic strain (Painter, P. C., and S. L. Shenoy, A Simple Model for the Swelling of Polymer Networks, *J. Chem. Phys.*, 99: 1409-1418 (1993)). Because of the strong interactions between molecular chains in the PU network, the storage modulus G' could be related to the cross-linking density $v_e$ using the affine network model (Eq. (1)). Using the time-temperature superposition principle (Ferry, J. D., *Viscoelastic Properties of Polymers*, New York chap 11, (1980)), it is possible to characterize the viocoelastic behavior of a polymer at various temperatures over an unapproachable experimental time or temperature range.

Isothermal oscillation measurements were performed in the $T_g$ region. The isothermal storage moduli (E') were obtained as a function of frequency. The curves obtained at different temperatures were superposed in the standard manner into respective master curves using the time—temperature superposition principle. FIG. 46 shows the master curve of E' at a reference temperature of $T_g+5°$ C. for GIII-PU The GIII-PU plastic sheets with $M_{ratio}$=1.0/1.1 had the highest $v_e$ (1.0×10$^{-3}$ mol/cm$^3$) and lowest $M_c$ (1217 g/mol). For $M_{ratio}$=1.0/1.0 and $M_{ratio}$=1.0/1.2, $v_e$ (6.8×10$^{-4}$ and 7.6× 10$^{-4}$ mol/cm$^3$ respectively) and $M_c$ (1662, and 1682 g/mol respectively) of the plastic sheets remained almost the same. This indicated that only a reasonable excess of isocyanates can improve the network structure by increasing cross-linking density.

$T_g$ of all the PU samples with different molar ratios was studied using DSC and DMA. The DSC curves of the GIII-PU plastic sheets with different molar ratios shown in FIG. 47, display a single feature: a glass transition ranging from 20° C. to 45° C. The $T_g$s were determined from the shift of heat capacity with temperature. Changes in the storage (E') and loss (E") moduli with temperature, obtained from DMA carried out at frequency of 1 Hz on the GIII-PU plastic sheets with different molar ratios are shown in FIG. 48 and FIG. 49 respectively. $T_g$ values as determined from the inflection point of E' vs. temperature obtained from DMA measurements were higher than those determined by DSC (see Table 8) by about 5 to 10° C. as generally found in the literature. The trend is however the same: the lowest $T_g$ was recorded for the GIII-PU plastic sheet with the OH/NCO molar ratio 1.0/1.0 and the highest $T_g$ was recorded for the GIII-PU plastic sheet with the OH/NCO molar ratio 1.0/1.2. $T_g$ value for the OH/NCO molar ratio 1.0/1.1 sample was closer to that of the OH/NCO molar ratio 1.0/1.2 sample.

The glass transition of a polymer network is affected by cross-linking density as well as chemical structure. In principle, increased aromatic content should result in higher $T_g$, and reduced crosslinking density $v_e$ would affect it oppositely (Petrovic, Z. S., M. J. Cevallos, I. Javni, D. W. Schaefer, and R. Justice, Soy-oil-based segmented polyurethanes, *Journal of Polymer Science Part B—Polymer Physics*, 43: 3178-3190 (2005)). The relatively large increase of $T_g$ (~20° C.) when $M_{ratio}$ decreased from 1.0/1.0 to 1.0/1.1 indicated that the flexibility of the polymer chains was reduced for the higher cross-linked networks shifting the rubbery state to higher temperatures. This could be explained by the high value of the cross linking density $v_e$ for the sample with $M_{ratio}$ of 1.0/1.1 as mentioned earlier. However, when the OH/NCO molar ratio further decreased from 1.0/1.1 to 1.0/1.2, the $T_g$ remained almost the same. This is thought to be due to several competing factors including primarily: (1) lower $v_e$ of the GIII-PU plastic sheets with OH/NCO molar ratio 1.0/1.2, and (2) increased phenyl ring content produced by larger amount of isocyanate in the later formulation.

A weak transition at about −70° C. was also observed for all the samples as illustrated by the first peak in the loss moduli curves (arrow in FIG. 49). This transition which has been detected in PU produced from other vegetable oils (Zlatanic, A., Z. S. Petrovic, and K. Dusek, Structure and properties of triolein-based polyurethane networks, *Biomacromolecules*, 3: 1048-1056 (2002)) has been identified as the β-transition. The β-transition may be related to the movements of a chain part containing the urethane group attached to crosslinker (Czech, P., L. Okrasa, G. Boiteux, F. Mechin, and J. Ulanski, Polyurethane networks based on hyperbranched polyesters: Synthesis and molecular relaxations, *J. Non-Cryst. Solids*, 351: 2735-2741 (2005)) or to the motion of the backbone chain of the short groups in the fatty acid chains (Nielsen, L. E., and R. F. Landel, *Mechanical properties of polymers and composites*, 2nd edition, Marcel Dekker, New York, USA., Chap. 4., (1994)).

The height and width of glass transition peaks may also be analyzed for each GIII-PU plastic sheet to observe trends in the cross-linking density and network homogeneity (Son, T. W., D. W. Lee, and S. K. Lim, Thermal and phase behavior of polyurethane based on chain extender, 2,2-bis-[4-(2-hydroxyethoxy)phenyl]propane, *Polym. J.*, 31: 563-568 (1999), Ishida, H., and D. J. Allen, Mechanical characterization of copolymers based on benzoxazine and epoxy, *Polymer*, 37: 4487-4495 (1996)). As shown in FIG. 50, the height of the tan δ peak measured by DMA was the lowest (0.98) for OH/NCO molar ratio 1.0/1.1 and had approximately the same value for the two other formulations (1.02 for OH/NCO molar ratio 1.0/1.0 and 1.03 for OH/NCO molar ratio 1.0/1.2). The full width at half maximum of tan δ peak was 19, 21 and 22° C. for samples with OH/NCO molar ratio 1.0/1.0, 1.0/1.1 and 1.0/1.2 respectively. Because tan δ is the ratio of viscous to elastic components of the modulus, it can be speculated that its increasing height is related to higher segmental mobility and thus indicative of a lower cross-linking density. The evolution of tan δ peak height with OH/NCO molar ratio mirrored that of $v_e$ and demonstrated consistency with what has been discussed in light of the theory of rubber elasticity. On the other hand, the slight broadening of the tan δ peak with decreasing OH/NCO molar ratio was probably due to the excess of isocyanate which may have reacted with the amine (produced by the side reactions of the isocyanate with moisture or carboxylic acids) to form urea. The formation of urea linkages increases the number of cross-linking joints and results in a wider distribution of network structures.

TGA curves of the GIII-PU plastic sheets with different OH/NCO molar ratios and their derivatives (DTGA) are shown in FIG. 51*a* and FIG. 51*b* respectively. For all the formulations, the decomposition started at approximately 200° C. and ended at 500° C. The shapes of the weight loss curves were similar in the temperature range of 200-320° C. but differed in the 320-420° C. temperature range. DTGA curves revealed three main degradation processes. In the first step, the sample lost 20% of its weight, in the second step it lost 20-70% and in the third it lost its remaining weight. In the case of OH/NCO molar ratio 1.0/1.1 and 1.0/1.2, the second step further split into two distinct steps.

Kinetic studies of the degradation process were performed in order to better understand the thermal degradation behavior of the GIII-PU plastic sheets. The kinetic data for thermal degradation, namely, the activation energy E, depends on heating rate (Thomas, T. J., V. N. Krishnamurthy, and U. S. Nandi, Thermogravimetric and Mass-Spectrometric Study of the Thermal-Decomposition of Pbct Resins, *J. Appl. Polym. Sci.*, 24: 1797-1808 (1979)). Because the kinetics of degradation is so complex, different methods applied to real polymers give substantially different results (Javni, I., Z. S. Petrovic, A. Guo, and R. Fuller, Thermal stability of polyurethanes based on vegetable oils, *J. Appl. Polym. Sci.*, 77: 1723-1734 (2000)). The values obtained for the activation energy depend significantly on the mathematical treatment used for the calculations (Cooney, J. D., M. Day, and D. M. Wiles, Thermal-Degradation of Poly(Ethylene-Terephthalate)—a Kinetic-Analysis of Thermogravimetric Data, *J. Appl. Polym. Sci.*, 28: 2887-2902 (1983)).

The two main methods applied to analyze TGA kinetic data are Kissinger method (Kissinger, H. E., Reaction Kinetics in Differential Thermal Analysis, *Anal. Chem.*, 29: 1702-1706 (1957)) and Coats-Redfern method (Coats, A. W., and J. P. Redfern, Kinetic Parameters from Thermogravimetric Data, *Nature*, 201: 68 (1964)).

The Kissinger method involves the temperature values ($T_m$) at the maxima of the first derivative weight loss of the DTGA curves. Kissinger assumed that pseudo-first order kinetics for the thermal decomposition could be used such that the following expression could be derived:

$$\frac{d[\ln(\beta/T_m^2)]}{d(1/T_m)} = \frac{-E}{R} \qquad (2)$$

where β is the heating rate, R the gas constant and E the activation energy. Thus, a plot of $\ln(\beta/T_m^2)$ vs. $1/T_m$ allows to calculate the activation energies for the main stages of decomposition. The values of activation energy using three different rates (5, 10, and 20° C.) obtained with Kissinger method are listed in Table 9.

TABLE 9

Activation energies calculated by Kissinger's method

| | Step I | | Step II | | Step III | | Step IV | |
|---|---|---|---|---|---|---|---|---|
| OH/NCO | α range | E (KJ/mol) | α range | E (KJ/mol) | α range | E (KJ/mol) | α range | E (KJ/mol) |
| 1.0/1.0 | 0.1-0.2 | 160 | | | 0.2-0.7 | 170 | 0.7-0.9 | 230 |
| 1.0/1.1 | 0.1-0.2 | 150 | 0.2-0.4 | 140 | 0.4-0.7 | 140 | 0.7-0.9 | 315 |
| 1.0/1.2 | 0.1-0.2 | 110 | | | 0.2-0.7 | 140 | 0.7-0.9 | 240 |

The Coats-Redfern method is an integral method which uses the following equation for the first order reaction:

$$\log\left[\frac{-\log(1-\alpha)}{T^2}\right] = \log\frac{AR}{\beta E}\left(1 - \frac{2RT}{E}\right) - \frac{E}{2.303RT} \quad (3)$$

where $\alpha$ is the fractional weight loss at time t, A the pre-exponential factor, T the absolute temperature. The remaining abbreviations have the same meaning as Eq. (2). Thus, activation energy for every degradation process can be determined from a plot of $$\log\left[\frac{-\log(1-\alpha)}{T^2}\right]$$

vs. 1/T. The lines obtained by this method have slopes equal to $-E/(2.303R)$ which conveniently characterize the different stages. The activation energies obtained by this method using kinetic data obtained at a rate of 5° C. are detailed in Table 10.

TABLE 10

Activation energies calculated by Coats-Redfern method

| OH/NCO | Step I α range | E (KJ/mol) | Step II + III α range | E (KJ/mol) | Step IV α range | E (KJ/mol) |
|---|---|---|---|---|---|---|
| 1.0/1.0 | 0.0-0.1 | 105 | 0.1-0.7 | 50 | 0.7-0.9 | 50 |
| 1.0/1.1 | 0.0-0.1 | 145 | 0.1-0.7 | 30 | 0.7-0.9 | 50 |
| 1.0/1.2 | 0.0-0.1 | 135 | 0.1-0.7 | 40 | 0.7-0.9 | 70 |

As indicated by both Kissinger and Coats-Redfern methods, all the GIII-PU plastic sheets decomposed in multiple stages. The first stage ($\alpha<0.2$) which is associated with E values in the range of 105-160 KJ/mol can be assigned to the cleavage of the urethane linkages (Javni, I., Z. S. Petrovic, A. Guo, and R. Fuller, Thermal stability of polyurethanes based on vegetable oils, *J. Appl. Polym. Sci.*, 77: 1723-1734 (2000)). The calculated activation energies for the intermediate stage ($\alpha=0.2-0.7$) using Coats-Redfern method are in the range 30-50 KJ/mol, were much lower than the values (140-170 KJ/mol) obtained by the Kissinger method.

The difference in the reported values of E highlights the sensitivity of the results to the methodologies used to analyze the data as mentioned earlier. Because the data obtained from methods based on multiple heating rates are more reliable than the methods which use a single heating rate as generally agreed (Cooney, J. D., M. Day, and D. M. Wiles, Thermal-Degradation of Poly(Ethylene-Terephthalate)—a Kinetic Analysis of Thermogravimetric Data, *J. Appl. Polym. Sci.*, 28: 2887-2902 (1983)), the results given by the Kissinger method may be closer to the actual values. It is to be noted that both methods gave very close E values for steps II and III. This shows that the complexity of the polymer degradation at each stage played a segregated role in the accuracy of the models.

A complete study of the kinetic behavior and use of other models may help clarify the degradation process of the PUs. In the last decomposition stage ($\alpha=0.7-0.9$), the E values calculated by Kissinger method were fairly high values (approximately 300 KJ/mol) close to the C—C bond dissociation energy of 348 KJ/mol suggesting a probable C—C bond cleavage (Darwent, B., *Bond dissociation energies in simple molecules*, [Washington] U.S. National Bureau of Standards, (1970)).

The stress vs. strain curves for the GIII-PU plastic sheets with different OH/NCO molar ratios are shown in FIG. 52. In the case of GIII-PU plastic sheet with OH/NCO molar ratio 1.0/1.0, the tensile strength at break was 14±2 MPa and maximum elongation was 75±10%. GIII-PU plastic sheet with OH/NCO molar ratio 1.0/1.1 displayed a yield point with yield strength 18±1 MPa followed by a slight decrease and then increase until break at elongation of 39±3%. GIII-PU plastic sheet with OH/NCO molar ratio 1.0/1.2 was more rigid but brittle with tensile strength at yield 32±2 MPa and elongation at break of 8±1%. Again this was probably due to the excess of aromatic content in this series as mentioned before. Since $T_g$ (23° C.) of the GIII-PU plastic sheet with OH/NCO molar ratio 1.0/1.0 coincided with the measuring temperature (25° C.), this polymer behaved as a hard rubber. The other two types of plastic sheets with $T_g$ around 40° C. had typical mechanical properties of rigid plastics (Petrovic, Z. S., W. Zhang, and I. Javni, Structure and properties of polyurethanes prepared from triglyceride polyols by ozonolysis, *Biomacromolecules*, 6: 713-719 (2005)).

Two types of PUs, elastomers and rigid foams, were prepared by mixing GII-Polyol (produced by the process of Example 2) or GIII-Polyol (produced by the process of Example 7) with appropriate diisocyanates, using the procedure as described in Example 4. The resulting samples are referred to as GII-PU and GIII-PU for the samples obtained with GII-Polyol and GIII-Polyol, respectively. Further details are provided in Example 11. The parameters of the polyols and diisocyanate used in the formulations to prepare the polyurethanes are listed in Table 11.

TABLE 11

Parameters of the polyols and diisocyanate used in the formulations to prepare polyurethanes. Errors are standard deviations; n = 3.

| | Equivalent weight (g/mole) | OH number (mg KOH/g) | Acidity number (mg KOH/g) |
|---|---|---|---|
| GII-Polyol | 368 | 152.4 ± 0.3 | 22.9 ± 0.3 |
| GIII-Polyol | 239 | 235.2 ± 4.6 | 15.8 ± 2.1 |
| HDI | 183 | | |
| MDI | 133 | | |

As can be seen, the hydroxyl number of GIII-Polyol was very close to the theoretical maximum value and much higher than that of GII-Polyol. The lower hydroxyl value obtained for the GII-Polyol may be due to an incomplete ozonolysis reaction at the end of which all the double bonds did not cleave on all the fatty acid chains. Moreover, for this generation of polyols, the hydrogenation process that follows produced more saturated TAGs which significantly affect the properties of produced PU.

To our knowledge, the cross-linking densities ($v_e$) of foams could not be calculated reliably by applying the known theories due to the effect of cellular structures. For elastomers however, $v_e$ can usually be estimated from equilibrium modulus of networks based on rubber-elasticity theory.

The equilibrium modulus of networks were investigated by creating master curves of the storage modulus vs. frequency following the time-temperature superposition principle (Ferry, J. D., *Viscoelastic Properties of Polymers*, New York chap 11, (1980)) using $T_g+5°$ C. as the reference temperature. FIG. 53 shows the master curve of E' at a reference temperature of 20° C. for GIII-PU elastomers as an example. The extended frequency range obtained by the superposition was $10^{-5}$ to $10^9$ Hz. The pseudo-equilibrium modulus of the cross-linking network, G' (G'=E'/3), is related to $v_e$ through Eq. (1). ρ was determined according to ASTM D 792-00 standards and assumed to be a constant when the $M_c$ was calculated. The results are listed in Table 12.

(Javni, I., W. Zhang, and Z. S. Petrovic, Soybean oil based polyisocyanurate cast resins, *Journal of Applied Polymer Science*, 90: 3333-3337 (2003)).

The glass transition of a polymer network is affected by cross-linking density and chemical structure as well. The increase of $T_g$ (~20° C. for GII-PU elastomers and ~3° C. for

TABLE 12

$T_g$ (° C.) obtained by DSC and DMA, density and parameters of cross-linking networks of the polyurethane elastomers.

| | $T_g$ (° C.) from DSC | $T_g$ (° C.) from DMA | E'(MPa)* | ρ at 23° C. (g/cm³) | $v_e$ (mol/cm³) | $M_c$ (g/mol) |
|---|---|---|---|---|---|---|
| GII-PU elastomers | −9.6 ± 1.0 | −5.3 ± 0.6 | 8.0 | 1.112 | $1.0 \times 10^{-3}$ | 1066 |
| GIII-PU elastomers | 8.3 ± 0.6 | 15.0 ± 0 | 10.1 | 1.110 | $1.4 \times 10^{-3}$ | 803 |

*E' at rubbery plateau from master curve

GIII-PU elastomers had larger $v_e$ and smaller $M_c$ confirming that polyols with higher functionality are more efficient at building network structure than those with lower functionality. Furthermore, the saturated fatty acids in GII-Polyol act as dangling chains causing significant steric hindrance to cross-linking which resulted in lower $v_e$ in the produced PU. As will be discussed later, cross-linking densities play an important role in the physical and mechanical properties of the PU networks.

The dynamic mechanical properties of both PU elastomers and foams were investigated as a function of temperature starting in the glassy state, through glass transition, and well into the rubbery plateau of each materials. The storage modulus measured at frequency of 1 Hz for PU elastomers and foams with different polyols are shown in FIG. 54(*a*) and FIG. 54 (*b*), respectively. For both elastomers and foams, the storage modulus dropped first gradually then exhibited a relatively rapid drop around −90° C. to −70° C. attributed to the β-transition (indicated by arrows in the figures), followed by another large drop during the transition from glassy to rubbery states. The storage moduli of the GII-PU decreased slightly with increasing temperature, while that of GIII-PU dropped abruptly in the glass transition region. In the glassy state, stiffness is related to changes in the stored elastic energy upon small deformation as the molecular segments resist motion.

The GII-PU with lower $v_e$ appeared less able to resist segmental motion and thus were not capable of storing elastic energy, resulting in a lower glass modulus than those of GIII-PU.

$T_g$ values for both elastomers and foams determined from the inflection point of E' vs temperature from DMA measurements are listed in Table 12 and Table 13, respectively. The $T_g$s of the PU elastomers were also determined by modulated DSC from the shift of heat capacity with temperature (see FIG. 55) and listed in Table 12 as well. No $T_g$ was observed in the case of PU foams with modulated DSC, because the recorded signal was very weak and did not reveal its existence.

The $T_g$ values determined by DSC and DMA showed the same trend: the $T_g$s of GIII-PU elastomers were about 20° C. higher than those of GII-PU elastomers. However, the values obtained from DMA were somewhat higher than those obtained by DSC which was due to the frequency effect GIII-PU foams) indicated that the flexibility of the polymer chains was reduced for the higher cross-linked networks shifting the rubbery state to higher temperatures. This could be explained by the high value of the cross-linking density $v_e$ for the GIII-PU sample as mentioned earlier. In addition, the dangling chains in GII-PU sample act as plasticizers which reduce the polymer rigidity and increase the flexibility, resulting in lower $T_g$ as well.

Plots of loss modulus (E") vs. temperature for the PU elastomers and foams are given in FIG. 56(*a*) and FIG. 56(*b*), respectively. A weak β-transition in the range −90° C. to −70° C. was observed for all the samples, which may be related to the movements of a chain part containing the urethane group attached to cross-linker (Czech, P., L. Okrasa, G. Boiteux, F. Mechin, and J. Ulanski, Polyurethane networks based on hyperbranched polyesters: Synthesis and molecular relaxations, *J. Non-Cryst. Solids*, 351: 2735-2741 (2005)) or to the motion of the backbone chain of the short groups in the fatty acid chains (Nielsen, L. E., and R. F. Landel, *Mechanical properties of polymers and composites*, 2nd edition, Marcel Dekker, New York, USA., Chap. 4., (1994)).

In the case of GIII-PUs, the strong peak in the loss modulus curve, which is associated with glass transition, appeared to be narrower, indicating a narrower distribution of cross-linking density. The β-transition has also been detected in other PUs (S. S. Narine, X. Kong, L. Bouzidi and P. Sporns, (In Press, January 2007), *Physical Properties of Polyurethanes Produced from Polyols from Seed Oils: I Elastomers*, J. Am. Oil Chem. Soc.; S. S. Narine, X. Kong, L. Bouzidi and P. Sporns, (In Press, January 2007), *Physical Properties of Polyurethanes Produced from Polyols from Seed Oils: II Foams*, J. Am. Oil Chem. Soc. and Petrovic 2005 Biomacromolecules 713) as well.

The network homogeneity for each PU may also be analyzed from the width of glass transition peaks in tangent δ (tan δ) curves (Son, T. W., D. W. Lee, and S. K. Lim, Thermal and phase behavior of polyurethane based on chain extender, 2,2-bis-[4-(2-hydroxyethoxy)phenyl]propane, *Polym. J.*, 31: 563-568 (1999)). The temperature dependence of tan δ from DMA for PU elastomers is given in FIG. 57 as an example.

The full width at half maximum (FWHM) of tan δ peak for GIII-PU elastomers, around 16° C., was much less than that of GII-PU elastomers, around 28° C. The broader peak width at half-height of tan δ peak for GII-PU elastomers indicated a wider distribution of network structures, which was due to the heterogeneities in the molecular weight between crosslink joints resulting from the heterogeneous nature of GII-Polyols as described elsewhere (S. S. Narine, J. Yue and X. Kong (In Press, February 2007), *Production of Polyols from Seed Oils and their Chemical Identification and Physical Properties*, J. Am. Oil Chem. Soc.).

The stress vs. strain curves for PU elastomers are shown in FIG. 58. GIII-PU elastomers displayed a higher Young's modulus, higher tensile strength and larger elongation at break (9.9±0.3 MPa, 6.9±0.1 MPa and 69±4% respectively) than those of GII-PU elastomers (5.7±0.2 MPa, 2.1±0.2 MPa and 44±3% respectively). Third generation PU elastomers exhibited better mechanical properties, which was due to the homogeneous nature of GIII-Polyols and therefore, the higher cross-linking density and narrower distribution of polymer network.

The results of compressive stress-strain testing for PU foams are depicted in FIG. 59. The plots can be divided into two regions, covering the strain range achieved; at low stress and for a resultant strain up to about 5%, both samples demonstrated near linear elastic behavior characterized by the Young's modulus (values are given in Table 13). Beyond the elastic limit, both specimens underwent plastic collapse of the cells (Gibson, L. J., M. F. Ashby, *Cellular solids: structure and properties*, Oxford; New York: Pergamon Press, 1988, (1988)) which appeared on the plots as along a region over which there was a slow increase in stress with increasing strain.

TABLE 13

$T_g$ (° C.) and compressive properties of polyurethane foams

|  | GII-PU foams | GIII-PU foams |
|---|---|---|
| $T_g$ (° C.) | 58.2 ± 0.6 | 61.3 ± 0.5 |
| Compressive strength (KPa) | 770 ± 145 | 1014 ± 36 |
| Modulus (MPa) | 22.2 ± 7.5 | 23.2 ± 2.3 |

The Young's modulus and another interesting parameter, i.e. compressive strength, were calculated according to the ASTM D1621-00 standard. With a density of 160 kg/m$^3$, the GII-PU foam had a compressive strength of 770±145 KPa and a modulus of 22.2±7.5 MPa. With the same density, the GIII-PU foam yielded higher compressive strength (1014±36 KPa) and modulus (23.2±2.3 MPa).

The dependence of both the compressive strength and the modulus of a cellular foam can be understood in terms of the mechanical properties of the polymer material from which the cell walls are made and from the size and shape of the cells themselves. The lower compressive strength of GII-PU foams was the result of the plasticizing effect of the dangling chains combined with the lower cross-linking density of the networks of the cell walls. Furthermore, the mechanical properties were affected by the cellular structures, such as diameter, diameter distribution, and shape of the cells as well, which will be discussed later.

Scanning electron micrographs of the PU foams were taken in low magnification to observe any distinct differences in the cellular structure. From these micrographs, important parameters as the mean cell size and the overall cell shape are usually obtained. Micrographs of GII-PU foam and of GIII-PU foam are shown in FIG. 60(*a*) and FIG. 60(*b*) respectively. The GII-PU foam had a cell size of approximately 500 µm, and was less uniformly distributed with relatively thick cell walls whereas GIII-PU foam had a cell size about 250 µm, uniformly distributed with smooth cell walls. The heterogeneous cellular structure and the less strong material from which the walls were made, led to poor mechanical properties in the case of GII-PU foam.

In summary, the lower functionality of GII-Polyols and therefore, the lower cross-linking density of its polymer network, combined with the presence of saturated TAG dangling chains acting as plasticizers, were the main reasons for the lower $T_g$ and poorer mechanical properties of GII-PU.

In another aspect of the invention, an alternate method for the production of hydroxyl wax esters via a step-wise reaction process has been developed. As previously noted, the formed transesterification product II of FIG. 15, namely nonyl-9-hydroxynonanoate (hydroxyl ester), was a hydroxyl wax ester. It is a member of a very important class of compounds used in cosmetics, lubricants, polishes, surface coatings, inks and many other applications. It is of great significance to realize the potential of the reaction processes of the invention to be tailored for the production of wax esters.

A method has been developed for the production of hydroxyl wax esters from a renewable feedstock comprising one or more unsaturated fatty acid triacylglycerols, wherein the method comprises the steps of:

a. ozonolysis of the double bonds in the unsaturated fatty acids of the one or more triacylglycerols of the feedstock;

b. subjecting the products of step (a) to reductive hydrogenation to produce at least one corresponding mono-ol, at least one corresponding polyol, or a mixture thereof, wherein the at least one mono-ol, the at least one polyol, or the mixture thereof comprises a triacylglycerol containing at least one terminal hydroxyl group; and c. subjecting the products of step (b) to transesterification with a short chain alcohol to produce said hydroxyl wax ester.

The foregoing method has been used to synthesize nonyl-9-hydroxynonanoate, and details are provided in Example 9 below. FIG. 61 illustrates the synthesis of this compound. It will be understood to those skilled in the art that a variety of hydroxyl wax esters can be produced using this method. A variety of feedstocks can be used for polyol production, including canola, flax, soybean and palm oils, and a variety of short chain alcohols including nonanol, hexanol, propanol, and 1,3-propanediol, etc. can be used to produce the hydroxyl wax esters.

To confirm the expected reaction products, flash chromatography was performed to collect the pure product and its structure was analyzed by IR, $^1$H-NMR, $^{13}$C-NMR and Electron Spay Mass spectrometry.

The FTIR spectrum of nonyl-9-hydroxynonanoate is shown in FIG. 62. The 3446.3 cm$^{-1}$ characteristic hydroxyl group stretch and 1737.5$^{-1}$ carbonyl group of ester are obvious. In $^1$H-NMR the integrations of protons are matching with its structure, and the peaks were assigned and labeled in the FIG. 63 and FIG. 64. In Mass spectrometry (FIG. 65), the peaks at 301.3 and 323.3 correspond to the protonated and sodium adduct of nonyl-9-hydroxynonanoate.

In another aspect of the invention, designer polyols were produced by using optimal conditions of ozonolysis and hydrogenation process as described in Example 7 and fixing ozonolysis time to 30 min, 40 min, 50 min, 60 min and 70 min. The obtained polyols are referred to as Polyol-30 min, Polyol-40 min, Polyol-50 min and Polyol-60 min. The content (in percentage mass) of triol, diol and mono-ol of these polyols and hydroxyl and acidity number are listed in Table 14.

TABLE 14

Composition and hydroxyl and acidity number of Designer Polyols. Maximum values theoretically obtainable when producing polyol with 3 primary alcohols from canola oil[1] are added for comparison.

| | Polyol-30 min | Polyol-40 min | Polyol-50 min | Polyol-60 min | Theoretical |
|---|---|---|---|---|---|
| Triol (%) | 16.8 ± 0.2 | 30.2 ± 0.8 | 50.6 ± 0.3 | 60.2 ± 1.2 | 75 |
| Diol (%) | 45.8 ± 0.8 | 46.8 ± 1.3 | 34.5 ± 1.1 | 26.0 ± 0.5 | 22 |
| Mono-ol (%) | 20.3 ± 1.1 | 14.1 ± 0.7 | 8.4 ± 0.1 | 4.7 ± 0.1 | 1 |
| Hydroxyl No. (mg KOH/g) | 163 ± 3 | 205 ± 4 | 225 ± 4 | 235 ± 5 | 251 |
| Acidity No. (mg KOH/g) | 6.1 ± 0.1 | 7.4 ± 0.3 | 9.1 ± 0 | 15.8 ± 2.1 | |

[1]. Neff, W. E., T. L. Mounts, W. M. Rinsch, H. Konishi, and M. A. Elagaimy, Oxidative Stability of Purified Canola Oil Triacylglycerols with Altered Fatty-Acid Compositions as Affected by Triacylglycerol Composition and Structure, J. Am. Oil Chem. Soc., 71: 1101-1109 (1994)

The content of triol and the final hydroxyl number increased with increasing ozonolysis time and reached its maximum value for $t_{ozonolysis}$=60 min. The highest hydroxyl number was 94% of the maximum value theoretically obtainable when producing polyols with 3 primary alcohols from canola oil (Neff, W. E., T. L. Mounts, W. M. Rinsch, H. Konishi, and M. A. Elagaimy, Oxidative Stability of Purified Canola Oil Triacylglycerols with Altered Fatty-Acid Compositions as Affected by Triacylglycerol Composition and Structure, J. Am. Oil Chem. Soc., 71: 1101-1109 (1994)). When increasing ozonolysis time, more double bonds on the fatty acid chains were cleaved leading to the production of more triol and less saturated (TAG), mono-ol and diol. The optimal yield of triol was achieved for 60 min ozonolysis (60.2% close to 75% theoretically possible). When ozonolysis time was further increased to 70 min, the ozonide tended to hydrolyze in the presence of ozone and oxygen to produce carboxylic acid which cannot be hydrogenated, which resulted in higher acid content. The polyol obtained using 70 min ozonolysis time was therefore discarded. No PU was made with it.

As expected, and due to hydrogen bonding induced by hydroxyl groups, the polyols with higher hydroxyl number demonstrated higher viscosities. The viscosity of the polyols decreased with increasing temperature (FIG. 66) as expected for such materials.

Polyols synthesized from canola oil by ozonolysis and hydrogenation based technology as per the general procedure as set out in Example 7 using ozonolysis times of 30 min, 40 min, 50 min, 60 min were reacted with aliphatic diisocyanates to produce polyurethane (PU) elastomers. Further details regarding methods for carrying out the procedure are set out as in Example 4. The polyol obtained using ozonolysis time of 70 min was not suitable to produce (PU) elastomer.

The glass transition temperatures ($T_g$s) of the PU samples were determined using DSC and DMA. The DSC curves of the PU elastomers shown in FIG. 67 display a single feature attributed to a glass transition. $T_g$ was determined from the shift of heat capacity with temperature. Changes in the storage (E') and loss (E") moduli with temperature, obtained from DMA carried out at frequency of 1 Hz on the PU elastomers are shown in FIG. 68 and FIG. 69 respectively. The $T_g$ value as determined from the inflection point of E' vs. temperature obtained from DMA measurements were higher than those determined by DSC (see Table 15) by about 2 to 5° C. as generally found in the literature. The trend is however the same: the lowest $T_g$ was recorded for the PU-30 min elastomer and the highest $T_g$ was recorded for the PU-60 min elastomer.

The glass transition of a polymer network is affected by cross-linking density. PU-60 min elastomers has the highest $T_g$ because polyol-60 min has the highest hydroxyl number and triol content which resulted in the highest crosslinking density.

TABLE 15

$T_g$ (° C.) obtained by DSC and DMA of the polyurethane elastomers prepared from polyols with different ozonolysis time.

| | DSC (° C.) | DMA (° C.) |
|---|---|---|
| PU-30 min elastomers | −0.6 ± 0.2 | 1.5 ± 0.4 |
| PU-40 min elastomers | −0.8 ± 0.6 | 4.0 ± 0.6 |
| PU-50 min elastomers | 1.3 ± 0.6 | 6.7 ± 0.6 |
| PU-60 min elastomers | 7.7 ± 0.6 | 13.7 ± 0.6 |

The stress vs. strain curves for PU elastomers prepared by using polyols with different ozonolysis time are shown in FIG. 70. PU-60 min elastomer displayed the highest Young's modulus, the highest tensile strength and largest elongation at break (9.5±0.6 MPa, 5.7±0.7 MPa and 57±7% respectively). PU-60 min elastomers exhibited better mechanical properties because of the homogeneous nature of Polyol-60 min and the subsequent higher cross-linking density and narrower distribution of polymer networks.

Polyols synthesized from canola oil via ozonolysis and hydrogenation methods and using ozonolysis times of 30 min, 40 min, 50 min, 60 min as described herein were prepared using the same general procedure as set out in Example 7. The so produced polyols were reacted with aromatic diisocyanates (MDI) as set out in Example 10 to produce polyurethane (PU). Polyols obtained using ozonolysis time of 70 min were not suitable to produce PUs.

$T_g$s of the PU were obtained with DSC and DMA (FIG. 71 and FIG. 72). The results are listed in Table 16. The highest $T_g$ was observed for the PU-60 min indicated that the flexibility of the polymer chains was reduced for the higher cross-linked networks shifting the rubbery state to higher temperatures. This could be explained by the highest cross-linking density for the PU-60 min sample as it has the highest triol content. For the other PUs, $T_g$ decreased as a result of increasing mono-ol and saturated TAGs content when ozonolysis time was decreased. It is known that mono-ol acts as a chain terminator when polyol is crosslinked with diisocyanate to produce polyurethane and that the saturated TAGs which are not involved in the reaction act as plasticizers which reduce polymer rigidity and increase the flexibility.

TABLE 16

T$_g$ (° C.) obtained by DSC and DMA of the polyurethane prepared from polyols with different ozonolysis time using the same procedure as set out in Example 7.

|  | DSC (° C.) | DMA (° C.) |
|---|---|---|
| PU-30 min | 5.0 ± 1.6 | 11.0 ± 1.4 |
| PU-40 min | 7.5 ± 1.0 | 14.3 ± 0.4 |
| PU-50 min | 16.8 ± 1.7 | 22.7 ± 2.6 |
| PU-60 min | 34.3 ± 0.6 | 41.3 ± 0.6 |

The stress vs. strain curves for the PU prepared by using polyols with different ozonolysis time are shown in FIG. 73. In the case of PU-30 min, the tensile strength at break was 5.2±0.4 MPa and maximum elongation was 123±5%. PU-40 min was harder with tensile strength at break of 16.7±2.5 MPa and maximum elongation of 100±4%. PU-50 min was more rigid with largest tensile strength at break (23.2±0.6 MPa). PU-60 min displayed a yield point with yield strength 21.0±1.0 MPa followed by a slight decrease and then increase until break at elongation of 29±3%.

Both PU-30 min and PU-40 min behaved as elastomers with T$_g$s much lower than the measuring temperature (room temperature was 25° C.). T$_g$ (23° C.) of the PU-50 min coincides with the measuring temperature indicating a hard rubber behavior. PU-60 min with T$_g$ around 40° C. had typical mechanical properties of rigid plastics.

The properties of the PU-60 min are attributable to the high density of crosslinks produced because of the high hydroxyl number of the starting polyol. The high density of crosslinks hindered molecular motion, increasing the rigidity. The low strength and modulus of PU-30 min was the result of imperfections in the final polymer network due to the large amount of dangling chains that the starting polyol contained.

The PUs obtained using the designer polyols described herein, range from soft to hard with a very wide range of mechanical properties. It is now demonstrated that by adjusting processing conditions, one can control the number of the double bonds that can be cleaved and therefore tailor the process to prepare "designer" polyols which can be used to prepare Designer PUs with specific physical properties.

Embodiments of the invention are described by reference to the following specific examples which are not to be construed as limiting.

EXAMPLES

Materials

Triolein (minimum 95% purity) and the Raney nickel 2800 (slurry in water) catalyst were obtained from Sigma-Aldrich Co. Tristearin was obtained from Applied Science Laboratories. Pentane, glacial acetic acid, ethyl ether, anhydrous sodium sulfate, Celite, dichloromethane (HPLC grade), heptane (HPLC grade), 2-propanol (isopropanol, HPLC grade), ethyl acetate and hexane were all obtained from Fisher. Tetrahydrofuran was obtained from Caledon and certified grade Tetrahydrofuran (THF) was purchased from Fisher Scientific, USA. Elemental zinc powder was obtained from Merck. Silica gel (230-400 mesh) was obtained from Rose Scientific Ltd, Alberta. Si-Diol Silica Gel (230-400 mesh) and the aluminum backed TLC plates (250 µm thickness) were obtained from Silicycle Chemistry Division, Quebec. All chemicals were reagent grade or better.

The canola vegetable oil used in this study was from a sample of "100% Pure Canola" supplied by Canbra Foods Limited, Lethbridge, Alberta, Canada and the flax vegetable oil was a sample of "Superb Flax Oil" supplied by Archer Daniels Midlands. Their main fatty acid profiles (Firestone, D., Editor, in *Physical and Chemical Characteristics of Oils, Fats, and Waxes*, AOCS press, Washington, D.C., 1999) are displayed in Table 17. Canola and flax oils are predominantly constituted of more than 90% of unsaturated fatty acids. Canola oil contains about 60% oleic acid, whereas flax oil contains over 50% of the more unsaturated linolenic acid.

TABLE 17

Fatty acid composition of canola and flax oil in weight %.

| Fatty acid | Canola (wt %) | Flax (wt %) |
|---|---|---|
| Oleic (C18:1 n9c) | 56.11 | 18.88 |
| Linoleic (C18:2 cc) | 21.01 | 16.10 |
| Linolenic (C18:3 n3c) | 7.89 | 53.73 |
| Palmitic (C16:0) | 4.09 | 5.48 |
| Stearic (C18:0) | 1.86 | 3.52 |

The gases used for the reactions were 99.5% Extra Dry Grade 2.6 oxygen gas and 99.995% pre-purified Grade 4.5 hydrogen gas, both from Praxair.

Example 1

Preparation of Polyols from Triolein (GI-Polyol)

Step A—Ozonolysis

Triolein (15 g) was dissolved in 150 mL of pentane and brought to −10° C. in a 500 mL three-necked flask using an external 50:50 mixture of glycol water from a Jeiotech VTRC-620 temperature bath from Rose Scientific. Ozone was produced in an Azcozon ozone generator Model number RMV16-16 from Azco Industries Ltd. In an attempt to minimize acid production the ozone treatments (10 min of air flow) were alternated with a nitrogen purge (5 min) at a gas flow rate of 5 L/min. These alternate gas flows were carried out seven times with the final nitrogen purge taking 20 min. The total ozonolysis time was therefore 70 min and the total nitrogen purging 50 min. During the gas flow pentane evaporated so it became necessary to continually top up the solvent level. In total, an additional 350 mL of pentane was required over the entire ozonolysis. The additional pentane was all added prior to the final nitrogen purge when the solution was allowed to warm to room temperature to remove any remaining ozone.

The remaining residue was quenched with 18 mL of glacial acetic acid and 6.65 g of zinc in the presence of constant agitation using a stir bar over a period of 10 minutes. During this addition the temperature was maintained lower than 30° C. with an ice bath and after 40 min the reaction mixture was dissolved in ethyl ether (150 mL). The ether layer was washed twice with 70 mL of deionized water and the remaining organic layer dried over anhydrous sodium sulfate. Finally the solvent was removed on a flash evaporator (Heidolph Laborota 4001) to yield 15.7 g of a viscous yellow oil.

Step B—Hydrogenation

The yellow oil from the ozonolysis step (15.7 g) was dissolved in 250 mL of tetrahydrofuran and 1.6 g of nickel catalyst added into a 2L Parr Instrument Co hydrogenation vessel fitted with a magnetic drive. This mixture was flushed 3 times (10 min for each) with nitrogen at 200 psi pressure. The reactor vessel was charged with hydrogen gas at 460 psi at room temperature and the temperature was increased over 15 min to 92° C. with a concomitant increase in pressure to 597 psi. The hydrogenation reaction was carried out at this temperature for 2 h and 10 min and then the temperature was reduced to room temperature with cooling water and a final pressure of 455 psi. The hydrogen was purged from the hydrogenation vessel with nitrogen gas. The remaining mixture was filtered over Celite and (about 3 mL) aqueous layer removed in a separatory funnel. The organic layer was concentrated on a flash evaporator.

To insure complete hydrogenation the above procedure was repeated. The remaining material was dissolved in 300 mL of tetrahydrofuran with 2.4 g of nickel catalyst added. After flushing with nitrogen the reactor vessel was charged with 410 psi of hydrogen and the temperature increased to 120 C. This reaction was carried out for 4 h and 15 min followed by a reduction in temperature (final psi of 408); flushed with nitrogen; filtered; water removed, and the remaining organic layer concentrated on a flash evaporator to a light yellow oil (11.4 g).

Step C—Column Chromatography

A column of dimensions 1.3 id×30 cm was packed with 11.02 g (about 17 mL volume) of Si-Diol silica gel. Material from the second hydrogenation (0.65 g) was dissolved in 7 mL of dichloromethane and 2 g of the Si-Diol silica gel added. The solvent was then removed with a flash evaporator and this material poured on top of the silica column. The column was then eluted with 50 mL heptane; 50 mL heptane containing 4% (v/v) isopropyl alcohol (IPA); 50 mL of heptane containing 8% IPA; 200 mL of heptane containing 12% IPA and finally, 100 mL of heptane containing 16% IPA. The column required about 14 mL of heptane to completely wet it. The fractions were collected as follows 1-19 (5 mL fractions; 20-43 (3 mL fractions) and 44-92 (5 mL fractions).

The presence of material was confirmed in fractions by thin layer chromatography (TLC) on silica gel plates using a solvent system of 10% ethyl acetate and 90% hexane (v/v). Spots were visualized using a 5% sulfuric acid in methanol dip followed by charring with a heat gun. On the basis of TLC and HPLC analysis fraction 76 was isolated and evaporated for further spectroscopic analysis.

Step D—HPLC System

The HPLC system developed was a modification of the procedure used by Elfman-Borjesson and Harrod (6 Elfman-Borjesson, I. and M. Harrod, Analysis of Non-Polar Lipids by HPLC on a Diol Column. *J. High Resol. Chromatogr.* 20: 516-518 (1997)) for analysis of lipid derivatives. The HPLC system consisted of a dual Milton Roy pump with a 20 μL auto-injector. The column was a Betasil Diol-100 (5 μm particle size) 250×4 mm produced by Thermo Hypersil-Keystone and maintained at 50° C. with a Biorad column heater. The detector was a Sedex SS SEDERE evaporative light scattering system maintained at 100° C. with a gain setting of 10 (on the 12 unit scale) and a nitrogen pressure of 2 bar.

A run consisted of a linear gradient of 100% heptane to 1:1 heptane, isopropyl alcohol in 30 min.; then back to 100% heptane in 10 minutes at a flow rate of 3 ml/min.

Step E—NMR and Mass Spectrometry

Spectral Data for Fraction 76. $^1$H NMR (CDCl$_3$) δ 5.27 (m, 1H), 4.30 (m, 2H), 4.16 (m, 2.5H), 4.05 (t, 1H), 3.65 (t, 5H), 2.30 (m, 7.5H), 2.03 (s, 4H), 1.60 (br m, 13.5H), 1.35 (br s, 28.5H). ESI (mass spectroscopy arbitrary ion intensity in brackets) m/z 583.4 (100%); 561.4 (60%), 739.6 (11%), 427.3 (9%), 717.6 (4%). Accurate mass spectroscopy m/z found 561.39933. Calculated for C$_{30}$H$_{57}$O$_9$ (protonated "triol") 561.39971. [NMR for Tristearin. $^1$H NMR (CDCl$_3$) δ 5.27 (m, 1H), 4.29 (m, 2H), 4.15 (m, 2H), 2.31 (m, 6H), 1.62 (m, 6H), 1.35 (br s, 84H), 0.95 (t, 9H)].

Example 2

Preparation of Polyols from Canola Oil (GII-Polyol)

Ozonolysis Reactor

The reactor 10 presently disclosed offers an improvement over prior art ozonolysis vessels, such as those utilized by Lin, S. H. and Wang, C. H. (Industrial wastewater treatment in a new gas-induced ozone reactor, *Journal of Hazardous Materials*, 98 295-309,(2003)) illustrated in FIG. 41 (Prior Art). The reactor of the present invention is fed with a motor 28, such as a Direct Current Permanent Magnet 1 HP Motor from Leeson electric-corporation, USA. The water, which temperature is controlled by a chiller, is rushed into the outer layer 14 of the reactor (entry labelled "H$_2$O in"; 16), circulated around the reaction vessel 12 and evacuated (labelled "H$_2$O out"; 18). The water is kept flowing during the reaction to keep the reaction system at a constant temperature. Ozone is generated in an ozone generator (such as Azcozon Model RMV16-16 from Azco Industries Ltd, Canada) with oxygen or air as the feed gas, and introduced into the reactor from the two apertures for ozone input at opposing ends of an ozone inlet channel 24 (the apertures being labelled as "O$_3$, O$_2$ in" (20) and "O$_3$, air in" (22) in FIG. 39). The ozone inlet channel 24 is disposed at the lower end of the reaction vessel 12 and extends across the diameter thereof. The gas is released from the ozone inlet channel 24 into the reaction vessel 12 through a plurality of pores 26, which are evenly spaced across the length of the ozone inlet channel 24. The non-return valves 36 prevent backflow of the reaction solution to the two apertures for ozone input (20, 22) and the aperture for nitrogen input, 38.

The two apertures for ozone input, 20 and 22, and the pores 26 in the ozone inlet channel 24, provide for substantially uniform distribution of ozone throughout the reaction vessel 12. This improved distribution of ozone increases the effectiveness of the ozonolysis reaction, allowing for shorter reaction times, higher reaction temperatures, and increased homogeneity of end products. This arrangement differs from prior art ozonolysis vessels, such as the embodiment illustrated in FIG. 41, which only have a single aperture for ozone input.

The magnet motor 28 is connected to a longitudinally disposed agitator 30 which extends into the reaction vessel 12. The motor 28 is kept rotating at high speed during the reaction. The agitator 30 comprises a plurality of pitched blades 32, which may be fixedly mounted or releasably mounted to the agitator 30 by means known to those skilled in the art. In one embodiment, the blades 32 may be welded to the agitator 30. In one embodiment, the blades 32 are trapezoidal in shape, which reduces the resistance. In another embodiment, the blades 32 are attached to the agitator 30 at an angle of from about 30 degrees to about 60 degrees. Such an angle of attachment has been found to reduce vortex formation and increase the rate of reaction. In yet another embodiment, the blades 32 contain a plurality of holes 34, which increase contact areas between the reagents and further reduce vortex formation. FIGS. 40(*a*) and 40(*b*) illustrate the blades 32 in greater detail in accordance with one embodiment of the invention. The plurality of pitched blades are oriented such as to direct the contents of said reaction vessel downward toward the ozone inlet channel.

Thus, in the reactor vessel of the current invention, the apertures for ozone input 20 and 22, the ozone inlet channel 24, the pores 26 within the ozone inlet channel 24, as well as the rotating blades 32 have been designed to ensure thorough contact and full reaction of ozone with the starting material.

In one embodiment, the blades 32, agitator 30, and reaction vessel 12 may be made of stainless steel, such as SS 316 L.

In one embodiment of the present invention, the reactor has the following characteristics, which are presently described by way of example and should not be interpreted as limiting. It has been found that a reaction vessel 12 having a volume of 1727 cm$^3$ (diameter=10 cm; height=22 cm) can accommodate 200 g of starting material (vegetable oil) in 1000 mL of solvent. The ozone inlet channel 24 comprises twelve pores 26 evenly spaced at 0.8 cm apart, wherein the pores have a diameter of 0.8 mm. The agitator 30 has six blades 32 having the dimensions illustrated in the embodiment shown in FIG. 40(a), and the blades 32 contain six holes 34 having a diameter of 0.3 cm. The angle of attachment of the blades 32 to the agitator 30 can vary from about 30 degrees to about 60 degrees. The blades 32, agitator 30, and reaction vessel 12 are made of SS 316 L.

Step A—Ozonolysis

Canola oil (100 g) and deionized water (400 g) were poured into a specially designed reactor (schematic shown in FIG. 39 and described above). The reaction was performed at 27° C., at 5 L/min O$_2$ flow rate and 80 rpm agitation rate. After 5 hours, the ozone generator was stopped and the reaction vessel was purged with N$_2$ for 10 minutes to remove the unreacted ozone from the vessel. 400 ml of tetrahydrofuran (THF) was then added into the vessel to dissolve the ozonide product. The product was then transferred to a separatory funnel where the organic part was collected for the hydrogenation step.

Step B—Hydrogenation 10.5 g of Raney nickel catalyst were added to the ozonide (490.8 g) in THF in a hydrogenation vessel (2L, Parr Instrument Co, USA) fitted with a magnetic drive. The reaction vessel was flushed 3 times with nitrogen at 200 psi pressure to remove the air and then was charged with hydrogen gas at 350 psi at room temperature. The temperature was increased over 30 minutes to 135° C. with a concomitant increase in pressure to 520 psi. The hydrogenation reaction was carried for 5 hours at this temperature and the pressure decreased with the consuming of hydrogen. The temperature was then reduced to room temperature with cooling water and to a final pressure of 290 psi. The unreacted hydrogen gas was removed from the reaction vessel with nitrogen gas. The remaining mixture was filtered over Celite and the aqueous layer removed in a separatory funnel To insure complete hydrogenation of the double bonds and ozonolysis products, the above procedure was repeated on the remaining organic material from the separatroy funnel. The final hydrogenation product was kept for distillation.

Step C—Gas Chromatography (GC)

To determine the amounts of short chain compounds present as by-products from the hydrogenation reaction, a Varian 3500 Capillary Gas Chromatograph equipped with a Flame Ionization Detector (GC-FID), a Varian 8200 Auto Sampler and a BP20025 column (30-m long, 0.25-mm internal diameter, and 0.25-µm thick silica wall) was used. The system was controlled with Varian's "Star Chromatography Workstation" software V.5.51. The injector and the detector temperature were fixed at 250° C. The temperature of the column initially set at 50° C. was increased to 250° C. in two successive steps: from 50° C. to 90° C. at a rate of 25° C./minute and from 90° C. to 250° C. at a rate of 10° C./minute.

Step D—Wiped-blade Molecular Distillation

The solvent was removed on a rotary evaporator (Heidolph Laborota 4001, UK) to yield a viscous yellow oil. GC analysis showed that the removed THF was 100% pure and no product was also removed with THF. The wiped blade molecular distillation unit (Model VKL 70/ICL-04, from Incon Processing) was set up at a jacket temperature of 115° C., and the temperature of the condenser 30° C. The pressure of the distillation system was reduced to 20 mTorr and the viscous oily product added into the distillation system through an addition funnel at a speed of 1 mL/min. After all the product had been added to the distillation system, the unit was kept running for 30 minutes, to allow the complete collection of the residue and distillate. Finally, distillate (31.1 g) and residue (47.0 g) were obtained. The distillate fractions from the flash evaporator and distillation were analyzed by GC, and the residue fraction analyzed by HPLC.

Step E—Flash Chromatography

A column of dimensions 3 id×30 cm was packed with 400 g (about 212 mL volume) of silica gel (230-400 mesh). Material from the residue fraction of distillation (4.3 g) was added. The column was then eluted under air pressure with gradient flow phase composed of hexane and ethyl acetate. The ratios (v/v) of hexane to ethyl acetate was started with 50:1, then gradually decreased to 20:1, 17:1, 10:1, 8:1, 5:1, 3:1, 2:1, 1:1, followed by 1:2, 1:3, 1:4. Finally pure ethyl acetate was used and the fractions were collected in 30 mL-test tubes. Ratios of flow phase of 20:1, 8:1, 2:1 and 1:4 were used on fractions 28-50, 131-143, 264-289, and 366-389 respectively. Thin layer chromatography (TLC) was run on each fraction using hexane and ethyl acetate as the developing system with ratios (v/v) of hexane and ethyl acetate of 3:1, 2:1, and 1:1. The glycerides and related compounds were detected by spraying the plates first with methanol containing 10% sulphuric acid (concentration 98%) and then heating them at 200° C. for 5 minutes.

Step F—High Performance Liquid Chromatography (HPLC)

The HPLC analysis protocol used was a modification of the procedure developed by Elfman-Borjesson and Harrod (Elfman-Borjesson, I. and M. Harrod, Analysis of Non-Polar Lipids by HPLC on a Diol Column. *J. High Resol. Chromatogr.* 20: 516-518 (1997)) for analysis of lipid derivatives. The HPLC system consisted of a dual Milton Roy pump with a 20 µL auto-injector. The column was packed by Betasil Diol-100 (5 µm particle size) 250×4 mm produced by Thermo Hypersi-Keytone and maintained at 50° C. with a Biorad column heater. The detector was an Alltech EDSL 2000 evaporative light scattering system maintained at 100° C. with a gain setting of 10 (on the 12 unit scale) and a nitrogen pressure of 2 bar. Two solvents were connected to the pump as the mobile phase. A was 100% heptane and B 50% heptane with 50% isopropyl alcohol (IPA). A run consisted of a linear gradient of 100% A to 83% A and 17% B in 30 min; then back to 100% A in 1 minute at a flow rate of 3 mL/min.

Example 3

Preparation of Polyols from Canola Oil and Flax Oil

Three grades of polyols were synthesized in this example: (i) polyols from canola oil using oxygen gas supply to generate the ozone, and referred to as canola-oxygen; (ii) polyols from canola oil using air supply to generate the ozone, and referred to as canola-air; and (iii) polyols from flax oil using air supply to generate the ozone, and referred to as flax-air.

Step A—Ozonolysis

The preparation of polyols from canola and flax was generally conducted as set out in the previous examples above. Briefly, the polyols were synthesized by ozonolysis of the vegetable oils followed by hydrogenation in the presence of a nickel catalyst. The ozonolysis was carried out in a reactor fed with ozone gas generated by a Model-RMU 16-16 generator from Azco Industries Ltd supplied either with air or oxygen. The hydrogenation was completed in a Parr-Pressure Reaction Apparatus (Parr Instrument Company Inc). The vessel temperature of the hydrogenator was controlled by a 4835-Parr controller. The distillation was carried out in a Model VKL 70/ICL-04 wipe-blade molecular distillation system from Incon Processing. The procedure was as follows: 100 g of triacylglycerol oil was mixed with 400 ml of de-ionized water in a high speed mixer and the mixture sonicated for 1 hr in a Sonic 300-Dismembrator sonicator at full power. The resulting solution was agitated at 500 rpm in the ozonolysis reactor vessel until the temperature of the vessel stabilizes at 0° C. This step took about 45 minutes to complete. The ozone generator was then supplied with air or oxygen at a constant flow rate of 5 L/min. The ozonolysis reaction was started by directly introducing the generated ozone gas in the reactor with the solution still agitated at 500 rpm. After about 8 hours, the water was removed and THF (or another suitable solvent) was added. The resulting solution was then transferred to the hydrogenation reactor where the reaction was carried out at 130° C. under pressure of 600 psi for about 8 hours. After the removal of the catalyst and the solvent, the hydrogenated crude was transferred to a wiped blade molecular distillation system to remove the short-chain by-products—i.e. the products were separated into a light fraction and a heavy fraction (polyols).

Step B—FTIR

The spectra were collected on a Nicolet Magna 750 spectrometer system, equipped with a room temperature MCT-B detector. The liquid samples were analyzed neat as a thin film between two KBr plates. The thickness of the film was manually adjusted to ensure that no peak absorbance was over 1.0 absorbance units. The spectra were recorded in the range 400-4000 cm$^{-1}$ with a nominal resolution of 4 cm$^{-1}$. A background spectrum of the clean, dry plates was first collected before each absorbance spectrum and 32 interferograms were co-added before Fourier transformation using Nicolet Omnic software.

Step C—GC

To determine the amounts of short chain compounds present as by-products of the ozonolysis and hydrogenation reactions, a Varian 3500 Capillary Gas Chromatograph equipped with a Flame Ionization Detector (GC-FID), a Varian 8200 Auto Sampler and a BP20025 column (30-m long, 0.25-mm internal diameter, and 0.25-μm thick silica wall) was used. The system was controlled with the Varian "Star Chromatography Workstation" software V.5.51. The injector and the detector temperature were fixed at 250° C. The temperature of the column initially set at 50° C. was increased to 250° C. in two successive steps: from 50° C. to 90° C. at a rate of 25° C./minute and from 90° C. to 250° C. at a rate of 10° C./minute.

Step D—HPLC

The molecular profile of the polyol products were obtained with a HPLC system using a modified procedure by Elfman-Borjesson and Harrod (11) for analysis of lipid derivatives. The HPLC system consisted of a dual Milton Roy pump with a 20 μL auto-injector. The column was a Betasil Diol-100 (5 μm particle size) 250×4 mm produced by Thenno Hypersil-Keystone and maintained at 50° C. with a Biorad column heater. The detector was an Alltech EDSL 2000 evaporative light scattering system maintained at 100° C. with a gain setting of 10 (on the 12 unit scale) and a nitrogen pressure of 2 bar. Two solvents reservoirs were connected to the pump as the mobile phase. Solvent A was 100% heptane and solvent B was 50% heptane with 50% isopropyl alcohol. A run consisted of a linear gradient of 100% A to 83% A and 17% B in 30 min.; then back to 100% A in 1 minutes at a flow rate of 2 mL/min.

Step E—Rheometric Measurements

The viscosities of the polyol samples were measured in shearing mode with the Universal Dynamic Rheometer PHYSICA UDS 200 (Paar Physica USA) with a constant shearing rate of 51.6 s$^{-1}$. The viscosities were recorded at 6 different temperatures, from 50° C. to 25° C. every 5° C. The viscosities were also measured at 25° C. as a function of time.

Step F—DSC

The "TA 2920 Modulated DSC" system from TA Instruments was used to study the thermal transitions of the polyols. The data sampling and temperature control procedures were fully automated and controlled by the "TA Instrument Control" software program and the data were analyzed using the "TA Universal Analysis" software. The procedure to record the crystallization and melting curves was as follows: Initially the sample was kept at 20° C. for 5 minutes to reach steady state and then was heated to 80° C. with a rate of 5° C./min to erase its thermal history. To record the crystallization curve, the sample was cooled down to −50° C. at a constant rate of 5° C./min and kept at this temperature for 5 minutes to allow the completion of the crystallization. The sample was then heated to 80° C. at a constant rate of 5° C./min to record the melting curve.

Step G—Refractometry

The refractive index of the materials was determined according to the ASTM method D1747-99, with a CARL Zeiss (Germany) refractometer.

Step H—Hydroxyl and Acidity Values

The hydroxyl numbers of the polyols were determined according to the ASTM titration method D1957-86 and the acidity values were determined according to the ASTM method D4662-98. Triplicate specimens were measured for each polyol and the average values and standard deviations are reported here.

Example 4

Polyurethane Produced from Polyols from Seed Oils

In this example, properties of PU elastomers and rigid foams prepared by reacting polyols synthesized from vegetable oils (canola, flax and soybean oils) and crude castor oil and two different classes of diisocyanate (aliphatic and aromatic diisocyanates) are described Using dynamic mechanical analysis (DMA), thermomechanical analysis (TMA), differential scanning calorimetry (DSC) and thermogravimetric analysis (TGA) techniques, their physical and thermal properties were studied and compared and the effect of the dangling chains assessed.

Step A: The canola and flax oil based polyols were synthesized by the method of Example 3, using air to generate the ozone. Soybean-based polyols with hydroxyl groups located in the middle of the fatty acid chains, were sourced from Urethane Soy Systems Company, IL. (USA). Soybean-based polyols with two hydroxyl functional groups were used to produce elastomers and soybean-based polyols with three hydroxyl functional groups were used to produce foams. Castor crude oil (which is a polyol) was obtained from CasChem Company, NJ (USA). The aliphatic 1,6-hexamethylene diisocyanate (HDI, Desmodur N-3200) and the aromatic diphenylmethane diisocyanate (MDI, Mondur MRS) were sourced from Bayer Corporation, Pittsburgh, Pa., USA. The relevant parameters of the polyols and diisocyanates are listed in Table 18.

TABLE 18

The parameters of the used polyols and diisocyanate. Errors are standard deviations, n = 3.

| | Equivalent weight (g/mole) | OH number (mg KOH/g) | Acidity number (mg KOH/g) |
|---|---|---|---|
| Canola based polyol | 368 | 152.4 ± 0.3 | 22.9 ± 0.3 |
| Flax based polyol | 436 | 128.7 ± 2.4 | 23.1 ± 0.2 |
| Soybean based polyol 1* | 902 | 62.2 ± 2.7 | 7.7 ± 0 |
| Soybean based polyol 2** | 302 | 185.5 ± 3.0 | 7.6 ± 0.4 |
| Castor oil | 340 | 165.2 ± 3.8 | 1.8 ± 0.1 |
| HDI | 183 | | |
| MDI | 133 | | |

*Soybean based polyol with two hydroxyl functional groups.
**Soybean based polyol with three hydroxyl functional groups.

Step B—Preparation of the Polyurethanes

The polyols were used to produce PU elastomers and PU foam samples. They are referred to as Canola Oil Based PU (COBPU), Flax Oil Based PU (FOBPU) and Soybean Oil Based PU (SOBPU) elastomers or Canola-PU, Castor-PU and Soybean-PU foams, respectively.

To prepare the elastomers, three formulations were used by fixing the molar ratio of the OH to the isocyanate (NCO) group to 1:0.8, 1:1.1 and 1:1.2 respectively. The weights of polyol and isocyanate were calculated on the basis of their respective known equivalent weights (the equivalent weight of polyol ($EW_{polyol}$)=56110/OH number in g/mole, the equivalent weight of the isocyanate ($EW_{isocyanate}$) was provided by the company (183 g/mole for HDI, and 133 g/mole for MDI). Given the total weight of PU ($W_{PU}$) to produce and the desired OH/NCO molar ratio ($M_{ratio}$), the weight of polyol ($W_{polyol}$) needed satisfy the equation below:

$$M_{ratio} = \frac{W_{polyol}/EW_{polyol}}{(W_{PU} - W_{Polyol})/EW_{Isocyanate}}$$

A suitable amount of polyols mixture and HDI were weighed in a plastic container, stirred slowly for 5 min, poured in a metallic mould previously greased with silicone release agent, and placed in a vacuum oven at 45° C. for 10 to 20 min to evacuate the $CO_2$ released during the side reaction. After this time, the sample was solid, but tacky and not fully cured. Air was then introduced to the oven and the sample post-cured for about 48 hours at 40-45° C.

The formulation to prepare the foams was chosen so that the final hydroxyl number lay between 450 to 500 mg KOH/g in order to obtain the desirable rigidity ((Guo, A., I. Javni, and Z. Petrovic, Rigid polyurethane foams based on soybean oil, Journal of Applied Polymer Science, 77: 467-473 (2000)). A typical foam formulation is shown in Table 19.

TABLE 19

Typical foam formulation

| Polyol | 100.0 part |
|---|---|
| Glycerin | 12.0-15.0 |
| Water | 2.0-3.0 |
| Surfactant | 2.0 |
| DBTDL T-12 | 1.0 |
| DABCO DMEA | 1.0 |
| Crude MDI Index | 1.2 |

The polyols were reacted with MDI, in the presence of Dibutin Dilaurate (DBTDL) from Aldrich Chemical (USA) as the main catalyst, N, N-Dimethylethanolamine (DMEA) from Aldrich Chemical (USA) as the co-catalyst, and glycerin from Fisher Chemicals (USA) as cross-linker agents and distilled water as blowing agent. The surfactant was B-8404 from Goldschmidt Chemical Canada. The specific polyol was first mixed (2 minutes) in a plastic container with suitable amounts of crosslinkers, catalyst, and surfactant. MDI was added and the mixture was stirred vigorously for 40 seconds in the case of Canola and Castor oil based PU foams and for 90 seconds in the case of Soybean oil based PU foams. The mixture was then poured into a home-made TEFLON mould which was greased with the silicon release agent and sealed with a hand-tightened clamp. After the reaction had been completed, the sample was post cured at room temperature for 4 days. Flax based polyols were found not suitable to produce usable foams. Without being bound by theory, it may be that this is due to a very low amount of triol in the flax-based polyol combined with a relatively high amount of saturated fatty acids.

For the compressive property measurements, foams samples were prepared in circular cylindrical TEFLON molds of 60-mm diameter and 36-mm long. For DMA measurements, rectangular samples were prepared with the same procedure by polymerizing the reactants in (18×13×4 mm)-TEFLON molds.

Step C—FTIR

The FTIR spectra were recorded on a Nicolet Magna 750 FTIR, equipped with an MCT-A detector and a Nicolet Nic-Plan IR microscope used in transmission mode. The spectra were recorded in the range 650-4000 $cm^{-1}$ with a nominal resolution of 4 $cm^{-1}$. A background spectrum was first collected before each absorbance spectrum. 128 interferograms were coadded before Fourier transformation using the Nicolet Omnic software.

Step D—Thermal Properties

DSC measurements were carried out on a TA Instruments MDSC Q100, equipped with a refrigerated cooling system. All the DSC measurements were performed following the ASTM E1356-03 standard. The samples were heated at a rate of 10° C./min from −90° C. to +100° C., under a dry nitrogen gas atmosphere. MDSC measurements were performed with a modulation amplitude of 0.5° C. and a modulation period of 60 s at a rate of 2° C./min for COBPU and with a modulation amplitude of 0.1° C. and a modulation period of 20 s at a rate of 1° C./min for FOBPU and SOBPU.

DMA measurements were carried out on a TA Instrument DMA Q800 equipped with a liquid nitrogen cooling apparatus, in the single cantilever mode, with a constant heating rate of 1° C./minute from −120° C. to +50° C. in the case of PU elastomers, and a constant heating rate of 2° C./minute from −120° C. to +150° C. in the case of PU foams. The measurements were performed following ASTM E1640-99 standard at a fixed frequency of 1 Hz and a fixed oscillation displacement of 0.015 mm.

A TA Instruments TMA (2940) was used to measure the change in dimensions of the PU elastomer while the material was subjected to a constant heating rate of 5° C./min through the glass transition from −120° C. to +150° C. The measurements were performed according to ASTM E1545-00 standard. The probe was kept in close contact with the specimen surface. The applied force on the specimen was 0.05 N.

TGA was carried out on a Dupont Instruments Thermogravimetric Analyzer (951) following the ASTM D3850-94 standard. The sample was ground to a powder after chilling with liquid nitrogen and approximately 20 mg of the specimen was loaded in the open platinum pan. The samples were heated from 25° C. to 600° C. under dry nitrogen at a constant heating rate of 5° C./min.

Step E—Mechanical Properties

The tensile property of the PU elastomers was conducted on an Instron 4202 tensile instrument according to the ASTM D882-97 standard. The cross-head speed was 50 mm/min with a load cell of 50 Kgf. At least five identical dumbbell-shaped specimens, prepared by cutting the material out of a polymer sheet, were tested and the results averaged.

The compressive properties of the foams were measured on an Instron universal testing machine (model 4202) according to the ASTM D1621-00 standard. The cross-head speed was 3.54 mm/min with a load cell of 500 Kgf. The load was applied until the foam was compressed to approximately 15% of its original thickness and the compressive strengths were calculated based on the "10% deformation" method according to the standard. The strengths of five identical specimens per sample were tested and the results averaged.

Step F—Scanning Electron Microscopy (SEM)

The microstructure of the obtained PU foams was examined using a Scanning Electron Microscope (Philips XL30 ESEM LaB$_6$ manufactured by FEI Company, Oregon, USA). Samples are examined uncoated and without processing, with a Gaseous Secondary electron Detector (GSED), within a gaseous environment and a partial vapor pressure of 1.2 mbar. The sample chamber vacuum was around $9.4 \times 10^{-5}$ mbar. The circular sample was cut into small strips and then snapped by hand to reveal a fracture surface for subsequent microscopy observation.

Step G—Density Test

The density of the PU foam was determined by averaging the mass/volume measurement results of five specimens per sample. All the samples were run in duplicate for thermomechanical property measurements and in sextuplicate for the tensile, compressive and density tests. The reported errors are the subsequent standard deviations.

Example 5:

Modified Methods of Preparation of Polyols from Canola Oil

Step A—Ozonolysis

Canola oil(100 g) and 500 ml of ethyl acetate were poured into a specially designed reactor (schematic shown in FIG. 39 and described above), fed with a Direct Current Permanent Magnet 1 HP Motor from Leeson electric-corporation, USA. Ozone was produced in an ozone generator (Azcozon Model RMV16-16 from Azco Industries Ltd, Canada) with oxygen as the feed gas. The reaction was performed at 10° C., at 5 L/min $O_2$ flow rate and 100 rpm agitation rate. After 1 hour, the ozone generator was stopped and the reaction vessel was purged with $N_2$ for 10 minutes to remove the unreacted ozone in the vessel. The product was poured out from the reaction vessel for hydrogenation.

Step B—Hydrogenation

Two catalysts systems were developed.

System A: Palladium-Carbon (10% of Weight of Pd in the Catalyst) and Raney Nickel Palladium catalyst (2 g) was added to the ozonide in ethyl acetate in a hydrogenation vessel (2L, Parr Instrument Co, USA) fitted with a magnetic drive. The reaction vessel was flushed 3 times with nitrogen and hydrogen to 200 psi pressure to remove the air and then was charged with hydrogen gas at 200 psi at room temperature. The temperature was increased to 50° C. The consumption of hydrogen was so fast that during the time period the temperature increasing, the pressure in the reaction vessel began to drop. Once the pressure dropped to 100 psi, more hydrogen was charged into the reaction vessel until the pressure reached 200 psi. After 2 times of recharging the hydrogen, the pressure was constant at 185 psi. The total reaction time was 1.5 hours. The temperature was then reduced to room temperature with cooling water and to a final pressure of 170 psi. The unreacted hydrogen gas was removed from the reaction vessel with nitrogen gas. The catalyst was filtrated out from the product.

The product was transferred to the reaction vessel again and 15 g Raney Nickel was added. The reaction vessel was flushed 3 times with nitrogen and hydrogen to 400 psi pressure to remove the air and then was charged with hydrogen gas at 300 psi at room temperature. The temperature was increased to 120° C. Once the pressure dropped to 150 psi, more hydrogen was charged into the reaction vessel until the pressure reached 200 psi. After 2 times of recharging the hydrogen, the pressure was constant at 225 psi. The total reaction time was 3 hours. The temperature was then reduced to room temperature with cooling water and to a final pressure of 120 psi. The unreacted hydrogen gas was removed from the reaction vessel with nitrogen gas. The catalyst was filtrated out from the product.

System B: Zinc Powder and Raney Nickel

The product from step A was transfer to the hydrogenation vessel and 30 g of zinc was also added. 20 psi of hydrogen was charged. The mixture was agitated at 4.8 RPM and room temperature for 30 mins. The unreacted hydrogen gas was removed from the reaction vessel with nitrogen gas. The catalyst was filtrated out from the product.

The product was transferred to the reaction vessel again and 15 g Raney Nickel was added. The reaction vessel was flushed 3 times with nitrogen and hydrogen to 300 psi pressure to remove the air and then was charged with hydrogen gas at 250 psi at room temperature. The temperature was increased to 100° C. Once the pressure dropped to 150 psi, more hydrogen was charged into the reaction vessel until the pressure reached 250 psi. After 5 times of recharging the hydrogen, the pressure remained constant at 225 psi. The total reaction time was 2.5 hours. The temperature was then reduced to room temperature with cooling water and to a final pressure of 130 psi. The unreacted hydrogen gas was removed from the reaction vessel with nitrogen gas. The catalyst was filtrated out from the product.

From GC analysis, the product was not fully hydrogenated. Then the product was transferred to the reaction vessel again and 10 g Raney Nickel was added. The reaction vessel was flushed 3 times with nitrogen and hydrogen to 300 psi pressure to remove the air and then was charged with hydrogen gas at 250 psi at room temperature. The temperature was increased to 100° C. Once the pressure dropped to 150 psi, more hydrogen was charged into the reaction vessel until the pressure reached 250 psi. After recharging the hydrogen once, the pressure was constant at 190 psi. The total reaction time was 2.5 hours. The temperature was then reduced to room temperature with cooling water and to a final pressure of 135 psi. The unreacted hydrogen gas was removed from the reaction vessel with nitrogen gas. The catalyst was filtrated out from the product.

The wiped-blade molecular distillation and GC, HPLC analysis methods were the same as in Example 2: Step C, Step D and Step F, except that A HPLC run consisted of a linear gradient of 100% solvent A to 70% A and 30% solvent B in 30 min.; then back to 100% A in 1 minutes at a flow rate of 2 mL/min.

It was also found that the ethyl acetate recycled by rotary evaporator could be successfully applied as a solvent for ozonolysis and hydrogenation reactions.

For both system A and system B, a batch of vegetable oils treated as described in the current example, i.e. full ozonolysis with an ozone flow of 5 L/min and subsequent full hydrogenation, resulted in a polyol product constituted by 95% triol and 5% of mono-ol and diol Step C—Rheometric Measurements The viscosities of the polyol samples were measured in shearing mode with the Universal Dynamic Rheometer PHYSICA UDS 200 (Paar Physica USA) with a constant shearing rate of 51.6 $s_{-5}$. The viscosities were recorded at 6 different temperatures, from 50° C. to 25° C. every 5° C. The viscosities were also measured at 25° C. as a function of time.

Step D—Hydroxyl and Acidity Values

The hydroxyl numbers of the polyols were determined according to the ASTM titration method D1957-86 and the acidity values were determined according to the ASTM method D4662-98. Triplicate specimens were measured for each polyol and the average values and standard deviations are reported here.

In this example, properties of PU rigid foams prepared by reacting polyols synthesized from canola oils by using ethyl acetate and recycled ethyl acetate with aromatic diisocyanates are described. The relevant parameters of the polyols and diisocyanates are listed in Table 20.

TABLE 20

The parameters of the used polyols and diisocyanate.

| | Equivalent weight (g/mole) | OH number (mg KOH/g) | Acidity number (mg KOH/g) |
|---|---|---|---|
| Canola based polyol (ethyl acetate) | 229 | 245.5 ± 2.2 | 10.6 ± 0.1 |
| Canola based polyol (recycled ethyl acetate) | 299 | 187.8 ± 2.6 | 25.6 ± 0.1 |
| MDI | 133 | | |

Step E—Preparation of the Polyurethanes

The polyols synthesized with the modified ozonolysis and hydrogenation methods set out in Example 5 were used to produce PU foam samples. They are referred to as Ethyl Acetate Canola Oil Based PU (EACOBPU) for the polyols synthesized using ethyl acetate as solvent and Recycled Ethyl Acetate Canola Oil Based PU (REACOBPU), for the polyols synthesized using recycled ethyl acetate respectively.

The formulation used to prepare foams was the same as shown in Table 19. The polyols were reacted with MDI, in the presence of Dibutin Dilaurate (DBTDL) from Aldrich Chemical (USA) as the main catalyst, N,N-Dimethylethanolamine (DMEA) from Aldrich Chemical (USA) as the co-catalyst, and glycerin from Fisher Chemicals (USA) as cross-linker agents and distilled water as blowing agent. The surfactant was B-8404 from Goldschmidt Chemical Canada. The specific polyol was first mixed (2 minutes) in a plastic container with suitable amounts of crosslinkers, catalyst, and surfactant. MDI was added and the mixture was stirred vigorously for 60 seconds in the case of EACOBPU foams and for 50 seconds in the case of REACOBPU foams. The mixture was then poured into a home-made TEFLON mould which was greased with the silicon release agent and sealed with a hand-tightened clamp. After the reaction had been completed, the sample was post cured at room temperature for 4 days.

For the compressive property measurements, foams samples were prepared in circular cylindrical TEFLON molds of 60-mm diameter and 36-mm long. For DMA measurements, rectangular samples were prepared with the same procedure by polymerizing the reactants in (18×13×4 mm)-TEFLON molds.

DMA measurements were carried out on a TA Instrument DMA Q800 equipped with a liquid nitrogen cooling apparatus, in the single cantilever mode, with a constant heating rate of 1° C./minute from −120° C. to +50° C. The measurements were performed following ASTM E1640-99 standard at a fixed frequency of 1 Hz and a fixed oscillation displacement of 0.015 mm.

The compressive properties of the foams were measured on an Instron universal testing machine (model 4202) according to the ASTM D1621-00 standard. The cross-head speed was 3.54 mm/min with a load cell of 500 Kgf. The load was applied until the foam was compressed to approximately 15% of its original thickness and the compressive strengths were calculated based on the "10% deformation" method according to the standard. The strengths of five identical specimens per sample were tested and the results averaged.

The density of the PU foam was determined by averaging the mass/volume measurement results of five specimens per sample. All the samples were run in duplicate for thermomechanical property measurements and in sextuplicate for the tensile, compressive and density tests. The reported errors are the subsequent standard deviations Example 6

General Procedure for Preparation of Hydroxyl Wax Esters

Step A: Ozonolysis

Canola oil (100 g) and 400 ml of distilled water were poured into the reactor (schematic shown in FIG. 39), fed with a Direct Current Permanent Magnet 1 HP Motor from Leeson electric-corporation, USA. Ozone was produced in an ozone generator (Azcozon Model RMV16-16 from Azco Industries Ltd, Canada) with oxygen as the feed gas. The reaction was performed at 27° C., at 5 L/min $O_2$ flow rate and 80 rpm agitation rate. After 5 hours, the ozone generator was stopped and the reaction vessel was purged with $N_2$ for 10 minutes to remove the unreacted ozone in the vessel. The product was poured out and transferred into a separatory funnel to remove the aqueous layer.

Step B: Hydrogenation

The short chain alcohols collected from the previous batches through the molecular blade distillation were used as the hydrogenation solvent. About 400 g of this solvent was added to the ozonide in the ozonolysis vessel and agitated under the nitrogen for 1 hour to ensure the ozonide was completely dissolved in the solvent. Then this solution was transferred to the hydrogenation vessel (2L, Parr Instrument Co, USA). 14.3 g of Raney nickel catalyst were added to the ozonide solution. The reaction vessel was flushed 3 times with nitrogen at 200 psi pressure to remove the air and then was charged with hydrogen gas at 350 psi at room temperature. The temperature was increased over 30 minutes to 135° C. with a concomitant increase in pressure to 490 psi. The hydrogenation reaction was carried for 5.5 hours at this temperature and the pressure decreased with the consumption of hydrogen. The temperature was then reduced to room temperature with cooling water and the pressure reduced to a final pressure of 235 psi. The unreacted hydrogen gas was removed from the reaction vessel with nitrogen gas. The remaining mixture was filtered over Celite and the aqueous layer removed in a separatory funnel.

Step C: Wiped-blade Molecular Distillation

The wiped blade molecular distillation unit (Model VKL 70/ICL-04, from Incon Processing) was set up at a jacket temperature of 115° C., and the temperature of the condenser 30° C. The pressure of the distillation system was reduced to 20 mTorr and the viscous oily product added into the distillation system through an addition funnel at a speed of 1 mL/min. After all the product had been added to the distillation system, the unit was kept running for 30 minutes, to allow the complete collection of the residue and distillate. Finally, distillate (140.0 g) and residue (52.0 g) were obtained.

Step D: Flash Chromatography

A column of dimensions 3 id×30 cm was packed with 400 g (about 212 mL volume) of silica gel (230-400 mesh). Material from the residue fraction of distillation (1.7 g) was added. The column was then eluted under air pressure with gradient flow phase composed of hexane and ethyl acetate. The ratios (v/v) of hexane to ethyl acetate was started with 50:1, then gradually decreased to 25:1, 20:1, 12:1, 10:1, 8:1, 7;1, 5:1, 3:1, followed by 2:1, 1:1, 1:2. Finally pure ethyl acetate was used and the fractions were collected in 20 mL-test tubes. Thin layer chromatography (TLC) was run on each fraction using hexane and ethyl acetate as the developing system with ratios (v/v) of hexane and ethyl acetate of 3:1, 2:1, and 1:1. The glycerides and related compounds were detected by spraying the plates first with methanol containing 10% sulphuric acid (concentration 98%) and then heating them at 200° C. for 5 minutes. A ratio of flow phase of 7:1 was used on fractions 110-130. The hydroxyl wax ester was in this fraction.

Example 7

Modified Method for the Preparation of GIII-Polyol from Canola Oil

Step A—Ozonolysis

Canola oil (100 g) and 700 ml of ethyl acetate were poured into the specially designed reactor (FIG. 39), fed with a Direct Current Permanent Magnet 1 HP Motor from Leeson electric-corporation, USA. Ozone was produced in an ozone generator (Azcozon Model RMV16-16 from Azco Industries Ltd, Canada) with oxygen as the feed gas. The reaction was performed at room temperature (around 22° C.), at 5 L/min $O_2$ flow rate and 100 rpm agitation rate. After 1 hour, the ozone generator was stopped and the reaction vessel was purged with $N_2$ for 5 minutes to remove the unreacted ozone in the vessel. The product was poured out from the reaction vessel for zinc treatment.

Two processes were developed: Process A using a separate Reduction Step with zinc after ozonolysis and before hydrogenation and Process B without a Reduction Step with zinc.

Step B—Reduction with Zinc

The product from ozonolysis was transferred to a 2L Parr Instrument Co reduction vessel fitted with a magnetic drive which was also a hydrogenation vessel and 30 g of zinc was added. The reaction was performed at room temperature and atmospheric pressure for 1 hour. Then the reaction product was filtrated with filtering paper.

Step C—Hydrogenation

The filtered product from step B was transferred into a 2L Parr Instrument Co hydrogenation vessel fitted with a magnetic drive. 300±125 ml of fresh ethyl acetate were added to make 950 to 1000 ml of Solution. 16±1 g of Ra—Ni catalyst were then added. The reaction was performed at a temperature of 70° C. and under 100 psi hydrogen pressure for 3 hr. The hydrogen was purged from the hydrogenation vessel with nitrogen gas. The catalyst was filtrated out from the product.

It was also found that the reaction can be successfully performed without the zinc reduction step using ethyl acetate (or other suitable solvent) for ozonolysis and hydrogenation reactions.

For both procedures (with and without zinc reduction step), a batch of 100 g of canola vegetable oil treated as described in the current example, i.e. full ozonolysis with an ozone flow of 5 L/min and subsequent full hydrogenation, resulted in a polyol product constituted by 95% triol and 5% of mono-ol, diol and saturated TAG.

Step D—Wiped-Blade Molecular Distillation

The unit (Model VKL 70/ICL-04, from Incon Processing, IL, USA) was set up at a jacket temperature of 115° C., and condenser temperature of 10° C. The pressure of the distillation system was reduced to 100 mTorr. After removing the solvent by rotary evaporation, the viscous oily product was added into the distillation system through an addition funnel. The distillate residue fraction was analyzed by HPLC.

Step E—Gas Chromatography (GC)

To determine the amounts of short chain compounds present as by-products from the ozonolysis, reduction and hydrogenation steps, a Varian 3500 Capillary Gas Chromatograph equipped with a Flame Ionization Detector (GC-FID), a Varian 8200 Auto Sampler and a BP20025 column (30-m long, 0.25-mm internal diameter, and 0.25-μm thick silica wall) was used. The system was controlled with Varian's "Star Chromatography Workstation" software V.5.51. The injector and the detector temperature were fixed at 250° C. The temperature of the column initially set at 50° C. was increased to 250° C. in two successive steps: from 50° C. to 90° C. at a rate of 25° C./minute and from 90° C. to 250° C. rate of 10° C./minute.

Step F—High Performance Liquid Chromatography (HPLC)

The HPLC analysis protocol used was a modification of the procedure developed by Elfman-Borjesson and Harrod (Elfman-Borjesson, I. and M. Harrod, Analysis of Non-Polar Lipids by HPLC on a Diol Column. *J. High Resol. Chromatogr.* 20: 516-518 (1997)) for analysis of lipid derivatives. The HPLC system consisted of a dual Milton Roy pump with a 20 μL auto-injector. The column was packed by Betasil Diol-100 (5 μm particle size) 250×4 mm produced by Thermo Hypersi-Keytone and maintained at 50° C. with a Biorad column heater. The detector was an Alltech EDSL 2000 evaporative light scattering system maintained at 100° C. with a gain setting of 10 (on the 12 unit scale) and a nitrogen pressure of 2 bar. Two solvents were connected to the pump as the mobile phase. A was 100% heptane and B 50% heptane with 50% isopropyl alcohol (IPA). A run consisted of a linear gradient of 100% A to 83% A and 17% B in 30 min; then back to 100% A in 1 minute at a flow rate of 3 mL/min.

Step G—Rheometric Measurements

The viscosities of the polyol samples were measured in shearing mode with the Universal Dynamic Rheometer PHYSICA UDS 200 (Paar Physica USA) with a constant shearing rate of 51.6 s$^{-1}$. The viscosities were recorded at 6 different temperatures, from 50° C. to 25° C. every 5° C. The viscosities were also measured at 25° C. as a function of time.

Step H—Hydroxyl and Acidity Values

The hydroxyl numbers of the polyols were determined according to the ASTM titration method D1957-86 and the acidity values were determined according to the ASTM method D4662-98. Triplicate specimens were measured for each polyol and the average values and standard deviations are reported here.

Example 8

Preparation of HPLC Standards

Step 1—Flash Chromatography

Pure triol and diol samples used as the standards were separated from the polyol product by flash chromatography (S. S. Narine, J. Yue and X. Kong (In Press, February 2007), *Production of Polyols from Seed Oils and their Chemical Identification and Physical Properties*, J. Am. Oil Chem. Soc.). A column of dimensions 3 id×30 cm was packed with 400 g (about 212 mL volume) of silica gel (230-400 mesh). Material from the residue fraction of distillation (4.3 g) was added.

The column was then eluted under air pressure with gradient flow phase composed of hexane and ethyl acetate. The ratios (v/v) of hexane to ethyl acetate was started with 50:1, then gradually decreased to 20:1, 17:1, 10:1, 8:1, 5:1, 3:1, 2:1, 1:1, followed by 1:2, 1:3, 1:4. Finally pure ethyl acetate was used and the fractions were collected in 30 mL test tubes. Ratios of flow phase of 20:1, 8:1, 2:1 and 1:4 were used on fractions 28-50, 131-143, 264-289, and 366-389 respectively.

Thin layer chromatography (TLC) was run on each fraction using hexane and ethyl acetate with ratios (v/v) of hexane and ethyl acetate of 3:1, 2:1, and 1:1 as the developing system. The glycerides and related compounds were detected by spraying the plates first with methanol containing 10% sulphuric acid (concentration 98%) and then heating them at 200° C. for 5 minutes. Fractions 264-289 were used for diol standard and fractions 366-389 were used for triol standard.

Step 2: HPLC Procedure

The HPLC analysis protocol used was a modification of the procedure developed by Elfman-Borjesson and Harrod for analysis of lipid derivatives. The HPLC system consisted of a dual Milton Roy pump with a 20 μL auto-injector. The column was packed by Betasil Diol-100 (5 μm particle size) 250×4 mm produced by Thermo Hypersi-Keytone and maintained at 50° C. with a Biorad column heater. The detector was an Alltech EDSL 2000 evaporative light scattering system maintained at 100° C. with a gain setting of 10 (on the 12 unit scale) and a nitrogen pressure of 2 bar. Two solvent reservoirs were used: (A) heptane, (B) heptane/isopropyl alcohol 50:50 (vol/vol). A run consisted of a linear gradient of 100% A to 83% A and 17% B in 30 min; then back to 100% A in 1 minute at a flow rate of 2 mL/min.

Step 3: Standard Curves

The standard curves were constructed by injecting in triplicate five known concentrations of triol, diol and mono-ol in DCM. The concentrations of triol sample were 423 μg/ml, 453 μg/ml, 481 μg/ml, 535 μg/ml, and 594 μg/ml; the concentrations of diol samples were 216 μg/ml, 288 μg/ml, 360 μg/ml, 432 μg/ml, 493 μg/ml; the concentrations of mono-ol samples were 193 μg/ml, 291 μg/ml, 386 μg/ml, 521 μg/ml, 581 μg/ml. Peak area versus substance concentration were then plotted and fit to a linear curve using SigmaPlot V9 software.

Example 9

Preparation of nonyl-9-hydroxynonanoate from Canola Oil

Materials

The canola vegetable oil used in this study was a "100% Pure Canola" supplied by Canbra Foods Limited, Lethbridge, AB, Canada. Raney nickel 2800 (slurry in water) catalyst was obtained from Sigma-Aldrich Co., USA. Ethyl acetate, hexane, 1-nonanol (97%) and hydrochloric acid (36.5-38%) were obtained from Fisher Scientific, USA. Silica gel (230-400 mesh) was obtained from Rose Scientific Ltd, AB, Canada. All chemicals were reagent grade or better.

Step 1—Ozonolysis

Canola oil (100 g) and 500 ml of ethyl acetate were poured into our specially designed reactor, fed with a Direct Current Permanent Magnet 1 HP Motor from Leeson electric-corporation, USA. Ozone was produced in an ozone generator (Azcozon Model RMV16-16 from Azco Industries Ltd, Canada) with oxygen as the feed gas. The reaction was performed at 10° C., at 5 L/min $O_2$ flow rate and 100 rpm agitation rate. After 1 hour, the ozone generator was stopped and the reaction vessel was purged with $N_2$ for 10 minutes to remove the unreacted ozone in the vessel. The product was poured out from the reaction vessel for hydrogenation.

Step 2—Hydrogenation

The product was transferred to the hydrogenation vessel and 15 g Raney Nickel was added. The vessel was charged with hydrogen and the reaction was performed at 70° C., 100 psi for 3 hours. The unreacted hydrogen gas was removed from the reaction vessel with nitrogen gas. The catalyst was filtrated out from the product.

Step 3—Wiped-Blade Molecular Distillation

The unit (Model VKL 70/ICL-04, from Incon Processing, IL, USA) was set up at a jacket temperature of 115° C., and condenser temperature of 30° C. The pressure of the distillation system was reduced to 20 mTorr. After removing the solvent by rotary evaporating, the viscous oily product was added into the distillation system through an addition funnel at a speed of 2 mL/min. After distillation, 61.6 g of product was collected.

Step 4—Transesterification

Product from Step 3 (3.1 g), nonanol (5.1 g) and hydrochloric acid (2 ml) were added into a 50 ml flask and heated up to 85° C. under agitation for 3 hours.

The product was transferred into a separatory funnel. The organic layer which was on the top was separated from the bottom aqueous layer and kept for further analysis.

Step 5—Flash Chromatography

A column of dimensions 3 id×30 cm was packed with 400 g (about 212 mL volume) of silica gel (230-400 mesh). Material from the top layer of separatory funnel (1.00 g) was added. The column was then eluted under air pressure with gradient flow phase composed of hexane and ethyl acetate. The ratios (v/v) of hexane to ethyl acetate was started with 25:1, then gradually decreased to 20:1, 15:1, 10:1, 8:1, 5:1, 3:1, followed by pure ethyl acetate. The presence of material was confirmed in fractions by thin layer chromatography (TLC) on silica gel plates using a solvent system of 25% ethyl acetate and 75% hexane (v/v). Spots were visualized using a 5% sulfuric acid in methanol dip followed by burning on a hot plate. Nonyl-9-hydroxynonanoate was in the fractions 64-84. After evaporation of solvent, 0.52 g of nonyl-9-hydroxynonanoate was collected.

Example 10

Production of Polyurethane Plastic Sheets from GIII-Polyol from Seed Oils

Step A: The polyols synthesized with the modified ozonolysis and hydrogenation methods set out in Example 7 were used to produce GIII-PU plastic sheet samples.

Step B—Preparation of the Polyurethanes Plastic Sheets

The GIII-PU plastic sheets were prepared by reacting the polyols with aromatic diphenylmethane diisocyanate. Three different molar ratios of the OH group to the isocyanate (NCO) group ($M_{ratio}$), i.e. OH/NCO of 1.0/1.0, 1.0/1.1 and 1.0/1.2 were chosen for the formulations. The weights of polyol and isocyanate were determined on the basis of their respective known equivalent weights i.e. $EW_{polyol}$=Molecule Weight of KOH×1000/OH number of polyol=56110/OH number in g/mole for the polyols, and $EW_{isocyanate}$=133 g/mole, provided by the supplier for the isocyanate. The desired OH/NCO molar ratio satisfies the following equation:

$$M_{ratio} = \frac{W_{polyol} / EW_{polyol}}{(W_{PU} - W_{polyol}) / EW_{isocyanate}}$$

where $W_{polyol}$ is the weight of the polyol and $W_{PU}$ the total weight of PU to produce.

A suitable amount of polyols mixture and MDI were weighed in a plastic container, stirred slowly for 2 min, poured in a metallic mould previously greased with silicone release agent and post-cured for about 48 hours at room temperature.

Step C—FTIR

The FTIR spectra were recorded on a Nicolet Magna 750 FTIR, equipped with an MCT-A detector and a Nicolet Nic-Plan IR microscope used in transmission mode. The spectra were recorded in the range 650-4000 cm$^{-1}$ with a nominal resolution of 4 cm$^{-1}$. A background spectrum was first collected before each absorbance spectrum. 128 interferograms were coadded before Fourier transformation using the Nicolet Omnic software.

Step D—Thermal Properties

DSC measurements were carried out on a DSC Q100 (TA Instruments), equipped with a refrigerated cooling system. All the DSC measurements were performed following the ASTM E1356-03 standard procedure. The samples were heated at a rate of 10° C./min from 25° C. to 80° C. to erase thermal memory, cooled down to −40° C. at a cooling rate of 5° C./min then heated again to 80° C. at a heating rate of 10° C./min. The second heating stage was selected to be analyzed for the collection of melting data. All the procedures were performed under a dry nitrogen gas atmosphere.

DMA measurements were carried out on a DMA Q800 (TA Instruments) equipped with a liquid nitrogen cooling apparatus in the single cantilever mode, with a constant heating rate of 1° C./minute from −120° C. to 80° C. The measurements were performed following ASTM E1640-99 standard at a fixed frequency of 1 Hz and a fixed oscillation displacement of 0.015 mm. In the case of multiple isothermal oscillation experiments, the isothermal evolution of theological parameters was recorded as a function of frequency ranging from 0.1 to 100 Hz. The measurements were performed, every 5° C., 30° C. below and above glass transition temperature.

TGA was carried out on a TGA Q50 (TA Instruments) following the ASTM D3850-94 standard. The sample was ground to a powder after chilling with liquid nitrogen and approximately 20 mg of the specimen was loaded in the open platinum pan. The samples were heated from 25° C. to 600° C. under dry nitrogen at constant heating rates of 5, 10 and 20° C./min.

All the samples were run in triplicate for thermal property measurements.

Step E—Mechanical Properties

Specimens for tensile measurements were cut out from the GIII-PU plastic sheets using an ASTM D638 Type IV cutter. The tests were performed at room temperature using an Instron (MA, USA) tensile testing machine (model 4202) equipped with a 500 Kgf load cell and activated grips which prevented slippage of the sample before break. The used cross-head speed was 100 mm/min, as suggested by the above mentioned ASTM standard. At least five identical dumbbell-shaped specimens for each sample were tested and their average mechanical properties are reported.

Step F—Density Test

The density of the GIII-PU plastic sheets with different molar ratio was determined according to ASTM D 792-00 standard.

Example 11

The Preparation of GIII-PU Elastomers and Foams.

Step A: Elastomers and rigid foams, were prepared by mixing GII-Polyol (produced by the process of Example 2) or GIII-Polyol (produced by the process of Example 7) with appropriate diisocyanates, using the procedure as described in Example 4. The resulting samples are referred to as GII-PU and GIII-PU for the samples obtained with GII-Polyol and GIII-Polyol, respectively.

Step B—Thermal Properties

DSC measurements were carried out on a DSC Q100 (TA Instruments), equipped with a refrigerated cooling system. All the DSC measurements were performed following the ASTM E1356-03 standard. The samples were heated at a rate of 10° C./min from +25° C. to +100° C. to eliminate the thermal history, cooled down to −50° C. at a cooling rate of 5° C./min then heated again to +100° C. at a rate of 10° C./min. Only the second heating step was select for data analysis. All the procedures were performed under a dry nitrogen gas atmosphere.

DMA measurements were carried out on a DMA Q800 (TA Instruments) equipped with a liquid nitrogen cooling apparatus in the single cantilever mode with a constant heating rate of 1° C./minute from −120° C. to 100° C. The measurements were performed following ASTM E1640-99 standard at a fixed frequency of 1 Hz and a fixed oscillation displacement of 0.015 mm. The isothermal evolution of rheological parameters was also recorded as a function of frequency in the range of 0.1 to 100 Hz. The isothermal oscillations were made, every 5° C., 30° C. below and above glass transition temperature.

All the samples were run in triplicate for thermal property measurements.

Step C—Mechanical Properties

Specimens for tensile measurements were cut out from the GIII-PU plastic sheets using an ASTM D638 Type IV cutter. The tests were performed at room temperature using an Instron (MA, USA) tensile testing machine (model 4202) equipped with a 500 Kgf load cell and activated grips which prevented slippage of the sample before break. The cross-head speed was 100 mm/min as suggested by the above mentioned ASTM standard. At least five identical dumbbell-shaped specimens for each sample were tested and their average mechanical properties are reported.

The compressive properties of the foams were measured on the same testing machine according to the ASTM D1621-00 standard. The cross-head speed was 3.54 mm/min with a load cell of 500 Kgf. The load was applied until the foam was compressed to approximately 15% of its original thickness and the compressive strengths were calculated based on the "10% deformation" method according to the standard. The strengths of five identical specimens per sample were tested and the results averaged.

Step D—Scanning Electron Microscopy (SEM)

The microstructure of the PU foams was examined using a Scanning Electron Microscope (SEM, Philips XL30 ESEM LaB$_6$ manufactured by FEI Company, Oregon, USA). Samples were examined uncoated and without processing, with a Gaseous Secondary Electron Detector (GSED), within a gaseous environment and a partial vapor pressure of 1.2 mbar. The sample chamber vacuum was around $9.4 \times 10^{-5}$ mbar. The sample was cut into small strips and then snapped by hand to reveal fresh fractured surface suitable for microscopy observation.

Every reference cited herein is hereby incorporated by reference in its entirety.

The invention claimed is:

1. A method for producing a polyol from a renewable feedstock comprising one or more unsaturated fatty acid triacylglycerols, wherein the method comprises the steps of:
   (a) dissolving the feedstock in a solvent consisting of ethyl acetate to form a solution;
   (b) supplying the solution of (a) with ozone to effect ozonolysis of two or more double bonds in the unsaturated fatty acids of the one or more triacylglycerols of the feedstock;
   (c) subjecting the solution containing the products of step (b) directly to reductive hydrogenation, without an intervening reduction step, under conditions effective to produce one or more corresponding polyols,
   wherein the one or more polyols comprise at least one triacylglycerol containing at least two primary hydroxyl groups.

2. The method of claim 1, wherein the one or more polyols comprise one or more dihydroxyl functionalized triacylglycerols, or one or more trihydroxyl functionalized triacylglycerols, or mixtures thereof.

3. The method of claim 1, wherein the feedstock comprises a vegetable oil or tallow.

4. The method of claim 2, wherein the vegetable oil is selected from the group comprising canola, linseed, sunflower, tung, lesqueralla, flaxseed, Jatupha, camelina sativa, hump, peanut, palm, soybean, cottonseed, corn, cashew nuts, calendula, mustard, sesame, safflower, sunflower, rapeseed, olive, castor, jojoba, brazil nuts, avocado, and kenaf.

5. The method of claim 1, wherein ozone used in the ozonolysis step (b) is substantially uniformly distributed throughout the reaction mixture.

6. The method of claim 1, wherein the ozonolysis conditions are selected to optimize the primary hydroxyl functionality of the one or more polyols.

7. The method of claim 6, wherein the ozonolysis conditions comprise ozonolysis time, ozone flow rate, and concentration of the renewable feedstock.

8. The method of claim 1, further comprising the step of isolating the one or more polyols from the reaction mixture of step (c).

9. The method of claim 8, wherein the one or more polyols are isolated in greater than about 90% purity relative to non-polyol components contained in or produced during the production of the one or more polyols.

10. The method of claim 1 wherein the ozonolysis reaction is performed at or above 0° C.

11. The method of claim 10, wherein the ozonolysis reaction is performed at room temperature.

12. The method of claim 8, wherein the separation step comprises the use of silica gel chromatography.

13. The method of claim 1, wherein said method further comprises the production of one or more short chain alcohols as a by-product, and said one or more short chain alcohols is separated from the one or more polyols.

14. The method of claim 13, wherein said separation of said one or more short chain alcohol by-products from the one or more polyols is carried out prior to isolating the one or more polyols from the reaction mixture of step (c).

15. The method of claim 13 or 14, wherein said separation of said one or more short chain alcohol by-products from the one or more polyols comprises the use of wiped-blade molecular distillation.

16. A method for producing nonanol, hexanol, propanol, and/or 1,3-propanediol from a renewable feedstock comprising a fatty acid triacylglycerol having at least one unsaturated fatty acid chain, the method comprising the steps of:
   (a) dissolving the feedstock in a solvent consisting of ethyl acetate to form a solutions;
   (b) supplying the solution of (a) with ozone to effect ozonolysis of the double bonds in the fatty acid chain of the triacylglycerol of the feedstock;
   (c) subjecting the solution containing the products of step (b) directly to reductive hydrogenation, without an intervening reduction step, to produce nonanol, hexanol, propanol, and/or 1,3-propanediol; and
   (d) separating nonanol, hexanol, propanol, and/or 1,3-propanediol from the products of step (c) by wiped-blade molecular distillation.

17. The method of claim 16, wherein the feedstock comprises canola oil.

* * * * *